(12) United States Patent
Nakajima et al.

(10) Patent No.: US 6,906,245 B1
(45) Date of Patent: Jun. 14, 2005

(54) METHOD FOR PRODUCING TRANSGENIC PLANTS RESISTANT TO WEED CONTROL COMPOUNDS WHICH DISRUPT THE PORPHYRIN PATHWAYS OF PLANTS

(75) Inventors: Hiroki Nakajima, Nishinomiya (JP); Akitsu Nagasawa, Kobe (JP)

(73) Assignee: Sumitomo Chemical Company, Limited, Osaka (JP)

( * ) Notice: Subject to any disclaimer, the term of this patent is extended or adjusted under 35 U.S.C. 154(b) by 497 days.

(21) Appl. No.: 09/697,719

(22) Filed: Oct. 27, 2000

Related U.S. Application Data

(63) Continuation-in-part of application No. 09/302,357, filed on Apr. 30, 1999, now Pat. No. 6,570,070.

(30) Foreign Application Priority Data

| Apr. 30, 1998 | (JP) | 10-120553 |
| Oct. 2, 1998 | (JP) | 10-281127 |
| Nov. 20, 1998 | (JP) | 10-330981 |
| Mar. 2, 1999 | (JP) | 11-054730 |

(51) Int. Cl.$^7$ .......................... A01H 5/00; C12N 15/82
(52) U.S. Cl. ..................... 800/300; 800/278; 435/410
(58) Field of Search ................ 800/278, 300; 435/410, 419, 468

(56) References Cited

FOREIGN PATENT DOCUMENTS

| EP | 0770682 A2 | 5/1997 |
| WO | WO9534659 | 12/1995 |
| WO | WO9704088 | 2/1997 |
| WO | WO9732011 | 9/1997 |
| WO | WO9849330 | 1/1998 |
| WO | WO9833927 | 8/1998 |

OTHER PUBLICATIONS

Lehninger 1982, in Principles of Biochemistry, Worth Publishers, Inc. New York, New York, p. 209.*
Kruse, E. et al; Planta (Heidelberg) 1995, vol. 196, No. 4, 1995, pp. 796–803.
Kruse, E. et al; Plant Molecular Biology Dec., 1997, vol. 35, No. 6, pp. 1053–1056.
Madsen, O. et al; Plant Molecular Biology 1993, vol. 23, No. 1, 1993, pp. 35–43.
G. della–Cioppa et al., *Bio/Technology*, vol. 5, pp. 579–584 (Jun. 1987).
M. A. W. Hinchee et al., *Bio/Technology*, vol. 6, pp. 915–922 (Aug. 1998).
M. De Block et al., *The EMBO Journal*, vol. 6, No. 9, pp. 2513–2518 (1987).
L. C. D. Gibson et al., *Proc. Natl. Acad. Sci. USA*, vol. 92, pp. 1941–1944 ( Mar. 1995).

\* cited by examiner

*Primary Examiner*—David H Kruse
(74) *Attorney, Agent, or Firm*—Birch, Stewart, Kolasch & Birch, LLP

(57) ABSTRACT

A method for producing a transgenic plant which is resistant to a weed control compound is disclosed. In the inventive method, a nucleotide sequence encoding a variant of plant protoporphyrinogen IX oxidase that lacks the FAD binding sequence is introduced into a plant cell. The nucleotide sequence is expressed and the plant cell is regenerated into a transgenic plant.

11 Claims, 13 Drawing Sheets

METHOD FOR PRODUCING TRANSGENIC PLANTS RESISTANT TO WEED CONTROL COMPOUNDS WHICH DISRUPT THE PORPHYRIN PATHWAYS OF PLANTS

This application is a Continuation-In-Part of application Ser. No. 09/302,357, filed on Apr. 30, 1999 now U.S. Pat. No. 6,570,070, and for which priority is claimed under 35 U.S.C. § 120; and this application claims priority of Application Nos. 120553/1998, 281127/1998, 330981/1998, and 054730/1999 filed in Japan on Apr. 30, 1998, Oct. 2, 1998, Nov. 20, 1998, and Mar. 2, 1999, respectively, under 35 U.S.C. § 119; the entire contents of all are hereby incorporated by reference.

BACKGROUND OF THE INVENTION

1. Fieled of the Invention

The present invention relates to a method for giving resistance to weed control compounds to plants.

2. Disclosure of the Related Art

Weed control is very important work for improving yields and quality of cultivated plants. For this purpose, weed control compounds such as herbicides are mainly used. However, for using weed control compounds, it is not always easy to distinguish cultivated plants from weeds of allied species to selectively control only weeds. Then, production of plants having resistance to weed control compounds (hereinafter referred to as weed control compound-resistance) has been attempted and some resistant plants have been put to practical use.

Recently, gene engineering techniques have been utilized for producing plants having weed control compound-resistance. As such a technique, for example, Hinchee, M. A. W. et al. disclose a method for producing a plant having resistance to a herbicide, glyphosate, wherein 5-enolpyruvylshikimate-3-phosphate synthase (EPSPS) gene which is a target enzyme of glyphosate is mutagenized so that an affinity for glyphosate is reduced, and the gene is introduced into a plant [Hinchee, M. A. W. et al., BIO/TECHNOLOGY, 6: p 915 (1988)].

OBJECTS OF THE INVENTION

Varieties of known methods for giving weed control compound-resistance to plants are not necessarily sufficient and it has been desired to develop further various kinds of methods for giving weed control compound-resistance to plants.

The main object of the present invention is to provide a new kind of a method for giving weed control compound-resistance to plants.

This object as well as other objects and advantages of the present invention will become apparent to those skilled in the art from the following description with reference to the accompanying drawings.

BRIEF DESCRIPTION OF THE DRAWINGS

FIG. 12 is the restriction map of plasmid pTVHVF1. HVF is barley ferrochelatase gene whose signal sequence has been deleted. lac pro represents the promoter sequence of a lactose operon. $Amp^r$ represents an ampicillin resistant gene and ori is the replication origin.

FIG. 13 is the restriction map of plasmid pBIHVF. HVF is barley ferrochelatase gene whose signal sequence has been deleted. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

FIG. 14 is the restriction map of plasmid pTVCSF. CSF is cucumber ferrochelatase gene whose signal sequence has been deleted. lac pro represents the promoter sequence of a lactose operon. $Amp^r$ is an ampicillin resistant gene, and ori is the replication origin.

FIG. 15 is the restriction map of plasmid pBICSF. CSF is cucumber ferrochelatase gene whose signal sequence has been deleted. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

BRIEF SUMMARY OF THE INVENTION

Figure 1:
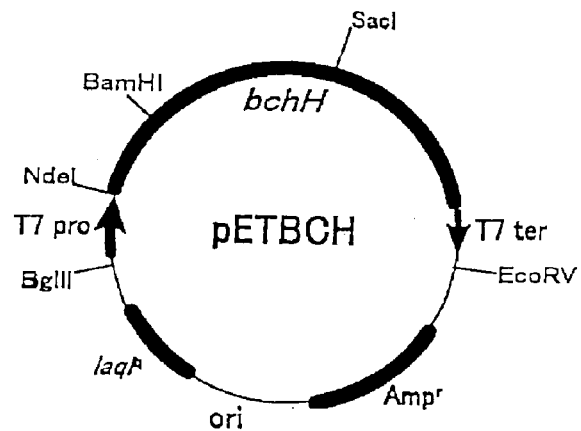
FIG. 1 is the restriction map of plasmid pETBCH. bchH is magnesium chelatase protoporphyrin IX binding subunit gene of a photosynthetic bacterium *Rhodobacter sphaeroides*. T7 pro represents the promoter sequence of T7 phage, and T7 ter represents the terminator sequence of T7 phage. Amp$^r$ is an ampicillin resistant gene, lacI$^q$ is a repressor protein gene of a lactose operon, and ori is the replication origin.

One aspect of the present invention relates to a method for giving weed control compound-resistance to a plant which comprises the steps of:
  introducing a gene encoding a protein having the following characteristics (a) to (c):
    (a) having a specific affinity for a substance which is concerned with the weed control activity of a weed control compound,
    (b) having substantially no capability of modifying a substance for which said protein has a specific affinity, and (c) being substantially free from framework regions of variable regions in an immunoglobulin, into a plant cell; and expressing the gene (hereinafter referred to as the first aspect of the method of the present invention).

The present invention also relates to a method according to the above, wherein the gene is introduced into the plant cell in the form that it is operably ligated to a promoter and a terminator both of which are functional in the plant cell;

The method according to the above, wherein the substance which is concerned with the weed control activity of the weed control compound is the weed control compound itself;

The method according to the above, wherein the substance which is concerned with the weed control activity of a weed control compound is an endogenous substance in a plant;

The method according to the above, wherein the weed control compound is that inhibiting porphyrin biosynthesis of a plant;

The method according to the above, wherein the weed control compound is a protoporphyrinogen IX oxidase inhibitory-type herbicidal compound;

The method according to the above, wherein the substance which is concerned with the weed control activity of the weed control compound is protoporphyrin IX;

The method according to the above, wherein the protein is protoporphyrin IX binding subunit protein of magnesium chelatase, or a variant of said protein having a specific affinity for protoporphyrin IX;

The method according to the above, wherein the protein is magnesium chelatase derived from a photosynthetic microorganism;

The method according to the above, wherein the protein is magnesium chelatase derived from a plant;

The method according to the above, wherein the protein is magnesium chelatase derived from tobacco;

The method according to the above, wherein the protein comprises the amino acid sequence of SEQ ID NO: 53;

The method according to the above, wherein the protein has the amino acid sequence of SEQ ID NO: 54;

The method according to the above, wherein the protein comprises the amino acid sequence of SEQ ID NO: 55;

The method according to the above, wherein the protein has the amino acid sequence of SEQ ID NO: 56;

The method according to the above, wherein the protein comprises the amino acid sequence of SEQ ID NO: 57;

The method according to the above, wherein the protein has the amino acid sequence of SEQ ID NO: 58;

The method according to the above, wherein the protein comprises the amino acid sequence of SEQ ID NO: 59;

The method according to the above, wherein the protein has the amino acid sequence of SEQ ID NO: 60;

The method according to the above, wherein the protein is composed of 4 to 100 amino acids;

The method according to the above, wherein the substance which is concerned with the weed control activity of the weed control compound is protoporphyrinogen IX;

The method according to the above, wherein the protein is a variant of protoporphyrinogen IX oxidase having no capability of oxidizing protoporphyrinogen IX and having a specific affinity for a protoporphyrinogen IX;

The method according to the above, wherein the protein is a variant of protoporphyrinogen IX oxidase having no capability of oxidizing protoporphyrinogen IX and having a specific affinity for a protoporphyrin IX oxidase inhibitory-type herbicidal compound;

The method according to the above, wherein the protein is a variant of protoporphyrinogen IX oxidase derived from a plant;

The method according to the above, wherein the protein is a variant of protoporphyrinogen IX oxidase derived from soybean;

The method according to the above, wherein the protein is a variant of protoporphyrinogen IX oxidase derived from an algae; and The method according to the above, wherein the protein is a variant of protoporphyrinogen IX oxidase derived from *Chlamydomonas.*

Another aspect of the present invention relates to a method for giving weed control compound-resistance to a plant which comprises the steps of:

introducing a gene encoding a protein having the following characteristics (a) to (c):
(a) having a specific affinity for protoporphyrin IX,
(b) having substantially no capability of modifying protoporphyrinogen IX, and
(c) being substantially free from framework regions of variable regions in an immunoglobulin, into a plant cell; and expressing the gene (hereinafter referred to as the second aspect of the method of the present invention).

The present invention also relates to a method according to the above, wherein the gene is introduced in the plant cell in the form that it is operably ligated to a promoter and a terminator both of which are functional in the plant cell;

The method according to the above, wherein the weed control compound is that inhibiting porphyrin biosynthesis of a plant;

The method according to the above, wherein the weed control compound is a protoporphyrinogen IX oxidase inhibitory-type herbicidal compound;

The method according to the above, wherein the protein is magnesium chelatase or a variant of said protein having a specific affinity for protoporphyrin IX;

The method according to the above, wherein the protein is ferrochelatase or a variant of said protein having an specific affinity for protoporphyrin IX;

The method according to the above, wherein the protein is ferrochelatase derived from a plant;

The method according to the above, wherein the protein is ferrochelatase derived from barley;

The method according to the above, wherein the protein is ferrochelatase derived from cucumber; and The method according to the above, wherein the protein is a peptide composed of 4 to 100 amino acids.

Another aspect of the present invention relates to a method for giving weed control compound-resistance to a plant which comprises the steps of:

introducing a gene encoding a protein having the following characteristics (a) to (c):
(a) having a specific affinity for protoporphyrinogen IX,
(b) having the capability for modifying coproporphyrinogen III, and
(c) being substantially free from framework regions of variable regions in an immunoglobulin, into a plant cell; and expressing the gene (hereinafter referred to as the third aspect of the method of the present invention).

The present invention also relates to the method according to the above, wherein the gene is introduced into the plant cell in the form that it is operably ligated to a promoter and a terminator both of which are functional in the plant cell;

The method according to the above, wherein the protein is coproporphyrinogen III oxidase or a variant of said protein having a specific affinity for protoporphyrinogen IX;

The method according to the above, wherein the protein is coproporphyrinogen III oxidase derived from a microorganism;

The method according to the above, wherein the protein is coproporphyrinogen III oxidase derived from *Escherichia coli*;

A weed control compound-resistant plant whose resistance is given by the method of the above;

A weed control compound-resistant plant whose resistance is given by the method of the above;

A method for protecting a plant which comprises applying the weed control compound to a growth area of the plant of the above;

A method for protecting a plant which comprises applying the weed control compound to a growth area of the plant of the above;

A method for selecting a plant which comprises applying a weed control compound to which the plant of the above is resistant to a growth area of the plant of the above and other plants, and selecting either plant on the basis of difference in growth between the plants;

A method for selecting a plant which comprises applying a weed control compound to which the plant of the above is resistant to a growth area of the plant of the above and other plants, and selecting either plant on the basis of difference in growth between the plants;

The method according to the above, wherein the plants are plant cells;

The method according to the above, wherein the plants are plant cells;

The method according to the above, wherein the weed control compound is a protoporphyrinogen IX oxidase inhibitory-type herbicidal compound selected from the compounds of (1) to (3) below, and the substance which is concerned with the weed control activity of the weed control compound is protoporphyrin IX, protoporphyrinogen IX or a protoporphyrinogen IX oxidase inhibitory-type herbicidal compound:

(1) chlormethoxynil, bifenox, chlornitrofen (CNP), acifluorfen (5-[2-chloro-4-(trifluoromethyl)phenoxy]-2-nitrobenzoic acid) and its ethyl ester, acifluorfen-sodium, oxyfluorfen(2-chloro-1-(3-ethoxy-4-nitrophenoxy)-4-trifluoromethylbenzene), oxadiazon (3-[2,4-dichloro-5-(1-methylethoxy)phenyl]-5-(1,1-dimethylethyl)-1,3,4-oxadiazol-2(3H)-one), 2-[4-chloro-2-fluoro-5-(prop-2-ynyloxy)phenyl]-2,3,4,5,6,7-hexahydro-1H-isoindol-1,3-dione, chlorphthalim (N-(4-chlorophenyl)-3,4,5,6-tetrahydrophtalimide), TNPP-ethyl(ethyl 2-[1-(2,3,4-trichlorophenyl)-4-nitropyrazolyl-5-oxy]propionate), or N3-(1-phenylethyl)-2,6-dimethyl-5-propyonylnicotinamide;

(2) a compound represented by the general formula: J-G (I), wherein G is a group represented by any one of the following general formulas G-1 to G-9 and J is a group represented by any one of the following general formulas of J-1 to J-30:

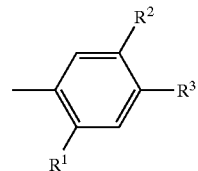
G-1

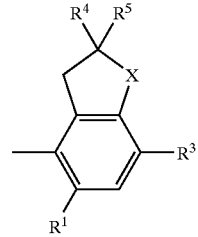
G-2

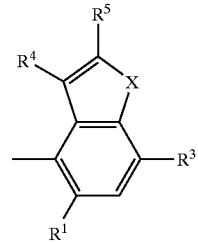
G-3

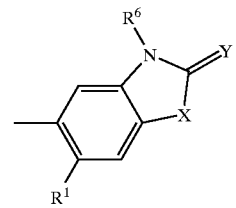
G-4

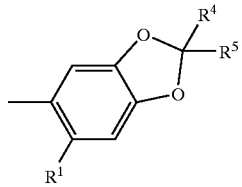
G-5

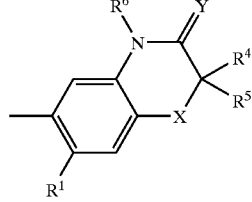
G-6

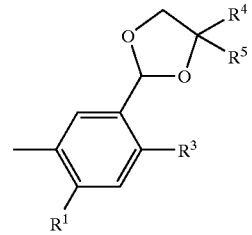
G-7

-continued
G-8
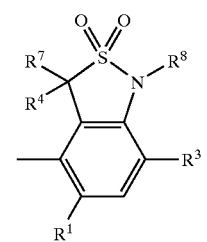
G-9
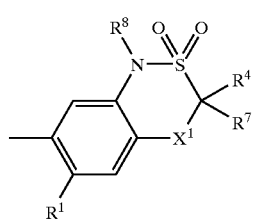
J-1
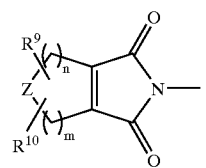
J-2
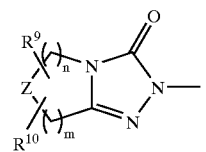
J-3
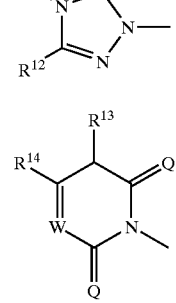
J-4
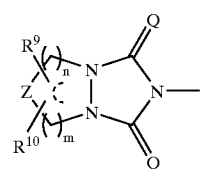
J-5
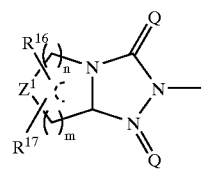
-continued
J-7
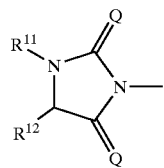
J-8
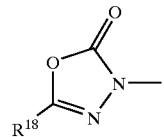
J-9
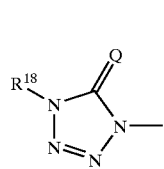
J-10
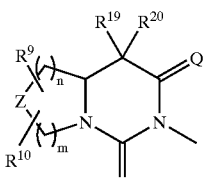
J-11
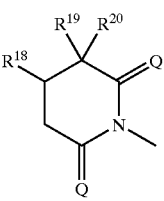
J-12
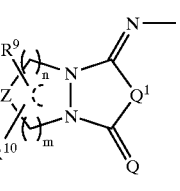
J-13
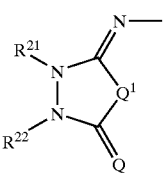
J-14
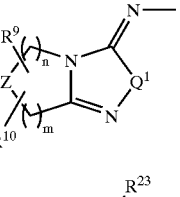
J-15
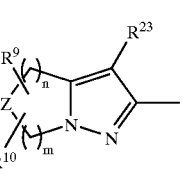

-continued

J-16 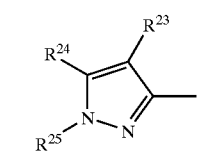

J-17 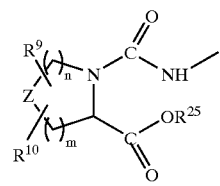

J-18 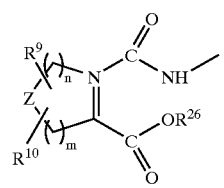

J-19 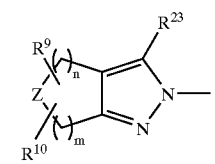

J-20 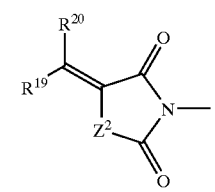

J-21 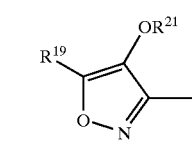

J-22 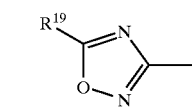

J-23 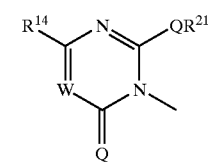

J-24 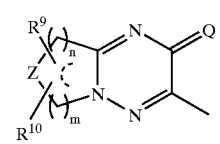

J-25 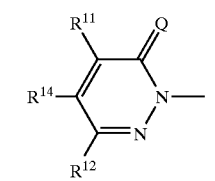

-continued

J-26 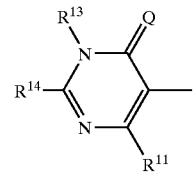

J-27 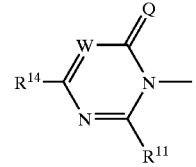

J-28 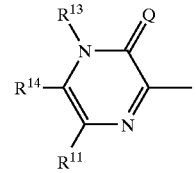

J-29 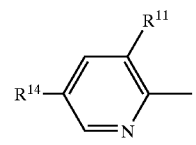

J-30 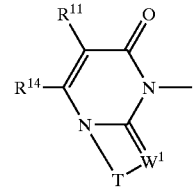

wherein the dotted lines in the formulas J-5, J-6, J-12 and J-24 represent that the left hand ring contains only single bonds, or one bond in the ring is a double bond between carbon atoms;

X is oxygen atom or sulfur atom;

Y is oxygen atom or sulfur atom;

$R^1$ is hydrogen atom or halogen atom;

$R^2$ is hydrogen atom, $C_1$–$C_8$ alkyl group, $C_1$–$C_8$ haloalkyl group, halogen atom, OH group, $OR^{27}$ group, SH group, $S(O)_pR^{27}$ group, $COR^{27}$ group, $CO_2R^{27}$ group, $C(O)SR^{27}$ group, $C(O)NR^{29}R^{30}$ group, CHO group, $CR^{27}$=$NOR^{36}$ group, CH=$CR^{37}CO_2R^{27}$ group, $CH_2CHR^{37}CO_2R^{27}$ group, $CO_2N$=$CR^{31}R^{32}$ group, nitro group, cyano group, $NHSO_2R^{33}$ group, $NHSO_2NHR^{33}$ group, $NR^{27}R^{38}$ group, $NH_2$ group or phenyl group optionally substituted with one or more and the same or different $C_1$–$C_4$ alkyl groups;

p is 0, 1 or 2;

$R^3$ is $C_1$–$C_2$ alkyl group, $C_1$–$C_2$ haloalkyl group, $OCH_3$ group, $SCH_3$ group, $OCHF_2$ group, halogen atom, cyano group or nitro group;

$R^4$ is hydrogen atom, $C_1$–$C_3$ alkyl group, $C_1$–$C_3$ haloalkyl group or halogen atom;

$R^5$ is hydrogen atom, $C_1$–$C_3$ alkyl group, halogen atom, $C_1$–$C_3$ haloalkyl group, cyclopropyl group, vinyl group, $C_2$ alkynyl group, cyano group, $C(O)R^{38}$ group, $CO_2R^{38}$ group, $C(O)NR^{38}R^{39}$ group, $CR^{34}R^{35}CN$ group, $CR^{34}R^{35}C(O)R^{38}$ group, $CR^{34}R^{35}CO_2R^{38}$ group, $CR^{34}R^{35}C(O)NR^{38}R^{39}$ group, $CHR^{34}OH$ group, $CHR^{34}OC(O)R^{38}$ group or $OCHR^{34}OC(O)NR^{38}R^{39}$ group, or, when G is G-2 or G-6, $R^4$ and $R^5$ may form C=O group together with the carbon atom to which they are attached;

$R^6$ is $C_1$–$C_6$ alkyl group, $C_1$–$C_6$ haloalkyl group, $C_2$–$C_6$ alkoxyalkyl group, $C_3$–$C_6$ alkenyl group or $C_3$–$C_6$ alkynyl group;

$X^1$ is single bond, oxygen atom, sulfur atom, NH group, $N(C_1$–$C_3$ alkyl) group, $N(C_1$–$C_3$ haloalkyl) group or N(allyl) group;

$R^7$ is hydrogen atom, $C_1$–$C_6$ alkyl group, $C_1$–$C_6$ haloalkyl group, halogen atom, $S(O)_2(C_1$–$C_6$ alkyl) group or $C(=O)R^{40}$ group;

$R^8$ is hydrogen atom, $C_1$–$C_8$ alkyl group, $C_3$–$C_8$ cycloalkyl group, $C_3$–$C_8$ alkenyl group, $C_3$–$C_8$ alkynyl group, $C_1$–$C_8$ haloalkyl group, $C_2$–$C_8$ alkoxyalkyl group, $C_3$–$C_8$ alkoxyalkoxyalkyl group, $C_3$–$C_8$ haloalkynyl group, $C_3$–$C_8$ haloalkenyl group, $C_1$–$C_8$ alkylsulfonyl group, $C_1$–$C_8$ haloalkylsulfonyl group, $C_3$–$C_8$ alkoxycarbonylalkyl group, $S(O)_2NH(C_1$–$C_8$ alkyl) group, $C(O)R^{41}$ group or benzyl group whose phenyl ring may be substituted with $R^{42}$;

n and m are independently 0, 1, 2 or 3 and m+n is 2 or 3;

Z is $CR^9R^{10}$ group, oxygen atom, sulfur atom, S(O) group, $S(O)_2$ group or $N(C_1$–$C_4$ alkyl) group;

each $R^9$ is independently hydrogen atom, $C_1$–$C_3$ alkyl group, halogen atom, hydroxyl group, $C_1$–$C_6$ alkoxy group, $C_1$–$C_6$ haloalkyl group, $C_1$–$C_6$ haloalkoxy group, $C_2$–$C_6$ alkylcarbonyloxy group or $C_2$–$C_6$ haloalkylcarbonyloxy group;

each $R^{10}$ is independently hydrogen atom, $C_1$–$C_3$ alkyl group, hydroxyl group or halogen atom;

$R^{11}$ and $R^{12}$ are independently hydrogen atom, halogen atom, $C_1$–$C_6$ alkyl group, $C_3$–$C_6$ alkenyl group or $C_1$–$C_6$ haloalkyl group;

$R^{13}$ is hydrogen atom, $C_1$–$C_6$ alkyl group, $C_1$–$C_6$ haloalkyl group, $C_3$–$C_6$ alkenyl group, $C_1$–$C_6$ haloalkenyl group, $C_3$–$C_6$ alkynyl group, $C_3$–$C_6$ haloalkynyl group, HC(=O) group, $(C_1$–$C_4$ alkyl)C(=O) group or $NH_2$ group;

$R^{14}$ is $C_1$–$C_6$ alkyl group, $C_1$–$C_6$ alkylthio group, $C_1$–$C_6$ haloalkyl group or $N(CH_3)_2$ group;

W is nitrogen atom or $CR^{15}$;

$R^{15}$ is hydrogen atom, $C_1$–$C_6$ alkyl group, halogen atom, or phenyl group optionally substituted with $C_1$–$C_6$ alkyl group, one or two halogen atoms, $C_1$–$C_6$ alkoxy group or $CF_3$ group;

each Q is independently oxygen atom or sulfur atom;

$Q^1$ is oxygen atom or sulfur atom;

$Z^1$ is $CR^{16}R^{17}$ group, oxygen atom, sulfur atom, S(O) group, $S(O)_2$ group or $N(C_1$–$C_4$alkyl) group;

each $R^{16}$ is independently hydrogen atom, halogen atom, hydroxyl group, $C_1$–$C_6$ alkoxy group, $C_1$–$C_6$ haloalkyl group, $C_1$–$C_6$ haloalkoxy group, $C_2$–$C_6$ alkylcarbonyloxy group or $C_2$–$C_6$ haloalkylcarbonyloxy group;

each $R^{17}$ is independently hydrogen atom, hydroxyl group or halogen atom;

$R^{18}$ is $C_1$–$C_6$ alkyl group, halogen atom or $C_1$–$C_6$ haloalkyl group;

$R^{19}$ and $R^{20}$ are independently hydrogen atom, $C_1$–$C_6$ alkyl group, or $C_1$–$C_6$ haloalkyl group;

$Z^2$ is oxygen atom, sulfur atom, $NR^9$ group or $CR^9R^{10}$ group;

$R^{21}$ and $R^{22}$ are independently $C_1$–$C_6$ alkyl group, $C_1$–$C_6$ haloalkyl group, $C_3$–$C_6$ alkenyl group, $C_3$–$C_6$ haloalkenyl group, $C_3$–$C_6$ alkynyl group or $C_3$–$C_6$ haloalkynyl group;

$R^{23}$ is hydrogen atom, halogen atom or cyano group;

$R^{24}$ is $C_1$–$C_6$ alkylsulfonyl group, $C_1$–$C_6$ alkyl group, $C_1$–$C_6$ haloalkyl group, $C_3$–$C_6$ alkenyl group, $C_3$–$C_6$ alkynyl group, $C_1$–$C_6$ alkoxy group, $C_1$–$C_6$ haloalkoxy group or halogen atom;

$R^{25}$ is $C_1$–$C_6$ alkyl group, $C_1$–$C_6$ haloalkyl group, $C_3$–$C_6$ alkenyl group or $C_3$–$C_6$ alkynyl group;

$R^{26}$ is $C_1$–$C_6$ alkyl group, $C_1$–$C_6$ haloalkyl group or phenyl group optionally substituted with $C_1$–$C_6$ alkyl, one or two halogen atoms, one or two nitro groups, $C_1$–$C_6$ alkoxy group or $CF_3$ group;

$W^1$ is nitrogen atom or CH group;

T is a group represented by any one of the following general formulas T-1, T-2 and T-3;

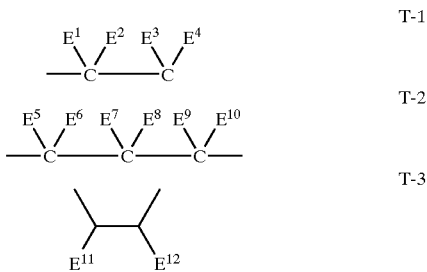

(wherein $E^1$, $E^2$, $E^3$, $E^4$, $E^5$, $E^6$, $E^7$, $E^8$, $E^9$, $E^{10}$, $E^{11}$ and $E^{12}$ are independently hydrogen atom or $C_1$–$C_3$ alkyl group);

$R^{27}$ is $C_1$–$C_8$ alkyl group, $C_3$–$C_8$ cycloalkyl group, $C_3$–$C_8$ alkenyl group, $C_3$–$C_8$alkynyl group, $C_1$–$C_8$ haloalkyl group, $C_2$–$C_8$ alkoxyalkyl group, $C_2$–$C_8$ alkylthioalkyl group, $C_2$–$C_8$ alkylsulfinylalkyl group, $C_2$–$C_8$ alkylsulfonylalkyl group, $C_1$–$C_8$ alkylsulfonyl group, phenylsulfonyl group whose phenyl ring may be substituted with at least one substituent selected from the group consisting of halogen atom and $C_1$–$C_4$ alkyl group, $C_4$–$C_8$ alkoxyalkoxyalkyl group, $C_4$–$C_8$ cycloalkylalkyl group, $C_6$–$C_8$ cycloalkoxyalkyl group, $C_4$–$C_8$ alkenyloxyalkyl group, $C_4$–$C_8$ alkynyloxyalkyl group, $C_3$–$C_8$ haloalkoxyalkyl group, $C_4$–$C_8$ haloalkenyloxyalkyl group, $C_4$–$C_8$ haloalkynyloxyalkyl group, $C_6$–$C_8$ cycloalkylthioalkyl group, $C_4$–$C_8$ alkenylthioalkyl group, $C_4$–$C_8$ alkynylthioalkyl group, $C_1$–$C_4$ alkyl group substituted with phenoxy group whose ring is substituted with at least one substituent selected from the group consisting of halogen atom, $C_1$–$C_3$ alkyl group and $C_1$–$C_3$ haloalkyl group, benzyloxy group whose ring is substituted with at least one substituent selected from the group consisting of halogen atom, $C_1$–$C_3$ alkyl group and $C_1$–$C_3$ haloalkyl group, $C_4$–$C_8$ trialkylsilylalkyl group, $C_3$–$C_8$ cyanoalkyl group, $C_3$–$C_8$ halocycloalkyl group, $C_3$–$C_8$ haloalkenyl group, $C_5$–$C_8$ alkoxyalkenyl group, $C_5$–$C_8$ haloalkoxyalkenyl group, $C_5$–$C_8$ alkylthioalkenyl group, $C_3$–$C_8$ haloalkynyl group, $C_5$–$C_8$ alkoxyalkynyl group, $C_5$–$C_8$ haloalkoxyalkynyl group, $C_5$–$C_8$ alkylthioalkynyl group, $C_2$–$C_8$ alkylcarbonyl group, benzyl group whose ring is substituted with at least one substituent selected from the group consisting of halogen atom, $C_1$–$C_3$ alkyl group and $C_1$–$C_3$ haloalkyl group, $CHR^{34}COR^{28}$ group, $CHR^{34}COOR^{28}$ group, $CHR^{34}P$ (O) (OR$^{28}$)$_2$ group, CHR$^{34}$P(S)(OR$^{28}$)$_2$ group, CHR$^{34}$C(O)NR$^{29}$R$^{30}$ group or CHR$^{34}$C(O)NH$_2$ group;

R$^{28}$ is C$_1$–C$_6$ alkyl group, C$_2$–C$_6$ alkenyl group, C$_3$–C$_6$ alkynyl group or tetrahydrofuranyl group;

R$^{29}$ and R$^{31}$ are independently hydrogen atom or C$_1$–C$_4$ alkyl group;

R$^{30}$ and R$^{32}$ are independently C$_1$–C$_4$ alkyl group or phenyl group whose ring may be substituted with at least one substituent selected from the group consisting of halogen atom, C$_1$–C$_3$ alkyl group and C$_1$–C$_3$ haloalkyl group; or, R$^{29}$ and R$^{30}$ together may form —(CH$_2$)$_5$—, —(CH$_2$)$_4$— or —CH$_2$CH$_2$OCH$_2$CH$_2$—, or the ring thus formed may be substituted with at least one substituent selected from the group consisting of C$_1$–C$_3$ alkyl group, phenyl group and benzyl group; or, R$^{31}$ and R$^{32}$ may from C$_3$–C$_8$ cycloalkyl group together with the carbon atom to which they are attached;

R$^{33}$ is C$_1$–C$_4$ alkyl group, C$_1$–C$_4$ haloalkyl group or C$_3$–C$_6$ alkenyl group;

R$^{34}$ and R$^{35}$ are independently hydrogen atom or C$_1$–C$_4$ alkyl group;

R$^{36}$ is hydrogen atom, C$_1$–C$_6$ alkyl group, C$_3$–C$_6$ alkenyl group or C$_3$–C$_6$ alkynyl group;

R$^{37}$ is hydrogen atom, C$_1$–C$_4$ alkyl group or halogen atom;

R$^{38}$ is hydrogen atom, C$_1$–C$_6$ alkyl group, C$_3$–C$_6$ cycloalkyl group, C$_3$–C$_6$ alkenyl group, C$_3$–C$_6$ alkynyl group, C$_2$–C$_6$ alkoxyalkyl group, C$_1$–C$_6$ haloalkyl group, phenyl group whose ring may be substituted with at least one substituent selected from the group consisting of halogen atom, C$_1$–C$_4$ alkyl group and C$_1$–C$_4$ alkoxy group, —CH$_2$CO$_2$(C$_1$–C$_4$ alkyl) group or —CH(CH$_3$)CO$_2$(C$_1$–C$_4$ alkyl) group;

R$^{39}$ is hydrogen atom, C$_1$–C$_2$ alkyl group or C(O)O (C$_1$–C$_4$ alkyl) group;

R$^{40}$ is hydrogen atom, C$_1$–C$_6$ alkyl group, C$_1$–C$_6$ alkoxy group or NH(C$_1$–C$_6$ alkyl) group;

R$^{41}$ is C$_1$–C$_6$ alkyl group, C$_1$–C$_6$ haloalkyl group, C$_1$–C$_6$ alkoxy group, NH(C$_1$–C$_6$ alkyl) group, phenyl group whose ring may be substituted with one substituent selected from the group consisting of R$^{42}$ group, benzyl group and C$_2$–C$_8$ dialkylamino group; and R$^{42}$ is C$_1$–C$_6$ alkyl group, one or two halogen atoms, C$_1$–C$_6$ alkoxy group or CF$_3$ group;

(3) a compound of the formula (II):

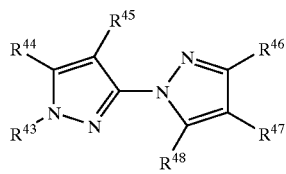

or nipilacrofen, wherein R$^{43}$ is C$_1$–C$_4$ alkyl group;

R$^{44}$ is C$_1$–C$_4$ alkyl group, C$_1$–C$_4$ alkylthio group, C$_1$–C$_4$ alkoxy group, C$_1$–C$_4$ haloalkyl group, C$_1$–C$_4$ haloalkylthio group or C$_1$–C$_4$ haloalkoxy group;

R$^{43}$ and R$^{44}$ together may form —(CH$_2$)$_3$— or —(CH$_2$)$_4$—;

R$^{45}$ is hydrogen atom or halogen atom;

R$^{46}$ is hydrogen atom or C$_1$–C$_4$ alkyl group;

R$^{47}$ is hydrogen atom, nitro group, cyano group, —COOR$^{49}$ group, —C(=X)NR$^{50}$R$^{51}$ group or —C(=X$^2$)R$^{52}$ group;

R$^{48}$ is hydrogen atom, halogen atom, cyano group, C$_1$–C$_4$ alkyl group optionally substituted with at least one substituent selected from the group consisting of halogen atom and hydroxyl group, C$_1$–C$_4$ alkoxy group, phenyl group optionally substituted with at least one substituent selected from the group consisting of halogen atom, nitro group, cyano group, C$_1$–C$_4$ alkyl group, C$_1$–C$_4$ alkoxy group and halo-C$_1$–C$_4$ alkyl group, pyrrolyl group, C$_2$–C$_8$ alkyl group, C$_3$–C$_8$ alkenyl group, C$_3$–C$_8$ alkynyl group, C$_3$–C$_8$ alkoxy group, a group selected from the group consisting of C$_2$–C$_8$ alkyl group, C$_3$–C$_8$ alkenyl group, C$_3$–C$_8$ alkynyl group and C$_3$–C$_8$ alkoxy group into which at least one oxygen atom is inserted, or any one of groups represented by the following formulas:

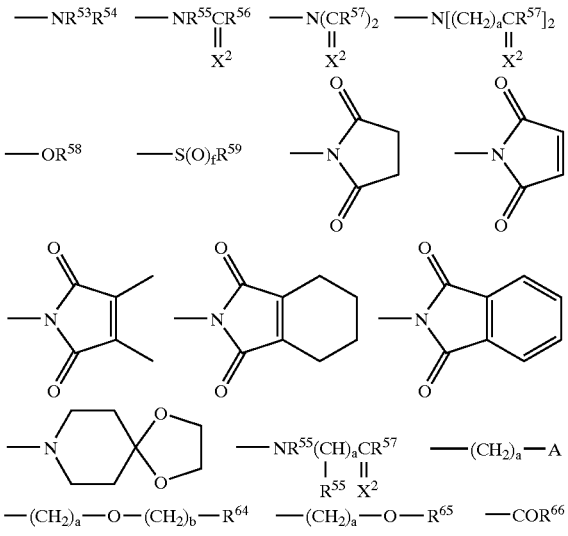

wherein R$^{49}$, R$^{50}$ and R$^{52}$ are, the same or different, hydrogen atom or C$_1$–C$_4$ alkyl group;

R$^{50}$ and R$^{51}$ may form saturated alicyclic 5 or 6 membered ring together with the nitrogen atom to which they are attached;

R$^{52}$ is hydrogen atom, C$_1$–C$_4$ alkyl group or C$_1$–C$_4$ alkyl group substituted with at least one halogen atom;

R$^{53}$ is hydrogen atom, C$_1$–C$_4$ alkyl group optionally substituted with at least one halogen atom, C$_2$–C$_6$ alkenyl group optionally substituted with at least one halogen atom, C$_3$–C$_6$ alkynyl group optionally substituted with at least one halogen atom, phenyl group optionally substituted with at least one halogen atom, C$_3$–C$_8$ cycloalkyl group, cyanomethyl group, or R$^{63}$CO— group;

R$^{54}$ is hydrogen atom, C$_1$–C$_6$ alkyl group optionally substituted with at least one halogen atom, C$_2$–C$_6$ alkenyl group optionally substituted with at least one halogen atom, C$_3$–C$_6$ alkynyl group optionally substituted with at least one halogen atom, phenyl group optionally substituted with halogen atom, C$_3$–C$_8$ cycloalkyl group, cyanomethyl group, C$_1$–C$_4$ alkoxy-C$_1$–C$_6$ alkyl group, di-C$_1$–C$_4$ alkylamino-C$_1$–C$_4$ alkyl group, tetrahydrofurfurylmethyl group, C$_3$–C$_6$ alkynyloxy-C$_1$–C$_4$ alkyl group, benzyl whose ring may be substituted with substituent selected from the group consisting of halogen atom, nitro group, cyano group, $C_1$–$C_4$ alkyl group, $C_1$–$C_4$ alkoxy group and halo-$C_1$–$C_4$ alkyl group, —C(=X²)R⁶³ group, —(CH₂)$_a$—(O)$_d$—R⁷⁰ group, —(CH₂)$_a$—O—(CH₂)$_b$—R⁷⁰ group, —(CH₂)$_a$—X²—R⁷⁶ group;

R⁵³ and R⁵⁴ together with the nitrogen atom to which they are attached may form saturated alicyclic 3, 5 or 6 membered ring or aromatic 5 or 6 membered ring in which a carbon atom may be optionally replaced with oxygen atom;

R⁵⁵ is hydrogen atom, $C_1$–$C_4$ alkyl group, $C_2$–$C_6$ alkenyl group or $C_3$–$C_6$ alkynyl group, or R⁵⁵ and R⁵⁶ together may form —(CH₂)$_e$—;

R⁵⁶ and R⁵⁷ are independently $C_1$–$C_4$ alkyl group optionally substituted with at least one halogen atom, $C_2$–$C_6$ alkenyl group optionally substituted with at least one halogen atom, $C_3$–$C_6$ alkynyl optionally substituted with at least one halogen atom or phenyl group optionally substituted with at least one halogen atom, hydrogen atom, $C_3$–$C_6$ cycloalkyl group, —XR⁶⁰ group or —NR⁶¹R⁶² group;

R⁵⁸ is hydrogen atom, $C_1$–$C_6$ alkyl group, $C_2$–$C_6$ alkenyl group, $C_3$–$C_6$ alkynyl group, $C_1$–$C_4$ alkylcarbonyl group, cyano-$C_1$–$C_3$ alkyl group, $C_1$–$C_4$ alkoxycarbonyl-$C_1$–$C_4$ alkyl group, di-$C_1$–$C_4$ alkoxycarbonyl-$C_1$–$C_4$ alkyl group, benzyl group, $C_1$–$C_4$ alkoxy-$C_1$–$C_4$ alkynyl group, —(CH₂)$_a$—R⁷⁵ group, —(CH₂)$_a$—X²—R⁷² group, —(CH₂)$_a$—X²—(CH₂)$_b$—R⁷² group or —(CH₂)$_a$—X²—(CH₂)$_b$—X²—(CH₂)$_c$—R⁷² group;

R⁵⁹ is hydrogen atom, $C_1$–$C_4$ alkyl group, $C_2$–$C_6$ alkenyl group, $C_3$–$C_6$ alkynyl group, cyano-$C_1$–$C_3$ alkyl group, $C_1$–$C_4$ alkylcarbonyl-$C_1$–$C_3$ alkyl group or phenyl group;

R⁶⁰ is $C_1$–$C_4$ alkyl group optionally substituted with at least one halogen atom;

R⁶¹ and R⁶² are, the same or different, hydrogen atom or $C_1$–$C_4$ alkyl group;

R⁶³ is $C_1$–$C_4$ alkyl group optionally substituted with at least one halogen atom, $C_1$–$C_4$ alkoxy-$C_1$–$C_4$ alkyl group, $C_1$–$C_4$ alkylthio-$C_1$–$C_4$ alkyl group, $C_3$–$C_6$ cycloalkyl group, phenyl group whose ring may be substituted with one substituent selected from the group consisting of halogen atom, nitro group, cyano group, $C_1$–$C_4$ alkyl group, $C_1$–$C_4$ alkoxy group and halo-$C_1$–$C_4$ alkyl group, —NR⁷³R⁷⁴ group or —(CH₂)$_a$—(O)$_d$—R⁷⁵ group;

R⁶⁴ is $C_1$–$C_4$ alkoxycarbonyl group or carboxyl group;

R⁶⁵ is chloromethyl group, cyanomethyl group, $C_3$–$C_6$ cycloalkyl group into which at least one oxygen atom may be inserted, or $C_1$–$C_4$ alkoxycarbonyl-$C_1$–$C_4$ alkyl group;

R⁶⁶ is hydroxyl group or —NR⁶⁷R⁶⁸ group;

A is —NR⁶⁷R⁶⁸ group or —S(O)$_f$—R⁶⁹ group;

R⁶⁷ and R⁶⁸ are, the same or different, hydrogen atom or $C_1$–$C_4$ alkyl group;

R⁶⁹ is $C_1$–$C_4$ alkyl group or $C_1$–$C_4$ haloalkyl group;

R⁷⁰ is hydrogen atom, hydroxyl group, halogen atom, $C_1$–$C_4$ alkyl group optionally substituted with at least one $C_1$–$C_4$ alkoxy group, $C_3$–$C_6$ cycloalkyl group into which at least one oxygen atom may be inserted, $C_3$–$C_6$ cycloalkyl group optionally substituted with one or two methyl groups, furyl group, thienyl group or —C(=O)R⁷¹ group;

R⁷¹ and R⁷² are, the same or different, $C_1$–$C_4$ alkyl group or $C_1$–$C_4$ alkoxy group;

R⁷³ and R⁷⁴ are, the same or different, $C_1$–$C_4$ alkyl group or phenyl group;

R⁷⁵ is $C_3$–$C_6$ cycloalkyl into which at least one oxygen atom may be inserted, $C_3$–$C_6$ cycloalkyl group optionally substituted with one or two methyl groups, furyl group, thienyl group or —C(=O)R⁷¹ group;

R⁷⁶ is $C_1$–$C_4$ alkyl group;

a, b and c is independently 1, 2 or 3;

d is 0 or 1;

e is 2 or 3;

f is 1 or 2; and

X² is oxygen atom or sulfur atom.

The method according to the above, additionally comprising the steps of:

introducing into the plant cell, a second gene selected from a gene encoding a protein substantially having protoporphyrinogen oxidase activity, a gene encoding a protein substantially having 5-enolpyruvylshikamate-3-phosphate synthase activity and a gene encoding a protein substantially having glyphosate oxidoreductase activity; and expressing said second gene.

Another aspect of the present invention relates to a plant cell having:

a gene encoding a protein having the following characteristics (a) to (c):

(a) having a specific affinity for a substance which is concerned with the weed control activity of a weed control compound, (b) having substantially no capability of modifying a substance for which said protein has a specific affinity, and (c) being substantially free from framework regions of variable regions in an immunoglobulin; and at least one altered form of an enzymatic activity which gives a resistance to a weed control compound in an amount inhibiting a naturally occurring form of said enzymatic activity, wherein said altered form of an enzymatic activity is a form of enzymatic activity selected from a protoporphyrinogen oxidase activity, 5-enolpyruvylshikamate-3-phosphate synthase activity and glyphosate oxidoreductase activity.

Another aspect of the present invention relates to a plant cell having:

a gene encoding a protein having the following characteristics (a) to (c):

(a) having a specific affinity for a substance which is concerned with the weed control activity of a weed control compound, (b) having substantially no capability of modifying a substance for which said protein has a specific affinity, and (c) being substantially free from framework regions of variable regions in an immunoglobulin; and an altered protoporphyrinogen oxidase activity which gives a resistance to a weed control compound in an amount inhibiting a natural occurring protoporphyrinogen oxidase activity.

Another aspect of the present invention relates to a plant cell having:

a gene encoding a protein having the following characteristics (a) to (c):

(a) having a specific affinity for a substance which is concerned with the weed control activity of a weed control compound, (b) having substantially no capability of modifying a substance for which said protein has a specific affinity, and (c) being substantially free from framework regions of variable regions in an immunoglobulin; and an altered 5-enolpyruvylshikamate-3-phosphate synthase activity which gives a resistance to a weed control compound in an amount inhibiting a natural occurring 5-enolpyruvylshikamate-3-phosphate synthase activity.

Another aspect of the present invention relates to a plant cell having:

a gene encoding a protein having the following characteristics (a) to (c):

(a) having a specific affinity for a substance which is concerned with the weed control activity of a weed control compound, (b) having substantially no capability of modifying a substance for which said protein has a specific affinity, and (c) being substantially free from framework regions of variable regions in an immunoglobulin; and an altered glyphosate oxidoreductase activity which gives a resistance to a weed control compound in an amount inhibiting a natural occurring glyphosate oxidoreductase activity.

The present invention also relates to the plant cell according to the above, wherein said altered form of an enzymatic activity is conferred by a second gene selected from a gene encoding a protein substantially having a protoporphyrinogen oxidase activity, a gene encoding a protein substantially having 5-enolpyruvylshikamate-3-phosphate synthase activity and a gene encoding a protein substantially having glyphosate oxidoreductase activity;

The plant cell according to the above, wherein the gene encoding a protein having the following characteristics (a) to (c):

(a) having a specific affinity for a substance which is concerned with the weed control activity of a weed control compound, (b) having substantially no capability of modifying a substance for which said protein has a specific affinity, and (c) being substantially free from framework regions of variable regions in an immunoglobulin; and the second gene are introduced into the plant cell in the form in that both of said genes are operably ligated to a promoter and a terminator both of which are functional in said plant cell;

The plant cell according to the above, wherein the protein substantially having a proto-porphyrinogen IX oxidase activity is protoporphyrinogen IX oxidase, the protein substantially having a 5-enol-pyruvylshikamate-3-phosphate synthase activity is 5-enolpyruvylshikamate-3-phosphate synthase and the protein substantially having glyphosate oxidoreductase activity is glyphosate oxidoreductase;

The plant cell according to the above, wherein the plant cell is derived from dicotyledones or monocotyledones;

A plant comprising the plant cell of the above;

A method for protecting a plant which comprises applying a protoporphyrinogen IX oxidase inhibitory-type compound to a growth area of the plant of the above;

A method for protecting a plant which comprises applying a protoporphyrinogen IX oxidase inhibitory-type compound and a compound inhibiting 5-enolpyruvylshikamate-3-phosphate synthase to a growth area of the plant of the above;

A method for protecting a plant which comprises applying a protoporphyrinogen IX oxidase inhibitory-type compound and a compound inhibiting 5-enolpyruvylshikamate-3-phosphate synthase to a growth area of the plant of the above;

A method for selecting a plant which comprises applying a protoporphyrinogen IX oxidase inhibitory-type compound to a growth area of the plant of the above and other plants, and selecting either plant on the basis of difference in growth between the plants;

A method for selecting a plant which comprises applying a protoporphyrinogen IX oxidase inhibitory-type compound and a compound inhibiting 5-enolpyruvylshikamate-3-phosphate synthase to a growth area of the plant of the above and other plants, and selecting either plant on the basis of difference in growth between the plants; and A method for selecting a plant which comprises applying a protoporphyrinogen IX oxidase inhibitory-type compound and a compound inhibiting 5-enolpyruvylshikamate-3-phosphate synthase to a growth area of the plant of the above and other plants, and selecting either plant on the basis of difference in growth between the plants.

DETAILED DESCRIPTION OF THE INVENTION

In the method of the present invention, substances which are concerned with weed control activities of weed control compounds (hereinafter referred to as weed control substances) are those constituting a part of metabolic reaction systems in organisms which are responsible for weed control activities upon applying the compounds to plants. Examples thereof include weed control compounds themselves, endogenous substances in plants, and the like. Specifically, as such endogenous substances in plants, for example, there are substrates of target enzymes on which weed control compounds act, or precursors or metabolites of the substrates which cause cellular dysfunction upon accumulating in plant cells; substances produced by the above substances in plant cells which cause cellular dysfunction; and the like. More specifically, it has been known that, when a compound having herbicidal activity (hereinafter referred to as herbicidal compound) which inhibits the activity of protoporphyrinogen IX oxidase (EC 1.3.3.4, hereinafter referred to as PPO) is applied to a plant, protoporphyrinogen IX which is the substrate of PPO is accumulated in the plant cells and it is metabolized to form protoporphyrin X, followed by formation of active oxygen in the presence of both protoporphyrin X and light in the cells, which damages cell functions [Junshi MIYAMOTO ed., Atarashii Noyaku no Kagaku (Chemistry of New Agrochemicals), Chapter 3, Section 3.3, p 106 (1993), Hirokawa Shoten, Tokyo]. Thus, protoporphyrinogen IX, protoporphyrin IX and active oxygen in these systems, and the like can be exemplified as these substances.

In the method of the present invention, weed control compounds include compounds having herbicidal activities, plant growth regulator activities, and the like.

Examples of the herbicidal compounds include compounds inhibiting porphyrin biosynthesis, compounds inhibiting electron transfer in photosynthesis, compounds inhibiting carotenoid biosynthesis, compounds inhibiting amino acid biosynthesis, compounds inhibiting lipid biosynthesis, compounds inhibiting cell wall biosynthesis, compounds influencing protein biosynthesis, nucleic acid biosynthesis and cell division, compounds having auxin antagonistic activity, and the like. More specifically, as the compounds inhibiting porphyrin biosynthesis, for example, there are compounds inhibiting PPO activity (PPO inhibitory-type herbicidal compound), and the like. As the compounds inhibiting electron transfer in photosynthesis, for example, there are compounds inhibiting electron transfer of photochemical system I or II, compounds inhibiting 4-hydroxyphenyl pyruvate dioxygenase (EC 1.13.11.27; hereinafter referred to as 4-HPPD) which influences biosynthesis of plastoquinone which transfers electrons, and the like. As the compounds inhibiting carotenoid biosynthesis, for example, there are compounds inhibiting phytoene desaturase (hereinafter referred to as PDS), and the like. As the compounds inhibiting amino acid biosynthesis, for example, there are compounds inhibiting EPSPS, acetolactate synthase (EC 4.1.3.18; hereinafter referred to as ALS), glutamine synthetase (EC 6.3.1.2; hereinafter referred to as GS), dihydropteroate synthase (EC 2.5.1.15; hereinafter referred to as DHP), and the like. As the compounds inhibiting lipid biosynthesis, for example, there are compounds inhibiting acetyl CoA carboxylase (EC 6.4.1.2; hereinafter referred to as ACC), and the like. As the compounds inhibiting cell wall biosynthesis, for example, there are compounds inhibiting cellulose biosynthesis, and the like. As the compounds influencing protein biosynthesis, nucleic acid biosynthesis or cell division, for example, there are compounds inhibiting formation of microtubules, and the like.

Examples of the compounds having plant growth regulator activities include compounds having antagonistic activities against plant hormones which enhance cell elongation and differentiation, and the like. Specifically, for example, there are 2,4-D, phenoxyalkane carboxylic acid, derivatives of benzoic acid, derivatives of picolinic acid, and the like.

As the above-described PPO inhibitory-type herbicidal compounds, for example, there are the compounds disclosed in Duke, S. O., Rebeiz, C. A., ACS Symposium Series 559, Porphyric Pesticides, Chemistry, Toxicology, and Pharmaceutical Applications, American Chemical Society, Washington D.C. (1994), and the like. Specifically, examples thereof include the following compounds:

(1) chlormethoxynil, bifenox, chlornitrofen (CNP), acifluorfen (5-[2-chloro-4-(trifluoromethyl)phenoxy]-2-nitorobenzoic acid) and its ethyl ester, acifluorfen-sodium, oxyfluorfen (2-chloro-1-(3-ethoxy-4-nitrophenoxy)-4-trifluorobenzene), oxadiazon (3-[2,4-dichloro-5-(1-methylethoxy)phenyl]-5-(1,1-dimethylethyl)-1,3,4-oxydiazol-2-(3H)-one), 2-[4-chloro-2-fluoro-5-(prop-2-ynyloxy)phenyl]-2,3,4,5,6,7-hexahydro-1H-isoindol-1,3-dione, chlorphthalim, (N-(4-chlorophenyl)-3,4,5,6-tetrahydrophtalimide), TNPP-ethyl(ethyl 2-[1-(2,3,4-trichlorophenyl)-4-nitropyrazolyl-5-oxy]propionate), or N3-(1-phenylethyl)-2,6-dimethyl-5-propyonylnicotinamide;

(2) a compound represented by the general fomrula: J-G (I), wherein G is a group represented by any one of the following general formulas G-1 to G-9 and J is a group represented by any one of the following general formulas J-1 to J-30:

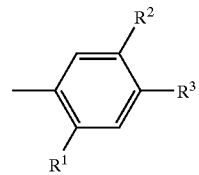
G-1

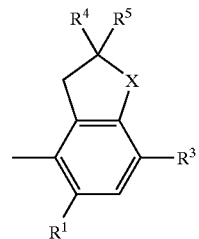
G-2

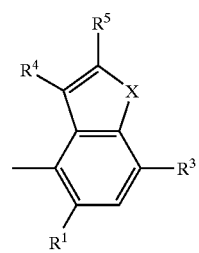
G-3

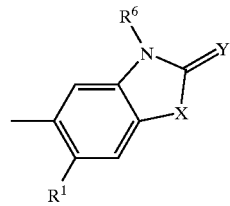
G-4

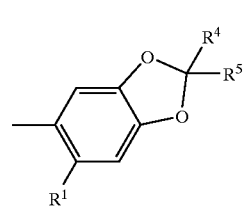
G-5

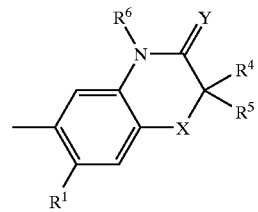
G-6

-continued
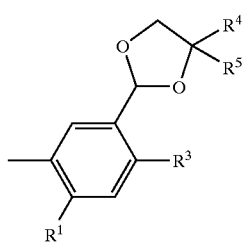
G-7
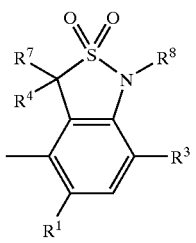
G-8
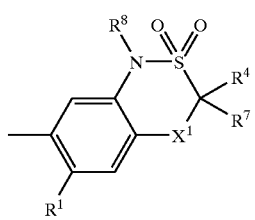
G-9
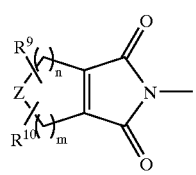
J-1
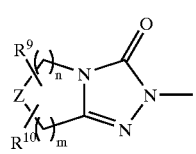
J-2
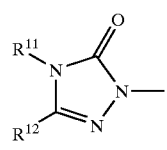
J-3
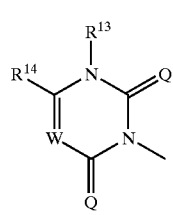
J-4
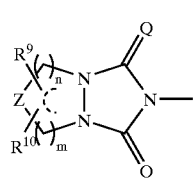
J-5
-continued
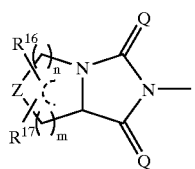
J-6
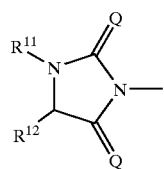
J-7
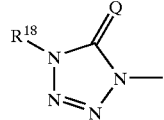
J-8
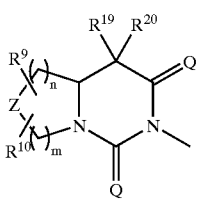
J-9
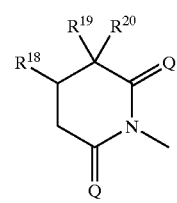
J-10
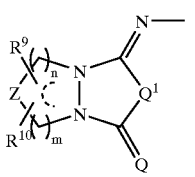
J-11
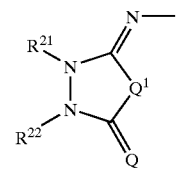
J-12
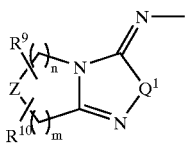
J-13
J-14

J-15 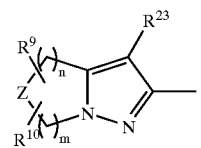

J-16 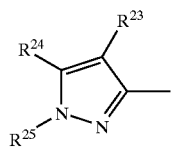

J-17 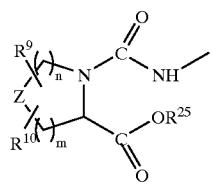

J-18 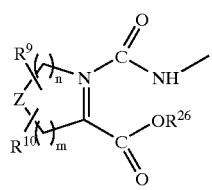

J-19 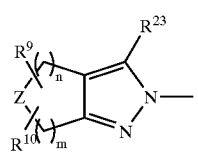

J-20 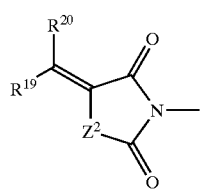

J-21 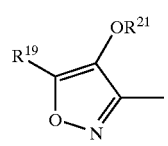

J-22 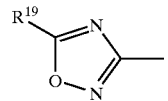

J-23 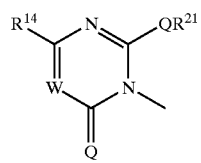

J-24 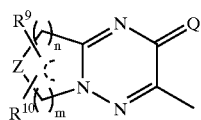

J-25 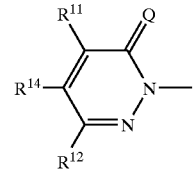

J-26 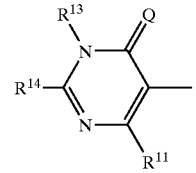

J-27 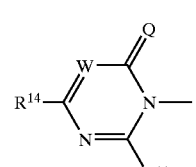

J-28 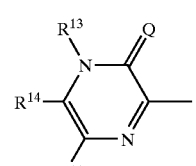

J-29 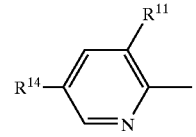

J-30 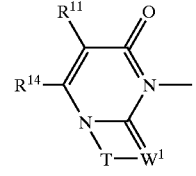

wherein the dotted lines in the formulas J-5, J-6, J-12 and J-24 represent that the left hand ring contains only single bonds, or one bond in the ring is a double bond between carbon atoms;

X is oxygen atom or sulfur atom;

Y is oxygen atom or sulfur atom;

$R^1$ is hydrogen atom or halogen atom;

$R^2$ is hydrogen atom, $C_1$–$C_8$ alkyl group, $C_1$–$C_8$ haloalkyl group, halogen atom, OH group, $OR^{27}$ group, SH group, $S(O)_pR^{27}$ group, $COR^{27}$ group, $CO_2R^{27}$ group, $C(O)SR^{27}$ group, $C(O)NR^{29}R^{30}$ group, CHO group, $CR^{27}\alpha NOR^{36}$ group, $CH=CR^{37}CO_2R^{27}$ group, $CH_2CHR^{37}CO_2R^{27}$ group, $CO_2N=CR^{31}R^{32}$ group, nitro group, cyano group, $NHSO_2R^{33}$ group, $NHSO_2NHR^{33}$ group, $NR^{27}R^{38}$ group, $NH_2$ group or phenyl group optionally substituted with one or more and the same or different $C_1$–$C_4$ alkyl groups;

p is 0, 1 or 2;

$R^3$ is $C_1$–$C_2$ alkyl group, $C_1$–$C_2$ haloalkyl group, $OCH_3$ group, $SCH_3$ group, $OCHF_2$ group, halogen atom, cyano group or nitro group;

$R^4$ is hydrogen atom, $C_1$–$C_3$ alkyl group, $C_1$–$C_3$ haloalkyl group or halogen atom;

R⁵ is hydrogen atom, $C_1$–$C_3$ alkyl group, halogen atom, $C_1$–$C_3$ haloalkyl group, cyclopropyl group, vinyl group, $C_2$ alkynyl group, cyano group, C(O)R³⁸ group, $CO_2R^{38}$ group, C(O)NR³⁸R³⁹ group, $CR^{34}R^{35}$CN group, $CR^{34}R^{35}$C(O)R³⁸ group, $CR^{34}R^{35}CO_2R^{38}$ group, $CR^{34}R^{35}$C(O)NR³⁸R³⁹ group, CHR³⁴OH group, CHR³⁴OC(O)R³⁸ group or OCHR³⁴OC(O)NR³⁸R³⁹ group, or, when G is G-2 or G-6, R⁴ and R⁵ may form C=O group together with the carbon atom to which they are attached;

R⁶ is $C_1$–$C_6$ alkyl group, $C_1$–$C_6$ haloalkyl group, $C_2$–$C_6$ alkoxyalkyl group, $C_3$–$C_6$ alkenyl group or $C_3$–$C_6$ alkynyl group;

X¹ is single bond, oxygen atom, sulfur atom, NH group, N($C_1$–$C_3$ alkyl) group, N($C_1$–$C_3$ haloalkyl) group or N(allyl) group;

R⁷ is hydrogen atom, $C_1$–$C_6$ alkyl group, $C_1$–$C_6$ haloalkyl group, halogen atom, $S(O)_2(C_1$–$C_6$alkyl) group or C(=O)R⁴⁰ group;

R⁸ is hydrogen atom, $C_1$–$C_8$ alkyl group, $C_3$–$C_8$ cycloalkyl group, $C_3$–$C_8$ alkenyl group, $C_3$–$C_8$ alkynyl group, $C_1$–$C_8$ haloalkyl group, $C_2$–$C_8$ alkoxyalkyl group, $C_3$–$C_8$ alkoxyalkoxyalkyl group, $C_3$–$C_8$ haloalkynyl group, $C_3$–$C_8$ haloalkenyl group, $C_1$–$C_8$ alkylsulfonyl group, $C_1$–$C_8$ haloalkylsulfonyl group, $C_3$–$C_8$ alkoxycarbonylalkyl group, $S(O)_2NH(C_1$–$C_8$ alkyl) group, C(O)R⁴¹ group or benzyl group whose phenyl ring may be substituted with R⁴²;

n and m are independently 0, 1, 2 or 3 and m+n is 2 or 3;

Z is CR⁹R¹⁰ group, oxygen atom, sulfur atom, S(O) group, $S(O)_2$ group or N($C_1$–$C_4$alkyl) group;

each R⁹ is independently hydrogen atom, $C_1$–$C_3$ alkyl group, halogen atom, hydroxyl group, $C_1$–$C_6$ alkoxy group, $C_1$–$C_6$ haloalkyl group, $C_1$–$C_6$ haloalkoxy group, $C_2$–$C_6$ alkylcarbonyloxy group or $C_2$–$C_6$ haloalkylcarbonyloxy group;

each R¹⁰ is independently hydrogen atom, $C_1$–$C_3$ alkyl group, hydroxyl group or halogen atom;

R¹¹ and R¹² are independently hydrogen atom, halogen atom, $C_1$–$C_6$ alkyl group, $C_3$–$C_6$ alkenyl group or $C_1$–$C_6$ haloalkyl group;

R¹³ is hydrogen atom, $C_1$–$C_6$ alkyl group, $C_1$–$C_6$ haloalkyl group, $C_3$–$C_6$ alkenyl group, $C_3$–$C_6$ haloalkenyl group, $C_3$–$C_6$ alkynyl group, $C_3$–$C_6$ haloalkynyl group, HC(=O) group, ($C_1$–$C_4$alkyl)C(=O) group or $NH_2$ group;

R¹⁴ is $C_1$–$C_6$ alkyl group, $C_1$–$C_6$ alkylthio group, $C_1$–$C_6$ haloalkyl group or N(CH₃)₂ group;

W is nitrogen atom or CR¹⁵;

R¹⁵ is hydrogen atom, $C_1$–$C_6$ alkyl group, halogen atom, or phenyl group optionally substituted with $C_1$–$C_6$ alkyl group, one or two halogen atoms, $C_1$–$C_6$ alkoxy group or $CF_3$ group;

each Q is independently oxygen atom or sulfur atom;

Q¹ is oxygen atom or sulfur atom;

Z¹ is CR¹⁶R¹⁷ group, oxygen atom, sulfur atom, S(O) group, $S(O)_2$ group or N($C_1$–$C_4$alkyl) group;

each R¹⁶ is independently hydrogen atom, halogen atom, hydroxyl group, $C_1$–$C_6$ alkoxy group, $C_1$–$C_6$ haloalkyl group, $C_1$–$C_6$ haloalkoxy group, $C_2$–$C_6$ alkylcarbonyloxy group or $C_2$–$C_6$ haloalkylcarbonyloxy group;

each R¹⁷ is independently hydrogen atom, hydroxyl group or halogen atom;

R¹⁸ is $C_1$–$C_6$ alkyl group, halogen atom or $C_1$–$C_6$ haloalkyl group;

R¹⁹ and R²⁰ are independently hydrogen atom, $C_1$–$C_6$ alkyl group, or $C_1$–$C_6$ haloalkyl group;

Z² is oxygen atom, sulfur atom, NR⁹ group or CR⁹R¹⁰ group;

R²¹ and R²² are independently $C_1$–$C_6$ alkyl group, $C_1$–$C_6$ haloalkyl group, $C_3$–$C_6$ alkenyl group, $C_3$–$C_6$ haloalkenyl group, $C_3$–$C_6$ alkynyl group or $C_3$–$C_6$ haloalkynyl group;

R²³ is hydrogen atom, halogen atom or cyano group;

R²⁴ is $C_1$–$C_6$ alkylsulfonyl group, $C_1$–$C_6$ alkyl group, $C_1$–$C_6$ haloalkyl group, $C_3$–$C_6$ alkenyl group, $C_3$–$C_6$ alkynyl group, $C_1$–$C_6$ alkoxy group, $C_1$–$C_6$ haloalkoxy group or halogen atom;

R²⁵ is $C_1$–$C_6$ alkyl group, $C_1$–$C_6$ haloalkyl group, $C_3$–$C_6$ alkenyl group or $C_3$–$C_6$ alkynyl group;

R²⁶ is $C_1$–$C_6$ alkyl group, $C_1$–$C_6$ haloalkyl group or phenyl group optionally substituted with $C_1$–$C_6$ alkyl, one or two halogen atoms, one or two nitro groups, $C_1$–$C_6$ alkoxy group or $CF_3$ group;

W¹ is nitrogen atom or CH group;

T is a group represented by any one of the following general formulas T-1, T-2 and T-3;

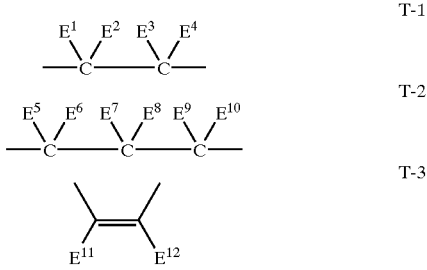

(wherein E¹, E², E³, E⁴, E⁵, E⁶, E⁷, E⁸, E⁹, E¹⁰, E¹¹ and E¹² are independently hydrogen atom or $C_1$–$C_3$ alkyl group);

R²⁷ is $C_1$–$C_8$ alkyl group, $C_3$–$C_8$ cycloalkyl group; $C_3$–$C_8$ alkenyl group, $C_3$–$C_8$alkynyl group, $C_1$–$C_8$ haloalkyl group, $C_2$–$C_8$ alkoxyalkyl group, $C_2$–$C_8$ alkylthioalkyl group, $C_2$–$C_8$ alkylsulfinylalkyl group, $C_2$–$C_8$ alkylsulfonylalkyl group, $C_1$–$C_8$ alkylsulfonyl group, phenylsulfonyl group whose phenyl ring may be substituted with at least one substituent selected from the group consisting of halogen atom and $C_1$–$C_4$ alkyl group, $C_4$–$C_8$ alkoxyalkoxyalkyl group, $C_4$–$C_8$ cycloalkylalkyl group, $C_6$–$C_8$ cycloalkoxyalkyl group, $C_4$–$C_8$ alkenyloxyalkyl group, $C_4$–$C_8$ alkynyloxyalkyl group, $C_3$–$C_8$ haloalkoxyalkyl group, $C_4$–$C_8$ haloalkenyloxyalkyl group, $C_4$–$C_8$ haloalkynyloxyalkyl group, $C_6$–$C_8$ cycloalkylthioalkyl group, $C_4$–$C_8$ alkenylthioalkyl group, $C_4$–$C_8$ alkynylthioalkyl group, $C_1$–$C_4$ alkyl group substituted with phenoxy group whose ring is substituted with at least one substituent selected from the group consisting of halogen atom, $C_1$–$C_8$ alkyl group and $C_1$, —$C_3$ haloalkyl group, benzyloxy group whose ring is substituted with at least one substituent selected from the group consisting of halogen atom, $C_1$–$C_3$ alkyl group and $C_1$–$C_3$ haloalkyl group, $C_4$–$C_8$ trialkylsilylalkyl group, $C_3$–$C_8$ cyanoalkyl group, $C_3$–$C_8$ halocycloalkyl group, $C_3$–$C_8$ haloalkenyl group, $C_5$–$C_8$ alkoxyalkenyl group, $C_5$–$C_8$ haloalkoxyalkenyl group, $C_5$–$C_8$ alkylthioalkenyl group, $C_2$–$C_8$ haloalkynyl group, $C_5$–$C_8$ alkoxyalkynyl group, $C_5$–$C_8$ haloalkoxyalkynyl group, $C_5$–$C_8$ alkylthioalkynyl group, $C_2$–$C_8$ alkylcarbonyl group, benzyl group whose ring is substituted with at least one substituent selected from the group consisting of halogen atom, $C_1$–$C_3$ alkyl group and $C_1$–$C_3$ haloalkyl group, $CHR^{34}COR^{28}$ group, $CHR^{34}COOR^{28}$ group, $CHR^{34}P(O)(OR^{28})_2$ group, $CHR^{34}P(S)(OR^{28})_2$ group, $CHR^{34}C(O)NR^{29}R^{30}$ group or $CHR^{34}C(O)NH_2$ group;

$R^{28}$ is $C_1$–$C_6$ alkyl group, $C_2$–$C_6$ alkenyl group, $C_3$–$C_6$ alkynyl group or tetrahydrofuranyl group;

$R^{29}$ and $R^{31}$ are independently hydrogen atom or $C_1$–$C_4$ alkyl group;

$R^{30}$ and $R^{32}$ are independently $C_1$–$C_4$ alkyl group or phenyl group whose ring may be substituted with at least one substituent selected from the group consisting of halogen atom, $C_1$–$C_3$ alkyl group and $C_1$–$C_3$ haloalkyl group; or, $R^{29}$ and $R^{30}$ together may form —$(CH_2)_5$—, —$(CH_2)_4$— or —$CH_2CH_2OCH_2CH_2$—, or the ring thus formed may be substituted with at least one substituent selected from the group consisting of $C_1$–$C_3$ alkyl group, phenyl group and benzyl group; or, $R^{31}$ and $R^{32}$ may from $C_3$–$C_8$ cycloalkyl group together with the carbon atom to which they are attached;

$R^{33}$ is $C_1$–$C_4$ alkyl group, $C_1$–$C_4$ haloalkyl group or $C_3$–$C_6$ alkenyl group;

$R^{34}$ and $R^{35}$ are independently hydrogen atom or $C_1$–$C_4$ alkyl group;

$R^{36}$ is hydrogen atom, $C_1$–$C_6$ alkyl group, $C_3$–$C_6$ alkenyl group or $C_3$–$C_6$ alkynyl group;

$R^{37}$ is hydrogen atom, $C_1$–$C_4$ alkyl group or halogen atom;

$R^{38}$ is hydrogen atom, $C_1$–$C_6$ alkyl group, $C_3$–$C_6$ cycloalkyl group, $C_3$–$C_6$ alkenyl group, $C_3$–$C_6$ alkynyl group, $C_2$–$C_6$ alkoxyalkyl group, $C_1$–$C_6$ haloalkyl group, phenyl group whose ring may be substituted with at least one substituent selected from the group consisting of halogen atom, $C_1$–$C_4$ alkyl group and $C_1$–$C_4$ alkoxy group, —$CH_2CO_2(C_1$–$C_4$ alkyl) group or —$CH(CH_3)CO_2(C_1$–$C_4$ alkyl) group;

$R^{39}$ is hydrogen atom, $C_1$–$C_2$ alkyl group or $C(O)O(C_1$–$C_4$ alkyl) group;

$R^{40}$ is hydrogen atom, $C_1$–$C_6$ alkyl group, $C_1$–$C_6$ alkoxy group or $NH(C_1$–$C_6$ alkyl) group;

$R^{41}$ is $C_1$–$C_6$ alkyl group, $C_1$–$C_6$ haloalkyl group, $C_1$–$C_6$ alkoxy group, $NH(C_1$–$C_6$ alkyl) group, phenyl group whose ring may be substituted with one substituent selected from the group consisting of $R^{42}$ group, benzyl group and $C_2$–$C_8$ dialkylamino group; and $R^{42}$ is $C_1$–$C_6$ alkyl group, one or two halogen atoms, $C_1$–$C_6$ alkoxy group or $CF_3$ group;

(3) a compound of the formula (II):

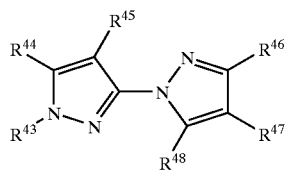

or nipilacrofen, wherein $R^{43}$ is $C_1$–$C_4$ alkyl group;

$R^{44}$ is $C_1$–$C_4$ alkyl group, $C_1$–$C_4$ alkylthio group, $C_1$–$C_4$ alkoxy group, $C_1$–$C_4$ haloalkyl group, $C_1$–$C_4$ haloalkylthio group or $C_1$–$C_4$ haloalkoxy group;

$R^{43}$ and $R^{44}$ together may form —$(CH_2)_3$— or —$(CH_2)_4$—;

$R^{45}$ is hydrogen atom or halogen atom;

$R^{46}$ is hydrogen atom or $C_1$–$C_4$ alkyl group;

$R^{47}$ is hydrogen atom, nitro group, cyano group, —$COOR^{49}$ group, —$C(=X)NR^{50}R^{51}$ group or —$C(=X^2)R^{52}$ group;

$R^{48}$ is hydrogen atom, halogen atom, cyano group, $C_1$–$C_4$ alkyl group optionally substituted with at least one substituent selected from the group consisting of halogen atom and hydroxyl group, $C_1$–$C_4$ alkoxy group, phenyl group optionally substituted with at least one substituent selected from the group consisting of halogen atom, nitro group, cyano group, $C_1$–$C_4$ alkyl group, $C_1$–$C_4$ alkoxy group and halo-$C_1$–$C_4$ alkyl group, pyrrolyl group, $C_2$–$C_8$ alkyl group, $C_3$–$C_8$ alkenyl group, $C_3$–$C_8$ alkynyl group, $C_3$–$C_8$ alkoxy group, a group selected from the group consisting of $C_2$–$C_8$ alkyl group, $C_3$–$C_8$ alkenyl group, $C_3$–$C_8$ alkynyl group and $C_3$–$C_8$ alkoxy group into which at least one oxygen atom is inserted, or any one of groups represented by the following formulas:

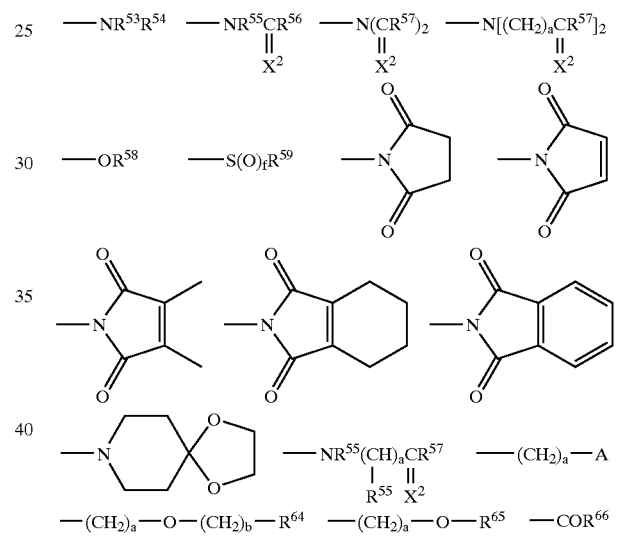

wherein $R^{49}$, $R^{50}$ and $R^{52}$ are, the same or different, hydrogen atom or $C_1$–$C_4$ alkyl group;

$R^{50}$ and $R^{51}$ may form saturated alicyclic 5 or 6 membered ring together with the nitrogen atom to which they are attached;

$R^{52}$ is hydrogen atom, $C_1$–$C_4$ alkyl group or $C_1$–$C_4$ alkyl group substituted with at least one halogen atom;

$R^{53}$ is hydrogen atom, $C_1$–$C_4$ alkyl group optionally substituted with at least one halogen atom, $C_2$–$C_6$ alkenyl group optionally substituted with at least one halogen atom, $C_3$–$C_6$ alkynyl group optionally substituted with at least one halogen atom, phenyl group optionally substituted with at least one halogen atom, $C_3$–$C_8$ cycloalkyl group, cyanomethyl group, or $R^{63}CO$— group;

$R^{54}$ is hydrogen atom, $C_1$–$C_6$ alkyl group optionally substituted with at least one halogen atom, $C_2$–$C_6$ alkenyl group optionally substituted with at least one halogen atom, $C_3$–$C_6$ alkynyl group optionally substituted with at least one halogen atom, phenyl group optionally substituted with halogen atom, $C_3$–$C_8$ cycloalkyl group, cyanomethyl group, $C_1$–$C_4$ alkoxy-$C_1$–$C_6$ alkyl group, di-$C_1$–$C_4$ alkylamino-$C_1$–$C_4$ alkyl group, tetrahydrofurfurylmethyl group, $C_3$–$C_6$ alkynyloxy-$C_1$–$C_4$ alkyl group, benzyl whose ring may be substituted with substituent selected from the group consisting of halogen atom, nitro group, cyano group, $C_1$–$C_4$ alkyl group, $C_1$–$C_4$ alkoxy group and halo-$C_1$–$C_4$ alkyl group, —C(=$X^2$)$R^{63}$ group, —$(CH_2)_a$—$(O)_d$—$R^{70}$ group, —$(CH_2)_a$—O—$(CH_2)_b$—$R^{70}$ group, —$(CH_2)_a$—$X^2$—$R^{76}$ group;

$R^{53}$ and $R^{54}$ together with the nitrogen atom to which they are attached may form saturated alicyclic 3, 5 or 6 membered ring or aromatic 5 or 6 membered ring in which a carbon atom may be optionally replaced with oxygen atom;

$R^{55}$ is hydrogen atom, $C_1$–$C_4$ alkyl group, $C_2$–$C_6$ alkenyl group or $C_3$–$C_6$ alkynyl group, or $R^{55}$ and $R^{56}$ together may form —$(CH_2)_e$—;

$R^{56}$ and $R^{57}$ are independently $C_1$–$C_4$ alkyl group optionally substituted with at least one halogen atom, $C_2$–$C_6$ alkenyl group optionally substituted with at least one halogen atom, $C_3$–$C_6$ alkynyl optionally substituted with at least one halogen atom or phenyl group optionally substituted with at least one halogen atom, hydrogen atom, $C_3$–$C_6$ cycloalkyl group, —$XR^{60}$ group or —$NR^{61}R^{62}$ group;

$R^{58}$ is hydrogen atom, $C_1$–$C_6$ alkyl group, $C_2$–$C_6$ alkenyl group, $C_1$–$C_6$ alkynyl group, $C_1$–$C_4$ alkylcarbonyl group, cyano-$C_1$–$C_3$ alkyl group, $C_1$–$C_4$ alkoxycarbonyl-$C_1$–$C_4$ alkyl group, di-$C_1$–$C_4$ alkoxycarbonyl-$C_1$–$C_4$ alkyl group, benzyl group, $C_1$–$C_4$ alkoxy-$C_1$–$C_4$ alkynyl group, —$(CH_2)_a$—$R^{75}$ group, —$(CH_2)_b$—$X^2$—$R^{72}$ group, —$(CH_2)_a$—$X^2$—$(CH_2)_b$—$R^{72}$ group or —$(CH_2)_a$—$X^2$—$(CH_2)_b$—$X^2$—$(CH_2)_c$—$R^{72}$ group;

$R^{59}$ is hydrogen atom, $C_1$–$C_4$ alkyl group, $C_2$–$C_6$ alkenyl group, $C_3$–$C_6$ alkynyl group, cyano-$C_1$–$C_3$ alkyl group, $C_1$–$C_4$ alkylcarbonyl-$C_1$–$C_3$ alkyl group or phenyl group;

$R^{60}$ is $C_1$–$C_4$ alkyl group optionally substituted with at least one halogen atom;

$R^{61}$ and $R^{62}$ are, the same or different, hydrogen atom or $C_1$–$C_4$ alkyl group;

$R^{63}$ is $C_1$–$C_4$ alkyl group optionally substituted with at least one halogen atom, $C_1$–$C_4$ alkoxy-$C_1$–$C_4$ alkyl group, $C_1$–$C_4$ alkylthio-$C_1$–$C_4$ alkyl group, $C_3$–$C_6$ cycloalkyl group, phenyl group whose ring may be substituted with one substituent selected from the group consisting of halogen atom, nitro group, cyano group, $C_1$–$C_4$ alkyl group, $C_1$–$C_4$ alkoxy group and halo-$C_1$–$C_4$ alkyl group, —$NR^{73}R^{74}$ group or —$(CH_2)_a$—$(O)_d$—$R^{75}$ group;

$R^{64}$ is $C_1$–$C_4$ alkoxycarbonyl group or carboxyl group;

$R^{65}$ is chloromethyl group, cyanomethyl group, $C_3$–$C_6$ cycloalkyl group into which at least one oxygen atom may be inserted, or $C_1$–$C_4$ alkoxycarbonyl-$C_1$–$C_4$ alkyl group;

$R^{66}$ is hydroxyl group or —$NR^{67}R^{68}$ group;

A is —$NR^{67}R^{68}$ group or —S(O)—R group;

$R^{67}$ and $R^{68}$ are, the same or different, hydrogen atom or $C_1$–$C_4$ alkyl group;

$R^{69}$ is $C_1$–$C_4$ alkyl group or $C_1$–$C_4$ haloalkyl group;

$R^{70}$ is hydrogen atom, hydroxyl group, halogen atom, $C_1$–$C_4$ alkyl group optionally substituted with at least one $C_1$–$C_4$ alkoxy group, $C_3$–$C_6$ cycloalkyl group into which at least one oxygen atom may be inserted, $C_3$–$C_6$ cycloalkyl group optionally substituted with one or two methyl groups, furyl group, thienyl group or —C(=O)$R^{71}$ group;

$R^{71}$ and $R^{72}$ are, the same or different, $C_1$–$C_4$ alkyl group or $C_1$–$C_4$ alkoxy group;

$R^{73}$ and $R^{74}$ are, the same or different, $C_1$–$C_4$ alkyl group or phenyl group;

$R^{75}$ is $C_3$–$C_6$ cycloalkyl into which at least one oxygen atom may be inserted, $C_3$–$C_6$ cycloalkyl group optionally substituted with one or two methyl groups, furyl group, thienyl group or —C(=O)$R^{71}$ group;

$R^{76}$ is $C_1$–$C_4$ alkyl group;

a, b and c is independently 1, 2 or 3;

d is 0 or 1;

e is 2 or 3;

f is 1 or 2; and $X^2$ is oxygen atom or sulfur atom.

In addition, as other N-substituted pyrazoles, there are the 3-substituted-2-aryl-4,5,6,7-tetrahydro-indazoles described in Lyga et al., Pesticide Sci., 42: p 29 (1994), and the like.

As specific examples of the compounds inhibiting electron transfer in photochemical system I, for example, there are paraquat, diquat, and the like. As specific examples of the compounds inhibiting electron transfer in photochemical system II, for example, there are triazine compounds (e.g., atrazine, etc.), urea compounds (e.g., diuron, etc.), nitrile compounds (e.g., bromoxynil and ioxynil) and the like. As specific examples of the compounds inhibiting 4-HPPD, for example, there are isoxazoles (e.g., isoxaflutole), pyrazoles, triketones, and the like. As specific examples of the compounds inhibiting PDS, for example, there are norflurazon, flurochloridone, fluridone, flurtamone, diflufenican, and the like. As specific examples of the compounds inhibiting EPSPS, for example, there are glyphosate, and the like. As specific examples of the compounds inhibiting ALS, for example, there are sulfonylureas, imidazolinones, pyrimidinylthiobenzoates, triazolopyrimidines, and the like. As specific examples of the compounds inhibiting GS, for example, there are bialaphos, glufosinate, and the like. As specific examples of the compounds inhibiting DHP, for example, there are asulam, and the like. As specific examples of the compounds inhibiting ACC, for example, there are cyclohexanediones, aryloxyphenoxypropionates, and the like. As specific examples of the compounds inhibiting cellulose, for example, there are dichlobenil, and the like.

Various examples of the weed control compounds useful in the present invention are shown by the following chemical structures:

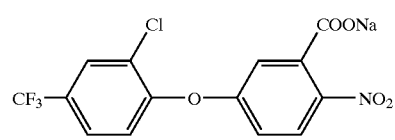

Structure 1

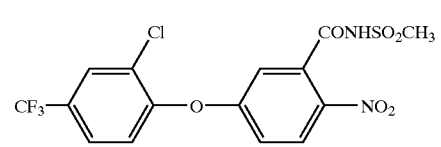

Structure 2

Structure 3
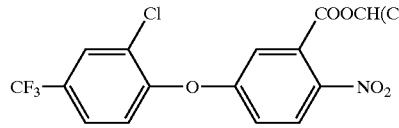
Structure 4
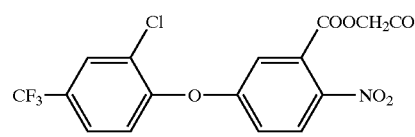
Structure 5
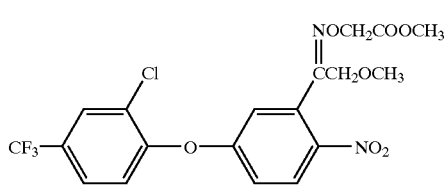
Structure 6
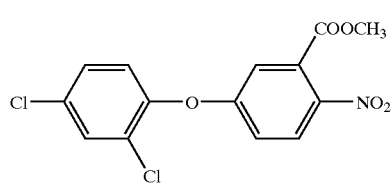
Structure 7
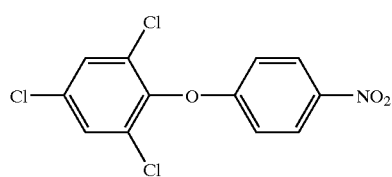
Structure 8
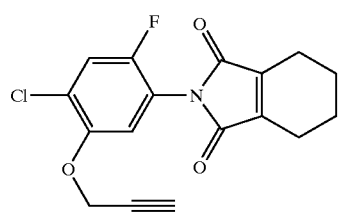
Structure 9
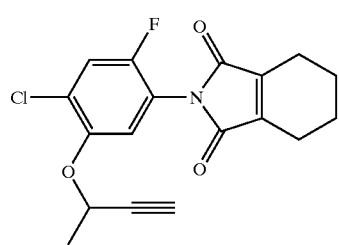
Structure 10
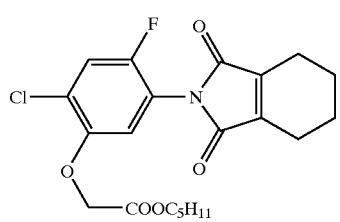
Structure 11
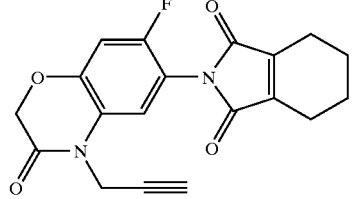
Structure 12
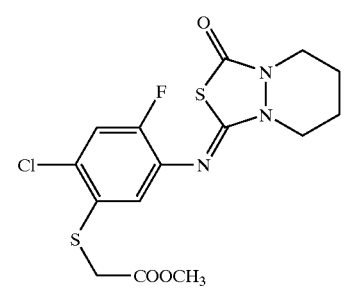
Structure 13
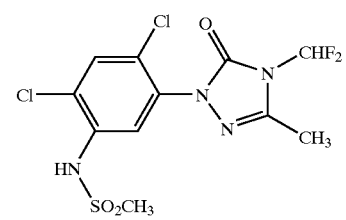
Structure 14
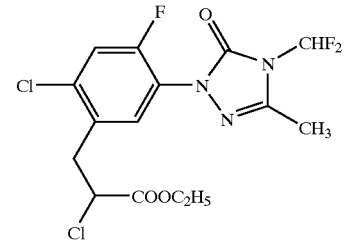
Structure 15
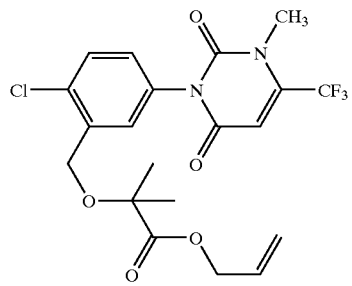
Structure 16
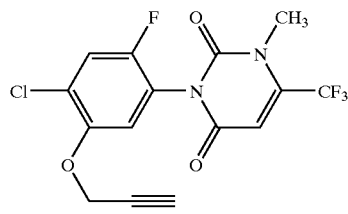

Structure 17
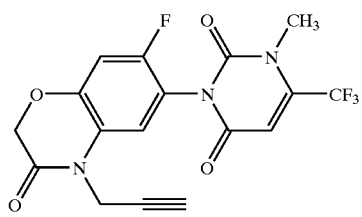
Structure 18
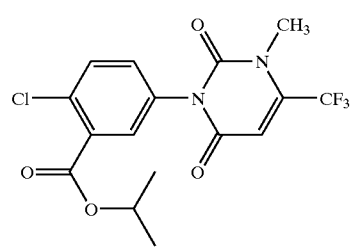
Structure 19
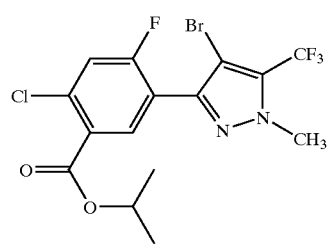
Structure 20
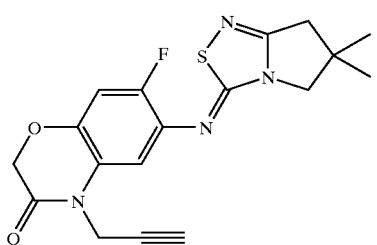
Structure 21
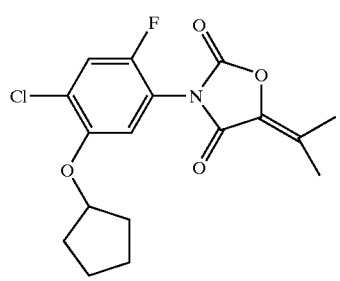
Structure 22
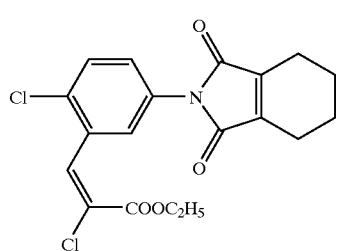
Structure 23
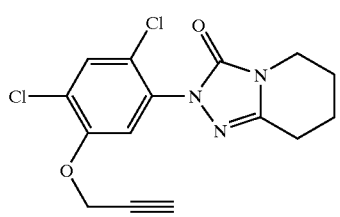
Structure 24
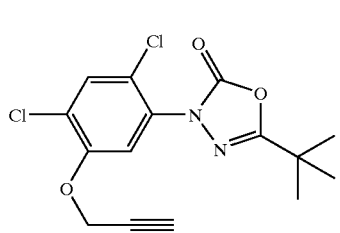
Structure 25
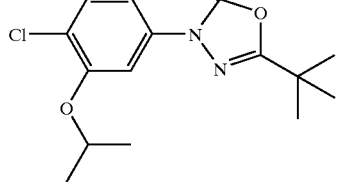
Structure 26
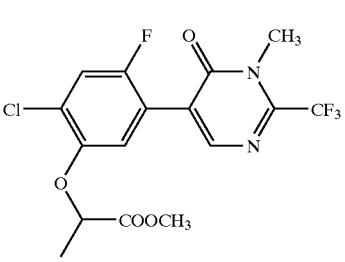
Structure 27
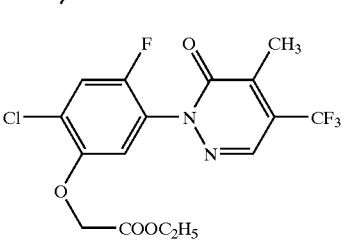
Structure 28
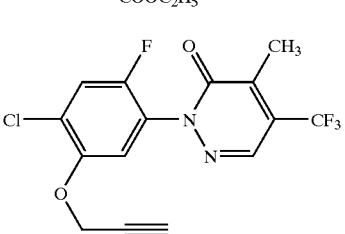
Structure 29
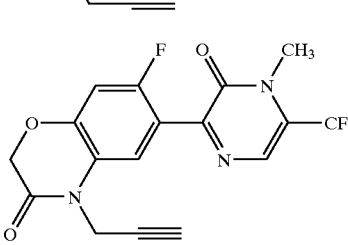

Structure 30
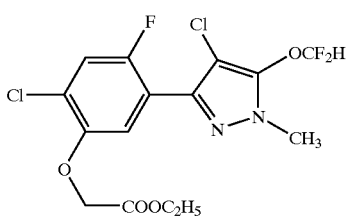

Structure 31
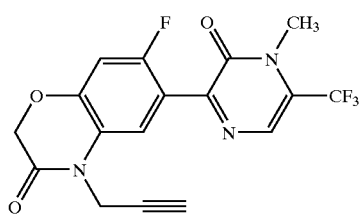

Structure 32
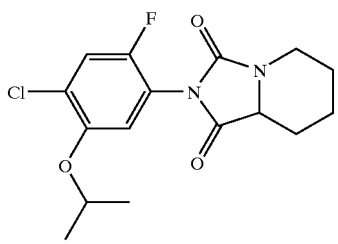

Structure 33
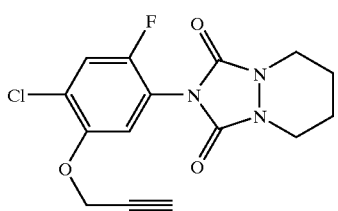

Structure 34
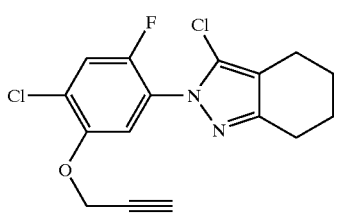

Structure 35
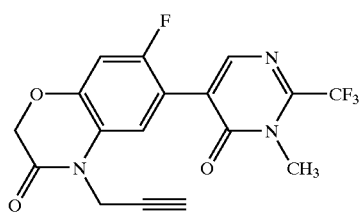

Structure 36
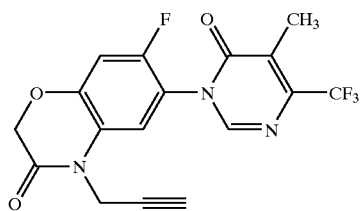

Structure 37
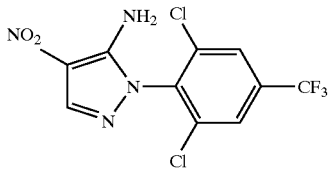

In the first aspect of the method of the present invention, the genes to be used are those encoding proteins having the following characteristics (a) to (c) (hereinafter sometimes referred to as the objective proteins):

(a) having a specific affinity for weed control substances;

(b) having substantially no capability of modifying substances for which said protein has a specific affinity; and (c) being substantially free from framework regions of variable regions of an immunoglobulin.

The term "a specific affinity" for weed control substances of the above characteristic (a) means that an enzyme (the objective protein) and a substrate (the weed control substance), or an enzyme (the objective protein) and an inhibitor or a regulator of an activity of the enzyme (the weed control substance) bind to each other, enzymatically; or that the objective protein and the weed control substance bind to each other on the basis of affinity and specificity, such as those shown in a receptor-chemical bond, for example, a bond between a receptor and a ligand, and the like. The objective proteins may be naturally occurring proteins; variants thereof obtained by introduction of amino acid substitution, addition, deletion, modification and the like into naturally occurring proteins; and artificially synthesized proteins having random amino acid sequences selected with the guidance of their affinity for weed control substances, in so far as they have structures specifically binding to weed control substances.

The term "having substantially no capability of modifying" in the characteristic (b) means that enzymatic reactivity with substances for which said protein has a specific affinity is substantially inactive or not existed (except the specific affinity for weed control substances in the characteristic (a)). Examples of this include a case that the objective protein does not have any capability of converting a substance for which said protein has a specific affinity such as a certain weed control substance or a substance having an essential part of the structure of the substrates on the basis of a specific affinity for said protein, and the like to a substance having a chemical structure different from that of the substance for which said protein has a specific affinity. The protein "having substantially no capability of modifying" can be, for example, identified by checking non-recovery of the growth of a microorganism whose gene encoding the said protein is deleted and thus cannot grow under a usual condition in a case where the gene encoding the said protein is introduced into the microorganism in such a state that the introduced gene is expressed in the microorganism.

The term "substantially free from the framework regions of variable regions of an immunoglobulin" in the characteristic (c) mean that the objective protein does not form a stereostructure specific for the variable regions of an immunoglobulin. The term "framework regions of variable regions of an immunoglobulin" mean regions remaining after removing the hypervariable regions from the variable regions of H chain and L chain which are the constituents of the immunoglobulin molecule. In these regions, conservation of the amino acid sequences is relatively high and these regions function for maintaining the highly conserved stereostructure of the variable regions. Due to formation of the above stereostructure, the hypervariable regions separately located at three sites on respective H chain and L chain are collected to one site on the stereostructure to form an antigen binding site [Alberts, B., et al. ed. (1983), Molecular Biology of the Cell, p 979, Garland Publishing, Inc., New York].

The objective protein having the above characteristic (c) can be selected on the basis of, for example, the amino acid sequences of the proteins. As specific examples of the protein, there are a protein which does not contain any amino acid sequence composed of about 30 amino acids or more and having about 60% or more homology with the known amino acid sequences of the framework regions of the variable regions of an immunoglobulin, and the like. For example, the presence or absence of the above framework regions can be confirmed by PCR using a gene encoding the protein as a template and DNAs having nucleotide sequences encoding the variable regions derived from H chain or L chain of the immunoglobulin as amplification primers, for example, the primers VH1BACK and VH1FOR-2, or VK2BACK and VK4FOR described by Clackson, T. et al., Nature 352; p 624 (1991), or primers contained in a commercially available kit for cloning recombinant antibody genes, for example, Heavy primer mix or Light primer mix of Recombinant Phage Antibody System (Pharmacia Biotech) to analyze presence or absence of amplification of DNA having a given length. Examples of the binding proteins having a specific affinity for weed control substances also include peptides having an affinity for the weed control substances.

Specific examples of the objective proteins having the above characteristics of (a) to (c) include inactive-type binding proteins having an affinity for protoporphyrin IX [e.g., inactive-type magnesium chelatase whose substrate is protoporphyrin IX (the weed control substance), inactive-type ferrochelatase (protoheme ferrolyase; EC 4.9.9.1), inactive-type cobalt chelatase which catalyzes a chelating reaction of a cobalt ion with a compound having tetrapyrrole ring as a substrate, peptides having an affinity for protoporphyrin IX, i.e., proteins composed of 4 to 100 amino acids (for example, peptide HASYS having an affinity for protoporphyrin IX, e.g., a protein comprising the amino acid sequence of SEQ ID NO: 53 and a protein having the amino acid sequence of SEQ ID NO: 54; peptide RASSL having an affinity for protoporphyrin IX, e.g., a protein comprising the amino acid sequence of SEQ ID NO: 55 and a protein having the amino acid sequence of SEQ ID NO: 56; peptide YAGY having an affinity for porphyrin compounds, e.g., a protein comprising the amino acid sequence of SEQ ID NO: 57 and a protein having the amino acid sequence of SEQ ID NO: 58; peptide YAGF having affinity for porphyrin compounds, e.g., a protein comprising the amino acid sequence of SEQ ID NO: 59 and a protein having the amino acid sequence of SEQ ID NO: 60; and the like)], inactive-type binding proteins having an affinity for protoporphyrinogen IX (e.g., inactive-type PPO, inactive-type coproporphyrinogen III oxidase), and the like.

The above inactive-type binding proteins include variants thereof whose activities have been lost by amino acid substitution, addition, deletion, modification and the like of naturally occurring active proteins under natural or artificial conditions.

Cellular dysfunction caused by weed control substances can be prevented by binding of these binding proteins to the weed control substances in plant cells to exhibit the desired weed control compound-resistance.

The inactive-type magnesium chelatase is protoporphyrin IX binding subunit protein of magnesium chelatase, or its variant having a specific affinity for protoporphyrin IX, and specific examples thereof include the subunit protein from which its organelle transit signal sequence has been deleted, and the like.

The inactive-type ferrochelatase is its variant having no capability of modifying protoporphyrin IX and having a specific affinity for protoporphyrin IX, and specific examples thereof include a ferrochelatase variant in which a region presumed to be a Fe ion binding site of ferrochelatse has been modified, and the like.

The inactive-type PPO is its variant having no capability of oxidizing protoporphyrinogen IX and having a specific affinity for protoporphyrinogen IX, and specific examples thereof include a PPO variant in which a region presumed to be FAD binding site of PPO (a region having the amino acid sequence GXGXXG (SEQ ID NO:77), wherein X is any amino acid, e.g., a region comprising the $63^{rd}$ to $68^{th}$ amino acids from the N-terminus of chloroplast localized PPO of mouse-ear cress (Arapidopsis thaliana) and having the amino acid sequence of GGGISG (SEQ ID NO:78)) has been deleted, and the like. The inactive-type coproporphyrinogen III oxidase is its variant having no capability of oxidizing protoporphyrinogen IX and having a specific affinity for protoporphyrinogen IX.

The inactive-type PPO is its variant having no capability of oxidizing protoporphyrinogen IX and having a specific affinity for protoporphyrinogen IX, and specific examples thereof include a PPO variant in which a region presumed to be FAD binding site of PPO (a region having the amino acid sequence GXGXXG wherein X is any amino acid, e.g., a region comprising the 63rd to 68th amino acids from the N-terminus of chloroplast localized PPO of mouse-ear cress (Arabidopsis thaliana) and having the amino acid sequence of GGGISG) has been deleted, and the like. The inactive-type coproporphyrinogen III oxidase is its variant having no capability of oxidizing protoporphyrinogen IX and having a specific affinity for protoporphyrinogen IX.

The genes encoding the above proteins can be obtained by, for example, as follows.

As the genes encoding protoporphyrin IX binding subunit protein of magnesium chelatase, for example, those derived from the photosynthetic bacterium, Rhodobacter capsulatus (Genebank accession M74001), mouse-ear cress (Genebank accession Z68495), barley (Genebank accession U96216), snapdragon (Antirrhinum majus) (Genebank accession U26916), Synechocystis P.C.C. 6803 (Genebank accession U29131) and the like have been known. For isolating such a known gene (its nucleotide sequence has been known), PCR can be carried out by using genomic DNA or cDNA of an organism having the desired gene as a template and primers produced on the basis of nucleotide sequences corresponding to those about the N- and C-termini of the protein encoded by the gene to amplify the desired gene. Further, genes encoding protoporphyrin IX binding subunit protein of magnesium chelatase can be obtained from photosynthetic organisms other than the above. For example, first, a cDNA library is constructed by obtaining mRNA from the desired photosynthetic organism, synthesizing cDNA by using the mRNA as a template with a reverse transcriptase, and integrating the cDNA into a phage vector such as ZAPII, etc. or a plasmid vector such as pUC, etc. For amplifying a DNA fragment containing at least a part of the gene encoding protoporphyrin IX binding subunit protein of magnesium chelatase, PCR can be carried out by using the above-constructed cDNA library as a template and primers designed and synthesized on the basis of nucleotide sequences well conserved among known genes such as the above-described genes. Screening of the cDNA library can be carried out by using the DNA fragment thus obtained as a probe to select positive clones. The desired gene of protoporphyrin IX binding subunit protein of magnesium chelatase can be confirmed by sequence determination of the nucleotide sequence of the selected clone.

For obtaining the gene encoding a variant of protoporhyrin IX binding subunit protein of magnesium chelatase having an specific affinity for protoporphyrin IX, for example, the gene encoding the subunit protein is mutagenized by introduction of nucleotide substitution, addition, deletion, modification and the like, followed by introducing the resultant gene into *Escherichia coli* BL21 (DE3) strain according to the method described by Gibson, L. C. D. et al., Proc. Natl. Acad. Sci. USA, 92; p 1941 (1995) and the like to obtain transformants, and culturing the transformants under conditions that high expression of the gene thus introduced occurs. The desired gene encoding a variant of the subunit protein having a specific affinity for protoporphyrin IX can be obtained by selecting a strain whose cultured cells have turned red and have the fluorescence absorption showing accumulation of protoporphyrin IX (excitation wavelength 405 nm, emission wavelength 630 nm).

As the genes encoding ferrochelatase, for example, those derived from *Escherichia coli* (Genebank accession D90259), *Bacillus subtilis* (Genebank accession M97208), *Bradyrhizobium japonicum* (Genebank accession M92427), yeast *Saccharomyces cerevisiae* (Genebank accession J05395), mouse (Genebank accession J05697), human being (Genebank accession D00726), barley (Genebank accession D26105), cucumber (Genebank accession D26106), and the like have been known. For isolating such a known gene (its nucleotide sequence has been known), PCR can be carried out by using genomic DNA or cDNA of an organism having the desired gene as a template and primers produced on the basis of nucleotide sequences corresponding to those about the N- and C-termini of the protein encoded by the gene to amplify the desired gene. Further, for obtaining other genes encoding ferrochelatase, for example, first, a cDNA library is constructed by obtaining mRNA from the desired organism, synthesizing cDNA by using the mRNA as a template with a reverse transcriptase, and integrating the cDNA into a phage vector such as ZAPII, etc. or a plasmid vector such as pUC, etc. The cDNA library can be introduced into ferrochelatase deficient mutant strain of *Escherichia coli* VS200 described by Miyamoto, K, et al., Plant Physiol., 105; p 769 (1994), followed by subjecting a complementation test to select clones containing ferrochelatase gene derived from the desired organism. Further, for amplifying a DNA fragment, PCR can be carried out by using the above-constructed cDNA library as a template and primers prepared on the basis of nucleotide sequences well conserved among known genes such as the above-described genes. Screening of the cDNA library can be carried out by using the DNA fragment thus obtained as a probe to select positive clones. The desired ferrochelatase gene can be confirmed by sequence determination of the nucleotide sequence of the selected clone.

For obtaining the gene encoding a variant of ferrochelatase having no capability of modifying protoporphyrin IX and having a specific affinity for protoporphyrin IX (for example, the gene encoding a ferrochelatase variant in which the region presumed to be a Fe ion binding site of ferrochelatase is modified), PCR can be carried out by preparing a mutagenesis primer for introduction of mutation into the region on the basis of nucleotide sequence encoding the amino acid sequence about the region, and using a commercially available site-directed mutagenesis kit (Mutan-Super Express, Takara Shuzo) to obtain the gene encoding the above variant. Specifically, a wild type ferrochelatase gene is inserted into the cloning site of plasmid vector pKF19K and PCR is carried out by using the resultant plasmid DNA as a template, the above-described mutagenesis primer and a selection primer for restoration of amber mutation located on kanamycin resistant gene of pKF19K. The gene amplified by PCR is introduced into *Escherichia coli* MV1184 (suppressor free strain) and the transformants are screened according to kanamycin resistance to isolate *Escherichia coli* having ferrochelatase gene in which the nucleotide sequence corresponding to the amino acid sequence which constitutes the desired region has been modified. The isolated gene can be confirmed as the gene encoding the desired protein by analyzing the nucleotide sequence of the plasmid DNA of the *Escherichia coli*.

The genes encoding the peptides having an affinity for protoporphyrin IX, i.e., the proteins composed of 4 to 100 amino acids can be obtained by synthesizing a peptide library according to, for example, the combinatorial chemistry method as described by Sugimoto, N., Nakano, S., Chem., Lett., p 939 (1997) and the like, selecting a peptide having an affinity for the weed control substance, analyzing the amino acid sequence of the peptide thus selected with a peptide sequencer, designing a gene containing a nucleotide sequence encoding the amino acid sequence, and synthesizing the nucleotide sequence with a DNA synthesizer or the like.

Further, a phase clone displaying a peptide having an affinity for the weed control substance can be selected from a phage library according to phage display method. Specifically, for example, a phage library displaying a protein having a random amino acid sequence on the surface of M13 phage particles is constructed by inserting a nucleotide sequence encoding the protein having the random amino acid sequence into the upstream from the region encoding the coat protein pIII of M13 phage gene. On the other hand, the weed control substance labeled with biotin is bound to a plate coated with avidin or streptoavidin to prepare a support coated with the weed control substance. A phage displaying the desired protein having an affinity for the weed control substance can be isolated by screening the above phage library on the plate coated with the weed control substance and the gene of the desired protein can be obtained from the isolated phage.

The gene encoding a protein containing the repetition of the amino acid sequence represented by SEQ ID NO: 53, 55, 57 or 59 four times or eight times can be produced by, for example, selecting a nucleotide sequence in which the nucleotide sequence encoding the above amino acid sequence is repeated the given times after the initiation codon ATG, synthesizing an oligonucleotide comprising the selected nucleotide sequence and an oligonucleotide comprising a nucleotide sequence complementary to the selected nucleotide sequence by a DNA synthesizer, and then subjecting them to annealing. Further, the genes encoding the amino acid sequence represented by SEQ ID NO: 54, 56, 58 or 60 can be produced by selecting a nucleotide sequence encoding the amino acid sequence, synthesizing an oligonucleotide comprising the selected nucleotide sequence and another oligonucleotide comprising a nucleotide sequence complementary to the selected nucleotide sequence by a DNA synthesizer, and then subjecting them to annealing. In this respect, for selecting the nucleotide sequence encoding the given amino acid sequence, for example, it is preferred to select codons frequently used in genes derived from plants.

As PPO genes, for example, those derived from *Escherichia coli* (Genebank accession X68660), *Bacillus subtilis* (Genebank accession M97208), *Haemophilus influenzae* (Genebank accession L42023), mouse (Genebank accession D45185), human being (Genebank accession D38537), mouse-ear cress (Genebank accession D83139), tobacco (Genebank accession Y13465, Y13466) and the like have been known. For isolating such a known gene (its nucleotide sequence has been known), PCR is carried out by using genomic DNA or cDNA of an organism having the desired gene as a template and primers produced on the basis of nucleotide sequences corresponding to those about the N- and C-termini of the protein encoded by the gene to amplify the desired gene. Further, for obtaining other PPO genes, for example, first, a cDNA library is constructed from an organism having the desired gene according to the above-described method. The cDNA library can be introduced into *Escherichia coli* PPO deficient mutant strain VSR800 described by Narita, S., et al., Gene, 182; p 169 (1996), followed by subjecting a complementation test to select clones containing PPO gene derived from the desired organism. Further, for amplifying a DNA fragment, PCR can be carried out by using the above-constructed cDNA library as a template and primers prepared on the basis of nucleotide sequences well conserved among known genes such as the above-described genes. Screening of the cDNA library can be carried out by using the DNA fragment thus obtained as a probe to select positive clones. The desired PPO gene can be confirmed by sequence determination of the nucleotide sequence of the selected clone.

For obtaining the gene encoding a variant of PPO having no capability of oxidizing protoporphyrinogen IX and having a specific affinity for protoporphyrinogen IX, for example, PPO gene is mutagenized by introducing nucleotide substitution, addition, deletion, modification, etc. and the resultant modified gene is introduced into the above *Escherichia coli* whose growth is inhibited light-dependently by treatment with a PPO inhibitory-type herbicidal compound. A gene encoding a protein having protoporphyrinogen IX binding capability can be selected by culturing the *Escherichia coli* thus obtained in the presence of hemin, aminolevulinic acid and a PPO inhibitory-type herbicidal compound to select a clone which can grow even in the light. A gene encoding a protein having no capability of oxidizing protoporphyrinogen IX can be selected by expressing the modified gene thus selected in a host such as *Escherichia coli*, etc. to prepare a protein encoded by the gene, and measuring its capability of oxidizing protoporphyrinogen IX according to the method described by Jacobs, N. J. and Jacobs, J. M. (1982) Enzyme, 28, 206–219 and the like. More specifically, the above modified gene is inserted into an expression vector for *Escherichia coli* and introduced into PPO gene (hemG locus) deficient mutant of *Escherichia coli* such as *Escherichia coli* BT3 strain described by Yamamoto, F., et al., Japanese J. Genet., 63; p 237 (1988) and the like. The *Escherichia coli* is cultured in a culture medium containing hemin and aminolevulinic acid in addition to the cell growth inhibitor corresponding to the selection marker of the vector introduced into the *Escherichia coli* to obtain transformants. The protein encoded by the modified gene can be produced from the transformant.

Further, a gene which does not complement PPO gene deficiency of its host cell can be obtained by culturing the transformant in a culture medium substantially free from hemin and aminolevulinic acid to identify a strain which does not grow. This latter method can also be used for selection of the gene encoding a protein having no capability of oxidizing protoporphyrinogen IX.

Further, for obtaining the gene encoding a variant of PPO in which the region presumed to be a FAD binding site of PPO (the region having the amino acid sequence GXGXXG, wherein X is any amino acid) is deleted, first, a mutagenesis primer for introduction of deletion mutation of the region is prepared on the basis of the nucleotide sequence encoding the amino acid sequence about the region. Then, PCR is carried out by using the mutagenesis primer and a commercially available site-directed mutagenesis kit (Mutan-Super Express, Takara Shuzo) as described above to obtain the gene encoding the above variant protein in which the region has been deleted.

The genes encoding peptide proteins such as the peptides HASYS and RASSL having an affinity for protoporphyrin IX, and the peptides YAGA and YAGF having an affinity for prophyrin compounds, and the like can be obtained by subjecting oligonucleotides synthesized by a DNA synthesizer to annealing.

Furthermore, genes encoding unknown peptide proteins having affinities for other weed control substances can be produced by the following methods and the like. For example, various peptide libraries can be constructed according to, for example, the combinatorial chemistry method as described by Sugimoto, N., Nakano, S., Chem., Lett., p 939 (1997), and the like. Peptides are selected from the peptide libraries thus constructed with the guidance of affinities for weed control substances, followed by analyzing the amino acid sequences of the peptides with a peptide sequencer. Thus, genes encoding the peptides can be synthesized by a DNA synthesizer. Alternatively, phase clones displaying peptides having affinities for weed control substances can be obtained by selecting phage libraries according to phage display method. Specifically, for example, a phage library displaying a protein having a random amino acid sequence on the surface of M13 phage particles is constructed by inserting a nucleotide sequence encoding the protein having the random amino acid sequence into the upstream from the region encoding the coat protein pIII of M13 phage gene. On the other hand, a weed control substance labeled with biotin is bound to a plate coated with avidin or streptoavidin to prepare a support coated with the weed control substance. A phage displaying the desired protein having an affinity for the weed control substance can be isolated by screening the above phage library on the plate coated with the weed control substance and the gene of the desired protein can be obtained from the isolated phage.

As the genes encoding coproporphyrinogen III oxidase, for example, those derived from *Escherichia coli* (Genebank accession X75413), *Salmonella typhimurium* (Genebank accession L19503), yeast *Saccharomyces cerevisiae* (Genebank accession J03873), mouse (Genebank accession D1633), human being (Genebank accession D16333), soybean (Genebank accession X71083), barley (Genebank accession X82830), tobacco (Genebank accession X82831) and the like have been known. For isolating such a known gene (its nucleotide sequence has been known), PCR is carried out by using genomic DNA or cDNA of an organism having the desired gene as a template and primers produced on the basis of nucleotide sequences corresponding to those about the N- and C-termini of the protein encoded by the gene to amplify the desired gene. Further, for obtaining other coproporphyrinogen III oxidase genes, for example, first, a cDNA library is constructed from an organism having the desired gene by preparing mRNA from the desired organism, synthesizing cDNA using the mRNA as a template with a reverse transcriptase and integrating this into a plasmid vector such as pRS313 described by Sikorski, R. S., et al., Genetics, 122; p 19 (1989), and the like. The cDNA library can be introduced into yeast coproporphyrinogen III oxidase deficient mutant strain HEM13 described by Troup, B., et al., Bacteriol., 176; p 673 (1994), followed by subjecting a complementation test to select clones containing coproporphyrinogen III oxidase derived from the desired organism. Further, for amplifying a DNA fragment, PCR can be carried out by using the above-constructed cDNA library as a template and primers prepared on the basis of nucleotide sequences well conserved among known genes such as the above-described genes. Screening of the cDNA library can be carried out by using the DNA fragment thus obtained as a probe to select positive clones. The desired coproporphyrinogen III oxidase gene can be confirmed by sequence determination of the nucleotide sequence of the selected clone.

For obtaining the gene encoding a variant of coporphyrinogen III oxidase having no capability of oxidizing protoporphyrinogen IX and having a specific affinity for protoporphyrinogen IX, for example, coproporphyrinogen III oxidase gene is mutagenized by introducing nucleotide substitution, addition, deletion, modification, etc. and the resultant gene is introduced into the above *Escherichia coli* whose growth is inhibited light-dependently by treatment with a PPO inhibitory-type herbicidal compound. A gene encoding a protein having protoporphyrinogen IX binding capability can be selected by culturing the *Escherichia coli* thus obtained in the presence of hemin, aminolevulinic acid and a PPO inhibitory-type herbicide to select a clone which can grow even in the light. A gene encoding a protein having no capability of oxidizing protoporphyrinogen IX can be selected by expressing the modified gene thus selected in a host such as *Escherichia coli*, etc. to prepare a protein encoded by the gene, and measuring its capability of oxidizing protoporphyrinogen IX according to the method described by Jacobs, N. J. and Jacobs, J. M. (1982) Enzyme, 28, 206–219 and the like.

The genes which is used in the second aspect of the method of the present invention are those encoding proteins having the following characteristics (a) to (c):

(a) having a specific affinity for protoporphyrin IX;

(b) having substantially no capability of modifying protoporphyrinogen IX; and (c) being substantially free from framework regions of variable regions of immunoglobulins.

The term "a specific affinity" for protoporphyrin IX in the characteristic (a) is substantially the same as that in the above first aspect of the method of the present invention and means that the protein and protoporphyrin IX bind to each other, enzymatically or the protein and protoporphyrin IX bind to each other on the basis of affinity and specificity as those shown in receptor chemical bond such as a bond between a receptor and a ligand and the like. The proteins may be naturally occurring proteins; variants thereof in which amino acid substitution, addition, deletion, modification and the like are introduced into naturally occurring proteins; and artificially synthesized proteins having random amino acid sequences which are selected with the guidance of an affinity for protoporphyrin IX in so far as they have structures specifically binding to protoporphyrin IX.

The term "having substantially no capability of modifying" protoporphyrinogen IX in the characteristic (b) means that enzymatic reactivity with protoporphyrinogen IX of the protein is substantially inactive or not existed. For example, this means that the protein does not have capability of converting protoporphyrinogen IX into a substance having a chemical structure different from that of protoporphyrinogen IX.

The term "substantially free from framework regions of variable regions of immunoglobulins" means the same as that in the above first aspect of the method of the present invention and the protein does not form the stereostructure specific for the variable regions in the immunoglobulin as is described hereinabove.

As specific examples of the proteins having the above characteristics (a) to (c), there are active or inactive-type binding proteins having an affinity for protoporphyrin IX [e.g., active or inactive-type magnesium chelatase whose substrate is protoporphyrin IX, active or inactive-type ferrochelatase, active or inactive-type cobalt chelatase which catalyzes a chelating reaction of a cobalt ion with a compound having tetrapyrrole ring as a substrate, peptides, i.e., proteins composed of 4 to 100 amino acids, having an affinity for protoporphyrin IX (for example, proteins containing at least one peptide selected from peptide HASYS having an affinity for protoporphyrin IX, e.g., a protein comprising the amino acid sequence of SEQ ID NO: 53 and a protein having the amino acid sequence of SEQ ID NO: 54; peptide RASSL having an affinity for protoporphyrin IX, i.e., a protein comprising the amino acid sequence of SEQ ID NO: 55 and a protein having the amino acid sequence of SEQ ID NO: 56; peptide YAGY having an affinity for porphyrin compounds, e.g., a protein comprising the amino acid sequence of SEQ ID NO: 57 and a protein having the amino acid sequence of SEQ ID NO: 58; peptide YAGF having affinity for porphyrin compounds, i.e., a protein comprising the amino acid sequence of SEQ ID NO: 59 and a protein having the amino acid sequence of SEQ ID NO: 60; and the like)], and the like.

The genes encoding the above proteins can be obtained by, for example, as follows.

Active-type magnesium chelatases are composed of three heterogenous subunit proteins, i.e., protoporhyrin IX binding subunit protein (H subunit protein), I subunit protein and D subunit protein, all of them are essential for catalytic acitivity. Three independent subunit proteins are encoded by different genes. The genes of protoporphyrin IX binding subunit protein can be obtained by PCR or screening of cDNA library as described hereinabove.

As the gene encoding I subunit protein of a magnesium chelatase, for example, those derived from photosynthetic bacterium, *Rhodobacter sphaeroides* (Genebank accession AF017642), *Rhodobacter capsulatus* (Genebank accession Z11165), *Arabidopsis* (Genebank accession D49426), barley (Genebank accession U26545), soybean (Genebank accession D45857), tobacco (Genebank accession AF14053), *Synechocystis* P.C.C. 6803 (Genebank accession U35144) and the like have been known. For isoltaing such a known gene (its nucleotide sequence has been known), PCR can be carried out by using genomic DNA or cDNA of an organism having the desired gene as a template and primers produced on the basis of nucleotide sequences corresponding to those about the N- and C-termini of the protein encoded by the desired gene. Further, genes encoding I subunit protein of a magnesium chelatase can be obtained from photosynthetic organisms other than the above. For example, first, a cDNA library is constructed by obtaining mRNA from the desired photosynthetic organisms, synthesizing cDNA by using the mRNA as a template with a reverse transcriptase, and integrating the cDNA into a phage vector such as ZAPII, etc. or plasmid vector such as pUC, etc. For amplifying a DNA fragment containing at least a part of the gene encoding I subunit protein of a magnesium chelatase, PCR can be carried out by using the above-constructed cDNA library as a template and primers designed and synthesized on the basis of nucleotide sequences well conserved among known genes such as the above described genes. Screening of the cDNA library can be carried out by using the DNA fragment thus obtained as a probe to select positive clones. The desired gene of I subunit protein of a magnesium chelatase can be confirmed by determination of the nucleotide sequence of the selected clone.

As the gene encoding D subunit protein of a magnesium chelatase, for example, those derived from photosynthetic bacterium, *Rhodobacter sphaeroides* (Genebank accession AJ001690), *Rhodobacter capsulatus* (Geneband accession Z11165), pea (Genebank accession AFO14399), tobacco (Genebank accession Y10022), *Synechocystis* P.C.C. 6803 (Genebank accession X96599) and the like have been known. The isolation of such a known gene (its nucleotide sequence has been known) or genes other than the above can be carried out in the same manner as described in that of the gene encoding I subunit protein of magnesium chelatase.

The genes used in the third aspect of the method of the present invention are those encoding proteins having the following characteristics (a) to (c):

(a) having a specific affinity for protoporphyrinogen IX;

(b) having the capability of modifying coproporphyrinogen III; and (c) being substantially free from framework regions of variable regions of immunoglobulins.

The term "a specific affinity" for protoporphyrinogen IX in the characteristic (a) is substantially the same as that in the above first or second aspect of the method of the present invention and means that the protein and protoporphyrinogen IX bind to each other, enzymatically or the protein and protoporphyrinogen IX are bound to each other on the basis of affinity and specificity as those shown in receptor-chemical bond such as a bond between a receptor and a ligand and the like. The proteins may be naturally occurring proteins; variants thereof in which amino acid substitution, addition, deletion, modification and the like are introduced into naturally occurring proteins; and artificially synthesized proteins having random amino acid sequences which are selected with the guidance of an affinity for protoporphyrinogen IX in so far as they have structures specifically binding to protoporphyrinogen IX.

The term "having the capability of modifying" coproporphyrinogen III in the characteristic (b) means that enzymatical reactivity with coproporphyrinogen III of the proteins is active. For example, this means that the protein has the capability of converting coproporphyrinogen III into a substance having a chemical structure different from that of coproporphyrinogen III.

The term "substantially free from framework regions of variable regions of immunoglobulins" means the same as that in the above first or second aspect of the method of the present invention and the protein does not form the stereo-structure specific for the variable regions in the immunoglobulin as is described hereinabove.

As specific examples of the proteins having the above characteristics (a) to (c), there are active or inactive-type binding proteins having an affinity for proporphyrinogen IX, for example, active-type coproporphyrinogen III oxidase whose substrate is proporphyrinogen IX, and the like.

As a reference, the activity of a magnesium chelatase, a ferrochelatase or a coproporphyrinogen III oxidase is, for example, measured by using the following method.

(1) A Magnesium Chelatase:

The genes encoding independent three subunit proteins are used to detect a magnesium chelatase activity according to the method by Gibson, L. C. D., et al. (Proc. Natl. Acad. Sci. USA, 92; p 1941 (1995)) and the like.

(2) A Ferrochelatse:

A ferrochelatase activity can, for example, be detected according to the method by Porra, R. J. (Anal. Biochem., 68; p 289 (1975)) and the like.

(3) A Coproporphyrinogen III Oxidase:

A coproporphyrinogen III oxidase activity can, for example, be detected according to the method by Yoshinaga, T., Sano, S., et al. (J. Biol. Chem., 255; p 4722 (1980)) and the like.

In the fourth aspect of the method of the present invention, there may be used in addition to the gene encoding the protein having the characteristics (a) to (c) (as described in the first to third aspects of the present invention), at least one altered form of an enzymatic activity selected from an altered PPO activity, an altered EPSPS activity and an altered glyphosate oxidoreductase (GOX) activity. Said altered form of the enzymatic activity in the plant cell can give a resistance to a weed control compound in an amount inhibiting a naturally occurring form of said enzymatic activity. Typically, such an amount of the weed control compound is an amount which can set forth a herbicidal control over the growth of a plant cell, which by inhibiting a naturally occurring form of the enzymatic activity. In this regard, to give the resistance to a PPO inhibitory-type herbicidal compound, it is preferable that the plant cell additionally comprises the altered PPO activity. Likewise, to give the resistance to glyphosate, it is preferable that the plant cell additionally comprises the altered EPSPS activity or the altered GOX activity.

Glyphosate is the common name given to the weed control compound, N-(phosponomethyl)glycine. In this regard, glyphosate includes the ammonium salt, sodium salt, isopropylamine salt, trimethylsulfonium salt, potassium salt or the like salt. Further, glyphosate is a compound encompassed by said compound inhibiting EPSPS, as described above.

The term "altered form of an enzymatic activity" means that the enzymatic activity is different from that which naturally occurs in a plant cell, which altered form of an enzymatic activity provides a resistance to a weed control compound that inhibits the naturally occurring activity thereof. Said naturally occurring enzymatic activity in the plant cell is the enzymatic activity which occurs naturally in the absence of direct or indirect manipulation by man of such naturally occurring enzymatic activity.

A second gene in the plant cell is useful to confer said altered form of the enzymatic activity therein. As such, the second gene typically provides in the plant cell, a gene providing for the altered PPO activity, for the altered EPSPS activity or for the altered GOX activity. Various proteins can be encoded by the second gene, so that the second gene can provide for said altered form of enzymatic activity when expressed in the plant cell.

In utilizing the second gene for the altered PPO activity, the second gene can encode a naturally occurring protein substantially having PPO activity. In the plant cell, such a protein substantially having PPO activity can be a protein having a capability of oxidizing protoporphyrinogen IX and which has a specific affinity for protoporphyrinogen IX.

In its amino acid sequence, the protein substantially having PPO activity preferably contains said region presumed to be FAD binding site of PPO. Such a protein substantially having PPO activity may be PPO. As genes encoding PPO, there can be utilized the known "PPO genes" as described above. Further, there can be utilized a naturally occurring protein substantially having PPO activity which activity is resistant to the PPO inhibitory-type herbicidal compound (as described in EP 0770682 or WO 9833927)

Further, the protein substantially having PPO activity can have substituted, deleted or added thereto amino acids, such that the resulting variant protein has substantially the PPO activity. Conventional methods well known in the art can be used to substitute, delete or add the amino acids thereto. U.S. Pat. No. 5,939,602 and WO 9704089 describe variant PPO substantially having PPO activity which activity is uninhibited by a PPO inhibitory-type herbicidal compound. The second gene may encode such a variant PPO.

In utilizing the second gene for the altered EPSPS activity, the second gene can encode a naturally occurring protein substantially having EPSPS activity. Such a protein substantially having EPSPS activity is a protein having a capability to modify in the plant cell, phosphoenolpyruvic acid (PEP) with 3-phosphoshikimic acid to 5-enolpyruvyl-3-phosphoshikimic acid.

Such a protein substantially having EPSPS activity may be EPSPS. As a polynucleotide encoding EPSPS, there can be utilized a known polynucleotide encoding EPSPS. Examples of such a polynucleotide encoding EPSPS include those derived from *Petunia hybrida* (Genebank accession M37029), Mitchell diploid petunia (as described in EP218571), *Salmonella typhymurium* (as described in EP508909), Tomato (strain VF36) pistil (Genebank accession M21071), *Arabidopsis thaliana* (Genebank accession X06613), soy beans, *Zea mays* (Genebank accession X63374), *Escherichia coli* (Genebank accession X00557), *Agrobacterium tumefaciens* sp. strain CP4 (class II) and the like. Additionally, the second gene can also encode a naturally occurring protein substantially having EPSPS activity which activity is resistant to glyphosate, such as a bacterial EPSPS which activity is resistant to glyphosate.

Further, the second gene when providing for the altered EPSPS activity in the plant cell can also encode a variant protein substantially having EPSPS activity. As such, the protein substantially having EPSPS activity can have substituted, deleted or added thereto amino acids such that the resulting protein substantially has the EPSPS activity. Examples of such a variant protein substantially having EPSPS activity include a variant EPSPS which activity is resistant to glyphosate, a variant EPSPS in which a chloroplast transit peptide is added thereto and the like.

The variant EPSPS which activity is resistant to glyphosate can be produced by substituting, deleting or adding nucleotides to a gene encoding EPSPS. For example, a substitutive mutation can be introduced to a polynucleotide encoding EPSPS to produce a variant polynucleotide. The protein encoded by the resulting variant gene can then be confirmed for a resistance to glyphosate and for the EPSPS activity.

The resistance to glyphosate may be confirmed by introducing the variant gene to a particular *Escherichia coli* mutant and by culturing the resulting particular *Escherichia coli* mutant in a specified minimal nutrient MOPS medium which has glyphosate added thereto. As the particular variant *Escherichia coli* in this case, there is utilized an *Escherichia coli* mutant which is deficient in its endogenous EPSPS gene (aroA locus) and which has the growth thereof inhibited in the specified minimal nutrient MOPS medium (in which there is no glyphosate therein). Further, in this case, the specified minimal nutrient MOPS medium is specified in that there is no aromatic amino acids present therein. When glyphosate is added to the minimal nutrient MOPS medium, the glyphosate is in an amount which would typically inhibit in normal growing conditions, the growth of an *Escherichia coli* mutant which is deficient in its endogenous EPSPS gene but which has introduced thereto a naturally occurring gene encoding herbicidally sensitive EPSPS. By selecting the resulting clones growable in such specified minimal nutrient MOPS medium containing glyphosate, there can be obtained a variant polynucleotide encoding a variant EPSPS having an activity which is resistant to glyphosate. The EPSPS activity can be confirmed by introducing said variant gene to a host cell and then by according to the method described in EP 409815. In this regard, there can be obtained the second gene encoding the variant EPSPS substantially having EPSPS activity which activity is resistant to glyphosate.

In utilizing the second gene for the altered GOX activity, the second gene can encode a naturally occurring protein substantially having GOX activity. Such a protein substantially having the GOX activity is a protein having a capability to degrade glyphosate to less herbicidal products, such as aminomethyl phosphonate (AMPA) and glyoxylate. In cases in which glyphosate is degraded into AMPA and glyoxylate, for example, the protein substantially having GOX activity may cleave the C—N bond of glyphosate.

Such a protein substantially having GOX activity may be GOX. As a polynucleotide encoding GOX, there can be utilized a known polynucleotide encoding GOX. Examples of naturally occurring GOX genes include those derived from *Pseudomonas* sp. strains LBAA, *Pseudomonas* sp. strains LBr, *Agrobacterium* sp. strain T10 and the like.

Further, the second gene when providing for the altered GOX activity in the plant cell can encode a variant protein substantially having GOX activity. As such, the protein substantially having GOX activity can have substituted, deleted or added thereto amino acids such that the resulting protein substantially has the GOX activity. As an example of such a variant protein substantially having GOX activity, there is mentioned a variant GOX in which a chloroplast transit peptide is added thereto. Conventional methods well known in the art can be used to substitute, delete or add the amino acids thereto.

The GOX activity of a protein substantially having GOX activity can be confirmed by introducing a gene encoding the protein substantially having GOX activity into a specified *Escherichia coli* mutant and by culturing the resulting specified *Escherichia coli* mutant in a minimal nutrient MOPS medium containing glyphosate as the sole nitrogenous source therein. As the specified *Escherichia coli* mutant in this case, there is utilized an *Escherichia coli* mutant which can grow in a minimal nutrient MOPS medium having a non-herbicidal aminophosphate compound as the sole nitrogenous source therein, such as *E. coli* SR2000 Mpu+. The glyphosate therein is in an amount which would typically inhibit the growth of the specified *Escherichia coli* mutant having no said gene encoding the protein substantially having GOX activity introduced thereto. By selecting the resulting clones growable in such minimal nutrient MOPS medium containing glyphosate as the sole nitrogenous source therein, there can be obtained a polynucleotide encoding a protein substantially having GOX activity. Such results suggest that in cases in which the protein substantially having GOX activity degrades glyphosate into AMPA, the growable clones use to grow, AMPA as a nitrogenous source. In practice, a 3-$^{14}$C labeled glyphosate may be used to confirm that said growable clone consumes and degrades glyphosate. For example, the growable clone may be cultured with the 3-$^{14}$C labeled glyphosate and the cell extract thereof may then be analyzed with HPLC.

The second gene encoding an above protein substantially having PPO activity, EPSPS activity or GOX activity can be obtained, for example, as follows.

For isolating a known gene encoding a protein substantially having PPO activity, EPSPS activity or GOX activity, PCR can be carried out by using genomic DNA or cDNA of an organism having the desired gene as a template and primers produced on the basis of nucleotide sequences corresponding to those about the N- and C-termini of the protein to amplify the desired gene. Further, genes encoding a protein substantially having PPO activity, EPSPS activity or GOX activity can be obtained from organisms other than the above. For example, first, a cDNA library is constructed by obtaining mRNA from an organism and synthesizing cDNA by using the mRNA as template with reverse transcriptase and integrating the cDNA into a phage vector such as ZAP II, etc. or a plasmid vector such as pUC, etc. For the protein substantially having PPO activity, the cDNA library may be introduced into *Escherichia coli* PPO deficient mutant strain VSR800 described by Narita, S., et al., Gene, 182; p 169 (1996), followed by subjecting a complementation test to select clones containing PPO gene derived from the desired organism. Further, for amplifying a DNA fragment containing at least a part of the desired gene, PCR can be carried out by using the above-constructed cDNA library as a template and primers designed and synthesized on the basis of nucleotide sequences well conserved among known genes such as the above-described genes. Screening of the cDNA library can be carried out by using the DNA fragment thus obtained as a probe to select positive clones. The desired gene, i.e., a gene encoding the protein substantially having the PPO activity, EPSPS activity or GOX activity, can be confirmed by determination of the nucleotide sequence of the selected clone.

Examples of methods used to confer the altered EPSPS activity or altered GOX activity include the following. An example may include a method of introducing into a cultivated plant a gene having a polynucleotide sequence encoding a petunia (Mitchell diploid petunia) EPSPS downstream of a high expression promoter such as a cauliflower mosaic virus 35S promoter (EP 218571). A further example may include a method of introducing into a cultivated plant a gene having a 35S promoter upstream of a polynucleotide sequence encoding an *Agrobacterium* (*Agrobacterium tumefaciens* sp. strain CP4) EPSPS fused with a chloroplast transit peptide of a petunia (*Petunia hybrida*) EPSPS (WO 9204449, U.S. Pat. No. 5,633,435). A furthermore example may include a method of introducing into a cultivated plant a gene having 2 continuous 35S promoters upstream a polynucleotide encoding a sunflower chloroplast transit peptide of small subunit of ribulose-1,5-bisphosphate carboxylase (ssRUBISCO), the 22 amino acids from the N-terminus of maize ssRUBISCO, maize chloroplast transit peptide of ssRUBISCO and a *Salmonella* (*Salmonella typhyrium*) EPSPS (EP 508909). Even furthermore, an example may include a method of introducing into a cultivated plant, a gene having downstream from a promoter of *Arabidopsis thaliana* alcohol dehydrogenase A, a polynucleotide encoding an *Arabidopsis thaliana* chloroplast transit peptide and GOX (WO 9706269). Yet even furthermore, an example may include a method of introducing into a cultivated plant, the above gene encoding GOX as well as a gene having downstream from a 35S promoter possessing an enhanced promoter activity with the omega sequence of tobacco mosaic virus, a polynucleotide sequence which encodes an *Agrobacterium* (*Agrobacterium tumefaciens* sp. strain CP4) EPSPS (class II) downstream a chloroplast transit peptide of Petunia (*Petunia hybrida*) EPSPS (WO 9706269). Still yet even furthermore, an example may include a method of introducing into a cultivated plant, a gene encoding a variant EPSPS having amino acid substitutions therein which augment the resistant to glyphosate [Hinchee, M. A. W. et al., BIO/TECHNOLOGY, 6: p 915 (1988), EP 389066, EP 409815, WO 9206201 and U.S. Pat. No. 5,312,910].

Examples of methods used to confer the altered PPO activity include the following. An example may include a method of over-expressing in a plant cell, a gene encoding wild-type, naturally occurring PPO (U.S. Pat. No. 5,767, 373). A further example may include a method of expressing in a plant cell, a variant protein substantially having PPO activity which activity is not inhibited by a PPO inhibitory-type herbicidal compound (U.S. Pat. No. 5,939,602). A furthermore example may include a method of expressing a PPO substantially having PPO activity which is not inhibited by a PPO inhibitory-type herbicidal compound, wherein the PPO is derived from bacteria (EP 0770682 or WO 9833927).

In the method (including the above first to third aspects) of the present invention, for introducing the gene encoding the protein having the characteristics of (a) to (c) into a plant cell, a gene encoding one protein can be introduced. Further, plural genes encoding different proteins can be introduced into a plant cell. When said altered form of enzymatic activity is given to the plant cell, the second gene encoding one protein may also be introduced. Further, plural genes of the second gene can be introduced into the plant cell to provide for said altered form of enzymatic activity therein. In introducing the gene encoding the protein having the characteristics of (a) to (c) and second gene thereto, the gene encoding the protein having the characteristics of (a) to (c) may be introduced into the plant cell with the second gene, or may be introduced before or after the second gene is introduced to the plant cell. Such gene introduction into plant cells can be carried out by conventional gene engineering techniques, for example, *Agrobacterium* infection (JP-B 2-58917 and JP-A 60-70070), electroporation into protoplasts (JP-A 60-251887 and JP-A 5-68575), particle gun methods (JP-A 5-508316 and JP-A 63-258525), and the like.

Preferably, the gene to be introduced into a plant cell is integrated into a vector having a selection marker gene such as a gene which can give cell growth inhibitor resistance to the plant cell. For example, the gene encoding the protein having the characteristics of (a) to (c) and the second gene, when utilized for the altered form of enzymatic activity, can be integrated into one of such vectors. Further, the gene encoding the protein having the characteristics of (a) to (c) and the second gene may also each be integrated, respectively, into such vectors having a selection marker gene. In integrating the gene encoding the protein having the characteristics (a) to (c) and the second gene into such respective vectors, the selection marker gene utilized for the vector for the second gene is typically different from the selection marker gene utilized for the vector for the gene encoding the protein having the characteristics (a) to (c).

For expression of the gene encoding the protein having the characteristics (a) to (c) in the plant cell, the gene can be introduced into a chromosome of a plant cell by homologous recombination [Fraley, R. T. et al., Proc. Natl. Acad. Sci. USA, 80; p 4803 (1983)] to select the plant cell expressing the gene. Alternatively, the gene can be introduced into a plant cell in the form that it is operably ligated to a promoter and a terminator both of which can function in the plant cell.

The term "operably ligated" used herein means that the above promoter and terminator are joined in such a state that the introduced gene is expressed in the plant cell under control of the promoter and the terminator.

To provide for the altered form of enzymatic activity, the second gene is expressed in a plant cell. For expression of the second gene in the plant cell, the second gene can likewise be introduced into a chromosome of a plant cell by homologous recombination to select the plant cell expressing the second gene. Alternatively, the second gene can be introduced into a plant cell in the form that it is operably ligated to a promoter and a terminator both of which can function in the plant cell. When utilized, the second gene is typically expressed at a level such that the amount of the protein encoded by the second gene provides for the altered form of enzymatic activity and further confer the resistance of the plant cell. It is preferable when the second gene encodes PPO or EPSPS, that the second gene provide for the altered form of enzymatic activity through over-expression. If so desired, a transcriptionally strong promoter which can function in the plant cell can be utilized with the second gene.

As the promoter which can function in a plant cell, for example, there are constitutive promoters derived from T-DNA such as nopaline synthase gene promoter, octopine synthase gene promoter, etc., promoters derived from plant viruses such as 19S and 35S promoters derived from cauliflower mosaic virus, etc., inductive promoters such as phenylalanine ammonia-lyase gene promoter, chalcone synthase gene promoter, pathogenesis-related protein gene promoter, etc., and the like. The promoter is not limited these promoters and other plant promoters can be used.

As the terminator which can function in a plant cell, for example, there are terminators derived from T-DNA such as nopaline synthase terminator, etc., terminators derived from plant viruses such as terminators derived from =garlic viruses GV1, GV2, etc., and the like. The terminator is not limited to these terminators and other plant terminators can be used.

As the plant cells into which the gene encoding the protein having the characteristics of (a) to (c) are introduced, for example, there are plant tissues, whole plants, cultured cells, seeds and the like. Examples of the plant species into which the genes are introduced include dicotyledones such as tobacco, cotton, rapeseed, sugar beet, mouse-ear cress, canola, flax, sunflower, potato, alfalfa, lettuce, banana, soybean, pea, legume, pine, poplar, apple, grape, citrus fruits, nuts, etc.; and monocotyledones such as corn, rice, wheat, barley, rye, oat, sorghum, sugar cane, lawn, etc. The second gene may also be introduced into such plant cells.

The transformant plant cells expressing the gene encoding the protein having the characteristics of (a) to (c) can be obtained by culturing cells into which the gene is transferred in a selection culture medium corresponding to a selection marker joined to the locus on the gene, for example, a culture medium containing a cell growth inhibitor, or the like, and isolating a clone capable of growing in the culture medium. Further, the selection culture medium should also correspond to a selection marker joined to the locus of the second gene when the altered form of enzymatic activity is also present in the transformant plant cells. Alternatively, the above transformant plant cells can be selected by culturing plant cells into which the gene is introduced in a culture medium containing the weed control compound to which the resistance is given, and isolating clones capable of growing in the culture medium.

The desired weed control compound-resistant plant can be obtained from the transformant cells thus obtained by regenerating the whole plant according to a conventional plant cell culture method, for example, that described in Plant Gene Manipulation Manual, Method for Producing Transgenic Plants, UCHIMIYA, Kodansha Scientific (1996). Thus, the transformed plants such as plant tissues, whole plants, cultured cells, seeds and the like can be obtained.

For example, rice and mouse-ear cress expressing the gene encoding the protein having the characteristics of (a) to (c) can be obtained according to the method described Experimental Protocol of Model Plants, Rice and Mouse-Ear Cress Edition, (Supervisors: Koh SHIMAMOTO and Kiyotaka OKADA, Shujun-sha, 1996), Chapter 4. Further, according to the method described in JP-A 3-291501, soybean expressing the gene encoding the binding protein by introducing the gene into soybean adventitious embryo with a particle gun. Likewise, according to the method described by Fromm, M. E., et al., Bio/Technology, 8; p 838 (1990), corn expressing the gene encoding the above protein can be obtained by introducing the gene into adventitious embryo with a particle gun. Wheat expressing the gene encoding the above protein can be obtained by introducing the gene into sterile-cultured wheat immature scutellum with a particle gun according to a conventional method described by TAKUMI et al., Journal of Breeding Society (1995), 44: Extra Vol. 1, p 57. Likewise, according to a conventional method described by HAGIO, et al., Journal of Breeding Society (1995), 44; Extra Vol. 1, p 67, barley expressing the gene encoding the above protein can be obtained by introducing the gene into sterile-cultured barley immature scutellum with a particle gun.

For confirmation of weed control compound-resistance of the plant expressing the gene encoding the above protein, preferably, the plant is reproduced with applying the weed control compound to which resistance is given to evaluate the degree of reproduction of the plant. For more quantitative confirmation, for example, in case of resistance to a compound having PPO inhibitory-type herbicidal activity, preferably, pieces of leaves of the plant are dipped in aqueous solutions containing the compound having PPO inhibitory-type herbicidal activity at various concentrations, or the aqueous solutions containing the compound having herbicidal activity are sprayed on pieces of leaves of the plant, followed by allowing to stand on an agar medium in the light at room temperature. After several days, chlorophyll is extracted from the plant leaves according to the method described by Mackenney, G., J. Biol. Chem., 140; p 315 (1941) to determine the content of chlorophyll.

Since the weed control compound-resistant plants (e.g., plant tissues, whole plants, cultured cells, seeds, etc.) obtained by the method of the present invention (including the first to fourth aspects) show resistance to weed control compounds, even in case that a weed control compound is applied to a growth area (e.g., cultivation area, proliferation area, etc.), the plant can grow. Therefore, when a weed control compound is applied to a growth area of the desired weed control compound resistant-plant, the desired plant can be protected from plants without resistance to the weed control plant. For example, weeds can be controlled efficiently by applying a weed control compound on a growth area of the plant having resistance to the weed control compound.

Further, by applying a weed control compound to a growth area of the weed control compound-resistant plant obtained by the method of the present invention (including the first to third aspects) and other plants (e.g., those having no or weak resistance to the weed control compound), one of the plants can be selected on the basis of the difference in growth between the plants. For example, by applying (adding) a weed control compound to a cultivation area (culture medium) of the weed control compound-resistant plant cells obtained by the method of the present invention and other plant cells (e.g., those having no or weak resistance to the weed control compound), one of the plant cells can be selected efficiently on the basis of the difference in growth between the plants.

The following Examples further illustrate the present invention in detail but are not to be construed to limit the scope thereof.

EXAMPLE 1

Isolation of Protoporphyrin IX Binding Subunit Protein Gene of Magnesium Chelatase.

Genomic DNA of photosynthetic bacterium *Rhodobacter sphaeroides* ATCC17023 was prepared using ISOPLANT kit for genomic DNA preparation (manufactured by Nippon Gene). Then, according to the description of Gibson, L. C. D. et al., Proc. Natl. Acad. Sci. USA, 92; p 1941 (1995), PCR was carried out by using about 1 µg of said genomic DNA as a template, and 10 pmol of an oligonucleotide composed of nucleotide sequence represented by SEQ ID NO: 1 and 10 pmol of an oligonucleotide composed of nucleotide sequence represented by SEQ ID NO: 2 as primers to amplify the DNA fragment containing protoporphyrin IX binding subunit protein gene bchH of magnesium chelatase. The oligonucleotides were prepared with a DNA synthesizer (PE Applied Biosystems: Model 394 DNA/RNA Synthesizer) and purified with an oligonucleotide purification cartridge (PE Applied Biosystems: OPC Cartridge). The PCR was carried out by maintaining at 94° C. for 2 minutes, at 96° C. for 40 seconds and then at 68° C. for 7 minutes, repeating a cycle for maintaining at 96° C. for 40 seconds and then at 68° C. for 7 minutes 28 times, and finally maintaining at 96° C. for 40 seconds, at 68° C. for 7 minutes and then at 72° C. for 10 minutes.

EXAMPLE 2

Expression of Protoporphyrin IX Binding Subunit Protein Gene of Magnesium Chelatase in *Escherichia Coli* (Hereinafter Abbreviated to *E. coli*)

According to the description of Gibson, L. C. D. et al., Proc. Natl. Acad. Sci. USA, 92; p 1941 (1995), the DNA fragment containing bchH gene prepared in Example 1 was digested with the restriction enzymes NdeI and BglII. The resultant DNA fragment was inserted between NdeI restriction site and BamHI restriction site of expression vector pET11a (manufactured by Stratagene) to obtain plasmid pETBCH (FIG. 1). This plasmid pETBCH was introduced into *E. coli* BL21(DE3) strain competent cells (manufactured by Stratagene) according to the manual attached to the competent cells to obtain *E. coli* BL21(DE3)/pETBCH strain. The strain was inoculated into 1.5 ml LB liquid culture medium (1% tryptone, 0.5% yeast extract, 0.5% NaCl) containing 100 µg/ml ampicillin in a tube (14×10 mm), and the tube was covered with aluminum foil (hereinafter referred to as dark conditions), cultured with shaking at 37° C. under light of fluorescent lamp (about 8000 lux). When the absorbance at 600 nm of the liquid culture medium became about 0.6, isopropyl β-D-thiogalactopyranoside (IPTG) was added to the liquid culture medium so that the final concentration was 0.4 mM, and the culture was continued for about additional 20 hours. At that time, the *Escherichia coli* turned red and fluorescent absorbance (excitation wavelength 405 nm, emission wavelength 630 nm) which showed the accumulation of protoporphyrin IX in *E. coli* was observed. When *E. coli* BL21 (DE3)/pETBCH strain was cultured according to the same manner except that IPTG was not added, *E. coli* did not turned red and the above fluorescent absorbance did not detected. In contrast to this, when *E. coli* BL21(DE3)/pETBCH strain was cultured according to the same manner (with IPTG) except that the tube was not covered with aluminum foil (hereinafter referred to as light conditions), *E. coli* grew and turned red as above.

EXAMPLE 3

Expression of PPO Gene Derived from Soybeans in hemG Gene Deficient *E. coli*

Soybeans (*Glycine max* var. Williams 82) were seeded and cultivated at 25° C. for 20 days and green leaves were collected. The collected green leaves were frozen with liquid nitrogen and the frozen leaves were ground in a mortar with a pestle. From the ground leaves, RNA were extracted by using RNA extracting reagent ISOGEN (manufactured by Nippon Gene) according to the manual attached thereto. The resultant RNA liquid extract was subjected to ethanol precipitation to collect total RNA, then the total RNA was fractionated by using poly(A)RNA fractionating kit BIOMAG mRNA Purification Kit (manufactured by Perceptive Bio System) according to the manual attached thereto to collect poly(A)RNA fraction. Using 1 µg of this poly(A)RNA fraction as a template, cDNA was synthesized with the cDNA synthetic reagent contained in Marathon cDNA amplification kit (manufactured by Clontech) according to the manual attached thereto. PCR was carried out by using the resultant cDNA as a template, and an oligonucleotide composed of nucleotide sequence of SEQ ID NO: 3 and an oligonucleotide composed of nucleotide sequence of SEQ ID NO: 4 as primers to amplify the DNA fragment containing chloroplast-type protoporphyrinogen IX oxidase gene. The above oligonucleotides were prepared with a DNA synthesizer (PE Applied Biosystems: Model 394 DNA/RNA Synthesizer) and purified with an oligonucleotide purification cartridge (PE Applied Biosystems: OPC Cartridge). The PCR was carried out by maintaining at 94° C. for 1 minutes and then at 65° C. for 5 minutes, repeating a cycle for maintaining at 94° C. for 15 seconds and then at 65° C. for 5 minutes 29 times. After the PCR, the amplified DNA fragment was purified by filtering the reaction mixture with MicroSpin S-400HR (manufactured by Pharmacia Biotech), and the DNA fragment was ligated to plasmid pCR2.1 (manufactured by Invitrogen) cleaved by restriction enzyme SalI to obtain plasmid pSPPO-P. Then, the plasmid was introduced into competent cells of *E. coli* INVαF' strain (manufactured by Invitrogen) and ampicillin resistant strains were selected. Then, the plasmid contained in selected ampicillin resistant strains was sequenced by using Dye terminator cycle sequencing kit (manufactured by PE Applied Biosystems) and DNA sequencer 373S (manufactured by PE Applied Biosystems). As a result, the nucleotide sequence of SEQ ID NO: 5 was revealed, thereby confirming that plasmid pSPPO-P contained chloroplast-type protoporphyrinogen IX oxidase gene of soybean.

Figure 2:
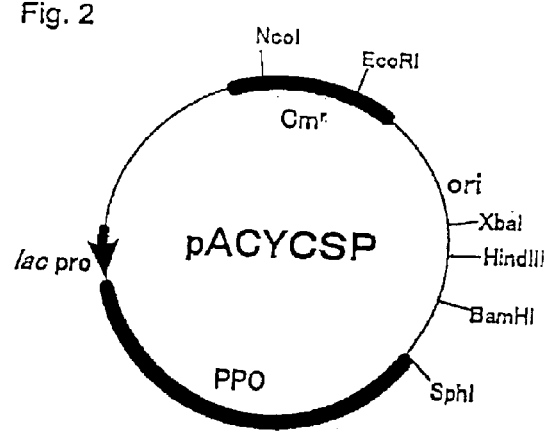
FIG. 2 is the restriction map of plasmid pACYCSP. PPO is protoporphyrinogen IX oxidase gene of soybean and lac pro represents the promoter sequence of a lactose operon. Cm$^r$ is a chloramphenicol resistant gene and ori is the replication origin.

The plasmid pSPPO-P was digested with restriction enzyme PshBI, the resultant DNA fragment was blunted by using T4 DNA polymerase and further digested with SphI to isolate the DNA fragment containing chloroplast-type PPO gene of soybean and lac promoter. Then, the plasmid pACYC184 (manufactured by Nippon Gene) was digested with the restriction enzymes NruI and SphI to remove a fragment of 410 bp and the above DNA fragment was inserted instead to obtain plasmid pACYCSP (FIG. 2). Then, the plasmid pACYCSP was introduced into PPO gene (hemG gene locus) deficient mutant *E. coli* BT3 strain (described in Yamamoto, F. et al., Japanese J. Genet., 63; p 237 (1988) etc.) according to the method described in Hanahan, D. J., Mol. Biol., 166; p 557 (1983). The resultant *E. coli* were cultured in YPT medium (5 g/liter yeast extract, 5 g/liter tryptone, 5 g/liter peptone, 10 g/liter NaCl, pH 7.0) containing 15 μg/ml chloramphenicol and 10 μg/ml kanamycin to select *E. coli* BT3/pACYCSP strain resistant to chloramphenicol and kanamycin whose hemG gene deficiency was complemented by PPO gene derived from soybean.

EXAMPLE 4

Test of Protoporphyrin IX Binding Subunit Protein of Magnesium Chelatase for Capability of Giving Weed Control Compound-Resistance

*E. coli* BT3/pACYCSP strain prepared in Example 3 was inoculated into YPT medium containing 10 or 1 ppm of PPO inhibitory type herbicidal compound represented by the above Structure 8, 10 μg/ml hemin, 50 μg/ml aminolevulinic acid, 15 μg/ml chloramphenicol and 10 μg/ml kanamycin, cultured under dark conditions or light conditions according to the same manner as in Example 2. As a control, *E. coli* BT3/pACYCSP strain was cultured in the same medium as above without the herbicidal compounds under the same conditions. Then, 18 hours after initiation of culture, the absorbance of the liquid culture medium was measured at 600 nm. By taking the absorbance of the medium without the herbicidal compound as 1, the relative value of the absorbance of the medium containing the herbicidal compound was calculated. The results are shown in Table 1.

TABLE 1

| E. coli strain | Culture conditions | Relative absorbance Concentration of test compound | | |
|---|---|---|---|---|
| | | 10 ppm | 1 ppm | 0 ppm |
| BT3/pACYCSP | in the light | 0.10 | 0.25 | 1.0 |
| BT3/pACYCSP | in the dark | 0.73 | 0.95 | 1.0 |

Figure 3:
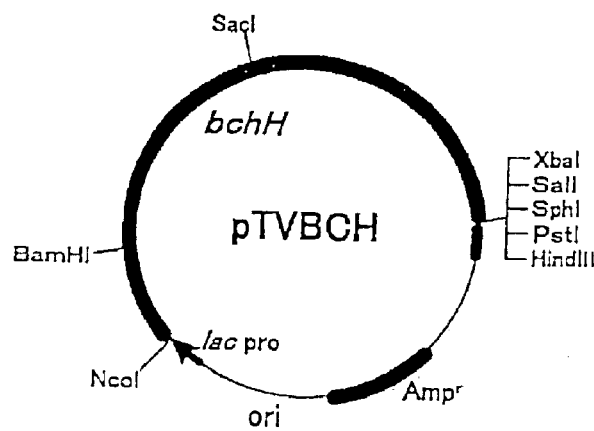
FIG. 3 is the restriction map of plasmid pTVBCH. bchH is magnesium chelatase protoporphyrin IX binding subunit gene of the photosynthetic bacterium *Rhodobacter sphaeroides*. lac pro represents the promoter sequence of a lactose operon. Amp$^r$ is an ampicillin resistant gene and ori is the replication origin.

Plasmid pTVBCH (FIG. 3) was constructed by amplification of the DNA fragment containing bchH gene derived from photosynthetic bacterium *Rhodobacter sphaeroides* using the oligonucleotide composed of the nucleotide sequence of SEQ ID NO: 1 and the oligonucleotide composed of the nucleotide sequence of SEQ ID NO: 2 according to the same manner as in Example 1, digestion of the resultant DNA fragment with the restriction enzymes NcoI and BglII and introducing the digested DNA fragment between NcoI restriction site and BamHI restriction site of plasmid pTV118N (manufactured by Takara Shuzo Co., Ltd.).

Plasmids pTVBCH and pTV118N respectively were introduced into *E. coli* BT3/pACYCSP strain prepared in Example 3 according to the method described in Hanahan, D. J., Mol. Biol., 166; p 557 (1983). The resultant *E. coli* were cultured in YPT medium containing 100 μg/ml ampicillin, 15 μg/ml chloramphenicol and 10 μg/ml kanamycin to obtain *E. coli* BT3/pACYCSP+pTVBCH strain bearing plasmids pACYCSP and pTVBCH, and *E. coli* BT3/pACYCSP+pTV118N strain bearing plasmids pACYCSP and pTV118N.

These strains were inoculated into YPT medium containing 10 or 1 ppm of the PPO inhibitory-type herbicidal compound represented by the above Structure 8, 100 μg/ml ampicillin, 15 μg/ml chloramphenicol, 10 μg/ml kanamycin, 10 μg/ml hemin and 50 μg/ml aminolevulinic acid, cultured under dark conditions or light conditions according to the same manner as in Example 2. Then, 18 hours after initiation of culture, the absorbance of the liquid culture medium was measured at 600 nm. By taking the absorbance of the medium without the herbicidal compound as 1, the relative value of the absorbance of the medium containing the herbicidal compound was calculated. The results are shown in Table 2.

TABLE 2

| E. coli strain | Culture conditions | Relative absorbance Concentration of test compound | | |
|---|---|---|---|---|
| | | 10 ppm | 1 ppm | 0 ppm |
| BT3/pACYCSP + pTVBCH | in the light | 0.80 | 0.77 | 1.0 |
| BT3/pACYCSP + pTVBCH | in the dark | 0.90 | 1.06 | 1.0 |
| BT3/pACYCSP + pTV118N | in the light | 0.18 | 0.31 | 1.0 |
| BT3/pACYCSP + pTV118N | in the dark | 0.68 | 0.77 | 1.0 |

Further, these strains were inoculated into YPT medium containing PPO inhibitory-type herbicidal compounds represented by the above Structures 1, 14, 15, 18–22, 29, 32, 33, 34 and 36, respectively, 100 μg/ml ampicillin, 15 μg/ml chloramphenicol, 10 μg/ml kanamycin, 10 μg/ml hemin and 50 μg/ml aminolevulinic acid, cultured under dark conditions or light conditions similar to the Example 2. Then, 18 hours after initiation of culture, the absorbance of liquid culture medium was measured at 600 nm. By taking the absorbance of the medium without the herbicidal compound as 1, the relative value of the absorbance of the medium containing the herbicidal compound was calculated. The results are shown in Table 3.

TABLE 3

| Test compound Structure No. | Test concentration | Relative absorbance | | | |
|---|---|---|---|---|---|
| | | BT3/ pACYCSP + pTVBCH | | BT3/ pACYCSP + pTV118N | |
| | | in the light | in the dark | in the light | in the dark |
| Structure 1 | 5.0 | 0.88 | 0.88 | 0.31 | 0.87 |
| Structure 14 | 10 | 0.47 | 0.93 | 0.12 | 0.81 |
| Structure 15 | 0.5 | 0.94 | 0.94 | 0.38 | 0.82 |
| Structure 18 | 2.0 | 0.68 | 1.0 | 0.33 | 0.91 |
| Structure 19 | 5.0 | 0.78 | 0.89 | 0.40 | 0.71 |
| Structure 20 | 5.0 | 0.57 | 0.88 | 0.11 | 0.75 |
| Structure 21 | 10 | 0.88 | 0.91 | 0.25 | 0.85 |
| Structure 22 | 10 | 0.55 | 0.93 | 0.29 | 0.94 |
| Structure 29 | 0.5 | 0.64 | 0.90 | 0.22 | 0.77 |
| Structure 32 | 2.0 | 0.70 | 0.94 | 0.37 | 0.87 |

TABLE 3-continued

| Test compound | Test concentration | BT3/ pACYCSP + pTVBCH in the light | BT3/ pACYCSP + pTVBCH in the dark | BT3/ pACYCSP + pTV118N in the light | BT3/ pACYCSP + pTV118N in the dark |
|---|---|---|---|---|---|
| Structure 33 | 2.0 | 0.81 | 0.92 | 0.41 | 0.91 |
| Structure 34 | 1.0 | 0.41 | 0.94 | 0.19 | 0.86 |
| Structure 36 | 0.5 | 0.55 | 0.95 | 0.28 | 0.96 |

EXAMPLE 5

Figure 4:
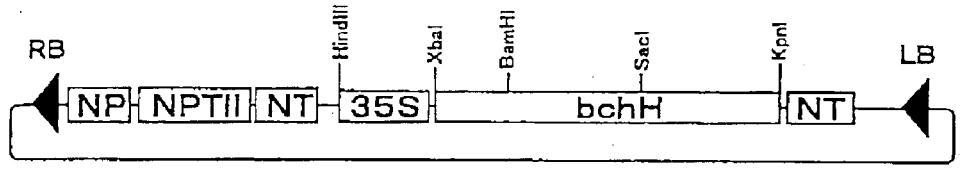
FIG. 4 is the restriction map of plasmid pBIBCH. bchH is magnesium chelatase protoporphyrin IX binding subunit gene of the photosynthetic bacterium *Rhodobacter sphaeroides*. NP is the promoter sequence of a nopaline synthase gene, NT is the terminator sequence of the nopaline synthase gene, and 35S is the 35S promoter of cauliflower mosaic virus. NPTII represents a kanamycin resistant gene, and RB and LB represent right and left border sequences of T-DNA, respectively.
Figure 5:
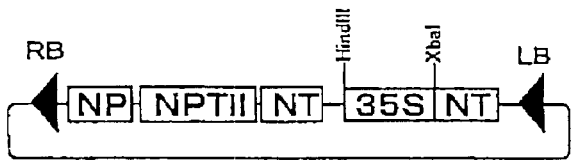
FIG. 5 is the restriction map of plasmid pNO. NP is the promoter sequence of a nopaline synthase gene, NT is the terminator sequence of the nopaline synthase gene, and 35S is the 35S promoter of cauliflower mosaic virus. NPTII represents a kanamycin resistant gene, and RB and LB represent right and left border sequences of T-DNA, respectively.

Introduction of Gene Encoding Protoporphyrin IX Binding Subunit Protein of Magnesium Chelatase into Tobacco A plasmid was constructed for introducing bchH gene into a plant by *Agrobacterium* infection method. First, binary vector pBI121 (manufactured by Clontech) was digested with restriction enzyme SacI, and KpnI linker (manufactured by Takara Shuzo Co., Ltd.) was inserted to prepare plasmid pBIK wherein SacI recognition site of pBI121 was removed and KpnI recognition site was added. On the other hand, according to the same manner as described in Example 1, PCR was carried out by using the genomic DNA of photosynthetic bacterium *Rhodobacter sphaeroides* as a template, and the oligonucleotide primer composed of the nucleotide sequence of SEQ ID NO: 7 and the oligonucleotide primer composed of the nucleotide sequence of SEQ ID NO: 8 to amplify the DNA fragment containing bchH gene. Then, the above plasmid pBIK was digested with restriction enzymes XbaI and KpnI to remove β-glucuronidase gene, and instead thereof, a DNA fragment which was obtained by digesting the above DNA fragment containing bchH gene with restriction enzymes XbaI and KpnI was inserted to produce plasmid pBIBCH (FIG. 4) in which bchH gene was joined downstream from 35S promoter. Binary vector pBI121 (manufactured by Clontech) was also digested with restriction enzymes BamHI and SacI to remove β-glucuronidase gene, the resultant DNA fragment was blunted by using T4 DNA polymerase, followed by self-cyclization with T4 DNA ligase to construct plasmid pNO (FIG. 5). The plasmid was used as a vector control of bchH expression plasmid pBIBCH.

The plasmid pBIBCH and pNO were introduced into *Agrobacterium tumefaciens* LBA4404, respectively. *Abrobacterium* strain bearing pBIBCH and that bearing pNO were isolated by culturing the resultant transformants in a medium containing 300 μg/ml streptomycin, 100 μg/ml rifampicin and 25 μg/ml kanamycin and selecting the desired transformants.

Then, according to the method described in Manual for Gene Manipulation of Plant (by Hirofumi UCHIMIYA, Kodan-sha Scientific, 1992), the gene was introduced into tobacco. *Agrobacterium* strain bearing plasmid pBIBCH was cultured at 28° C. overnight in LB medium and then leaf pieces of tobacco cultured sterilely were dipped in the liquid culture medium. The leaf pieces were cultured at room temperature for 2 days in Murashige-Skoog medium (MS-medium, described in Murasige T. and Skoog F., Physiol. Plant. (1962) 15, p 473) containing 0.8% agar, 0.1 mg/liter naphthalene acetic acid and 1.0 mg/liter benzyl aminopurine. Then, the leaf pieces were washed with sterilized water and cultured for 7 days on MS medium containing 0.8% agar, 0.1 mg/liter naphthalene acetic acid, 1.0 mg/liter benzyl aminopurine and 500 μg/ml cefotaxime. The leaf pieces were transplanted onto MS medium containing 0.8% agar, 0.1 mg/liter naphthalene acetic acid, 1.0 mg/liter benzyl aminopurine, 500 μg/ml cefotaxime and 100 μg/ml kanamycin (hereinafter referred to as selective MS medium) and cultured on the medium continuously for 4 months with transplanting the tobacco leaf pieces onto fresh selective MS medium every 1 month. During culture, stem-leaf differentiated shoots were appeared from the tobacco leaf pieces, these shoots were transplanted to MS medium containing 0.8% agar, 300 μg/ml cefotaxime and 50 μg/ml kanamycin to induce roots to obtain regenerated plants. The resultant regenerated plant was transplanted and cultured on MS medium 0.8% agar and 50 μg/ml kanamycin to obtain tobacco plant into which bchH gene was introduced. Similarly, tobacco leaf pieces were infected with *Agrobacterium* strain bearing pNO to obtain regenerated plant from the tobacco leaf pieces and tobacco plant (hereinafter referred to as control recombinant tobacco).

EXAMPLE 6

Test of Tobacco Bearing Introduced Gene Encoding Protoporphyrin IX Binding Subunit Protein of Magnesium Chelatase for Resistance to Herbicidal Compounds The tobacco leaves into which bchH gene was introduced and control recombinant tobacco leaves obtained in Example 5 were collected and each leaf was divided into the right and left equivalent pieces along the main vein, respectively. To one piece was applied an aqueous solution containing 0.3 ppm PPO inhibitory-type herbicidal compound of Structure 8, while, to the other piece was not applied the compound. These leaf pieces were placed on MS medium containing 0.8% agar and allowed to stand at room temperature for 7 days in light place. Then, each leaf piece was ground with pestle and mortar in 5 ml of 80% aqueous acetone solution to extract chlorophyll. The extract liquid was diluted with 80% aqueous acetone solution and the absorbance was measured at 750 nm, 663 nm and 645 nm to calculate total chlorophyll content according to the method described by Macknney G., J. Biol. Chem. (1941) 140, p 315. The results obtained from 4 clones of tobacco into which bchH gene was introduced (BCH1 to 4) and control recombinant tobacco is shown in Table 4. In the table, the resistant level to the herbicidal compound was represented by percentages of the total chlorophyll content of leaf pieces treated with herbicidal compound to that of untreated leaf pieces.

TABLE 4

| Recombinant tobacco | Total chlorophyll content (mg/ g-fresh weight) untreated-leaf | Total chlorophyll content (mg/ g-fresh weight) treated-leaf | Resistant level to test compound (%) |
|---|---|---|---|
| control | 2.49 | 0.19 | 7.63 |
| BCH-1 | 1.35 | 1.70 | 126 |
| BCH-2 | 2.06 | 2.14 | 104 |
| BCH-3 | 1.93 | 1.57 | 81.3 |
| BCH-4 | 1.51 | 1.06 | 70.2 |

The tobacco clone into which bchH gene was introduced and control recombinant tobacco were also treated in the same manner with the solution containing PPO inhibitory-type herbicidal compound represented by the above Structure 3, 7, 10, 11, 13, 17, 23, 24, 25, 27, 28, 30 or 35, and the resistant level to each herbicidal compound was measured. The results are shown in Table 5. In the table, the resistant levels to the herbicidal compound were represented by percentages of the total chlorophyll content of leaf pieces treated with the herbicidal compound to that of untreated leaf pieces.

TABLE 5

| Test compound Structure No. | Test concentration (ppm) | Resistant level to test compound (%) | |
|---|---|---|---|
| | | bchH recombinant tobacco | control recombinant tobacco |
| Structure 3 | 10 | 114 | 9.94 |
| Structure 7 | 30 | 89.3 | 8.62 |
| Structure 10 | 10 | 84.0 | 14.9 |
| Structure 11 | 0.30 | 78.1 | 5.51 |
| Structure 13 | 30 | 95.2 | 14.8 |
| Structure 17 | 0.30 | 80.4 | 14.3 |
| Structure 23 | 3.0 | 106 | 5.58 |
| Structure 24 | 10 | 129 | 5.18 |
| Structure 25 | 10 | 104 | 16.0 |
| Structure 27 | 10 | 86.8 | 16.8 |
| Structure 28 | 0.30 | 72.2 | 8.79 |
| Structure 30 | 3.0 | 102 | 4.24 |
| Structure 35 | 0.30 | 83.3 | 17.4 |

EXAMPLE 7

Figure 6:
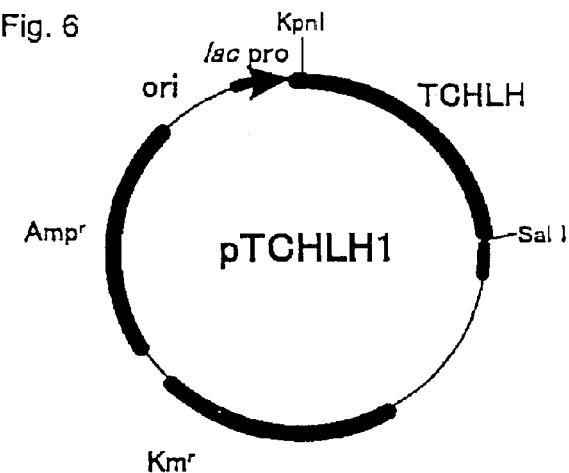
FIG. 6 is the restriction map of plasmid pTCHLH. TCHLH is protoporphyrin IX binding subunit gene of tobacco magnesium chelatase whose chloroplast transit signal has been deleted. lac pro represents the promoter sequence of a lactose operon. Amp$^r$ is an ampicillin resistant gene, Km$^r$ is a kanamycin resistant gene and ori is the replication origin.

Isolation of Gene Encoding Variant Protein of Protoporphyrin IX Binding Subunit Protein of Tobacco Magnesium Chelatase Total RNAs were prepared from leaf tissues of tobacco (*Nicotiana tabacum* cv. SR1) by using RNeasy Plant Kit (manufactured by QIAGEN) according to the manual attached thereto. The DNA fragment containing the gene encoding protoporphyrin IX binding subunit protein of tobacco magnesium chelatase whose chloroplast transit signal had been deleted (hereinafter referred to as the variant tobacco chelatase subunit) was obtained by using RNA LA PCR Kit (AMV) Ver 1.1 (manufactured by Takara Shuzo Co., Ltd.) according to the manual attached thereto. First, 1st strand cDNA was synthesized by using tobacco total RNAs as templates and Oligo dT-Adaptor Primer contained in the above kit as the primer with the reverse transcriptase contained in the above kit. Then, PCR was carried out by using the 1st strand cDNA as a template and LA Taq polymerase contained in the above kit to amplify the DNA fragment containing the gene encoding the variant tobacco chelatase subunit protein. In this PCR, oligonucleotide primer composed of the nucleotide sequence of SEQ ID NO: 9 and the oligonucleotide primer composed of the nucleotide sequence of SEQ ID NO: 10 were used. These oligonucleotides were synthesized by using a DNA synthesizer (PE Applied Biosystems; Model 394 DNA/RNA Synthesizer) and purified with an oligonucleotide purification cartridge (PE Applied Biosystems; OPC cartridge). The PCR was carried out by maintaining at 94° C. for 2 minutes and then repeating a cycle for maintaining at 94° C. for 30 seconds, at 50° C. for 30 seconds and then at 72° C. for 7 minutes 30 times. After the PCR, the DNA fragment amplified by the PCR was cloned into plasmid pCR2.1 by using TA Cloning Kit (manufactured by Invitrogen) according to the manual attached thereto. The resultant plasmid was digested with restriction enzyme KpnI and analyzed by agarose gel electrophoresis. The plasmid from which 8.0 kb DNA fragment was detected was named pTCHLH. The plasmid had the structure that the gene encoding the variant tobacco chelatase subunit has been inserted in the direction expressible under the control of lac promoter. Plasmid pTCHLH was digested with restriction enzyme KpnI followed by self-ligaiton to obtain plasmid pTCHLH1 (FIG. 6) in which DNA fragment composed of about 60 nucleotides had been deleted from plasmid pTCHLH.

EXAMPLE 8

Test of Variant Tobacco Magnesium Chelatase Subunit Protein for Capability of Giving Resistance to Herbicidal Compounds The plasmid pTCHLH1 and pCR2.1 prepared in Example 7 were introduced into *E. coli* BT3/pACYCSP strain prepared in Example 3, respectively according to the method described in Hanahan, D. J., Mol. Biol., 166; p 557 (1983). *E. coli* BT3/pACYCSP+pTCHLH1 strain bearing plasmids pACYCSP and pTCHLH1, and *E. coli* BT3/pACYCSP+pCR2.1 strain bearing plasmids pACYCSP and pCR2.1 were obtained by culturing the above strains in YPT medium containing 100 μg/ml ampicillin, 15 μg/ml chloramphenicol and 50 μg/ml kanamycin, respectively.

These *E. coli* strains were inoculated into YPT medium containing 10 or 1 ppm of the PPO inhibitory-type herbicidal compound represented by Structure 8, 100 μg/ml ampicillin, 15 μg/ml chloramphenicol, 50 μg/ml kanamycin, 10 μg/ml hemin and 50 μg/ml aminolevulinic acid, cultured under dark conditions or light conditions according to the same manner as in Example 2. Then, 18 hours after initiation of culture, the absorbance of the liquid culture medium was measured at 600 nm. By taking the absorbance of the medium without the herbicidal compound as 1, the relative value of the absorbance of the medium containing the herbicidal compound was calculated. The results are shown in Table 6.

TABLE 6

| E. coli strain | Culture conditions | Relative absorbance concentration of test compound | | |
|---|---|---|---|---|
| | | 10 ppm | 1 ppm | 0 ppm |
| BT3/pACYCSP + pTCHLH1 | in the light | 0.69 | 0.89 | 1.0 |
| BT3/pACYCSP + pTCHLH1 | in the dark | 0.92 | 0.93 | 1.0 |
| BT3/pACYCSP + pCR2.1 | in the light | 0.03 | 0.08 | 1.0 |
| BT3/pACYCSP + pCR2.1 | in the dark | 1.0 | 1.0 | 1.0 |

EXAMPLE 9

Figure 7:
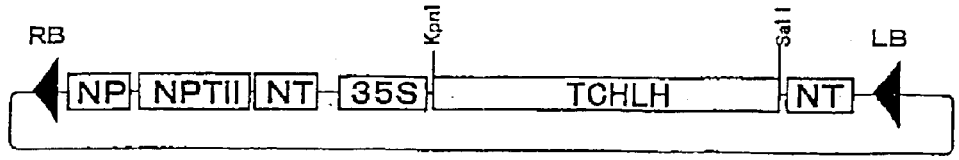
FIG. 7 is the restriction map of plasmid pBITCHLH. TCHLH is protoporphyrin IX binding subunit gene of tobacco magnesium chelatase whose chloroplast transit signal has been deleted. NP is the promoter sequence of a nopaline synthase, NT is the terminator sequence of the nopaline synthase and 35S is the 35S promoter of cauliflower mosaic virus. NPTII represents a kanamycin resistant gene, and RB and LB represent right and left border sequences of T-DNA, respectively.

Introduction of Gene Encoding Variant Tobacco Magnesium Chelatase Subunit Protein into Tobacco A plasmid for introducing the gene encoding a variant tobacco magnesium chelatase subunit protein into is tobacco by *Agrobacterium* infection method was constructed. First, the DNA fragment containing the gene encoding the variant tobacco magnesium chelatase subunit protein was prepared by digesting plasmid pTCHLH1 prepared in Example 7 with restriction enzymes KpnI and SalI. On the other hand, binary vector pBI121 (manufactured by Clonetech) was digested with restriction enzyme SmaI and KpnI linker (manufactured by Takara Shuzo Co., Ltd.) was inserted into this portion to prepare plasmid pBI121K in which SmaI recognition site of pBI121 was removed and KpnI recognition site was added. The plasmid pBI121K was digested with restriction enzyme SacI followed by blunting the DNA by adding nucleotides to the double-stranded DNA gap with DNA Polymerase I. Then, the DNA was dephosphorylated with alkaline phosphatase derived from calf intestine and cyclized by inserting phosphorylated SalI linker (4680P, manufactured by Takara Shuzo Co., Ltd.) to construct plasmid pBI121KS. The binary vector pBI121KS was digested with restriction enzymes KpnI and SalI to remove β-glucuronidase gene and the gene encoding the variant tobacco magnesium chelatase subunit protein was inserted into this portion to prepare plasmid pBITCHLH (FIG. 7).

The plasmid pBITCHLH was introduced into *Agrobacterium tumefaciens* LBA4404. The resultant transformants were cultured in a medium containing 300 μg/ml streptomycin, 100 μg/ml rifampicin and 25 μg/ml kanamycin, followed by selecting the desired transformants to isolate a *Agrobacterium* strain bearing pBITCHLH.

Leaf pieces of tobacco cultured sterilely are infected with the *Agrobacterium* strain and, according to the same manner as in Example 5, tobacco into which the gene encoding the variant tobacco magnesium chelatase subunit protein is introduced is obtained.

EXAMPLE 10

Confirmation of Resistance to Herbicidal Compounds of Tobacco Bearing Introduced Gene Encoding Variant Tobacco Magnesium Chelatase Subunit Protein The levels of resistance to herbicidal compounds are confirmed quantitatively by testing tobacco introduced with the gene encoding the variant tobacco magnesium chelatase subunit protein prepared in Example 9 according to the same manner as in Example 6.

EXAMPLE 11

Figure 8:
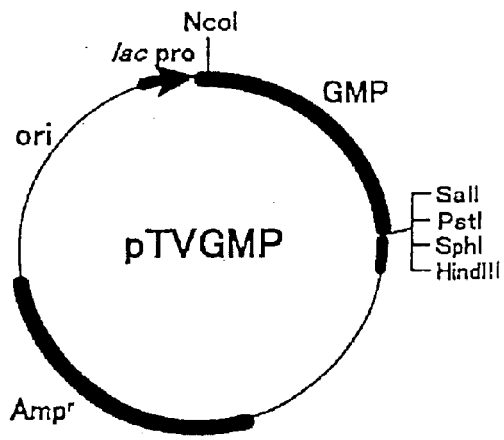
FIG. 8 is the restriction map of plasmid pTVGMP. GMP is soybean protoporphyrinogen IX oxidase gene whose chloroplast transit signal and FAD binding sequence have been deleted. lac pro represents the promoter sequence of a lactose operon. Amp$^r$ represents an ampicillin resistant gene and ori is the replication origin.

Isolation of Gene Encoding Variant Protein of Soybean PPO Having No Capability of Oxidizing Protoporphyrinogen IX and Having Specific Affinity for Protoporphyrinogen IX PCR was carried out by using plasmid pSPPO-P prepared in Example 3 as a template and an oligonucleotide composed of the nucleotide sequence of SEQ ID NO: 11 and an oligonucleotide composed of the nucleotide sequence of SEQ ID NO: 12 as primers to amplify the DNA fragment encoding soybean PPO whose chloroplast transit signal and FAD binding sequence had been deleted (hereinafter referred to as the variant soybean PPO). The oligonucleotides were prepared with a DNA synthesizer (PE Applied Biosystems; Model 394 DNA/RNA synthesizer) and purified with an oligonucleotide purification cartridge (PE Applied Biosystems; OPC cartridge). The PCR was carried out by repeating a cycle for maintaining at 94° C. for 1 minute, at 55° C. for 2 minutes and the 72° C. for 3 minutes 30 times. The amplified DNA fragments were digested with restriction enzymes NcoI and SalI, and introduced between NcoI restriction site and SalI restriction site of plasmid pTV118N (manufactured by Takara Shuzo Co., Ltd.) to construct plasmid pTVGMP (FIG. 8).

The plasmid pTVGMP was introduced into *E. coli* PPO gene deficient mutant BT3 strain according to the method described in Hanahan, D. J., Mol. Biol., 166; p 557 (1983). When the resultant *E. coli* were cultured in YPT medium containing 100 μg/ml ampicillin and 10 μg/ml kanamycin, no growth complemented clone was obtained.

EXAMPLE 12

Test for Effect of Giving Resistance to Herbicidal Compounds of Variant Soybean PPO Plasmids pTVGMP and pTV118N prepared in Example 11 were introduced into *E. coli* BT3/pACYCSP strain prepared in Example 3 respectively according to the method described in Hanahan, D. J., Mol. Biol., 166; p 557 (1983). *E. coli* BT3/pACYCSP+pTVGMP strain bearing plasmids pACYCSP and pTVGMP, and *E. coli* BT3/pACYCSP+pTV118N strain bearing plasmids pACYCSP and pTV118N were obtained by culturing the above strains in YPT medium containing 100 μg/ml ampicillin, 15 μg/ml chloramphenicol and 10 μg/ml kanamycin.

These *E. coli* strains were inoculated into YPT medium containing 10 or 1 ppm of PPO inhibitory-type herbicidal compound represented by Structure 8, 100 μg/ml ampicillin, 15 μg/ml chloramphenicol, 10 μg/ml kanamycin, 10 μg/ml hemin and 0.50 μg/ml aminolevulinic acid, cultured under dark conditions or light conditions according to the same manner as in Example 2. Then, 18 hours after initiation of culture, the absorbance of liquid culture medium was measured at 600 nm. By taking the absorbance of the medium without the herbicidal compound as 1, the relative value of the absorbance of the medium containing the herbicidal compound was calculated. The results are shown in Table 7.

TABLE 7

| | | Relative absorbance Concentration of test compound | | |
|---|---|---|---|---|
| *E. coli* strain | Culture conditions | 10 ppm | 1 ppm | 0 ppm |
| BT3/pACYCSP + pTVGMP | in the light | 0.33 | 0.85 | 1.0 |
| BT3/pACYCSP + pTVGMP | in the dark | 0.91 | 0.94 | 1.0 |
| BT3/pACYCSP + pTV118N | in the light | 0.05 | 0.09 | 1.0 |
| BT3/pACYCSP + pTV118N | in the dark | 0.89 | 0.91 | 1.0 |

EXAMPLE 13

Introduction of the Gene Encoding Variant Soybean PPO into Tobacco

Figure 9:
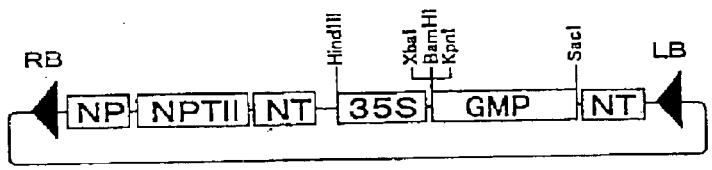
FIG. 9 is the restriction map of plasmid pBIGMP. GMP is soybean protoporphyrinogen oxidase gene whose chloroplast transit signal and FAD binding sequence have been deleted. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

A plasmid for introducing the gene encoding the variant soybean PPO into a plant by *Agrobacterium* infection method was constructed. PCR was carried out by using the plasmid pSPPO-P prepared in Example 3 as a template, an oligonucleotide primer composed of the nucleotide sequence of SEQ ID NO: 13 and an oligonucleotide primer composed of the nucleotide sequence of SEQ ID NO: 14 to amplify the DNA fragment containing the gene encoding the variant soybean PPO. Then, plasmid pBI121K prepared in Example 9 was digested with the restriction enzymes KpnI and SacI to remove β-glucuronidase gene, and the DNA fragment which was obtained by digesting the DNA fragment containing the above gene encoding the variant soybean PPO with restriction enzymes KpnI and Sac I was inserted into this portion to prepare plasmid pBIGMP (FIG. 9) in which the gene was joined downstream from 35S promoter.

The plasmid pBIGMP was introduced into *Agrobacterium tumefaciens* LBA4404. The resultant transformants were cultured in a medium containing 300 μg/ml streptomycin, 100 μg/ml rifampicin and 25 μg/ml kanamycin, followed by selecting the desired transformants to isolate *Agrobacterium* strain bearing pBIGMP.

Leaf pieces of tobacco cultured sterilely were infected with the *Agrobacterium* strain and, according to the same manner as in Example 5, tobacco into which the gene encoding the variant soybean PPO was introduced was obtained.

EXAMPLE 14

Confirmation of Resistance to Herbicidal Compounds of Tobacco Bearing Introduced Gene Encoding Variant Soybean PPO The level of resistance to PPO inhibitory type herbicidal compound represented by Structure 8 was confirmed quantitatively by testing tobacco into which the gene encoding the variant soybean PPO prepared in Example 13 was introduced according to the same manner as in Example 6. The results obtained from 4 clones (GMP 1–4) of tobacco introduced with the gene encoding the variant soybean PPO and control recombinant tobacco are shown in Table 8. In the table, the resistant level to herbicidal compound is represented by percentage of the total chlorophyll content of leaf pieces treated with the herbicidal compound to that of untreated leaf pieces.

TABLE 8

| Recombinant tobacco | Total chlorophyll content (mg/ g-fresh weight) untreated-leaf | treated-leaf | Resistant level to test compound (%) |
|---|---|---|---|
| control | 3.49 | 0.35 | 10.0 |
| GMP-1 | 1.89 | 2.55 | 135 |
| GMP-2 | 0.89 | 0.96 | 108 |
| GMP-3 | 1.50 | 1.49 | 99.3 |
| GMP-4 | 2.91 | 2.34 | 80.4 |

EXAMPLE 15

Isolation of PPO Gene of Chlamydomonas

*Chlamydomonas reinhardtii* CC407 strain was obtained from *Chlamydomonas* Genetics Center (address: DCMB Group, Department of Botany, Box 91000, Duke University, Durham, N.C. 27708-1000, USA), cultured under 200 $\mu E/m^2/s$ photosynthesis active light for 5 days in TAP liquid culture medium (E. H. Harris, The *Chlamydomonas* Sourcebook, Academic Press, San Diego, 1989, p 576–577) containing 7 mM $NH_4Cl$, 0.4 mM $MgSO_4.7H_2O$, 0.34 mM $CaCl_2.2H_2O$, 25 mM potassium phosphate, 0.5 mM Tris (pH 7.5), 1 ml/liter Hatner miner element and 1 ml/liter glacial acetic acid to obtain 200 ml ($1.0 \times 10^6$ cells/ml) liquid culture medium containing early stationary growth phase cells.

Total RNAs were prepared from these cells by using ISOGEN (manufactured by Nippon Gene) according to the manual attached thereto. Also, poly(A)RNA was fractionated using BioMag mRNA Purification Kit (manufactured by Perceptive Bio System) according to the manual attached thereto. cDNA was synthesized from the resultant poly(A) RNA by using Marathon cDNA Amplification Kit (manufactured by Clontech) according to the manual attached thereto and the cDNA was used as a template for PCR.

As PCR primers, an oligonucleotide composed of the nucleotide sequence of SEQ ID NO: 15 and an oligonucleotide composed of the nucleotide sequence of SEQ ID NO: 16 were prepared. The oligonucleotides were prepared with a DNA synthesizer (PE Applied Biosystems; Model 394 DNA/RNA synthesizer) and purified with an oligonucleotide purification cartridge (PE Applied Biosystems; OPC cartridge).

PCR was carried out by preparing a reaction liquid using Advantage cDNA PCR kit (manufactured by Clontech) according to the manual attached thereto, and then, after maintaining at 94° C. for 1 minute and then at 65° C. for 5 minutes, repeating a cycle for maintaining at 94° C. for 15 seconds and the 65° C. for 5 minutes 29 times. After the PCR, the amplified DNA fragments were purified by filtering the reaction liquid with MicroSpin S-400HR (manufactured by Pharmacia Biotech), and the DNA fragment was cloned into plasmid pCR2.1 by using TA Cloning Kit (manufactured by Invitrogen) according to the manual attached thereto to construct plasmid pCPPO.

The nucleotide sequence of DNA fragment contained in the resultant plasmid pCPPO was determined by using Dye terminator cycle sequencing kit (manufactured by PE applied Biosystems) and DNA sequencer 373S (manufactured by PE applied Biosystems). As a result, the nucleotide sequence of SEQ ID NO: 17 was revealed, thereby confirming that plasmid pCPPO contained the full length PPO cDNA of *Chlamydomonas reinhardtii*.

EXAMPLE 16

Figure 10:
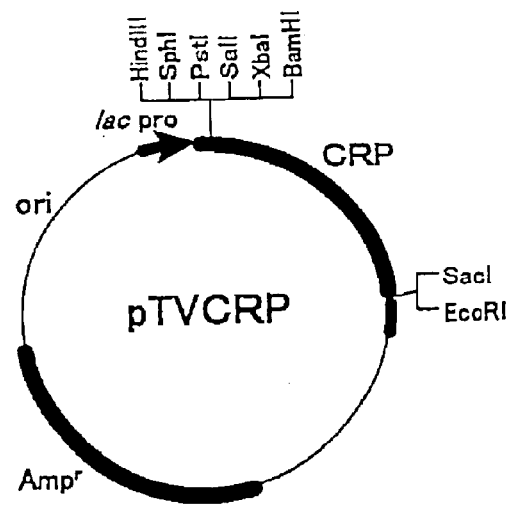
FIG. 10 is the restriction map of plasmid pTVCRP. CRP is protoporphyrinogen oxidase gene of *Chlamydomonas reinhardtii* whose chloroplast transit signal and FAD binding sequence have been deleted. lac pro represents the promoter sequence of a lactose operon. Amp$^r$ is an ampicillin resistant gene and ori is the replication origin.

Isolation of Gene Encoding Variant Protein of *Chlamydomonas reinhardtii* PPO Having No Capability of Oxidizing Protoporphyrinogen IX and Specific Affinity for Protoporphyrinogen IX PCR was carried out by using plasmid pCPPO prepared in Example 15 as a template, and an oligonucleotide composed of the nucleotide sequence of SEQ ID NO: 19 and an oligonucleotide composed of the nucleotide SEQ ID NO: 20 as primers to amplify the DNA fragment encoding *Chlamydomonas reinhardtii* PPO whose chloroplast transit signal and FAD binding sequence had been deleted (hereinafter referred to as the variant *Chlamydomonas reinhardtii* PPO). The oligonucleotides were prepared with a DNA synthesizer (PE Applied Biosystems; Model 394 DNA/RNA synthesizer) and purified with an oligonucleotide purification cartridge (PE Applied Biosystems; OPC cartridge). The PCR was carried out by repeating a cycle for maintaining at 94° C. for 1 minute, at 55° C. for 2 minutes and then at 72° C. for 3 minutes 30 times. The amplified DNA fragment was digested with restriction enzymes BamHI and SacI, and inserted between BamHI restriction site and SacI restriction site of plasmid pTV119N (manufactured by Takara Shuzo Co., Ltd.) to construct plasmid pTVCRP (FIG. 10).

The plasmid pTVCRP was introduced into *E. coli* PPO gene deficient mutant BT3 strain according to the method described in Hanahan, D. J., Mol. Biol., 166; p 557 (1983). When the resultant *E. coli* were cultured in YPT medium containing 100 µg/ml ampicillin and 10 µg/ml kanamycin, no growth complemented clone was obtained.

EXAMPLE 17

Test of Variant Modified *Chlamydomonas reinhardtii* PPO for Capability of Giving Resistance to Herbicidal Compounds Plasmids pTVCRP and pTV118N prepared in Example 16 were introduced into *E. coli* BT3/pACYCSP strain prepared in Example 3 respectively according to the method described in Hanahan, D. J., Mol. Biol., 166; p 557 (1983). *E. coli* BT3/pACYCSP+pTVCRP strain bearing plasmids pACYCSP and pTVCRP, and *E. coli* BT3/pACYCSP+ pTV118N strain bearing plasmids pACYCSP and pTV118N were obtained by culturing the above strains in YPT medium containing 100 µg/ml ampicillin, 15 µg/ml chloramphenicol and 10 µg/ml kanamycin.

These *E. coli* strains were inoculated into YPT medium containing 10 or 1 ppm of the PPO inhibitory-type herbicidal compound represented by Structure 8, 100 μg/ml ampicillin, 15 μg/ml chloramphenicol, 10 μg/ml kanamycin, 10 μg/ml hemin and 50 μg/ml aminolevulinic acid, cultured under dark conditions or light conditions in the same manner as in Example 2. Then, 18 hours after initiation of culture, the absorbance of liquid culture medium was measured at 600 nm. By taking the absorbance of the medium containing no herbicidal compound as 1, the relative value of the absorbance of the medium containing the herbicidal compound was calculated. The results are shown in Table 9.

TABLE 9

| E. coli strain | Culture conditions | Relative absorbance Concentration of test compound | | |
|---|---|---|---|---|
| | | 10 ppm | 1 ppm | 0 ppm |
| BT3/pACYCSP + pTVCRP | in the light | 0.23 | 0.42 | 1.0 |
| BT3/pACYCSP + pTVCRP | in the dark | 0.81 | 0.82 | 1.0 |
| BT3/pACYCSP + pTV118N | in the light | 0.12 | 0.24 | 1.0 |
| BT3/pACYCSP + pTV118N | in the dark | 0.80 | 0.91 | 1.0 |

EXAMPLE 18

Figure 11:
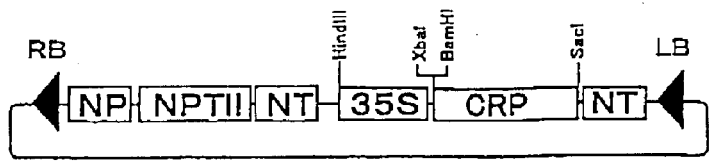
FIG. 11 is the restriction map of plasmid, pBICRP. CRP is protoporphyrinogen oxidase gene of *Chlamydomonas reinhardtii* whose chloroplast transit signal and FAD binding sequence have been deleted. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Introduction of Gene Encoding Variant *Chlamydomonas reinhardtii* PPO into Tobacco A plasmid for introducing the gene encoding the variant *Chlamydomonas reinhardtii* PPO into a plant by *Agrobacterium* infection method was constructed. The DNA fragment containing the gene encoding the variant *Chlamydomonas reinhardtii* PPO was prepared by digesting plasmid pTVCRP prepared in Example 16 with restriction enzymes BamHI and SacI. Binary vector pBI121 (manufactured by Clontech) was digested with restriction enzymes BamHI and SacI to remove β-glucuronidase gene and the above gene encoding the variant *Chlamydomonas reinhardtii* PPO was inserted into this portion to prepare plasmid pBICRP (FIG. 11).

The plasmid pBICRP was introduced into *Agrobacterium tumefaciens* LBA4404. The resultant transformants were cultured in a medium containing 300 μg/ml streptomycin, 100 μg/ml rifampicin and 25 μg/ml kanamycin, followed by selecting the desired transformants to isolate *Agrobacterium* strain bearing pBICRP.

Leaf pieces of tobacco cultured sterilely were infected with the *Agrobacterium* strain and, according to the same manner as in Example 5, tobacco into which the gene encoding the variant *Chlamydomonas reinhardtii* PPO was introduced was obtained.

EXAMPLE 19

Confirmation of Resistance to Herbicidal Compounds of Tobacco Bearing Introduced Gene Encoding Variant *Chlamydomonas reinhardtii* PPO The level of resistance to the PPO-inhibitory type herbicidal compound represented by Structure 8 was confirmed quantitatively by testing tobacco into which the gene encoding the variant *Chlamydomonas reinhardtii* PPO prepared in Example 18 was introduced according to the same manner as in Example 6. The results obtained from 4 clones (CRP 1–4) of tobacco into which the gene encoding the variant *Chlamydomonas reinhardtii* PPO was introduced and control recombinant tobacco is shown in Table 10. In the table, the resistant levels to the herbicidal compound are represented by percentages of the total chlorophyll content of leaf pieces treated with the herbicidal compound to that of untreated leaf pieces.

TABLE 10

| Recombinant tobacco | Total chlorophyll content (mg/ g-fresh weight) | | Resistant level to test compound (%) |
|---|---|---|---|
| | untreated-leaf | treated-leaf | |
| control | 2.28 | 0.42 | 18.4 |
| CRP-1 | 1.27 | 1.54 | 121 |
| CRP-2 | 1.50 | 1.67 | 111 |
| CRP-3 | 1.10 | 1.11 | 101 |
| CRP-4 | 1.58 | 1.57 | 99.4 |

EXAMPLE 20

Figures 12, 13, 14, 15:
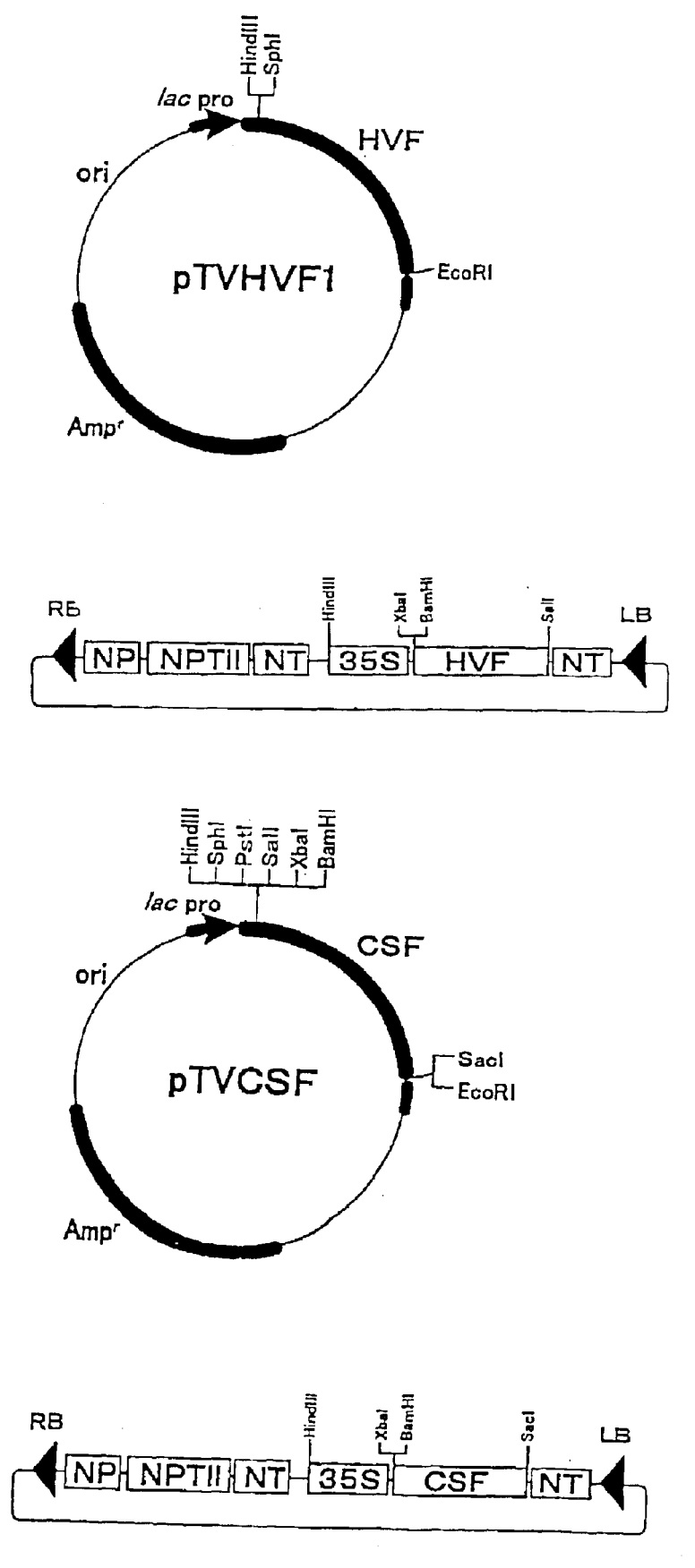

Test of Variant Protein of Barley Ferrochelatase Having Affinity for Protoporphyrin IX Specifically for Capability of Giving Resistance to Herbicidal Compounds A plasmid bearing barley ferrochelatase gene was prepared by the method described in Miyamoto, K. et al., Plant Physiol. 105; p 769 (1994). The resultant plasmid was digested with restriction enzymes NspI and EcoRI to obtain the DNA fragment containing the gene encoding barley ferrochelatase whose signal sequence had been deleted (hereinafter referred to as the variant barley ferrochelatase). This DNA fragment was inserted between SphI restriction site and EcoRI restriction site of plasmid pTV119N (manufactured by Takara Shuzo Co., Ltd.) to construct plasmid pTVHVF1 (FIG. 12).

The plasmids pTVHVF1 and pTV118N were introduced into *E. coli* BT3/pACYCSP strains prepared in Example 3 respectively according to the method described in Hanahan, D. J., Mol. Biol., 166; p 557 (1983). *E. coli* BT3/pACYCSP+pTVHVF1 strain bearing plasmid pACYCSP and pTVHVF1, and *E. coli* BT3/pACYCSP+pTV118N strain bearing plasmid pACYCSP and pTV118N were obtained by culturing the above strains in YPT medium containing 100 μg/ml ampicillin, 15 μg/ml chloramphenicol and 10 μg/ml kanamycin.

These *E. coli* strains were inoculated into YPT medium containing 10 or 1 ppm of the PPO inhibitory-type herbicidal compound represented by Structure 8, 100 μg/ml ampicillin, 15 μg/ml chloramphenicol, 10 μg/ml kanamycin, 10 μg/ml hemin and 50 μg/ml aminolevulinic acid, cultured under dark conditions or light conditions according to the same manner as in Example 2. Then, 18 hours after initiation of culture, the absorbance of liquid culture medium was measured at 600 nm. By taking the absorbance of the medium without the herbicidal compound as 1, the relative value of the absorbance of the medium containing the herbicidal compound was calculated. The results are shown in Table 11.

TABLE 11

| E. coli strain | Culture conditions | Relative absorbance Concentration of test compound | | |
|---|---|---|---|---|
| | | 10 ppm | 1 ppm | 0 ppm |
| BT3/pACYCSP + pTVHVF1 | in the light | 0.39 | 0.94 | 1.0 |
| BT3/pACYCSP + pTVHVF1 | in the dark | 0.94 | 0.96 | 1.0 |

TABLE 11-continued

| | | Relative absorbance Concentration of test compound | | |
|---|---|---|---|---|
| E. coli strain | Culture conditions | 10 ppm | 1 ppm | 0 ppm |
| BT3/pACYCSP + pTV118N | in the light | 0.12 | 0.24 | 1.0 |
| BT3/pACYCSP + pTV118N | in the dark | 0.80 | 0.91 | 1.0 |

EXAMPLE 21

Introduction of the Gene Encoding Variant Barley Ferrochelatase into Tobacco

A plasmid for introducing the gene encoding barley ferrochelatase into tobacco by *Agrobacterium* infection method was constructed. The plasmid pTVHVF1 described in Example 20 was digested with restriction enzyme Nco I followed by blunting the DNA with DNA polymerase I by adding nucleotides to the double-stranded DNA gap. Then, the DNA was dephosphorylated with alkaline phosphatase derived from calf intestine and cyclized by inserting phosphorylated BamHI linker (4610P, manufactured by Takara Shuzo Co., Ltd.) to construct plasmid pTVHVF2. Then, pTVHVF2 was digested with restriction enzyme EcoRI followed by blunting of the DNA with DNA polymerase I by adding nucleotides to the double-stranded DNA gap. Further, the DNA was dephosphorylated with alkaline phosphatase derived from calf intestine and cyclized by inserting phosphorylated SalI linker (4680P, manufactured by Takara Shuzo Co., Ltd.) to construct plasmid pTVHVF3. Plasmid pBI121KS prepared in Example 9 was digested with restriction enzymes BamHI and SalI to remove β-glucuronidase gene. The DNA fragment containing the gene encoding the variant barley ferrochelatase was prepared by digesting the above pTVHVF3 with restriction enzymes BamHI and SalI. The resultant DNA fragment was inserted into plasmid pBI121KS with replacing β-glucuronidase gene to prepare plasmid pBIHVF (FIG. 13) in which variant barley gene joined downstream from 35S promoter.

The plasmid pBIHVF was introduced into *Agrobacterium tumefaciens* LBA4404. The resultant transformants were cultured in a medium containing 300 μg/ml streptomycin, 100 μg/ml rifampicin and 25 μg/ml kanamycin, followed by selecting the desired transformants to isolate *Agrobacterium* strain bearing pBIHVF.

Leaf pieces of tobacco cultured sterilely were infected with said *Agrobacterium* strain and, according to the same manner as in Example 5, tobacco into which the gene encoding the variant barley ferrochelatase was introduced was obtained.

EXAMPLE 22

Confirmation of Resistance to Herbicidal Compounds of Tobacco Bearing Introduced Gene Encoding Variant Barley Ferrochelatase The level of resistance to the PPO inhibitory-type herbicidal compound represented by Structure 8 was confirmed quantitatively by testing tobacco into which the gene encoding the variant barley ferrochelatase prepared in Example 21 was introduced according to the same manner as in Example 6. The results obtained from 4 clones (HVF 1–4) of tobacco introduced with the gene encoding the variant barley ferrochelatase and control recombinant tobacco are shown in table 12. In the table, the resistant levels to the herbicidal compound are represented by percentages of the total chlorophyll content of leaf pieces treated with herbicidal compound to that of untreated leaf pieces.

TABLE 12

| Recombinant tobacco | Total chlorophyll content (mg/ g-fresh weight) | | Resistant level to test compound (%) |
|---|---|---|---|
| | untreated-leaf | treated-leaf | |
| control | 1.93 | 0.160 | 8.29 |
| HVF-1 | 0.876 | 0.930 | 106 |
| HVF-2 | 1.14 | 1.16 | 102 |
| HVF-3 | 1.06 | 1.04 | 98.1 |
| HVF-4 | 1.48 | 1.42 | 95.9 |

EXAMPLE 23

Test of Variant Protein of Cucumber Ferrochelatase Having Specific Affinity for Protoporphyrin IX for Capability of Giving Resistance to Herbicidal Compounds PCR was carried out by using cucumber ferrochelatase cDNA clone isolated by the method described in Miyamoto, K. et al., Plant Physiol., 105; p 769 (1994) as a template, an oligonucleotide composed of the nucleotide sequence of SEQ ID NO: 21 and an oligonucleotide composed of the nucleotide sequence of SEQ ID NO: 22 as primers to amplify the DNA fragment encoding cucumber ferrochelatase whose signal sequence had been deleted (hereinafter referred to as the variant cucumber ferrochelatase). The oligonucleotides were prepared with a DNA synthesizer (PE Applied Biosystems; Model 394 DNA/RNA synthesizer) and purified with an oligonucleotides purification cartridge (PE Applied Biosystems; OPC cartridge). The PCR was carried out by repeating a cycle for maintaining at 94° C. for 1 minute, at 55° C. for 2 minutes and then at 72° C. for 3 minutes 30 times. The amplified DNA fragments were digested with restriction enzymes BamHI and SacI, and inserted between BamHI restriction site and SacI restriction site of plasmid pTV119N (manufactured by Takara Shuzo Co., Ltd.) to construct pTVCSF (FIG. 14).

The plasmids pTVCSF and pTV118N were introduced into *E. coli* BT3/pACYCSP strain prepared in Example 3 respectively according to the method described in Hanahan, D. J., Mol. Biol., 166; p 557 (1983). *E. coli* BT3/pACYCSP+pTVCSF strain bearing plasmid pACYCSP and pTVCSF, and *E. coli* BT3/pACYCSP+pTV118N strain bearing plasmid pACYCSP and pTV118N were obtained by culturing the above strains in YPT medium containing 100 μg/ml ampicillin, 15 μg/ml chloramphenicol and 10 μg/ml kanamycin.

These *E. coli* strains were inoculated into YPT medium containing 10 or 1 ppm of the PPO inhibitory-type herbicidal compound represented by Structure 8, 100 μg/ml ampicillin, 15 μg/ml chloramphenicol, 10 μg/ml kanamycin, 10 μg/ml hemin and 50 μg/ml aminolevulinic acid, cultured under dark conditions or light conditions according to the same manner as in Example 2. Then, 18 hours after initiation of culture, the absorbance of liquid culture medium was measured at 600 nm. By taking the absorbance of the medium without the herbicidal compound as 1, the relative value of the absorbance of the medium containing the herbicidal compound was calculated. The results are shown in Table 13.

TABLE 13

| E. coli strain | Culture conditions | Relative absorbance Concentration of test compound | | |
|---|---|---|---|---|
| | | 10 ppm | 1 ppm | 0 ppm |
| BT3/pACYCSP + pTVCSF | in the light | 0.73 | 0.78 | 1.0 |
| BT3/pACYCSP + pTVCSF | in the dark | 0.89 | 0.92 | 1.0 |
| BT3/pACYCSP + pTV118N | in the light | 0.06 | 0.08 | 1.0 |
| BT3/pACYCSP + pTV118N | in the dark | 0.81 | 0.91 | 1.0 |

EXAMPLE 24

Introduction of the Gene Encoding Variant Cucumber Ferrochelatase into Tobacco

A plasmid for introducing the gene encoding the modified cucumber ferrochelatase into tobacco by *Agrobacterium* infection method was constructed. Plasmid pBI121 (manufactured by Colntech) was digested with restriction enzymes BamHI and SacI to remove β-glucuronidase gene. A DNA fragment containing the gene encoding the variant cucumber ferrochelatase was prepared by digesting plasmid pTVCSF described in Example 23 with restriction enzymes BamHI and SacI. The resultant DNA fragment was introduced into plasmid pBI121 with replacing β-glucuronidase gene to prepare plasmid pBICSF (FIG. 15) in which variant cucumber ferrochelatase gene was joined downstream from 35S promoter.

The plasmid pBICSF was introduced into *Agrobacterium tumefaciens* LBA4404. The resultant transformants were cultured in a medium containing 300 μg/ml streptomycin, 100 μg/ml rifampicin and 25 μg/ml kanamycin, followed by selecting the desired transformants to isolate *Agrobacterium* strain bearing pBICSF.

Leaf pieces of tobacco cultured sterilely were infected with said *Agrobacterium* strain to obtain tobacco introduced with the gene encoding the modified cucumber ferrochelatase according to the same manner as in Example 5.

EXAMPLE 25

Confirmation of Resistance to Herbicidal Compounds of Tobacco Bearing Introduced Gene Encoding Variant Cucumber Ferrochelatase The level of resistance to PPO inhibitory-type herbicidal compounds is confirmed quantitatively by testing tobacco introduced with the gene encoding the modified cucumber ferrochelatase prepared in Example 24 according to the same manner as in Example 6.

EXAMPLE 26

Isolation of *E. coli* Coproporphyrinogen III Oxidase (hemF) Gene

Genomic DNA was prepared from *E. coli* LE392 strain using Kit ISOPLANT for genome DNA preparation (manufactured by Nippon Gene). An oligonucleotide primer composed of the nucleotide sequence of SEQ ID NO: 23 and an oligonucleotide primer composed of the nucleotide sequence of SEQ ID NO: 24 were synthesized according to nucleotide sequences of its 5' and 3' regions of *E. coli* hemF gene registered in GenBank (Accession X75413). The oligonucleotides were prepared with a DNA synthesizer (PE Applied Biosystems; Model 394 DNA/RNA synthesizer) and purified with an oligonucleotides purification cartridge (PE Applied Biosystems; OPC cartridge). PCR was carried out by using about 1 μg of *E. coli* LE392 strain genomic DNA as a template and the above oligonucleotides (each 10 pmol) as primers to amplify the DNA fragment containing *E. coli* hemF gene. The PCR was carried out by repeating a cycle for maintaining at 96° C. for 1 minute, at 55° C. for 2 minutes and then at 72° C. for 3 minutes 30 times.

EXAMPLE 27

Figure 16:
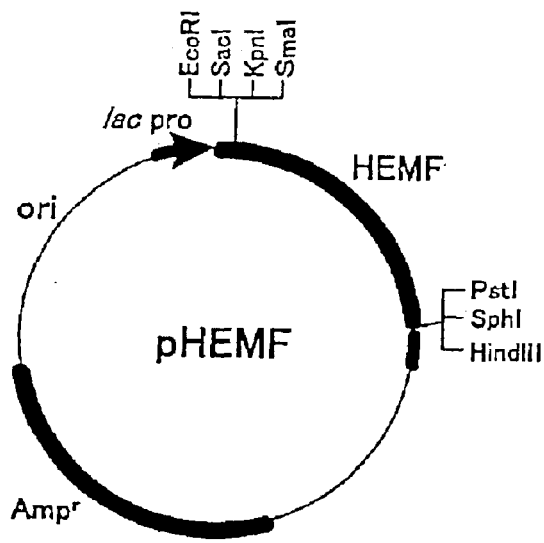
FIG. 16 is the restriction map of plasmid pHEMF. HEMF is coproporphyrinogen III oxidase gene (hemF) of *Escherichia coli*. lac pro is the promoter sequence of a lactose operon. $Amp^r$ is an ampicillin resistant gene, and ori is the replication origin.

Test of *E. coli* hemF Protein for Capability of Giving Resistance to Herbicidal Compounds The DNA fragment containing hemF gene amplified by the method described in Example 26 was digested with restriction enzymes FbaI and PstI, and inserted between BamHI restriction site and PstI restriction site of commercially available plasmid pUC118N (manufactured by Takara Shuzo Co., Ltd.) to construct plasmid pHEMF (FIG. 16).

The plasmid pHEMF and pTV118N were introduced into *E. coli* BT3/pACYCSP strain prepared in Example 3 respectively according to the method described in Hanahan, D. J., Mol. Biol., 166; p 557 (1983). *E. coli* BT3/pACYCSP+pHEMF strain bearing plasmid pACYCSP and pHEMF, and *E. coli* BT3/pACYCSP+pTV118N strain bearing plasmid pACYCSP and pTV118N were obtained by culturing the above strains in YPT medium containing 100 μg/ml ampicillin, 15 μg/ml chloramphenicol and 10 μg/ml kanamycin.

These *E. coli* strains were inoculated into YPT medium containing 10 or 1 ppm of the PPO inhibitory-type herbicidal compound represented by Structure 8, 100 μg/ml ampicillin, 15 μg/ml chloramphenicol, 10 μg/ml kanamycin, 10 μg/ml hemin and 50 μg/ml aminolevulinic acid, cultured under dark conditions or light conditions according to the same manner as in Example 2. Then, 18 hours after initiation of culture, the absorbance of liquid culture medium was measured at 600 nm. By taking the absorbance of the medium without the herbicidal compound as 1, the relative value of the absorbance of the medium containing the herbicidal compound was calculated. The results are shown in Table 14.

TABLE 14

| E. coli strain | Culture conditions | Relative absorbance Concentration of test compound | | |
|---|---|---|---|---|
| | | 10 ppm | 1 ppm | 0 ppm |
| BT3/pACYCSP + pHEMF | in the light | 0.48 | 1.0 | 1.0 |
| BT3/pACYCSP + pHEMF | in the dark | 0.94 | 0.95 | 1.0 |
| BT3/pACYCSP + pTV118N | in the light | 0.06 | 0.16 | 1.0 |
| BT3/pACYCSP + pTV118N | in the dark | 0.96 | 0.98 | 1.0 |

EXAMPLE 28

Introduction of *E. coli* hemF Gene into Tobacco

A plasmid for introducing *E. coli* hemF gene into a plant by *Agrobacterium* infection method was constructed. First, for obtaining *E. coli* hemF gene, an oligonucleotide primer composed of the nucleotide sequence of SEQ ID NO: 25 and an oligonucleotide primer composed of the nucleotide sequence of SEQ ID NO: 26 were synthesized with a DNA synthesizer (PE Applied Biosystems; Model 394 DNA/RNA synthesizer) and purified with an oligonucleotide purification cartridge (PE Applied Biosystems; OPC cartridge). PCR was carried out by using the oligonucleotide primers according to the same manner as in Example 26 to amplify the DNA fragment containing *E. coli* hemF gene.

Figure 17:
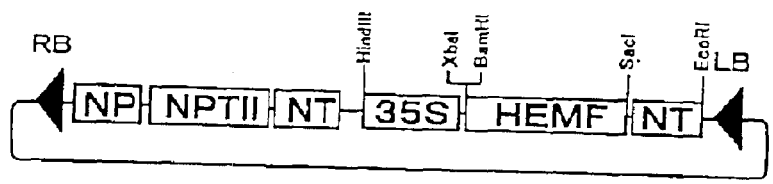
FIG. 17 is the restriction map of plasmid pBIHEMF. HEMF is coproporphyrinogen III oxidase gene (hemF) of *Escherichia coli*. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Plasmid pBI121 (manufactured by Clontech) was digested with restriction enzymes BamHI and SacI to remove β-glucuronidase gene. The DNA fragment containing the gene encoding the *E. coli* hemF gene was prepared by digesting the above PCR-amplified DNA fragment with restriction enzymes BamHI and SacI. The resultant DNA fragment was introduced into plasmid pBI121 with replacing β-glucuronidase gene to prepare plasmid pBIHEMF (FIG. 17) in which *E. coli* hemF gene was joined downstream from 35S promoter.

The plasmid pBIHEMF was introduced into *Agrobacterium tumefaciens* LBA4404. The resultant transformants were cultured in a medium containing 300 µg/ml streptomycin, 100 µg/ml rifampicin and 25 µg/ml kanamycin, followed by selecting the desired transformants to isolate *Agrobacterium* strain bearing pBIHEMF.

Leaf pieces of tobacco cultured sterilely were infected with the *Agrobacterium* strain to obtain tobacco introduced with *E. coli* hemF gene according to the same manner as in Example 5.

EXAMPLE 29

Confirmation of Resistance to Herbicidal Compounds of Tobacco Introduced with the *E. coli* hemF Gene The level of resistance to the PPO inhibitory-type herbicidal compounds is confirmed quantitatively by testing tobacco introduced with the *E. coli* hemF gene (prepared in Example 28) according to the same manner as in Example 6.

EXAMPLE 30

Binding Test of Porphyrin Compound-Binding Protein to Protoporphyrin IX

A phage library presenting a protein containing an amino acid sequence composed of 5 random amino acids and a phage clone displaying a protein containing an amino acid sequence HASYS or RASSL (wherein H is histidine, A is alanine, S is serine, Y is tyrosine, R is arginine and L is leucine) which can specifically bind to porphyrin compound 5, 10, 15, 20-tetrakis(N-methylpyridinium-4-yl)-21H, 23H-porphine ($H_2TMpyP$) were prepared according to the method described in KITANO et al., Nihon Kagakukai (Chemical Society of Japan) 74th Spring Annual Meeting Pre-Published Abstracts of Presentation II, p 1353, 4G511 (1998).

First, the phage library displaying a protein containing an amino acid sequence composed of 5 random amino acids was constructed. Mixed oligonucleotides composed of the nucleotide sequence of SEQ ID NO: 27 and mixed oligonucleotides composed of the nucleotide sequence of SEQ ID NO: 28 were synthesized. The mixed oligonucleotides were synthesized with a DNA synthesizer (PE Applied Biosystems; Model 394 DNA/RNA synthesizer) and purified with an oligonucleotide purification cartridge (PE Applied Biosystems; OPC cartridge). The above mixed oligonucleotides (each 50 pmol) were phosphorylated at 5' end by treating with T4 DNA kinase respectively. They were mixed and, after heating at 70° C. for 10 minutes, subjected to annealing by cooling slowly to room temperature at rate of 0.5° C./minute. Plasmid pCANTAB5E (manufactured by Pharmacia Biotech) was digested with restriction enzymes SfiI and NotI to remove the recombinant antibody gene ScFv. The above phosphorylated and annealed oligonucleotide pair was inserted into the portion of the above recombinant antibody gene ScFv to prepare a plasmid containing a nucleotide sequence encoding a protein composed of a 5 random amino acid sequence upstream from a protein comprising an amino acid sequence of M13 phage coat protein. The plasmid was introduced into *E. coli* TG-1 strain according to the method described in Hanahan, D. J., Mol. Biol. 166; p 557 (1983) and cultured in 2×YT medium (10 g/liter yeast extract, 15 g/liter tryptone and 5 g/liter NaCl, pH 7.2) containing 100 µg/ml ampicillin to obtain recombinant *E. coli* TG-1 strain. The recombinant *E. coli* TG-1 strain was inoculated into 2×YT medium containing 100 µg/ml ampicillin and cultured with shaking at 37° C. Then, 1 hour after initiation of culture, $6 \times 10^{10}$ pfu helper-phage M13K07 (manufactured by Pharmacia Biotech) was inoculated to the medium, and culture was continued for additional 18 hours with shaking. Then, the liquid culture medium was centrifuged at 1,000×g for 20 minutes to collect the phage library displaying a protein containing the amino acid sequence composed of 5 random amino acids.

For preparing the phage clone displaying a protein containing the amino acid sequence HASYS (SEQ ID NO: 53), an oligonucleotide composed of the nucleotide sequence of SEQ ID NO: 29 and an oligonucleotide composed of the nucleotide sequence of SEQ ID NO: 30 were synthesized. And, for preparing the phage clone displaying a protein containing the amino acid sequence RASSL (SEQ ID No: 55), an oligonucleotide composed of the nucleotide sequence of SEQ ID NO: 31 and an oligonucleotide composed of the nucleotide sequence of SEQ ID NO: 32 were synthesized. These oligonucleotides were synthesized with a DNA synthesizer (PE Applied Biosystems; Model 394 DNA/RNA synthesizer) and purified with an oligonucleotide purification cartridge (PE Applied Biosystems; OPC cartridge). The phage clone displaying the protein containing the amino acid sequence HASYS or RASSL was obtained by the same operation as the above that for obtaining the phage library displaying a protein containing the amino acid sequence composed of 5 random amino acids.

A phage suspension containing the phage clone displaying the protein containing the amino acid sequence HASYS, the phage clone displaying the protein containing the amino acid sequence RASSL or the phage library displaying the protein containing the amino acid sequence consisting of 5 random amino acids (titer $10^5$ pfu) was respectively spotted to nitro cellulose filter (manufactured by Schleicher & Schuell), and then the nitro cellulose filter was blocked by shaking it in PBT buffer (137 mM NaCl, 8.10 mM $Na_2HPO_4$, 2.68 mM KCl, 1.47 mM $KH_2PO_4$, 0.05% Tween 20, pH 7.2) containing 1% bovine serum albumin. The nitro cellulose filter was washed with PBT buffer and shaken for 18 hours in 2×SSC buffer (0.3 M NaCl, 0.03M sodium citric acid) containing 10 µM protoporphyrin IX. Further, said nitro cellulose filter was washed with 2×SSC buffer, dried, and fluorescence derived from protoporphyrin IX was detected under ultraviolet light (365 nm).

The spots of the phage library did not show fluorescence, while the spots of both phage clones displaying the protein containing the amino acid sequence HASYS and that containing the amino acid sequence RASSL showed clear fluorescence.

EXAMPLE 31

Test of Protoporphyrin IX Binding Protein for Capability of Giving Resistance to Herbicidal Compounds First, a plasmid which could express the gene encoding the protein containing the amino acid sequence HASYS (SEQ ID NO: 53), or the amino acid sequence RASSL (SEQ ID NO: 55) was prepared. For preparing the plasmid capable of expressing the gene encoding the protein composed of the amino acid sequence of SEQ ID NO: 54 (hereinafter referred to as the protein MGHASYS), an oligonucleotide composed of the nucleotide sequence of SEQ ID NO: 33 and an oligonucleotide composed of the nucleotide sequence of SEQ ID NO: 34 were synthesized. The oligonucleotides were synthesized with a DNA synthesizer (PE Applied Biosystems; Model 394 DNA/RNA synthesizer) and purified with an oligonucleotide purification cartridge (PE Applied Biosystems; OPC cartridge). The above oligonucleotides (each 50 pmol) were phosphorylated at 5' end by treating with T4 DNA kinase, respectively. They were mixed and then, after heating for 10 minutes at 70° C., subjected to annealing by cooling slowly to room temperature at rate of 0.5° C./minute. Plasmid pTV118N was digested with restriction enzymes NcoI and EcoRI to remove the gene fragment consisting of 16 base pairs. Plasmid pHASYS capable of expressing the gene encoding protein MGHASYS was prepared by inserted the above phosphorylated and annealed oligonucleotide pairs into the position of the above 16 base pairs.

Then, for preparing the plasmid capable of expressing the gene encoding the protein consisting of amino acid sequence of SEQ ID NO: 56 (hereinafter referred to as protein MGRASSL), an oligonucleotide composed of the nucleotide sequence of SEQ ID NO: 35 and an oligonucleotide composed of the nucleotide sequence of SEQ ID NO: 36 were synthesized. The oligonucleotides were synthesized with a DNA synthesizer (PE Applied Biosystems; Model 394 DNA/RNA synthesizer) and purified with an oligonucleotide purification cartridge (PE Applied Biosystems; OPC cartridge). Plasmid pRASSL capable of expressing the gene encoding protein MGRASSL was prepared by the same procedure as that for plasmid pHASYS.

A plasmid capable of expressing the gene encoding the protein containing the amino acid sequence YAGY or YAGF (wherein Y is tyrosine, A is alanine, G is glycine, F is phenylalanine) (Sugimoto, N., Nakano. S., Chem. Lett. p 939, 1997) capable of binding to porphyrin compound $H_2TMPyP$ was prepared. For preparing the plasmid capable of expressing the gene encoding the protein consisting of the amino acid sequence of SEQ ID NO: 58 (hereinafter referred to as protein MGYAGY), an oligonucleotide composed of the nucleotide sequence of SEQ ID NO: 37 and an oligonucleotide composed of the nucleotide sequence of SEQ ID NO: 38 were synthesized. For preparing the plasmid capable of expressing the gene encoding the protein composed of the amino acid sequence of SEQ ID NO: 60 (hereinafter referred to as protein MGYAGF), an oligonucleotide composed of the nucleotide sequence of SEQ ID NO: 39 and an oligonucleotide composed of the nucleotide sequence of SEQ ID NO: 40 were also synthesized. These oligonucleotides were synthesized with a DNA synthesizer (PE Applied Biosystems; Model 394 DNA/RNA synthesizer) and purified with an oligonucleotide purification cartridge (PE Applied Biosystems; OPC cartridge). Plasmid pYAGY capable of expressing the gene encoding the protein MGYAGY and plasmid pYAGF capable of expressing the gene encoding protein MGYAGF were prepared by the same procedure as that for plasmid pHASYS.

The above plasmids pHASYS, pRASSL, pYAGY, pYAGF and pTV118N were introduced into E. coli BT3/pACYCSP strain prepared in Example 3 respectively according to the method described in Hanahan, D. J., Mol. Biol., 166; p 557 (1983). E. coli BT3/pACYCSP+pHASYS strain bearing plasmid pACYCSP and pHASYS, E. coli BT3/pACYCSP+pRASSL strain bearing plasmid pACYCSP and pRASSL, E. coli BT/pACYCSP+pYAGY strain bearing plasmid pACYCSP and pYAGY, E. coli BT3/pACYCSP+pYAGF strain bearing plasmid pACYCSP and pYAGF and E. coli BT3/pACYCSP+pTV118N strain bearing plasmid pACYCSP and pTV118N were obtained by culturing the above strains in YPT medium containing 100 µg/ml ampicillin, 15 µg/ml chloramphenicol and 10 µg/ml kanamycin.

These E. coli strains were inoculated into YPT medium containing 1 ppm of the PPO inhibitory-type herbicidal compound represented by Structure 8, 100 µg/ml ampicillin, 15 µg/ml chloramphenicol, 10 µg/ml kanamycin, 10 µg/ml hemin and 50 µg/ml aminolevulinic acid, cultured under dark conditions or light conditions according to the same manner as in Example 2. Then, 18 hours after initiation of culture, the absorbance of liquid culture medium was measured at 600 nm. By taking the absorbance of the medium without the herbicidal compound as 1, the relative value of the absorbance of the medium containing the herbicidal compound was calculated. The results are shown in Table 15.

TABLE 15

| E. coli strain | Culture conditions | Relative absorbance Concentration of test compound | |
|---|---|---|---|
| | | 1 ppm | 0 ppm |
| BT3/pACYCSP + pHASYS | in the light | 0.65 | 1.0 |
| BT3/pACYCSP + pHASYS | in the dark | 0.96 | 1.0 |
| BT3/pACYCSP + pRASSL | in the light | 0.59 | 1.0 |
| BT3/pACYCSP + pRASSL | in the dark | 1.0 | 1.0 |
| BT3/pACYCSP + pYAGY | in the light | 0.48 | 1.0 |
| BT3/pACYCSP + pYAGY | in the dark | 0.99 | 1.0 |
| BT3/pACYCSP + pYAGF | in the light | 0.62 | 1.0 |
| BT3/pACYCSP + pYAGF | in the dark | 0.96 | 1.0 |
| BT3/pACYCSP + pTV118N | in the light | 0.07 | 1.0 |
| BT3/pACYCSP + pTV118N | in the dark | 0.93 | 1.0 |

Further, a plasmid capable of expressing a gene encoding a protein containing an amino acid sequence in which one unit of the amino acid sequences HASYS or RASSL were repeatedly joined. For preparing the plasmid capable of expressing the gene encoding the protein composed of the amino acid sequence of SEQ ID NO: 61 (hereinafter referred to as protein $MG(HASYS)_4$, $(HASYS)_n$ referred to as a sequence in which peptide HASYS was repeatedly joined to each other n times), an oligonucleotide composed of the nucleotide sequence of SEQ ID NO: 41, SEQ ID NO: 42, SEQ ID NO: 43 or SEQ ID NO: 44 was synthesized. These oligonucleotides were synthesized with a DNA synthesizer (PE Applied Biosystems; Model 394 DNA/RNA synthesizer) and purified with an oligonucleotide purification cartridge (PE Applied Biosystems; OPC cartridge). First, the oligonucleotide composed of the nucleotide sequence of SEQ ID NO. 42 and the oligonucleotide composed of the nucleotide sequence of SEQ ID NO: 43 were phosphorylated respectively at 5' end by treating with T4 DNA kinase. Thereafter, the oligonucleotide composed of the nucleotide sequence of SEQ ID NO: 41 and the oligonucleotide composed of the phosphorylated nucleotide sequence of SEQ ID NO: 42 or the oligonucleotide composed of the phosphorylated nucleotide sequence of SEQ ID NO: 43 and the oligonucleotide composed of the nucleotide sequence of SEQ ID NO: 44 were mixed (each 300 pmol), and after heating for minutes at 70° C., annealed by cooling slowly to room temperature at rate of 0.5° C./minute. The above two annealed oligonucleotide pairs were mixed and ligated with T4 DNA ligase, then the resultant DNA fragment was phosphorylated with T4 DNA kinase at 5' end. On the other hand, vector pTV118N was digested with restriction enzymes NcoI and EcoRI to remove a DNA fragment of 16 base pairs and the above phosphorylated DNA fragment was inserted into this portion to obtain plasmid pHASYS4 expressing the gene encoding protein MG(HASYS)$_4$.

Further, for preparing the plasmid capable of expressing the gene encoding the protein composed of the amino acid-sequence of SEQ ID NO: 62 (hereinafter referred to as protein MG(HASYS)$_8$), an oligonucleotide composed of the nucleotide sequence of SEQ ID NO: 45 and an oligonucleotide composed of the nucleotide sequence of SEQ ID NO: 46 were synthesized. These oligonucleotides were synthesized with a DNA synthesizer (PE Applied Biosystems; Model 394 DNA/RNA synthesizer) and purified with an oligonucleotide purification cartridge (PE Applied Biosystems; OPC cartridge). First, the above oligonucleotides were phosphorylated at 5' end by treating with T4 DNA kinase. Thereafter, an oligonucleotide composed of the nucleotide sequence of SEQ ID NO: 41 and an oligonucleotide composed of the phosphorylated nucleotide sequence of SEQ ID NO: 42 were mixed (each 300 pmol), an oligonucleotide composed of the phosphorylated nucleotide sequence of SEQ ID NO: 43 and an oligonucleotide composed of the nucleotide sequence of SEQ ID NO: 44 were mixed (each 300 pmol), and further, an oligonucleotide composed of the phosphorylated nucleotide sequence of SEQ ID NO: 45 and an oligonucleotide composed of the phosphorylated nucleotide sequence of SEQ ID NO: 46 were mixed (each 600 pmol). These three mixtures were heated for 5 minutes at 70° C., and annealed by cooling slowly to room temperature at rate of 0.5° C./minute, respectively. The above three annealed oligonucleotide pairs were mixed, and ligated with T4 DNA ligase, and then the resultant DNA fragment was phosphorylated with T4 DNA kinase at 5' end. Plasmid pHASYS8 capable of expressing protein MG(HASYS)$_8$ were prepared in the same manner as that for the above plasmid pHASYS4.

Then, for preparing a plasmid capable of expressing the gene encoding the protein composed of the amino acid sequence of SEQ ID NO: 63 (hereinafter referred to as protein MG(RASSL)$_4$, (RASSL)$_n$ referred to as a sequence in which peptide RASSL was repeatedly joined to each other n times), an oligonucleotide composed of the nucleotide sequence of SEQ ID NO: 47, SEQ ID NO: 48, SEQ ID NO: 49 or SEQ ID NO: 50 were synthesized. Also, for preparing a plasmid capable of expressing the gene encoding the protein composed of the amino acid sequence of SEQ ID NO: 64 (hereinafter referred to as protein MG(RASSL)$_8$), an oligonucleotide composed of the nucleotide sequence of SEQ ID NO: 51 and an oligonucleotide composed of the nucleotide sequence of SEQ ID No: 52 were synthesized. These oligonucleotides were synthesized with a DNA synthesizer (PE Applied Biosystems; Model 394 DNA/RNA synthesizer) and purified with an oligonucleotide purification cartridge (PE Applied Biosystems; OPC cartridge).

Plasmid pRASSL4 capable of expressing protein MG(RASSL)$_4$ were prepared according to the same manner as that for the above plasmid pHASYS4. Plasmid pRASSL8 capable of expressing protein MG(RASSL)$_8$ were also prepared according to the same manner as that for the above plasmid pHASYS8.

The above plasmids pHASYS4, pHASYS8, pRASSL4, pRASSL8 and pTV118N were introduced into *E. coli* BT3/pACYCSP strain prepared in Example 3 respectively according to the method described in Hanahan, D. J., Mol. Biol., 166; p 557 (1983). *E. coli* BT3/pACYCSP+pHASYS4 strain bearing plasmid pACYCSP and pHASYS4, *E. coli* BT3/pACYCSP+pHASYS8 strain bearing plasmid pACYCSP and pHASYS8, *E. coli* BT3/pACYCSP+pRASSL4 strain bearing plasmid pACYCSP and pRASSL4, *E. coli* BT3/pACYCSP+pRASSL8 strain bearing plasmid pACYCSP and pRASSL8 and *E. coli* BT3/pACYCSP+pTV118N strain bearing plasmid pACYCSP and pTV118N were obtained by culturing the above strains in YPT medium containing 100 μg/ml ampicillin, 15 μg/ml chloramphenicol and 10 μg/ml kanamycin.

These *E. coli* strains were inoculated into YPT medium containing 1 ppm of the PPO inhibitory-type herbicidal compound represented by Structure 8, 100 μg/ml ampicillin, 15 μg/ml chloramphenicol, 10 μg/ml kanamycin, 10 μg/ml hemin and 50 μg/ml aminolevulinic acid, cultured under dark conditions or light conditions according to the same manner as in Example 2. Then, 18 hours after initiation of culture, the absorbance of the liquid culture medium was measured at 600 nm. By taking the absorbance of the culture medium without the herbicidal compound as 1, the relative value of the absorbance of the culture medium containing the herbicidal compound was calculated. The results are shown in Table 16.

TABLE 16

|  |  | Relative absorbance Concentration of test compound | |
| --- | --- | --- | --- |
| *E. coli* strain | Culture condition | 1 ppm | 0 ppm |
| BT3/pACYCSP + pHASYS4 | in the light | 0.91 | 1.0 |
| BT3/pACYCSP + pHASYS4 | in the dark | 1.0 | 1.0 |
| BT3/pACYCSP + pHASYS8 | in the light | 0.57 | 1.0 |
| BT3/pACYCSP + pHASYS8 | in the dark | 1.0 | 1.0 |
| BT3/pACYCSP + pRASSL4 | in the light | 1.1 | 1.0 |
| BT3/pACYCSP + pRASSL4 | in the dark | 0.98 | 1.0 |
| BT3/pACYCSP + pRASSL8 | in the light | 0.79 | 1.0 |
| BT3/pACYCSP + pRASSL8 | in the dark | 1.0 | 1.0 |
| BT3/pACYCSP + pTV118N | in the light | 0.15 | 1.0 |
| BT3/pACYCSP + pTV118N | in the dark | 0.81 | 1.0 |

EXAMPLE 32

Figure 18:
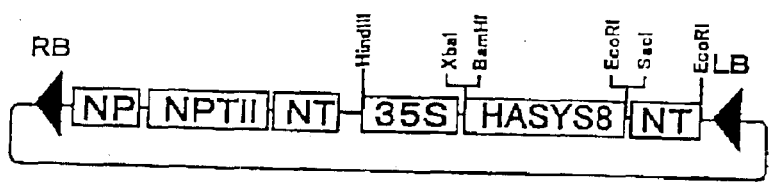
FIG. 18 is the restriction map of plasmid pBIHASYS8. HASYS8 is a gene encoding $MG(HASYS)_8$ protein. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Introduction of the Gene Encoding Protoporphyrin IX Binding Peptide into Tobacco A plasmid for introducing the gene encoding the protoporphyrin IX binding peptide into tobacco by *Agrobacterium* method was constructed. The plasmid pHASYS8 prepared in Example 31 was digested with restriction enzyme NcoI followed by blunting the DNA with DNA polymerase I with addition of nucleotides to the double-stranded DNA gap. Then, the DNA was dephosphorylated with alkaline phosphatase derived from calf intestine and cyclized by inserting phosphorylated BamH I linker (4610P, manufactured by Takara Syuzo Co., Ltd.) to construct plasmid pHASYS8B. Plasmid pBI121 (manufactured by Clonetech) was digested with restriction enzymes BamHI and SacI to remove β-glucuronidase gene. On the other hand, plasmid pHASYS8B was digested with restriction enzymes BamHI and SacI to prepare the DNA fragment containing the gene encoding protein MG(HASYS)$_8$, the resultant DNA fragment was inserted into plasmid pBI121 with replacing β-glucuronidase gene to prepare plasmid pBIHASYS8 (FIG. 18) in which the gene encoding protoporphyrin IX binding protein MG(HASYS)$_8$ was joined downstream from 35S promoter.

Figure 19:
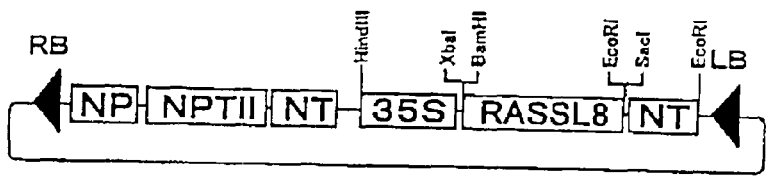
FIG. 19 is the restriction map of plasmid pBIRASSL8. RASSL8 is $MG(RASSL)_8$ protein. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

A plasmid for introducing the gene encoding the protoporphyrin IX binding peptide MG(RASSL)$_8$ into a plant by Agrobacterium infection method was constructed. Plasmid pBIRASSL8 (FIG. 19) in which the gene encoding protoporphyrin IX binding protein MG(RASSL)$_8$ was joined downstream from 35S promoter was prepared from pRASSL8 according to the same procedure as that for pBIHASYS8.

The above plasmid pBIHASYS8 and pBIRASSL8 were introduced into *Agrobacterium tumefaciens* LBA4404 respectively. The resultant transformants were cultured in a medium containing 300 μg/ml streptomycin, 100 μg/ml rifampicin and 25 μg/ml kanamycin, followed by selecting the desired transformants to isolate *Agrobacterium* strains bearing pBIHASYS8 and pBIRASSL8, respectively.

Leaf pieces of tobacco cultured sterilely are infected with said *Agrobacterium* strains to obtain tobacco introduced with the gene encoding protoporphyrin IX binding protein MG(HASYS)$_8$, and the tobacco introduced with the gene encoding protoporphyrin IX binding protein MG(RASSL)$_8$ in the same manner as in Example 5.

EXAMPLE 33

Confirmation of Resistance to Herbicidal Compounds of Tobacco Bearing Introduced Gene Encoding the Protoporphyrin IX Binding Peptide The level of resistance to herbicidal compounds is confirmed quantitatively by testing tobacco introduced with the gene encoding the protoporphyrin IX binding peptide prepared in Example 32 according to the same manner as in Example 14.

EXAMPLE 34

Isolation of PPO Gene of *Arabidopsis thaliana* Having Herbicidal Compound-Resistant Mutation A plasmid containing PPO gene of *Arabidopsis thaliana* obtained by the method described by Narita, S. et al., Gene, 182; p 169 (1996) was digested with the restriction enzyme NcoI, and nucleotides were added to the gap of the double-stranded DNA by using DNA Polymerase I to blunt the end of the DNA. Then, the 5'-end of the DNA was dephosphorylated with an alkaline phosphatase derived from calf small intestine, followed by insertion of a phosphorylated BamHI linker (4810P manufactured by Takara Shuzo Co., Ltd.) therein and cyclization to construct plasmid pAGE17B. The plasmid pAGE17B was digested with BamHI and SacI to obtain a gene fragment containing PPO gene of *Arabidopsis thaliana*. The fragment was inserted between BamHI and SacI of a commercially available vector, pKF19k for site-directed mutagenesis (manufactured by Takara Shuzo Co., Ltd.), to construct plasmid pKFATP.

Then, for conversion of the 220th alanine into valine, a PPO inhibitory-type herbicidal compound-resistant mutation in PPO protein of *Arabidopsis thaliana* disclosed in WO 9534659, base substitution (substitution of "T" for the 659 base "C") of DNA was introduced into the above PPO gene of *Arabidopsis thaliana*. First, an oligonucleotide primer for mutagenesis represented by SEQ ID NO: 65 was synthesized. The oligonucleotide primer was synthesized with a DNA synthesizer (PE Applied Biosystems: Model 394 DNA/RNA Synthesizer) and purified with an oligonucleotide purification cartridge (PE Applied Biosystems: OPC Cartridge). The 5'-end of the oligonucleotide primer was phosphorylated with T4 DNA kinase. According to the manual attached to a commercially available site-directed mutagenesis kit, Mutan-Super Express Km (manufactured by Takara Shuzo Co., Ltd.), a reaction mixture containing 10 ng of the above plasmid pKFATP as template DNA, 5 pmol of the attached selection primer, 5 pmol of the above phosphorylated oligonucleotide primer for mutagenesis and the like was prepared and PCR was carried out. The PCR was carried by repeating a cycle for maintaining at 94° C. for 1 minute, at 55° C. for 1 minute and then at 72° C. for 3 minutes 30 times. The resultant reaction mixture was purified by ethanol precipitation and the precipitate was dissolved in 5 μl of sterilized-distilled water. According to the attached manual, its 2 μl portion was used for introduction into a commercially available *E. coli* competent cell, MV1184 (manufactured by Takara Shuzo Co., Ltd.), and plated on LB agar culture medium (1% tryptone, 0.5% yeast extract, 0.5% NaCl, 1% agar) containing 50 μg/ml of kanamycin. After incubation at 37° C., the resultant clone was cultured in LB liquid medium containing 50 μg/ml of kanamycin to prepare plasmid DNA. The introduction of the desired herbicidal compound-resistant mutation A220V was confirmed by analyzing the nucleotide sequence of the PPO gene of *Arabidopsis thaliana* having herbicidal compound-resistant mutation contained in the resultant plasmid pKFATP1.

EXAMPLE 35

Figure 20:
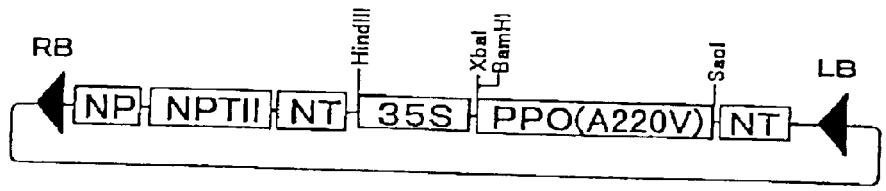
FIG. 20 is the restriction map of plasmid pNATP. PPO (A220V) is a PPO gene having a herbicidal compound-resistant mutation (A220V). NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Introduction of PPO Gene of *Arabidopsis thaliana* Having Herbicidal Compound-Resistant Mutation into Tobacco A plasmid was constructed for introducing the PPO gene of *Arabidopsis thaliana* having herbicidal compound-resistant mutation (hereinafter referred to as *Arabidopsis thaliana* PPO(A220V) gene) into a plant by *Agrobacterium* infection method. Binary vector pBI121 (manufactured by Clontech) was digested with the restriction enzymes BamHI and SacI to remove β-glucuronidase gene. On the other hand, the plasmid pKFATP1 described in Example 34 was digested with restriction enzymes BamHI and SacI to prepare a DNA fragment containing *Arabidopsis thaliana* PPO (A220V) gene. Instead of the above β-glucuronidase gene, the resultant DNA fragment was inserted in the binary vector pBI121 to construct the plasmid pNATP (FIG. 20).

The plasmid pNATP was introduced into *Agrobacterium tumefaciens* LBA4404 and this was cultured in LB culture medium containing 300 μg/ml of streptomycin, 100 μg/ml of rifampicin and 25 μg/ml of kanamycin, followed by selection of a transformant to isolate an *Agrobacterium* strain bearing pNATP.

Tobacco leaf pieces cultured sterilely were infected with the *Agrobacterium* strain and, according to the same manner as described in Example 5, tobacco bearing the introduced *Arabidopsis thaliana* PPO(A220V) gene was obtained.

EXAMPLE 36

Production of Recombinant Tobacco Having *Arabidopsis thaliana* PPO(A220V) Gene and Gene Encoding Variant Tobacco Chelatase Subunit A plasmid was constructed for introducing both *Arabidopsis thaliana* PPO(A220V) gene and gene encoding a variant tobacco chelatase subunit into a plant by *Agrobacterium* infection method. First, oligonucleotide primers composed of the nucleotide sequence represented by SEQ ID NO: 66 and the nucleotide sequence represented by SEQ ID NO: 67, respectively, were synthesized. The oligonucleotide primers were synthesized by a DNA synthesizer (PE Applied Biosystems: Model 394 DNA/RNA Synthesizer) and purified with an oligonucleotide purification cartridge (PE Applied Biosystems: OPC Cartridge). PCR was carried out by using the primers and the plasmid pKFATP1 constructed in Example 34 as template DNA to prepare a DNA fragment containing *Arabidopsis thaliana* PPO(A220V) gene. The PCR was carried out by repeating a cycle for maintaining at 94° C. for 1 minute, 55° C. for 2 minutes and then 72° C. for 3 minutes 30 times. The amplified DNA fragment was digested by the restriction enzymes HindIII and SalI to obtain a DNA fragment containing *Arabidopsis thaliana* PPO(A220V) gene. The fragment was inserted between HindIII and SalI restriction sites of a commercially available vector, pUC19, to construct plasmid pAP.

Figure 29:
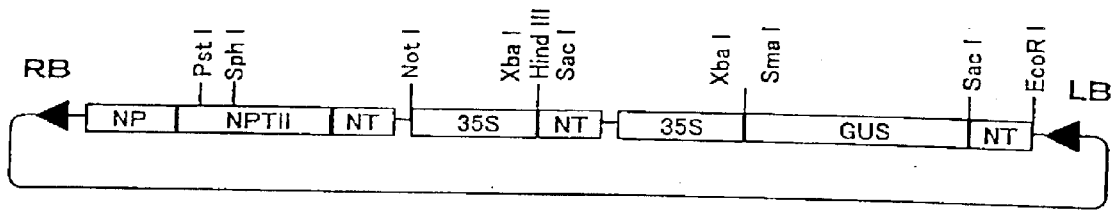
FIG. 29 is the restriction map of plasmid pNG01. NP is the promoter sequence of a nopaline synthase, NT is the terminator sequence of a nopaline synthase, and 35S is the 35S promoter of cauliflower mosaic virus. NPTII is a kanamycin resistant gene, GUS is β-glucuronidase gene, and RB and LB are the right and left border sequences of T-DNA, respectively.
Figure 30:
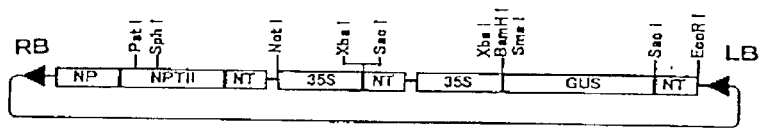
FIG. 30 is the restriction map of plasmid pNG04. NP is the promoter sequence of a nopaline synthase, NT is the terminator sequence of a nopaline synthase, and 35S is the 35S promoter of cauliflower mosaic virus. NPTII is a kanamycin resistant gene, GUS is β-glucuronidase gene, and RB and LB are the right and left border sequences of T-DNA, respectively.

On the other hand, the plasmid pNG01 (FIG. 29) described in Shiota, N. et al., Plant Physiol., 106; p 17 (1994) was digested with the restriction enzyme HindIII and nucleotides were added to the gap of the double-stranded DNA with DNA Polymerase I to blunt the end of the DNA, followed by self-cyclization to construct the plasmid pNG04 (FIG. 30). The plasmid pNG04 was digested with the restriction enzyme XbaI to isolate a DNA fragment of about 1.1 kb composed of the terminator of a nopaline synthase and 35S promoter. The DNA fragment was inserted into the XbaI restriction site of the above plasmid pAP. For selecting plasmid pAPNS wherein the terminator of the nopaline synthase was ligated to the downstream of *Arabidopsis thaliana* PPO(A220V) gene, digestion with the restriction enzymes HindIII and PstI was carried out to select a clone producing a DNA fragment of about 2.0 kb composed of *Arabidopsis thaliana* PPO(A220V) gene and the terminator of the nopaline synthase. Further, the plasmid pAPNS was digested with the restriction enzyme HindIII and nucleotides were added to the gap of the double-stranded DNA with DNA polymerase I to blunt the end of the DNA. The 5'-end of the DNA was dephosphorylated with an alkaline phosphatase derived from calf small intestine and a phosphorylated KpnI linker (4668P manufactured by Takara Shuzo Co., Ltd.) was inserted therein, followed by cyclization to construct plasmid pAPNSK.

Figure 21:
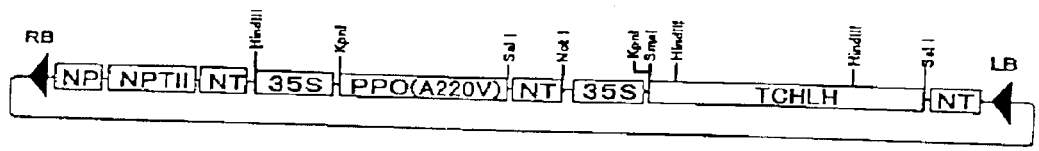
FIG. 21 is the restriction map of plasmid pBIAPTCH. PPO(A220V) is a PPO gene having a herbicidal compound-resistant mutation (A220V) and TCHLH is a tabacco magnesium chelatase subunit gene whose chloroplast transit singal has been deleted. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

The plasmid pAPNSK was digested with the restriction enzymes KpnI and DraI to isolate a DNA fragment of about 2.8 kb composed of *Arabidopsis thaliana* PPO(A220V) gene, the terminator of the nopaline synthase located at the downstream of the gene and 35S promoter located at the downstream of the terminator. The fragment was inserted in KpnI restriction site of the plasmid pBITCHLH constructed in Example 9. For selecting the plasmid pBIAPTCH (FIG. 21) wherein *Arabidopsis thaliana* PPO(A220V) gene and a gene encoding a variant tobacco chelatase subunit were ligated to the downstream of 35S promoter, respectively, the resultant plasmid was digested with the restriction enzyme BamHI to select a clone producing a DNA fragment of about 2.8 kb composed of *Arabidopsis thaliana* PPO(A220V) gene, the terminator of the nopaline synthase and the 35S promoter.

The plasmid pBIAPTCH was introduced into *Agrobacterium tumefaciens* LBA4404 and this was cultured in LB medium containing 300 μg/ml of streptomycin, 100 μg/ml rifampicin and 25 μg/ml kanamycin, followed by selection of a transformant to isolate an *Agrobacterium* strain bearing pBIAPTCH.

Tobacco leaf pieces cultured sterilely were infected with the *Agrobacterium* strain and, according to the same manner as in Example 5, tobacco bearing the introduced both *Arabidopsis thaliana* PPO(A220V) gene and gene encoding the variant tobacco chelatase subunit was obtained.

EXAMPLE 37

Confirmation of Resistance to Herbicidal Compound of Tobacco Bearing Introduced *Arabidopsis thaliana* PPO (A220V) Gene and Gene Encoding Variant Tobacco Chelatase Subunit Leaves of the tobacco bearing the introduced both *Arabidopsis thaliana* PPO(A220V) gene and gene encoding the variant tobacco chelatase subunit produced in Example 36, those bearing the introduced *Arabidopsis thaliana* PPO (A220V) gene produced in Example 35, and the control recombinant tobacco leaves produced in Example 5 were collected, and each leaf was divided into the right and left equivalent pieces along the main vein. One of the pieces was treated with an aqueous solution containing 2.0 ppm PPO inhibitory-type herbicidal compound of Structure 8, while the other piece was not treated with the compound. These leaf pieces were placed on MS medium containing 0.8% agar and allowed to stand at room temperature for 7 days in a light place. Then, each leaf piece was ground in 5 ml of 80% aqueous acetone solution in a mortar with a pestle to extract chlorophyll. The extract was diluted 10 times with 80% aqueous acetone solution and the absorbance was measured at 750 nm, 663 nm and 645 nm to calculate the total chlorophyll content according to the method described by Mackinney G., J. Biol. Chem. (1941) 140, p 315. The resistant level to the herbicidal compound tested was represented by the percentage of the total chlorophyll content of the leave pieces treated with the herbicidal compound to that of untreated leaf pieces. The resistant level of the control recombinant tobacco was 2.88% and that of the tobacco bearing the introduced *Arabidopsis thaliana* PPO(A220V) gene was 12.2%. On the other hand, the resistant level of the tobacco bearing introduced both *Arabidopsis thaliana* PPO (A220V) gene and gene encoding the variant tobacco chelatase subunit was 61.6%.

EXAMPLE 38

Isolation of Gene Encoding Chloroplast-Localized Type Ferrochelatase of *Arabidopsis thaliana*

Figure 22:
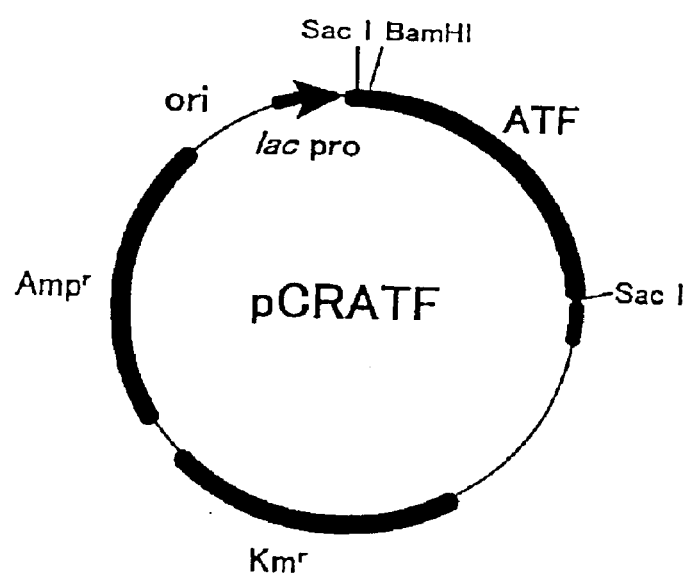
FIG. 22 is the restriction map of plasmid pCRATF. ATF is a chloroplast-localized type ferrochelatase gene of *Arabidopsis thaliana*. lac pro represents the promoter sequence of a lactose operon. $Amp^r$ is an ampicillin resistant gene, $Km^r$ is kanamycin resistant gene and ori is the replication origin.

Total RNAs were prepared from leaf tissues of *Arabidopsis thaliana* ecotype WS by using RNeasy Plant Kit (manufactured by QIAGEN) according to the manual attached thereto. A DNA fragment containing a chloroplast-localized type ferrochelatase gene of *Arabidopsis thaliana* was obtained by using RNA LA PCR Kit (AMV) Ver 1.1 (manufactured by Takara Shuzo Co., Ltd.) according to the manual attached thereto. First, 1st strand cDNA was synthesized by using *Arabidopsis thaliana* total RNAs as a template and Oligo dT-Adaptor Primer contained in the above kit as the primer with the reverse transcriptase contained in the above kit. Then, PCR was carried out by using the 1st strand cDNA as a template and LA Taq polymerase contained in the above kit to amplify a DNA fragment containing the gene encoding the chloroplast-localized type ferrochelatase of *Arabidopsis thaliana*. In this PCR, the primers used were the oligonucleotide primer composed of the nucleotide sequence of SEQ ID NO: 68 and the oligonucleotide primer composed of the nucleotide sequence of SEQ ID NO: 69. The oligonucleotides were synthesized by a DNA synthesizer (PE Applied Biosystems: Model 394 DNA/RNA Synthesizer) and purified with an oligonucleotide purification cartridge (PE Applied Biosystems: OPC Cartridge). The PCR was carried by maintaining at 94° C. for 2 minutes and then repeating a cycle for maintaining at 94° C. for 30 seconds, at 50° C. for 30 seconds and then at 72° C. for 7 minutes 30 times. After the PCR, the DNA fragment amplified by the PCR was cloned into the plasmid pCR2.1 by using TA Cloning Kit (manufactured by Invitrogen) according to the manual attached thereto. The resultant plasmid was digested with the restriction enzyme BamHI and analyzed by agarose gel electrophoresis. The plasmid from which 5.3 kb DNA fragment was detected was named pCRATF (FIG. 22). The plasmid has such a structure that the chloroplast-localized type ferrochelatase gene of *Arabidopsis thaliana* is inserted in a DNA strand complementary to the lac promoter. When the nucleotide sequence of the chloroplast-localized type ferrochelatase gene of *Arabidopsis thaliana* was analyzed, it agreed with the nucleotide sequence of the chloroplast-localized type ferrochelatase gene of *Arabidopsis thaliana* described by Smith, A. G. et al., J. Biol. chem., 269; p 13405 (1994).

EXAMPLE 39

Introduction of Gene Encoding Chloroplast-Localized Type Ferrochelatase of *Arabidopsis thaliana*

Figure 23:
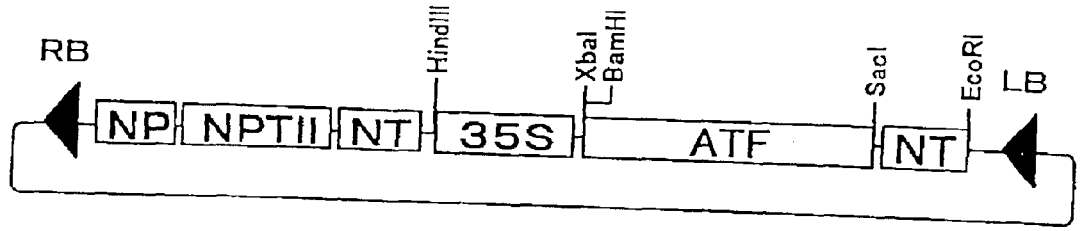
FIG. 23 is the restriction map of plasmid pBIATF. ATF is a chloroplast-localized type ferrochelatse gene of *Arabidopsis thaliana*. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

A plasmid was constructed for introducing a gene encoding chloroplast-localized type ferrochelatase of *Arabidopsis thaliana* into a plant by *Agrobacterium* infection method. First, the plasmid pCRATF constructed in Example 38 was digested with the restriction enzymes BamHI and SacI to prepare a DNA fragment containing chloroplast-localized type ferrochelatase gene of *Arabidopsis thaliana*. Binary vector pBI121 (manufactured by Clontech) was digested with the restriction enzymes BamHI and SacI to remove β-glucuronidase gene and, instead of this gene, the above DNA fragment containing the chloroplast-localized type ferrochelatase gene of *Arabidopsis thaliana* was inserted therein to construct the plasmid pBIATF (FIG. 23) wherein the ferrochelatase gene was ligated to the downstream of the 35S promoter.

The plasmid pBIATF was inserted into *Agrobacterium tumefaciens* LBA4404 and this was cultured in LB medium containing 300 μg/ml of streptomycin, 100 μg/ml of rifampicin and 25 μg/ml of kanamycin, followed by selection of a transformant to isolate an *Agrobacterium* strain bearing pBIATF.

Tobacco leaf pieces cultivated sterilely are infected with the *Agrobacterium* strain and tobacco bearing the introduced chloroplast-localized type ferrochelatase gene of *Arabidopsis thaliana* is obtained according to the same manner as in Example 5.

EXAMPLE 40

Production of Recombinant Tobacco Bearing Both *Arabidopsis thaliana* PPO(A220V) Gene and Chloroplast-Localized Type Ferrochelatase Gene of *Arabidopsis thaliana*

A plasmid is constructed for introducing both *Arabidopsis thaliana* PPO(A220V) gene and chloroplast-localized type ferrochelatase gene of *Arabidopsis thaliana* into a plant by *Agrobacterium* infection method. First, the plasmid pAPNS constructed in Example 36 are digested with the restriction enzyme HindIII and nucleotides are added to the gap of the double-stranded DNA with DNA Polymerase I to blunt the end of the DNA. The 5'-end of the DNA is dephosphorylated with an alkaline phosphatase derived from calf small intestine and a phosphorylated BamHI linker (4610P manufactured by Takara Shuzo Co., Ltd.) is inserted therein, followed by cyclization to construct plasmid pAPNSB.

Figure 24:
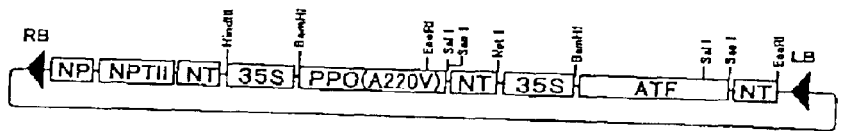
FIG. 24 is the restriction map of plasmid pBIAPATF. PPO(A220V) is PPO gene hvaing a herbicidal compound-resistant mutation (A220V). ATF is a chloroplast-localized type ferrochelatase gene of *Arabidopsis thaliana*. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

The plasmid pAPNSB is digested with the restriction enzymes BamHI and DraI to isolate a DNA fragment of about 2.8 kb composed of *Arabidopsis thaliana* PPO (A220V) gene, the terminator of nopaline synthase and 35S promoter. The fragment is inserted in the BamHI restriction site of the plasmid pBIATF constructed in Example 39. For selecting the plasmid pBIAPATF (FIG. 24) wherein *Arabidopsis thaliana* PP(A220V) gene and chloroplast-localized type ferrochelatase gene of *Arabidopsis thaliana* are ligated to the downstream of 35S promoter, the resultant plasmid is digested with the restriction enzymes NotI and SacI to select a clone producing a DNA fragment of about 2.2 kb composed of the 35S promoter and the chloroplast-localized type ferrochelatase gene of *Arabidopsis thaliana*.

The plasmid pBIAPATF is introduced into *Agrobacterium tumefaciens* LBA44044 and this is cultured in LB medium containing 300 μg/ml of streptomycin, 100 μg/ml of rifampicin and 25 μg/ml of kanamycin, followed by selection of a transformant to isolate an *Agrobacterium* strain bearing pBIAPATF.

Tobacco leaf pieces cultivated sterilely are infected with the *Agrobacterium* strain and tobacco bearing the introduced *Arabidopsis thaliana* PPO(A220V) gene and chloroplast-localized type ferrochelatase gene of *Arabidopsis thaliana* is obtained according to the same manner as in Example 5.

EXAMPLE 41

Confirmation of Resistance to Herbicidal Compounds of Tobacco Bearing Introduced *Arabidopsis thaliana* PPO (A220V) Gene and Chloroplast-Localized Type Ferrochelatase Gene of *Arabidopsis thaliana*

The levels of resistance to herbicidal compounds are confirmed quantitatively by testing the tobacco bearing the introduced *Arabidopsis thaliana* PPO(A220V) gene and chloroplast-localized type ferrochelatase gene of *Arabidopsis thaliana* produced in Example 40 according to the same manner as in Example 37.

EXAMPLE 42

Isolation of Soybean Coproporphyrinogen III Oxidase Gene

Figure 25:
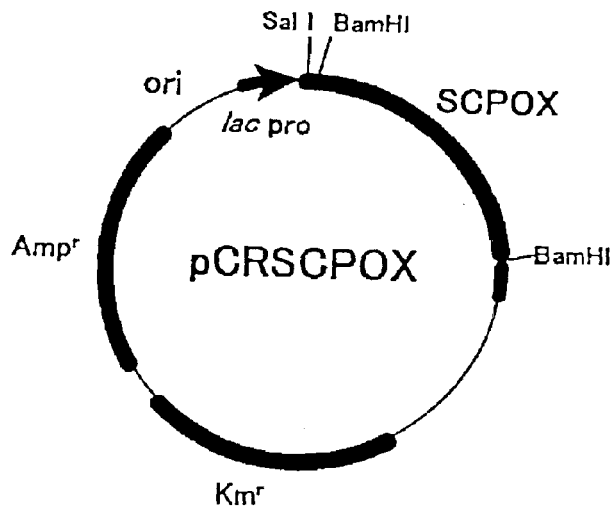
FIG. 25 is the restriction map of plasmid pCRSCPOX. SCPOX is soybean coproporphyrinogen III oxidase gene and lac pro represents the promoter sequence of a lactose operon. $Amp^r$ is an ampicillin resistant gene, $Km^r$ is a kanamycin resistant gene and ori is the replication origin.

Total RNAs were prepared from leaf tissues of soybean (*Glycine max* cv. Jack) by using RNeasy Plant Kit (manufactured by QIAGEN) according to the manual attached thereto. Further, a DNA fragment containing a gene encoding soybean coproporphyrinogen III oxidase (hereinafter referred to as the present soybean CPOX) was obtained by using RNA LA PCR Kit (AMV) Ver 1.1 (manufactured by Takara Shuzo Co., Ltd.) according to the manual attached thereto. First, 1st strand cDNA was synthesized by using the soybean total RNAs as a template and Oligo dT-Adaptor Primer contained in the above kit as a primer with the reverse transcriptase contained in the above kit. Then, PCR was carried out by using the 1st strand cDNA as a template and LA Taq polymerase contained in the above kit to amplify a DNA fragment containing the present soybean CPOX gene. In this PCR, an oligonucleotide primer composed of the nucleotide sequence represented by SEQ ID NO: 70 and an oligonucleotide primer composed of the nucleotide sequence represented by SEQ ID NO: 71 were used. These oligonucleotides were synthesized by using a DNA synthesizer (PE Applied Biosystems: Model 394 DNA/RNA Synthesizer) and purified with an oligonucleotide purification cartridge (PE Applied Biosystems: OPC Cartridge). The PCR was carried out by maintaining at 94° C. for 2 minutes and then repeating a cycle for maintaining at 94° C. for 30 seconds, at 50° C. for 30 seconds and then at 72° C. for 7 minutes 30 times. After the PCR, the DNA fragment amplified by the PCR was cloned into plasmid pCR2.1 by using TA Cloning Kit (manufactured by Invitrogen) according to the manual attached thereto. The resultant plasmid was digested with the restriction enzyme BamHI and analyzed by agarose gel electrophoresis. The plasmid from which 1.2 kb DNA fragment was detected was named pCRSCPOX (FIG. 25). The plasmid pCRSCPOX has such a structure that the present soybean CPOX gene is inserted into a DNA strand complementary to the lac promoter. When the nucleotide sequence of the DNA fragment in the plasmid was analyzed, it was confirmed to be the present soybean CPOX gene.

EXAMPLE 43

Introduction of Present Soybean CPOX Gene into Tobacco

Figure 26:
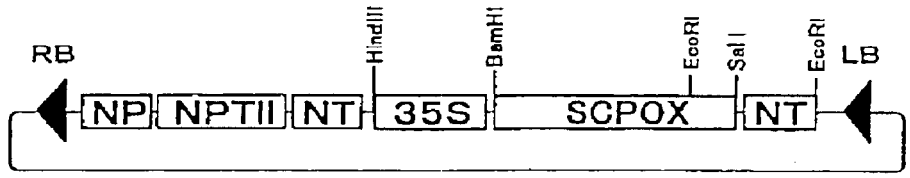
FIG. 26 is the restriction map of plasmid pBISCPOX. SCPOX is soybean coproporphyrinogen III oxidase gene. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequecnes of T-DNA, respectively.

A plasmid was constructed for introducing the present soybean CPOX gene into a plant by *Agrobacterium* infection method. First, the plasmid pCRSCPOX constructed in Example 42 was digested with the restriction enzymes BamHI and SalI to prepare a DNA fragment containing the present soybean CPOX gene. The plasmid pBI121KS constructed in Example 9 was digested with the restriction enzymes BamHI and SalI to remove β-glucuronidase gene and, instead thereof, the above DNA fragment containing the present soybean CPOX gene was inserted therein to construct the plasmid pBISCPOX (FIG. 26) wherein the gene was ligated to the downstream of 35S promoter.

The plasmid pBISCPOX was introduced into *Agrobacterium tumefaciens* LBA4404 and it was cultured in LB medium containing 300 μg/ml of streptomycin, 100 μg/ml of rifampicin and 25 μg/ml of kanamycin, followed by selection of a transformant to isolate an *Agrobacterium* strain bearing pBISCPOX.

Tobacco leaf pieces cultured sterilely is infected with the *Agrobacterium* strain and, according to the same manner as in Example 5, tobacco bearing the introduced present soybean CPOX gene is obtained.

EXAMPLE 44

Figure 27:
FIG. 27 is the restriction map of plasmid pBIAPSCP. PPO(A220V) is PPO gene having a herbicidal compound-resistant mutation (A220V). SCPOX is soybean coproporphyrinogen III oxidase gene. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Production of Recombinant Tobacco Bearing *Arabidopsis thaliana* PPO(A220V) Gene and Present Soybean CPOX Gene A plasmid is constructed for introducing both *Arabidopsis thaliana* PPO(A220V) gene and present soybean CPOX gene into a plant by *Agrobacterium* infection method. The plasmid pAPNSB constructed in Example 40 is digested with the restriction enzymes BamHI and DraI to isolate a DNA fragment of about 2.8 kb composed of *Arabidopsis thaliana* PPO(A220V) gene, the terminator of a nopaline synthase and 35S promoter. The fragment is inserted into the BamHI restriction site of the plasmid pBISCPOX constructed in Example 43. For selecting the plasmid pBIAPSCP (FIG. 27) wherein *Arabidopsis thaliana* PPO(A220V) gene and the present soybean CPOX gene are ligated to the downstream of the 35S promoter, respectively, the resultant plasmid is digested with the restriction enzymes NotI and SalI to select a clone producing a DNA fragment of about 2.0 kb composed of the 35S promoter and the present CPOX gene.

The plasmid pBIAPSCP is introduced into *Agrobacterium tumefaciens* LBA4404 and this is cultured in LB medium containing 300 μg/ml of streptomycin, 100 μg/ml of rifampicin and 25 μg/ml of kanamycin, followed by selection of a transformant to isolate an *Agrobacterium* strain bearing pBIAPSCP.

Tobacco leaf pieces cultivated sterilely is infected with the *Agrobacterium* strain and, according to the same manner as in Example 5, tobacco bearing the introduced both *Arabidopsis thaliana* PPO(A220V) gene and present soybean CPOX gene is obtained.

EXAMPLE 45

Confirmation of Resistance to Herbicidal Compounds of Tobacco Bearing Introduced Both *Arabidopsis thaliana* PPO(A220V) Gene and Present Soybean CPOX Gene The levels of resistance to herbicidal compounds are confirmed quantitatively by testing the tobacco bearing the introduced both *Arabidopsis thaliana* PPO(A220V) gene and present soybean CPOX gene produced in Example 44 according to the same manner as in Example 37.

EXAMPLE 46

Isolation of Glyphosate Resistant Gene

Figure 28:
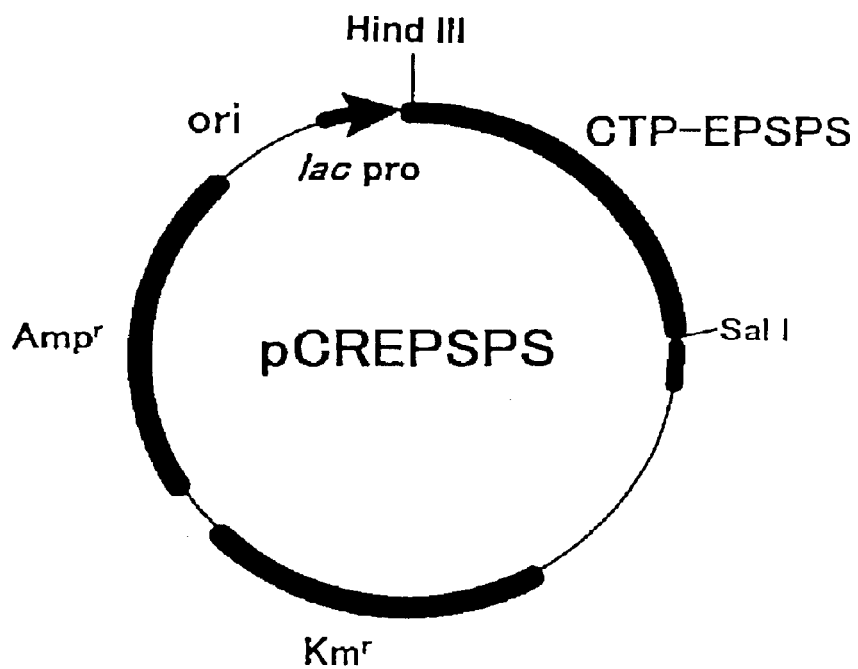
FIG. 28 is the restriction map of plasmid pCREPSPS. CTP-EPSPS is a variant gene in which EPSPS gene derived from *Agrobacterium* is ligated to the downstream of a nucleotide sequence encoding a chloroplast transit peptide of EPSPS derived from petunia. lac pro represents the promoter sequence of a lactose operon. $Amp^r$ is an ampicillin resistant gene, $Km^r$ is kanamycin resistant gene and ori is the replication origin.

Glyphosate resistant soybean (*Glycine max*) was seeded and cultivated at 27° C. for 30 days. The first leaves of germinated individuals were collected, were frozen in liquid Nitrogen and were grounded in a mortar with a pestle. Genomic DNA was extracted from the ground material with a genomic DNA extracting reagent ISOPLANT (manufactured by NIPPON GENE) according to the manual attached thereto. PCR was carried out by using the genomic DNA as a template, an oligonucleotide primer composed of the nucleotide sequence represented by SEQ ID NO: 72 and an oligonucleotide primer composed of the nucleotide sequence represented by SEQ ID NO: 73 to amplify a DNA fragment (hereinafter referred to as the present CTP-CP4 EPSPS gene) containing a nucleotide sequence encoding a chloroplast transit peptide sequence of EPSPS of petunia (*Petunia hybrida*) (hereinafter referred to as CTP) and EPSPS gene of *Agrobacterium* (*Agrobacterium* sp. Strain CP4). The oligonucleotides were synthesized by using a DNA synthesizer (PE Applied Biosystems: Model 394 DNA/RNA Synthesizer) and purified with an oligonucleotide purification cartridge (PE Applied Systems: OPS Cartridge). The PCR was carried out by maintaining at 94° C. for 5 minutes, 55° C. for 2 minutes and then at 72° C. for 3 minutes, and further repeating a cycle for maintaining at 94° C. for 1 minute, at 55° C. for 2 minutes and then 72° C. for 3 minutes 38 times, and, finally, further maintaining at 94° C. for 1 minute, at 55° C. for 2 minutes and then 72° C. for 10 minutes. The amplified DNA fraction was ligated to a PCR product cloning site of plasmid pCR2.1 (manufactured Invitrogen), to construct the plasmid pCREPSPS (FIG. 28). Then, the plasmid was introduced in a competent cell of *E. coli* JM109 strain (manufactured by Takara Shuzo Co., Ltd.) to select an ampicillin resistant strain. The nucleotide sequence of the plasmid contained in the selected ampicillin resistant strain was determined by using Thermo Sequence II Dye Terminator kit (manufacture by Amersham Pharmacia Biotech) and DNA Sequencer 373S (manufactured by PE Applied Biosystems). As a result, the nucleotide sequence represented by SEQ ID NO: 74 was revealed and it was confirmed that the plasmid pCREPSPS contained the present CTP-CP4 EPSPS gene.

EXAMPLE 47

Introduction of Present CTP-CP4 EPSPS Gene into Tobacco

Figure 31:
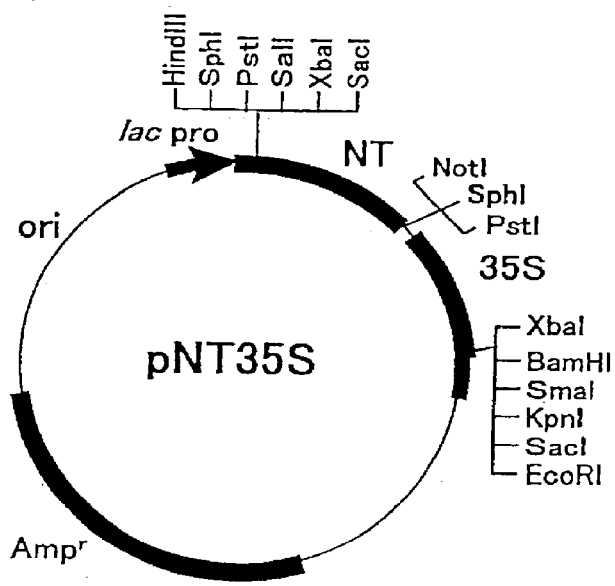
FIG. 31 is the restriction map of plasmid pNT35S. NT is the terminator sequence of a nopaline synthase, 35S is the 35S promoter of cauliflower mosaic virus, and lac pro is the promoter sequence of a lactose operon. Amp$^r$ is an ampicillin resistant gene and ori is the replication origin.
Figure 32:
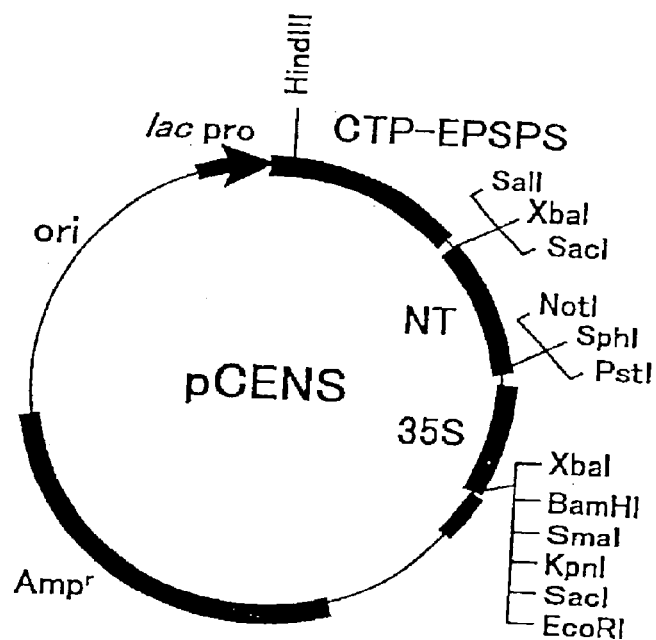
FIG. 32 is the restriction map of plasmid pCENS. CTP-EPSPS is a variant gene in which EPSPS gene derived from Agrobacterium is ligated to the downstream of a nucleotide sequence encoding a chloroplast transit peptide of EPSPS derived from petunia. NT is the terminator sequence of a nopaline synthase, 35S is the 35S promoter of cauliflower mosaic virus, and lac pro is the promoter sequence of a lactose operon. Amp$^r$ is an ampicillin resistant gene, ori is the replication origin.
Figure 33:
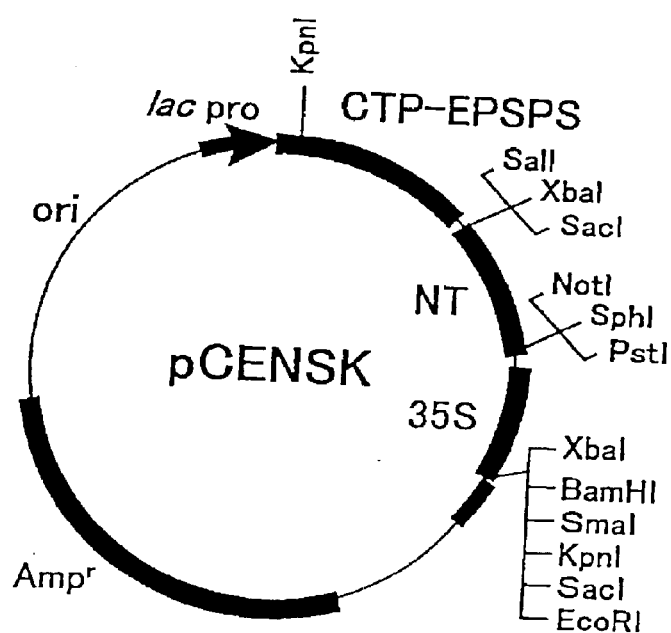
FIG. 33 is the restriction map of plasmid pCENSK. CTP-EPSPS is a variant gene in which EPSPS gene derived from Agrobacterium is ligated to the downstream of a nucleotide sequence encoding a chloroplast transit peptide of EPSPS derived from petunia. NT is the terminator sequence of a nopaline synthase, 35S is the 35S promoter of cauliflower mosaic virus, and lac pro is the promoter sequence of a lactose operon. Amp$^r$ is an ampicillin resistant gene, ori is the replication origin.
Figure 34:
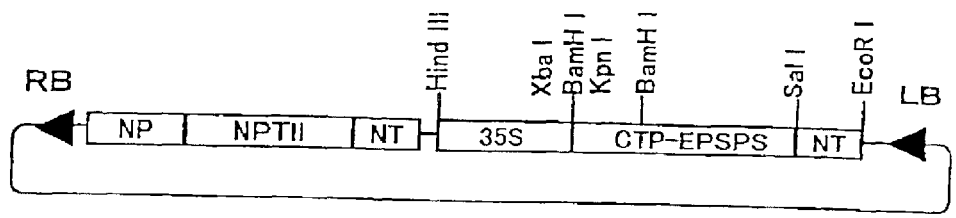
FIG. 34 is the restriction map of plasmid pBICE. CTP-EPSPS is a variant gene in which EPSPS gene derived from Agrobacterium is ligated to the downstream of a nucleotide sequence encoding a chloroplast transit peptide of EPSPS derived from petunia. NP is the promoter sequence of a nopaline synthase, NT is the terminator sequence of a nopaline synthase, and 35S is the 35S promoter of cauliflower mosaic virus. NPTII is a kanamycin resistant gene, and PB and LB are the right and left border sequences of T-DNA, respectively.

A plasmid was constructed for introducing the present CTP-CP4 EPSPS gene into a plant by *Agrobacterium* infection method. First, pNG01 [Shiota et al., (1994) Plant Physiol., 106:17–23] (FIG. 29) was digested with the restriction enzyme HindIII and nucleotides were added to the gap of the double-stranded DNA with DNA Polymerase I to blunt the end of the DNA, followed by self-cyclization with T4 DNA ligase to obtain pNG04 (FIG. 30). The plasmid pNG04 was digested with the restriction enzyme XbaI to obtain a DNA fragment containing the terminator of a nopaline synthase and 35S promoter located at the downstream thereof. The fragment was inserted in the XbaI restriction site of plasmid pUC19 (manufactured by Takara Shuzo Co., Ltd.) to obtain pNT35S (FIG. 31). Then, the plasmid pCREPSPS constructed in Example 46 was digested with the restriction enzymes HindIII and SalI and the resultant DNA fragment containing the present CTP-CP4 EPSPS gene was inserted between HindIII and SalI restriction sites of pNT35S to obtain the plasmid pCENS (FIG. 32). The plasmid pCENS was digested with the restriction enzyme HindIII and nucleotides were added to the gap of the double-stranded DNA with DNA Polymerase I to blunt the end of the DNA. The 5'-end of the DNA was dephosphorylated with treatment of alkaline phosphatase derived from calf small intestine, followed by insertion of phosphorylated KpnI linker (4668A manufactured by Takara Shuzo Co., Ltd.) therein and cyclization to obtain the plasmid pCENSK (FIG. 33). The plasmid pBI121KS constructed in Example 9 was digested with the restriction enzymes KpnI and SalI to remove β-glucuronidase gene and, instead thereof, a DNA fragment containing the present CTP-CP4 EPSPS gene, which was obtained by digesting the above plasmid pCENSK with the restriction enzymes KpnI and SalI, was inserted therein to construct the plasmid pBICE (FIG. 34) wherein the present CTP-CP4 EPSPS gene was ligated to the downstream of 35S promoter.

The plasmid pBICE was introduced into *Agrobacterium tumefaciens* LBA44044 (manufactured by Clontech) and this was cultured in LB medium (0.5% yeast extract, 1.0% Bacto tryptone, 0.5% NaCl) containing 300 µg/ml of streptomycin, 100 µg/ml of rifampicin and 25 µg/ml of kanamycin, followed by selection of a transformant to isolate an *Agrobacterium* strain bearing pBICE.

Tobacco leaf pieces cultivated sterilely were infected with the *Agrobacterium* strain and, according to the same manner as in Example 5, tobacco bearing the inserted present CTP-CP4 EPSPS gene was obtained.

EXAMPLE 48

Figure 35:
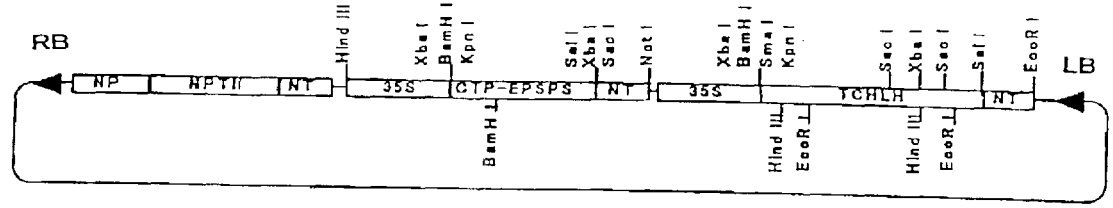
FIG. 35 is the restriction map of plasmid pBICETCH. CTP-EPSPS is a variant gene in which EPSPS gene derived from Agrobacterium is ligated to the downstream of a nucleotide sequence encoding a chloroplast transit peptide of EPSPS derived from petunia. TCHLH is protoporphyrin IX binding subunit gene of tabacco magnesium chelatase whose chloroplast transit singal has been deleted. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Introduction of Present CTP-CP4 EPSPS Gene and Gene Encoding Variant Tobacco Chelatase Subunit into Tobacco A plasmid was constructed for introducing the present CTP-CP4 EPSPS gene and a gene encoding a variant tobacco chelatase subunit into a plant by *Agrobacterium* infection method. First, the plasmid pCENSK constructed in Example 47 was digested with the restriction enzyme KpnI to obtain a DNA fragment containing the present CTP-CP4 EPSPS gene, a terminator of a gene encoding nopaline synthase located at the downstream thereof and 35S promoter located at the downstream of the terminator. This was inserted into the KpnI restriction site of the plasmid pBITCHLH constructed in Example 9 to construct the plasmid pBICETCH (FIG. 35) wherein the present CTP-CP4 EPSPS gene and the gene encoding the variant tobacco chelatase subunit were ligated to the downstream of 35S promoter, respectively.

The plasmid pBICETCH was introduced into *Agrobacterium tumefaciens* LBA44044 and this was cultured in LB medium containing 300 µg/ml of streptomycin, 100 µg/ml of rifampicin and 25 µg/ml of kanamycin, followed by selection of a transformant to isolate an *Agrobacterium* strain bearing pBICETCH.

Tobacco leaf pieces cultivated sterilely were infected with the *Agrobacterium* strain and, according to the same manner as described in Example 5, tobacco bearing the inserted present CTP-CP4 EPSPS gene and gene encoding the variant tobacco chelatase subunit was obtained.

EXAMPLE 49

Confirmation of Resistance to Herbicidal Compounds of Tobacco Bearing Introduced Present CTP-CP4 EPSPS Gene as well as Tobacco Bearing Introduced Present CTP-CP4 EPSPS Gene and Gene Encoding Variant Tobacco Chelatase Subunit Leaves of the tobacco bearing the introduced present CTP-CP4 EPSPS gene produced in Example 47, those of the control recombinant tobacco obtained in Example 5 and those bearing the introduced present CTP-CP4 gene and gene encoding the variant tobacco chelatase subunit produced in Example 48 are collected, and each leaf is divided into the right and left equivalent pieces along the main vein. One of the pieces is treated with an aqueous solution containing 0.3 ppm PPO inhibitory-type herbicidal compound of Structure 8, while to the other piece is not treated with the compound. These leaf pieces are placed on MS medium containing 0.8% agar and allowed to stand at room temperature for 7 days in a light place. Then, each leaf piece is ground in 5 ml of 80% aqueous acetone solution in a mortar with a pestle to extract chlorophyll. The extract is diluted 10 times with 80% aqueous acetone solution and the absorbance is measured at 750 nm, 663 nm and 645 nm to calculate the total chlorophyll content according to the method described by Macknney G., J. Biol. Chem. (1941) 140, p 315. The resistant level to the herbicidal compound tested is represented by the percentage of the total chlorophyll content of the leave piece treated with the herbicidal compound to that of untreated leaf piece.

Similarly, the tobacco bearing the introduced present CTP-CP4 EPSPS gene, the tobacco bearing the introduced both present CTP-CP4 EPSPS gene and gene encoding the variant tobacco chelatase subunit, and the control recombinant tobacco are treated with an aqueous solution containing 100 ppm of a glyphosate to determine the resistant level to the glyphosate. The resistant level to the glyphosate is represented by the percentage of the total chlorophyll content of the leave piece treated with the glyphosate to that of untreated leaf piece.

EXAMPLE 50

Figure 36:
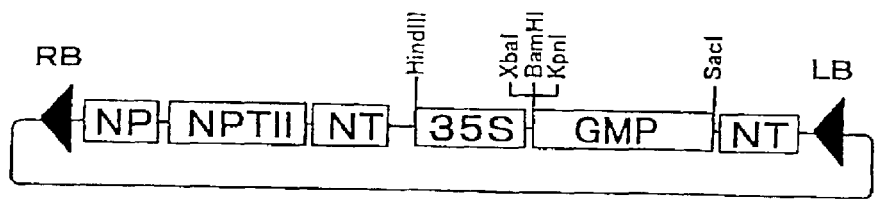
FIG. 36 is the restriction map of plasmid pBIGMP. GMP is soybean PPO gene whose chloroplast transit signal and FAD binding sequence have been deleted. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Introduction of Present CTP-CP4 EPSPS Gene and Gene Encoding Variant Soybean PPO into Tobacco A plasmid was constructed for introducing the present CTP-CP4 EPSPS gene and a gene encoding a variant soybean PPO into a plant by *Agrobacterium* infection method. According to the same manner as described in Example 11, PCR was carried out by using an oligonucleotide primer composed of the nucleotide sequence represented by SEQ ID NO: 75, an oligonucleotide primer composed of the nucleotide sequence represented by SEQ ID NO: 76, and the plasmid pSPPO-P constructed in Example 3 as a template to amplify a DNA fragment containing the gene encoding the variant soybean PPO. Then, the plasmid pBI121K constructed in Example 9 was digested with restriction enzymes KpnI and SacI to remove β-glucuronidase gene and, instead thereof, a DNA fragment obtained by digesting the above DNA fragment containing the gene encoding the variant soybean PPO with the restriction enzymes KpnI and SacI was inserted therein to construct the plasmid pBIGMP (FIG. 36) wherein the gene was ligated to the downstream of the 35S promoter.

Figure 37:
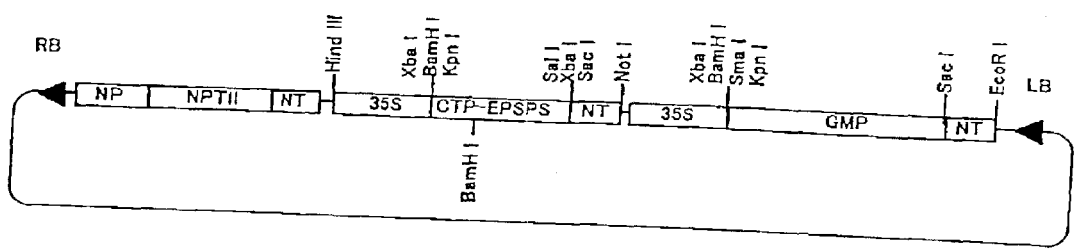
FIG. 37 is the restriction map of plasmid pBICEGMP. CTP-EPSPS is a chimera gene in which EPSPS gene derived from Agrobacterium is ligated to the downstream of a nucleotide sequence encoding a chloroplast transit peptide of EPSPS derived from petunia. GMP is soybean PPO gene whose chloroplast transit signal and FAD binding gene have been deleted. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Then, the plasmid pCENSK constructed in Example 47 is digested with the restriction enzyme KpnI to obtain a DNA fragment containing the present CTP-CP4 EPSPS gene, the terminator of the gene encoding nopaline synthase located at the downstream of the gene and the 35S promoter located at the downstream of the terminator, followed by insertion of it in the KpnI restriction site of the above plasmid pBIGMP to construct the plasmid pBICEGMP (FIG. 37) wherein the present CTP-CP4 EPSPS gene and the gene encoding the variant soybean PPO are ligated to the downstream of the 35S promoter, respectively.

The plasmid pBICEGMP is introduced into *Agrobacterium tumefaciens* LBA44044 and this is cultured in LB medium containing 300 μg/ml of streptomycin, 100 μg/ml of rifampicin and 25 μg/ml of kanamycin, followed by selection of a transformant to isolate an *Agrobacterium* strain bearing pBICEGMP.

Tobacco leaf pieces cultivated sterilely are infected with the *Agrobacterium* strain and, according to the same manner as in Example 5, tobacco bearing the introduced present CTP-CP4 EPSPS gene and gene encoding the variant soybean PPO is obtained.

EXAMPLE 51

Confirmation of Resistance to Herbicidal Compound of Tobacco Bearing Introduced Present CTP-CP4 EPSPS Gene and Gene Encoding Variant Soybean PPO The levels of resistance to the PPO inhibitory-type herbicidal compound represented by structure 8 are confirmed quantitatively by testing the tobacco bearing the introduced present CTP-CP4 EPSPS gene and gene encoding the variant soybean PPO obtained in Example 50, and the control recombinant tobacco obtained in Example 5 according to the same manner as in Example 49.

Further the levels of resistance to glyphosate are confirmed quantitatively by testing the tobacco bearing introduced the present CTP-CP4 EPSPS gene and the gene encoding the variant soybean PPO and the control recombinant tobacco according to the same manner as in Example 49.

EXAMPLE 52

Figure 38:
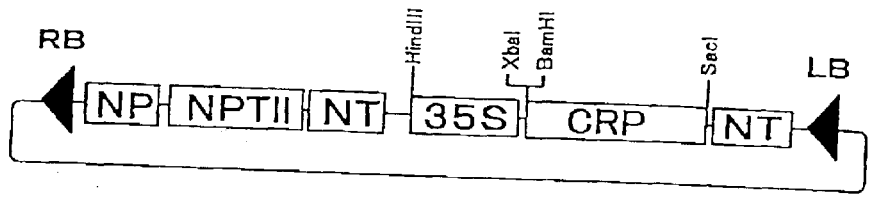
FIG. 38 is the restriction map of plasmid pBICRP. CRP is PPO gene of Chlamydomonas reinhardtii whose chloroplast transit signal and FAD binding sequence have been deleted. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Introduction of Present CTP-CP4 EPSPS Gene and Gene Encoding Variant *Chlamydomonas reinhardtii* PPO into Tobacco A plasmid was constructed for introducing the present CTP-CP4 EPSPS gene and a gene encoding a variant *Chlamydomonas reinhardtii* PPO into a plant by *Agrobacterium* infection method. The plasmid pTVCRP constructed in Example 16 was digested with the restriction enzymes BamHI and SacI to prepare a DNA fragment containing a gene encoding a variant *Chlamydomonas reinhardtii* PPO. Binary vector pBI121 (manufactured by Clontech) was digested with the restriction enzymes BamHI and SacI to remove β-glucuronidase gene and, instead thereof, the above DNA fragment containing the gene encoding the variant *Chlamydomonas reinhardtii* PPO was inserted therein to construct the plasmid pBICRP (FIG. 38) wherein the gene was ligated to the downstream of the 35S promoter.

Figure 39:
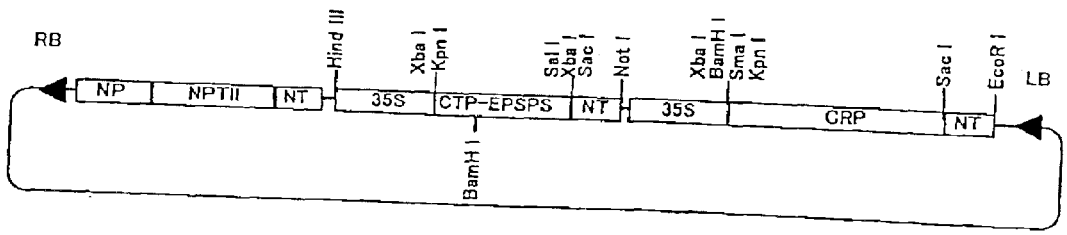
FIG. 39 is the restriction map of plasmid pBICECRP. CTP-EPSPS is a variant gene in which EPSPS gene derived from Agrobacterium is ligated to the downstream of a nucleotide sequence encoding a chloroplast transit peptide of EPSPS derived from petunia. CRP is PPO gene of Chlamydomonas reinhardtii whose chloroplast transit signal and FAD binding sequence have been deleted. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Then, the plasmid pBICRP is digested with the restriction enzyme BamHI and nucleotides are added to the gap of the double-stranded DNA with DNA Polymerase I to blunt the end of the DNA. The 5'-end of the DNA is dephosphorylated by treatment with an alkaline phosphatase derived from calf small intestine, followed by inserting a phosphorylated KpnI linker (4668A manufactured by Takara Shuzo Co., Ltd.) and cyclization to obtain plasmid pBICRPK. Then, the plasmid pCENSK constructed in Example 47 is digested with the restriction enzyme KpnI to obtain a DNA fragment containing the present CTP-CP4 EPSPS gene, the terminator of the gene encoding nopaline synthase located at the downstream of the present CTP-CP4 EPSPS gene and the 35S promoter located at the downstream of the terminator. This is inserted in the KpnI restriction site of the above plasmid pBICRPK to construct the plasmid pBICECRP (FIG. 39) wherein the present CTP-CP4 EPSPS gene and the gene encoding the variant *Chlamydomonas reinhardtii* PPO are ligated to the downstream of 35S promoter, respectively.

The plasmid pBICECRP is introduced into *Agrobacterium tumefaciens* LBA44044 and this is cultured in LB medium containing 300 μg/ml of streptomycin, 100 μg/ml of rifampicin and 25 μg/ml of kanamycin, followed by selection of a transformant to isolate an *Agrobacterium* strain bearing pBICECRP.

Tobacco leaf pieces cultivated sterilely are infected with the *Agrobacterium* strain and, according to the same manner as described in Example 5, tobacco bearing the introduced present CTP-CP4 EPSPS gene and gene encoding the variant *Chlamydomonas reinhardtii* PPO is obtained.

EXAMPLE 53

Confirmation of Resistance to Herbicidal Compounds of Tobacco Bearing Introduced Present CTP-CP4 EPSPS Gene and Gene Encoding Variant *Chlamydomonas reinhardtii* PPO The levels of resistance to the above PPO inhibitory-type herbicidal compound represented by Structure 8 are confirmed quantitatively by testing the tobacco bearing the introduced present CTP-CP4 EPSPS gene and gene encoding the variant *Chlamydomonas reinhardtii* PPO obtained in Example 52 and the control recombinant tobacco obtained in Example 5 according to the same manner as in Example 49.

Further the levels of resistance to glyphosate are confirmed quantitatively by testing the tobacco bearing the introduced present CTP-CP4 EPSPS gene and gene encoding the variant *Chlamydomonas reinhardtii* PPO and the control recombinant tobacco according to the same manner as in Example 49.

EXAMPLE 54

Figure 40:
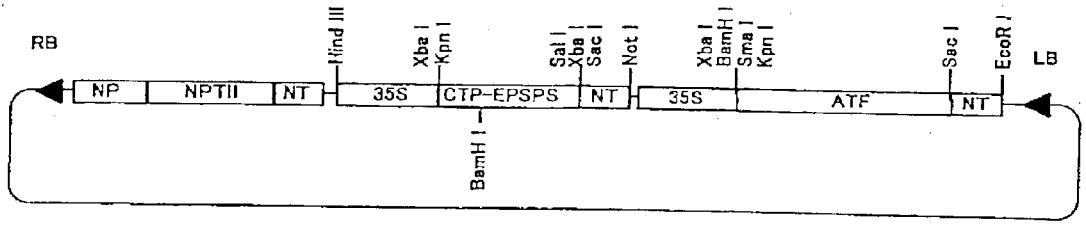
FIG. 40 is the restriction map of plasmid pBICEATF. CTP-EPSPS is a variant gene in which EPSPS gene derived from Agrobacterium is ligated to the downstream of a nucleotide sequence encoding a chloroplast transit peptide of EPSPS originated from petunia. ATF is chloroplast-localized type ferrochelatase gene of Arobidopsis thliana. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Introduction of Present CTP-CP4 EPSPS Gene and Gene Encoding Chloroplast-Localized Type Ferrochelatase of *Arabidopsis thaliana* into Tobacco The plasmid pBIATF constructed in Example 39 is digested with the restriction enzyme BamHI and then nucleotides are added in the gap of the double-stranded DNA with DNA polymerase I to blunt the end of the DNA. The 5'-end of the DNA is dephosphorylated by treatment with an alkaline phosphatase derived from calf small intestine, followed by insertion of a phosphorylated KpnI linker (4668A manufactured by Takara Shuzo Co., Ltd.) and cyclization to obtain the plasmid pBIATFK. Then, the plasmid pCENSK constructed in Example 47 is digested with the restriction enzyme KpnI to obtain a DNA fragment containing the present CTP-CP4 EPSPS gene, the terminator of the gene encoding nopaline synthase located at the downstream of the present CTP-CP4 EPSPS gene and the 35S promoter located at the downstream of the terminator. This is inserted in the KpnI restriction site of the above plasmid pBIATFK to construct the plasmid pBICEATF (FIG. 40) wherein the present CTP-CP4 EPSPS gene and the gene encoding the chloroplast-localized type ferrochelatase of *Arabidopsis thaliana* are ligated to the downstream of 35S promoter, respectively.

The plasmid pBICEATF is introduced into *Agrobacterium tumefaciens* LBA44044 and this is cultured in LB medium containing 300 µg/ml of streptomycin, 100 µg/ml of rifampicin and 25 µg/ml of kanamycin, followed by selection of a transformant to isolate an *Agrobacterium* strain bearing pBICEATF.

Tobacco leaf pieces cultivated sterilely are infected with the *Agrobacterium* strain and, according to the same manner as described in Example 5, tobacco bearing the inserted present CTP-CP4 EPSPS gene and gene encoding the chloroplast-localized type ferrochelatase of *Arabidopsis thaliana* is obtained.

EXAMPLE 55

Confirmation of Resistance to Herbicidal Compounds of Tobacco Bearing Introduced Present CTP-CP4 EPSPS Gene and Gene Encoding Chloroplast-Localized Type Ferrochelatase of *Arabidopsis thaliana*

The levels of resistance to the above PPO inhibitory-type herbicidal compound represented by Structure 8 are confirmed quantitatively by testing the tobacco bearing the introduced present CTP-CP4 EPSPS gene and gene encoding the chloroplast-localized type ferrochelatase of *Arabidopsis thaliana* obtained in Example 54, and the control recombinant tobacco obtained in Example 5 according to the same manner as in Example 49.

Further the levels of resistance to glyphosate are confirmed quantitatively by testing the tobacco bearing the introduced present CTP-CP4 EPSPS gene and gene encoding the chloroplast-localized type ferrochelatase of *Arabidopsis thaliana* and the control recombinant tobacco according to the same manner as in Example 49.

EXAMPLE 56

Figure 41:
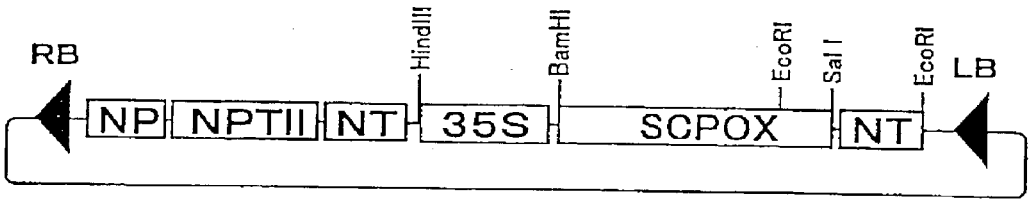
FIG. 41 is the restriction map of plasmid pBISCPOX. SCPOX is soybean coproporphyrinogen III oxydase gene. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Introduction of Present CTP-CP4 EPSPS Gene and Gene Encoding Present Soybean CPOX into Tobacco A plasmid was constructed for introducing the present CTP-CP4 EPSPS gene and a gene encoding the present soybean CPOX into a plant by *Agrobacterium* infection method. First, the plasmid pCRSCPOX constructed in Example 42 was digested with the restriction enzyme BamHI to prepare a DNA fragment containing a gene encoding the present soybean CPOX. The DNA fragment was inserted in the BamHI restriction site of the plasmid pBI121KS constructed in Example 9 to obtain the plasmid pBISCPOXGUS. This plasmid was digested with the restriction enzyme SalI to remove β-glucuronidase gene, followed by self-cyclization to construct the plasmid pBISCPOX (FIG. 41) wherein the gene was ligated to the downstream of the 35S promoter.

Figure 42:
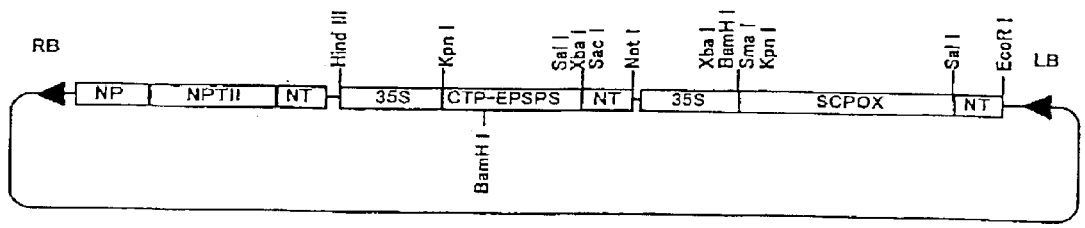
FIG. 42 is the restriction map of plasmid pBICESCPOX. CTP-EPSPS is a variant gene in which EPSPS gene derived from Agrobacterium is ligated to the downstream of a nucleotide sequence encoding a chloroplast transit peptide of EPSPS derived from petunia. SCPOX is soybean coproporphyrinogen III oxydase gene. NP is the promoter sequence of a nopaline synthase, NT is the terminator sequence of a nopaline synthase, and 35S is the 35S promoter of cauliflower mosaic virus. NPTII is a kanamycin resistant gene, and RB and LB are the right and left border sequences of T-DNA, respectively.

Then, the plasmid pBISCPOX is digested with the restriction enzyme BamHI and nucleotides are added to the gap of the double-stranded DNA with DNA polymerase I to blunt the end of the DNA. The 5'-end of the DNA is dephosphorylated by treatment with an alkaline phosphatase derived from calf small intestine, followed by inserting a phosphorylated KpnI linker (4668A manufactured by Takara Shuzo Co., Ltd.) therein and cyclization to obtain the plasmid pBISCPOXK. Then, the plasmid pCENSK constructed in Example 47 is digested with the restriction enzyme KpnI to obtain a DNA fraction containing the present CTP-CP4 EPSPS gene, the terminator of the gene encoding nopaline synthase located at the downstream of the present CTP-CP4 EPSPS gene and the 35S promoter located at the downstream of the terminator. This is inserted in the KpnI restriction site of the above plasmid pBISCPOXK to construct the plasmid pBICESCPOX (FIG. 42) wherein the present CTP-CP4 EPSPS gene and the gene encoding the present soybean CPOX are ligated to the downstream of 35S promoter, respectively.

The plasmid pBICESCPOX is introduced into *Agrobacterium tumefaciens* LBA44044 and this is cultured in LB medium containing 300 µg/ml of streptomycin, 100 µg/ml of rifampicin and 25 µg/ml of kanamycin, followed by selection of a transformant to isolate an *Agrobacterium* strain bearing pBICESCPOX.

Tobacco leaf pieces cultivated sterilely are infected with the *Agrobacterium* strain and, according to the same manner as described in Example 45, tobacco bearing the inserted present CTP-CP4 EPSPS gene and gene encoding the present soybean CPOX is obtained.

EXAMPLE 57

Confirmation of Resistance to Herbicidal Compounds of Tobacco Bearing Introduced Present CTP-CP4 EPSPS Gene and Gene Encoding Present Soybean CPOX The levels of resistance to the above PPO inhibitory-type herbicidal compound represented by Structure 8 are confirmed quantitatively by testing the tobacco bearing the introduced present CTP-CP4 EPSPS gene and gene encoding the present soybean CPOX obtained in Example 56, and the control recombinant tobacco according to the same manner as in Example 49.

Further the levels of resistance to glyphosate are confirmed quantitatively by testing the tobacco bearing the introduced present CTP-CP4 EPSPS gene and gene encoding the present soybean CPOX and the control recombinant tobacco according to the same manner as in Example 49.

As described hereinabove, according to the present invention, weed control compound-resistant plant can be produced.

What is claimed is:

1. A method for producing a transgenic plant which is resistant to a weed control compound, comprising the steps of:

introducing into a plant cell, a nucleotide sequence encoding a variant of plant protoporphyrinogen IX oxidase that lacks the FAD binding sequence;

expressing the nucleotide sequence; and regenerating said plant cell into a transgenic plant.

2. The method according to claim 1, wherein the nucleotide sequence is operably ligated to a promoter sequence and a terminator sequence both of which are functional in the plant cell.

3. The method according to claim 1, wherein the variant of plant protoporphyrinogen IX oxidase is derived from soybean.

4. The method according to claim 1, wherein the weed control compound inhibits porphyrin biosynthesis of a plant.

5. The method according to claim 1, wherein the weed control compound is a protoporphyrinogen IX oxidase inhibitory-type herbicidal compound.

6. The method according to claim 1, wherein said variant further lacks the chloroplast transit signal.

7. The method according to claim 1, wherein the weed control compound is a protoporphyrinogen IX oxidase inhibitory-type herbicidal compound selected from the compounds of (1) to (3) below:

(1) chlormethoxynil, bifenox, chlornitrofen, acifluorfen and its ethyl ester, acifluorfen-sodium, oxyfluorfen, oxadiazon, 2-[4-chloro-2-fluoro-5-(prop-2-ynyloxy) phenyl]-2,3,4,5,6,7 hexahydro-1H-isoindol-1,3-dione, chlorphthalim, TNPP-ethyl, or N3-(1-phenylethyl)-2,6-dimethyl-5-propyonylnicotinamide;

(2) a compound represented by the general formula: J-G (I), wherein G is a group represented by any one of the following general formulas G-1 to G-9 and J is a group represented by any one of the following general formulas J-1 to J-30:

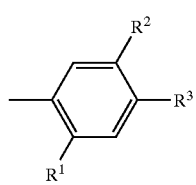

G-1

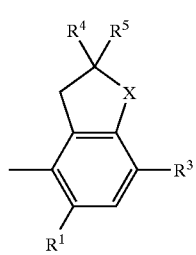

G-2

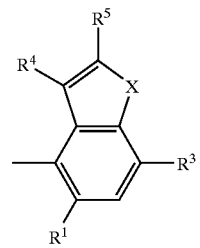

G-3

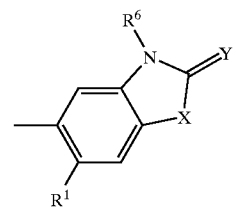

G-4

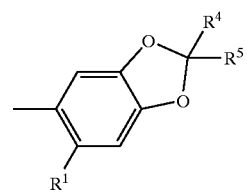

G-5

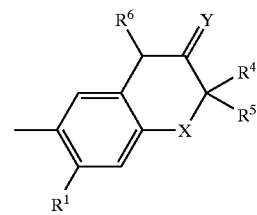

G-6

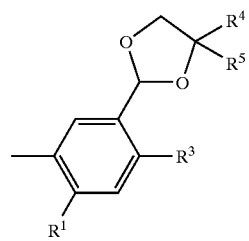

G-7

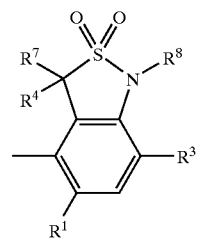

G-8

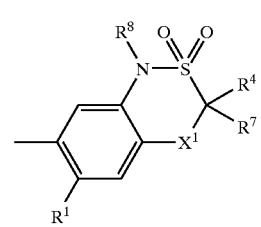

G-9

-continued
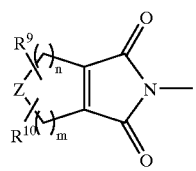 J-1
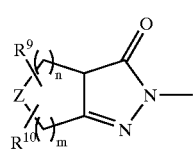 J-2
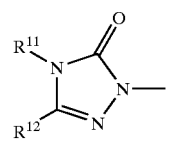 J-3
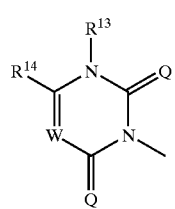 J-4
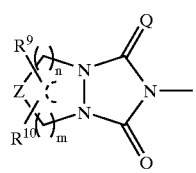 J-5
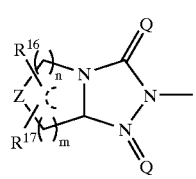 J-6
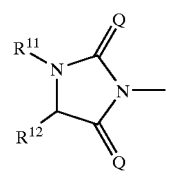 J-7
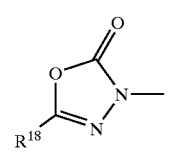 J-8
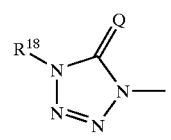 J-9
-continued
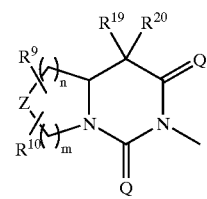 J-10
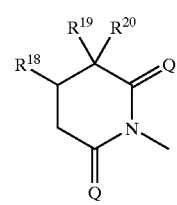 J-11
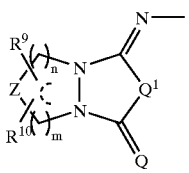 J-12
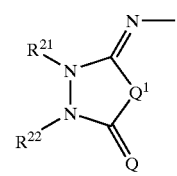 J-13
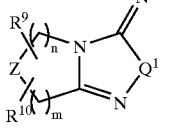 J-14
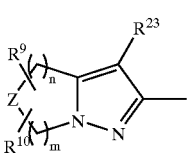 J-15
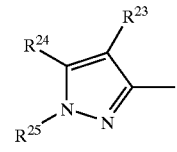 J-16
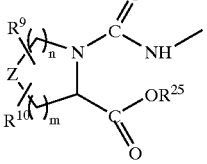 J-17
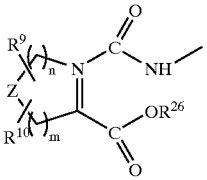 J-18

J-19

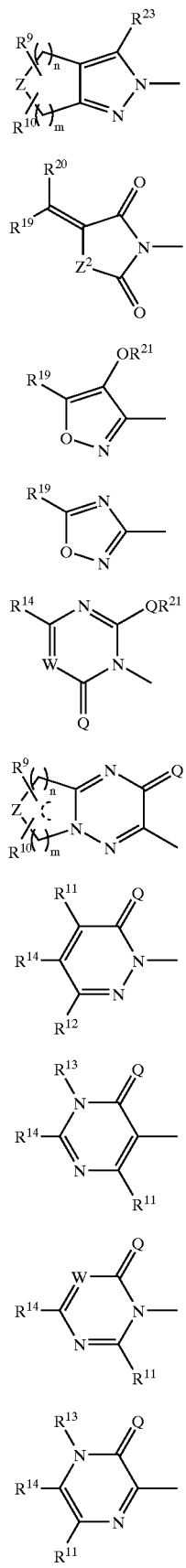

J-20

J-21

J-22

J-23

J-24

J-25

J-26

J-27

J-28

J-29

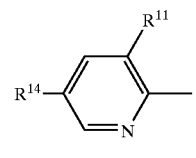

J-30

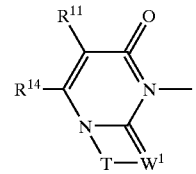

wherein the dotted lines in the formulas J-5, J-6, J-12 and J-24 represent that the left hand ring contains only single bonds, or one bond in the ring is a double bond between carbon atoms;

X is oxygen atom or sulfur atom;

Y is oxygen atom or sulfur atom;

R1 is hydrogen atom or halogen atom;

R2 is hydrogen atom, C1–C8alkyl group, C1–C8 haloalkyl group, halogen atom, OH group, OR27 group, SH group, S(O)pR27 group, COR27 group, CO2R27 group, C(O)SR27 group, C(O)NR29R30 group, CHO group, CR27=NOR36 group, CH=CR37CO2R27 group, CH2CHR37CO2R27 group, CO2N=CR31R32 group, nitro group, cyano group, NHSO2R33 group, NHSO2NHR33 group, NR27R38 group, NH2 group or phenyl group optionally substituted with one or more and the same or different C1–C4 alkyl groups;

p is 0, 1 or 2;

R3 is C1–C2 alkyl group, C1–C2 haloalkyl group, OCH3 group, SCH3 group, OCHF2 group, halogen atom, cyano group or nitro group;

R4 is hydrogen atom, C1–C3 alkyl group, C1–C3 haloalkyl group or halogen atom;

R5 is hydrogen atom, C1–C3 alkyl group, halogen atom, C1–C3 haloalkyl group, cyclopropyl group, vinyl group, C2 alkynyl group, cyano group, C(O)R38 group, CO2R38 group, C(O)NR38R39 group, CR34R35CN group, CR34R35C(O)R38 group, CR34R35CO2R38 group, CR34R35C(O)NR38R39 group, CHR34OH group, CHR34OC(O)R38 group or OCHR34OC(O)NR38R39 group, or, when G is G-2 or G-6, R4 and R5 may form C=O group together with the carbon atom to which they are attached;

R6 is C1–C6 alkyl group, C1–C6 haloalkyl group, C2–C6 alkoxyalkyl group, C3–C6 alkenyl group or C3–C6 alkynyl group;

X1 is single bond, oxygen atom, sulfur atom, NH group, N(C1–C3 alkyl), N(C1–C3 haloalkyl) group or N(allyl) group;

R7 is hydrogen atom, C1–C6 alkyl group, C1–C6 haloalkyl group, halogen atom, S(O)2(C1–C6alkyl) group or C(=O)R40 group;

R8 is hydrogen atom, C1–C8 alkyl group, C3–C8 cycloalkyl group, C3–C8 alkenyl group, C3–C8 alkynyl group, C1–C8 haloalkyl group, C2–C8 alkoxyalkyl group, C3–C8 alkoxyalkoxyalkyl group, C3–C8 haloalkynyl group, C3–C8 haloalkenyl group, C1–C8 alkylsulfonyl group, C1–C8 haloalkylsulfonyl group, C3–C8 alkoxycarbonylalkyl group, S(O)2NH(C1–C8 alkyl) group, C(O)R41 group or benzyl group whose phenyl ring may be substituted with R42;

n and m are independently 0, 1, 2 or 3 and m+n is 2 or 3;

Z is CR9R10 group, oxygen atom, sulfur atom, S(O) group, S(O)2 group or N(C1–C4 alkyl) group;

each R9 is independently hydrogen atom, C1–C3 alkyl group, halogen atom, hydroxyl group, C1–C6 alkoxy group, C1–C6 haloalkyl group, C1–C6 haloalkoxy group, C2–C6 alkylcarbonyloxy group or C2–C6 haloalkylcarbonyloxy group;

each R10 is independently hydrogen atom, C1–C3 alkyl group, and hydroxyl group or halogen atom;

R11 and R12 are independently hydrogen atom, halogen atom, C1–C6 alkyl group, C3–C6 alkenyl group or C1–C6 haloalkyl group;

R13 is hydrogen atom, C1–C6 alkyl group, C1–C6 haloalkyl group, C3–C6 alkenyl group, C3–C6 haloalkenyl group, C3–C6 alkynyl group, C3–C6 haloalkynyl group, HC(=O) group, (C1–C4 alkyl)C(=O) group or NH2 group;

R14 is C1–C6 alkyl group, C1–C6 alkylthio group, C1–C6 haloalkyl group or N(CH3)2 group;

W is nitrogen atom or CR15;

R15 is hydrogen atom, C1–C6 alkyl group, halogen atom, or phenyl group optionally substituted with C1–C6 alkyl group, one or two halogen atoms, C1–C6 alkoxy group or CF3 group;

each Q is independently oxygen atom or sulfur atom;

Q1 is oxygen atom or sulfur atom;

Z1 is CR16R17 group, oxygen atom, sulfur atom, S(O) group, S(O)2 group or N(C1–C4alkyl) group;

each R16 is independently hydrogen atom, halogen atom, hydroxyl group, C1–C6 alkoxy group, C1–C6 haloalkyl group, C1–C6 haloalkoxy group, C2–C6 alkylcarbonyloxy group or C2–C6 haloalkylcarbonyloxy group;

each R17 is independently hydrogen atom, hydroxyl group or halogen atom;

R18 is C1–C6 alkyl group, halogen atom or C1–C6 haloalkyl group;

R19 and R20 are independently hydrogen atom, C1–C6 alkyl group, or C1–C6 haloalkyl group;

Z2 is oxygen atom, sulfur atom, NR9 group or CR9R10 group;

R21 and R22 are independently C1–C6 alkyl group, C1–C6 haloalkyl group, C3–C6 alkenyl group, C3–C6 haloalkenyl group, C3–C6 alkynyl group or C3–C6 haloalkynyl group;

R23 is hydrogen atom, halogen atom or cyano group;

R24 is C1–C6 alkylsulfonyl group, C1–C6 alkyl group, C1–C6 haloalkyl group, C3–C6 alkenyl group, C3–C6 alkynyl group, C1–C6 alkoxy group, C1–C6 haloalkoxy group or halogen atom;

R25 is C1–C6 alkyl group, C1–C6 haloalkyl group, C3–C6 alkenyl group or C3–C6 alkynyl group;

R26 is C1–C6 alkyl group, C1–C6 haloalkyl group or phenyl group optionally substituted with C1–C6 alkyl, one or two halogen atoms, one or two nitro groups, C1–C6 alkoxy group or CF3 group;

W1 is nitrogen atom or CH group;

T is a group represented by any one of the following general formulas T-1, T-2 and T-3;

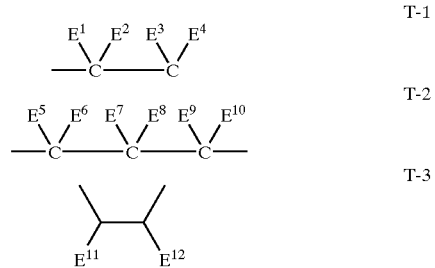

(wherein E1, E2, E3, E4, E5, E6, E7, E8, E9, E10, E11 and E12 are independently hydrogen atom or C1–C3 alkyl group);

R27 is C1–C8 alkyl group, C3–C8 cycloalkyl group, C3–C8 alkenyl group, C3–C8alkynyl group, C1–C8 haloalkyl group, C2–C8 alkoxyalkyl group, C2–C8 alkylthioalkyl group, C2–C8 alkylsulfinylalkyl group, C2–C8 alkylsulfonylalkyl group, C1–C8 alkylsulfonyl group, phenylsulfonyl group whose phenyl ring may be substituted with at least one substituent selected from the group consisting of halogen atom and C1–C4 alkyl group, C4–C8 alkoxyalkoxyalkyl group, C4–C8 cycloalkylalkyl group, C6–C8 cycloalkoxyalkyl group, C4–C8 alkenyloxyalkyl group, C4–C8 alkynyloxyalkyl group, C3–C8 haloalkoxyalkyl group, C4–C8 haloalkenyloxyalkyl group, C4–C8 haloalkynyloxyalkyl group, C6–C8 cycloalkylthioalkyl group, C4–C8 alkenylthioalkyl group, C4–C8 alkynylthioalkyl group, C1–C4 alkyl group substituted with phenoxy group whose ring is substituted with at least one substituent selected from the group consisting of halogen atom, C1–C3 alkyl group and C1–C3 haloalkyl group, benzyloxy group whose ring is substituted with at least one substituent selected from the group consisting of halogen atom, C1–C3 alkyl group and C1–C3 haloalkyl group, C4–C8 trialkylsilylalkyl group, C3–C8 cyanoalkyl group, C3–C8 halocycloalkyl group, C3–C8 haloalkenyl group, C5–C8 alkoxyalkenyl group, C5–C8 haloalkoxyalkenyl group, C5–C8 alkylthioalkenyl group, C3–C8 haloalkynyl group, C5–C8 alkoxyalkynyl group, C5–C8 haloalkoxyalkynyl group, C5–C8 alkylthioalkynyl group, C2–C8 alkylcarbonyl group, benzyl group whose ring is substituted with at least one substituent selected from the group consisting of halogen atom, C1–C3 alkyl group and C1–C3 haloalkyl group, CHR34COR28 group, CHR34COOR28 group, CHR34P(O) (OR28)2 group, CHR34P(S) (OR28)2 group, CHR34C(O)NR29R30 group or CHR34C(O)NH2 group;

R28 is C1–C6 alkyl group, C2–C6 alkenyl group, C3–C6 alkynyl group or tetrahydrofuranyl group;

R29 and R31 are independently hydrogen atom or C1–C4 alkyl group;

R30 and R32 are independently C1–C4 alkyl group or phenyl group whose ring may be substituted with at least one substituent selected from the group consisting of halogen atom, C1–C3 alkyl group and C1–C3 haloalkyl group; or, R29 and R30 together may form —(CH2)5-, —(CH2)4- or —CH2CH2OCH2CH2-, or the ring thus formed may be substituted with at least one substituent selected from the group consisting of C1–C3 alkyl group, phenyl group and benzyl group; or, R31 and R32 may from C3–C8 cycloalkyl group together with the carbon atom to which they are attached;

R33 is C1–C4 alkyl group, C1–C4 haloalkyl group or C3–C6 alkenyl group;

R34 and R35 are independently hydrogen atom or C1–C4 alkyl group;

R36 is hydrogen atom, C1–C6 alkyl group, C3–C6 alkenyl group or C3–C6 alkynyl group;

R37 is hydrogen atom, C1–C4 alkyl group or halogen atom;

R38 is hydrogen atom, C1–C6 alkyl group, C3–C6 cycloalkyl group, C3–C6 alkenyl group, C3–C6 alkynyl group, C2–C6 alkoxyalkyl group, C1–C6 haloalkyl group, phenyl group whose ring may be substituted with at least one substituent selected from the group consisting of halogen atom, C1–C4 alkyl group and C1–C4 alkoxy group, —CH2CO2(C1–C4 alkyl) group or —CH(CH3)CO2(C1–C4 alkyl) group;

R39 is hydrogen atom, C1–C2 alkyl group or C(O)O (C1–C4 alkyl) group;

R40 is hydrogen atom, C1–C6 alkyl group, C1–C6 alkoxy group or NH(C1–C6 alkyl) group;

R41 is C1–C6 alkyl group, C1–C6 haloalkyl group, C1–C6 alkoxy group, NH(C1–C6 alkyl) group, phenyl group whose ring may be substituted with one substituent selected from the group consisting of R42 group, benzyl group and C2–C8 dialkylamino group; and R42 is C1–C6 alkyl group, one or two halogen atoms, C1–C6 alkoxy group or CF3 group;

(3) a compound of the formula (II):

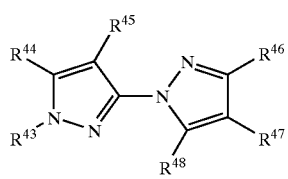

or nipilacrofen, wherein R43 is C1–C4 alkyl group;

R44 is C1–C4 alkyl group, C1–C4 alkylthio group, C1–C4 alkoxy group, C1–C4 haloalkyl group, C1–C4 haloalkylthio group or C1–C4 haloalkoxy group;

R43 and R44 together may form —(CH2)3- or —(CH2)4-;

R45 is hydrogen atom or halogen atom;

R46 is hydrogen atom or C1–C4 alkyl group;

R47 is hydrogen atom, nitro group, cyano group, —COOR49 group, —C(=X)NR50R51 group or —C(=X2)R52 group;

R48 is hydrogen atom, halogen atom, cyano group, C1–C4 alkyl group optionally substituted with at least one substituent selected from the group consisting of halogen atom and hydroxyl group, C1–C4 alkoxy group, phenyl group optionally substituted with at least one substituent selected from the group consisting of halogen atom, nitro group, cyano group, C1–C4 alkyl group, C1–C4 alkoxy group and halo-C1–C4 alkyl group, pyrrolyl group, C2–C8 alkyl group, C3–C8 alkenyl group, C3–C8 alkynyl group, C3–C8 alkoxy group, a group selected from the group consisting of C2–C8 alkyl group, C3–C8 alkenyl group, C3–C8 alkynyl group and C3–C8 alkoxy group into which at least one oxygen atom is inserted, or any one of groups represented by the following formulas:

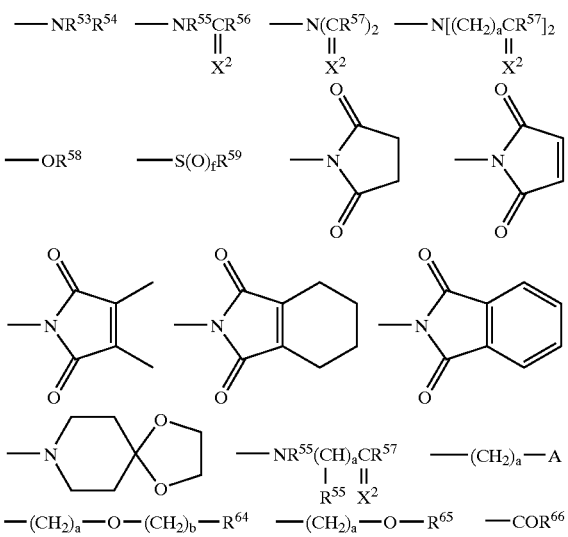

wherein R49, R50 and R52 are, the same or different, hydrogen atom or C1–C4 alkyl group;

R50 and R51 may form saturated alicyclic 5 or 6 membered ring together with the nitrogen atom to which they are attached;

R52 is hydrogen atom, C1–C4 alkyl group or C1–C4 alkyl group substituted with at least one halogen atom;

R53 is hydrogen atom, C1–C4 alkyl group optionally substituted with at least one halogen atom, C2–C6 alkenyl group optionally substituted with at least one halogen atom, C3–C6 alkynyl group optionally substituted with at least one halogen atom, phenyl group optionally substituted with at least one halogen atom, C3–C8 cycloalkyl group, cyanomethyl group, or R63CO— group;

R54 is hydrogen atom, C1–C6 alkyl group optionally substituted with at least one halogen atom, C2–C6 alkenyl group optionally substituted with at least one halogen atom, C3–C6 alkynyl group optionally substituted with at least one halogen atom, phenyl group optionally substituted with halogen atom, C3–C8 cycloalkyl group, cyanomethyl group, C1–C4 alkoxy-C1–C6 alkyl group, di-C1–C4 alkylamino-C1–C4 alkyl group, tetrahydrofurfurylmethyl group, C3–C6 alkynyloxy-C1–C4 alkyl group, benzyl whose ring may be substituted with substituent selected from the group consisting of halogen atom, nitro group, cyano group, C1–C4 alkyl group, C1–C4 alkoxy group and halo-C1–C4 alkyl group, —C(=X2)R63 group, —(CH2)a-(O)d-R70 group, —(CH2)a-O—(CH2)b-R70 group, —(CH2)a-X2-R76 group;

R53 and R54 together with the nitrogen atom to which they are attached may form saturated alicyclic 3, 5 or 6 membered ring or aromatic 5 or 6 membered ring in which a carbon atom may be optionally replaced with oxygen atom;

R55 is hydrogen atom, C1–C4 alkyl group, C2–C6 alkenyl group or C3–C6 alkynyl group, or R55 and R56 together may form —(CH2)e-;

R56 and R57 are independently C1–C4 alkyl group optionally substituted with at least one halogen atom, C2–C6 alkenyl group optionally substituted with at least one halogen atom, C3–C6 alkynyl optionally substituted with at least one halogen atom or phenyl group optionally substituted with at least one halogen atom, hydrogen atom, C3–C6 cycloalkyl group, —XR60 group or —NR61R62 group;

R58 is hydrogen atom, C1–C6 alkyl group, C2–C6 alkenyl group, C3–C6 alkynyl group, C1–C4 alkylcarbonyl group, cyano-C1–C3 alkyl group, C1–C4 alkoxycarbonyl-C1–C4 alkyl group, di-C1–C4 alkoxycarbonyl-C1–C4 alkyl group, benzyl group, C1–C4 alkoxy-C1–C4 alkynyl group, —(CH2)a-R75 group, —(CH2)a-X2-R72 group, —(CH2)a-X2-(CH2)b-R72 group or —(CH2)a-X2-(CH2)b-X2-(CH2)c-R72 group;

R59 is hydrogen atom, C1–C4 alkyl group, C2–C6 alkenyl group, C3–C6 alkynyl group, cyano-C1–C3 alkyl group, C1–C4 alkylcarbonyl-C1–C3 alkyl group or phenyl group;

R60 is C1–C4 alkyl group optionally substituted with at least one halogen atom;

R61 and R62 are, the same or different, hydrogen atom or C1–C4 alkyl group;

R63 is C1–C4 alkyl group optionally substituted with at least one halogen atom, C1–C4 alkoxy-C1–C4 alkyl group, C1–C4 alkylthio-C1–C4 alkyl group, C3–C6 cycloalkyl group, phenyl group whose ring may be substituted with one substituent selected from the group consisting of halogen atom, nitro group, cyano group, C1–C4 alkyl group, C1–C4 alkoxy group and halo-C1–C4 alkyl group, —NR73R74 group or —(CH2)a-(O)d-R75 group;

R64 is C1–C4 alkoxycarbonyl group or carboxyl group;

R65 is chloromethyl group, cyanomethyl group, C3–C6 cycloalkyl group into which at least one oxygen atom may be inserted, or C1–C4 alkoxycarbonyl-C1–C4 alkyl group;

R66 is hydroxyl group or —NR67R68 group;

A is —NR67R68 group or —S(O)f-R69 group;

R67 and R68 are, the same or different, hydrogen atom or C1–C4 alkyl group;

R69 is C1–C4 alkyl group or C1–C4 haloalkyl group;

R70 is hydrogen atom, hydroxyl group, halogen atom, C1–C4 alkyl group optionally substituted with at least one C1–C4 alkoxy group, C3–C6 cycloalkyl group into which at least one oxygen atom may be inserted, C3–C6 cycloalkyl group optionally substituted with one or two methyl groups, furyl group, thienyl group or —C(=O)R71 group;

R71 and R72 are, the same or different, C1–C4 alkyl group or C1–C4 alkoxy group;

R73 and R74 are, the same or different, C1–C4 alkyl group or phenyl group;

R75 is C3–C6 cycloalkyl into which at least one oxygen atom may be inserted, C3–C6 cycloalkyl group optionally substituted with one or two methyl groups, furyl group, thienyl group or —C(=O)R71 group;

R76 is C1–C4 alkyl group;

a, b and c is independently 1, 2 or 3;

d is 0 or 1;

e is 2 or 3;

f is 1 or 2; and

X2 is oxygen atom or sulfur atom.

8. A weed control compound-resistant plant produced by the method of claim 1.

9. A method for protecting a plant which comprises applying a weed control compound to a growth area of the plant of claim 8.

10. A method for selecting a plant which comprises applying a weed control compound to which the plant of claim 8 is resistant to a growth area of the plant of claim 8 and other plants, and selecting either plant on the basis of difference in growth between the plants.

11. The method according to claim 10, wherein the plants are plant cells.

* * * * *

SEQUENCE LISTING

<160> NUMBER OF SEQ ID NOS: 78

<210> SEQ ID NO 1
<211> LENGTH: 39
<212> TYPE: DNA
<213> ORGANISM: Artificial Sequence
<220> FEATURE:

-continued

```
<223> OTHER INFORMATION: Designed oligonucleotide primer to amplify bchH
      gene

<400> SEQUENCE: 1
gacatctaga ggagacgacc atatgcacgg tgaagtctc                              39

<210> SEQ ID NO 2
<211> LENGTH: 31
<212> TYPE: DNA
<213> ORGANISM: Artificial Sequence
<220> FEATURE:
<223> OTHER INFORMATION: Designed oligonucleotide primer to amplify bchH
      gene

<400> SEQUENCE: 2
acggaagctt agatcttcac tcggcggcaa t                                     31

<210> SEQ ID NO 3
<211> LENGTH: 39
<212> TYPE: DNA
<213> ORGANISM: Artificial Sequence
<220> FEATURE:
<223> OTHER INFORMATION: Designed oligonucleotide primer to amplify
      soybean PPO gene

<400> SEQUENCE: 3
tcgagctcca tggtttccgt cttcaacgag atcctattc                             39

<210> SEQ ID NO 4
<211> LENGTH: 36
<212> TYPE: DNA
<213> ORGANISM: Artificial Sequence
<220> FEATURE:
<223> OTHER INFORMATION: Designed oligonucleotide primer to amplify
      soybean PPO gene

<400> SEQUENCE: 4
ttgtcgacaa ctgctactat ttgtacactc tatttg                                36

<210> SEQ ID NO 5
<211> LENGTH: 1632
<212> TYPE: DNA
<213> ORGANISM: Glycine max var. Williams82
<220> FEATURE:
<221> NAME/KEY: CDS
<222> LOCATION: (1)...(1632)

<400> SEQUENCE: 5 atg gtt tcc gtc ttc aac gag atc cta ttc ccg ccg aac caa acc ctt        48
Met Val Ser Val Phe Asn Glu Ile Leu Phe Pro Pro Asn Gln Thr Leu
 1               5                  10                  15 ctt cgc ccc tcc ctc cat tcc cca acc tct ttc ttc acc tct ccc act        96
Leu Arg Pro Ser Leu His Ser Pro Thr Ser Phe Phe Thr Ser Pro Thr
             20                  25                  30 cga aaa ttc cct cgc tct cgc cct aac cct att cta cgc tgc tcc att       144
Arg Lys Phe Pro Arg Ser Arg Pro Asn Pro Ile Leu Arg Cys Ser Ile
         35                  40                  45 gcg gag gaa tcc acc gcg tct ccg ccc aaa acc aga gac tcc gcc ccc       192
Ala Glu Glu Ser Thr Ala Ser Pro Pro Lys Thr Arg Asp Ser Ala Pro
     50                  55                  60 gtg gac tgc gtc gtc gtc ggc gga ggc gtc agc ggc ctc tgc atc gcc       240
Val Asp Cys Val Val Val Gly Gly Gly Val Ser Gly Leu Cys Ile Ala
 65                  70                  75                  80 cag gcc ctc gcc acc aaa cac gcc aat gcc aac gtc gtc gtc acg gag       288
Gln Ala Leu Ala Thr Lys His Ala Asn Ala Asn Val Val Val Thr Glu
```

```
                         85                  90                  95
gcc cga gac cgc gtc ggc ggc aac atc acc acg atg gag agg gac gga        336
Ala Arg Asp Arg Val Gly Gly Asn Ile Thr Thr Met Glu Arg Asp Gly
                100                 105                 110 tac ctc tgg gaa gaa ggc ccc aac agc ttc cag cct tct gat cca atg        384
Tyr Leu Trp Glu Glu Gly Pro Asn Ser Phe Gln Pro Ser Asp Pro Met
        115                 120                 125 ctc acc atg gtg gtg gac agt ggt tta aag gat gag ctt gtt ttg ggg        432
Leu Thr Met Val Val Asp Ser Gly Leu Lys Asp Glu Leu Val Leu Gly
    130                 135                 140 gat cct gat gca cct cgg ttt gtg ttg tgg aac agg aag ttg agg ccg        480
Asp Pro Asp Ala Pro Arg Phe Val Leu Trp Asn Arg Lys Leu Arg Pro
145                 150                 155                 160 gtg ccc ggg aag ctg act gat ttg cct ttc ttt gac ttg atg agc att        528
Val Pro Gly Lys Leu Thr Asp Leu Pro Phe Phe Asp Leu Met Ser Ile
                165                 170                 175 ggt ggc aaa atc agg gct ggc ttt ggt gcg ctt gga att cgg cct cct        576
Gly Gly Lys Ile Arg Ala Gly Phe Gly Ala Leu Gly Ile Arg Pro Pro
        180                 185                 190 cct cca ggt cat gag gaa tcg gtt gaa gag ttt gtt cgt cgg aac ctt        624
Pro Pro Gly His Glu Glu Ser Val Glu Glu Phe Val Arg Arg Asn Leu
    195                 200                 205 ggt gat gag gtt ttt gaa cgg ttg ata gag cct ttt tgt tca ggg gtc        672
Gly Asp Glu Val Phe Glu Arg Leu Ile Glu Pro Phe Cys Ser Gly Val
210                 215                 220 tat gca ggc gat cct tca aaa tta agt atg aaa gca gca ttc ggg aaa        720
Tyr Ala Gly Asp Pro Ser Lys Leu Ser Met Lys Ala Ala Phe Gly Lys
225                 230                 235                 240 gtt tgg aag ctg gaa aaa aat ggt ggc agc att att ggt gga act ttc        768
Val Trp Lys Leu Glu Lys Asn Gly Gly Ser Ile Ile Gly Gly Thr Phe
                245                 250                 255 aaa gca ata caa gag aga aat gga gct tca aaa cca cct cga gat ccg        816
Lys Ala Ile Gln Glu Arg Asn Gly Ala Ser Lys Pro Pro Arg Asp Pro
        260                 265                 270 cgt ctg cca aaa cca aaa ggt cag act gtt gga tct ttc cgg aag gga        864
Arg Leu Pro Lys Pro Lys Gly Gln Thr Val Gly Ser Phe Arg Lys Gly
    275                 280                 285 ctt acc atg ttg cct gat gca att tct gcc aga cta ggc aac aaa gta        912
Leu Thr Met Leu Pro Asp Ala Ile Ser Ala Arg Leu Gly Asn Lys Val
290                 295                 300 aag tta tct tgg aag ctt tca agt att agt aaa ctg gat agt gga gag        960
Lys Leu Ser Trp Lys Leu Ser Ser Ile Ser Lys Leu Asp Ser Gly Glu
305                 310                 315                 320 tac agt ttg aca tat gaa aca cca gaa gga gtg gtt tct ttg cag tgc       1008
Tyr Ser Leu Thr Tyr Glu Thr Pro Glu Gly Val Val Ser Leu Gln Cys
                325                 330                 335 aaa act gtt gtc ctg acc att cct tcc tat gtt gct agt aca ttg ctg       1056
Lys Thr Val Val Leu Thr Ile Pro Ser Tyr Val Ala Ser Thr Leu Leu
        340                 345                 350 cgt cct ctg tct gct gct gct gca gat gca ctt tca aag ttt tat tac       1104
Arg Pro Leu Ser Ala Ala Ala Ala Asp Ala Leu Ser Lys Phe Tyr Tyr
    355                 360                 365 cct cca gtt gct gca gtt tcc ata tcc tat cca aaa gaa gct att aga       1152
Pro Pro Val Ala Ala Val Ser Ile Ser Tyr Pro Lys Glu Ala Ile Arg
370                 375                 380 tca gaa tgc ttg ata gat ggt gag ttg aag ggg ttt ggt caa ttg cat       1200
Ser Glu Cys Leu Ile Asp Gly Glu Leu Lys Gly Phe Gly Gln Leu His
385                 390                 395                 400 cca cgt agc caa gga gtg gaa aca tta gga act ata tac agc tca tca       1248
```

```
                Pro Arg Ser Gln Gly Val Glu Thr Leu Gly Thr Ile Tyr Ser Ser Ser
                            405                 410                 415 cta ttc ccc aac cga gca cca cct gga agg gtt cta ctc ttg aat tac    1296
Leu Phe Pro Asn Arg Ala Pro Pro Gly Arg Val Leu Leu Leu Asn Tyr
            420                 425                 430 att gga gga gca act aat act gga att tta tcg aag acg gac agt gaa    1344
Ile Gly Gly Ala Thr Asn Thr Gly Ile Leu Ser Lys Thr Asp Ser Glu
            435                 440                 445 ctt gtg gaa aca gtt gat cga gat ttg agg aaa atc ctt ata aac cca    1392
Leu Val Glu Thr Val Asp Arg Asp Leu Arg Lys Ile Leu Ile Asn Pro
        450                 455                 460 aat gcc cag gat cca ttt gta gtg ggg gtg aga ctg tgg cct caa gct    1440
Asn Ala Gln Asp Pro Phe Val Val Gly Val Arg Leu Trp Pro Gln Ala
465                 470                 475                 480 att cca cag ttc tta gtt ggc cat ctt gat ctt cta gat gtt gct aaa    1488
Ile Pro Gln Phe Leu Val Gly His Leu Asp Leu Leu Asp Val Ala Lys
                485                 490                 495 gct tct atc aga aat act ggg ttt gaa ggg ctc ttc ctt ggg ggt aat    1536
Ala Ser Ile Arg Asn Thr Gly Phe Glu Gly Leu Phe Leu Gly Gly Asn
            500                 505                 510 tat gtg tct ggt gtt gcc ttg gga cga tgc gtt gag gga gcc tat gag    1584
Tyr Val Ser Gly Val Ala Leu Gly Arg Cys Val Glu Gly Ala Tyr Glu
        515                 520                 525 gta gca gct gaa gta aac gat ttt ctc aca aat aga gtg tac aaa tag    1632
Val Ala Ala Glu Val Asn Asp Phe Leu Thr Asn Arg Val Tyr Lys
    530                 535                 540         543

<210> SEQ ID NO 6
<211> LENGTH: 543
<212> TYPE: PRT
<213> ORGANISM: Glycine max var. Williams82

<400> SEQUENCE: 6

Met Val Ser Val Phe Asn Glu Ile Leu Phe Pro Pro Asn Gln Thr Leu
 1               5                  10                  15

Leu Arg Pro Ser Leu His Ser Pro Thr Ser Phe Phe Thr Ser Pro Thr
                20                  25                  30

Arg Lys Phe Pro Arg Ser Arg Pro Asn Pro Ile Leu Arg Cys Ser Ile
            35                  40                  45

Ala Glu Glu Ser Thr Ala Ser Pro Pro Lys Thr Arg Asp Ser Ala Pro
        50                  55                  60

Val Asp Cys Val Val Gly Gly Val Ser Gly Leu Cys Ile Ala
65                  70                  75                  80

Gln Ala Leu Ala Thr Lys His Ala Asn Ala Asn Val Val Thr Glu
                85                  90                  95

Ala Arg Asp Arg Val Gly Gly Asn Ile Thr Thr Met Glu Arg Asp Gly
            100                 105                 110

Tyr Leu Trp Glu Glu Gly Pro Asn Ser Phe Gln Pro Ser Asp Pro Met
        115                 120                 125

Leu Thr Met Val Val Asp Ser Gly Leu Lys Asp Glu Leu Val Leu Gly
    130                 135                 140

Asp Pro Asp Ala Pro Arg Phe Val Leu Trp Asn Arg Lys Leu Arg Pro
145                 150                 155                 160

Val Pro Gly Lys Leu Thr Asp Leu Pro Phe Phe Asp Leu Met Ser Ile
                165                 170                 175

Gly Gly Lys Ile Arg Ala Gly Phe Gly Ala Leu Gly Ile Arg Pro Pro
            180                 185                 190
```

Pro Pro Gly His Glu Glu Ser Val Glu Glu Phe Val Arg Arg Asn Leu
        195                 200                 205

Gly Asp Glu Val Phe Glu Arg Leu Ile Glu Pro Phe Cys Ser Gly Val
    210                 215                 220

Tyr Ala Gly Asp Pro Ser Lys Leu Ser Met Lys Ala Ala Phe Gly Lys
225                 230                 235                 240

Val Trp Lys Leu Glu Lys Asn Gly Gly Ser Ile Ile Gly Gly Thr Phe
                245                 250                 255

Lys Ala Ile Gln Glu Arg Asn Gly Ala Ser Lys Pro Pro Arg Asp Pro
                260                 265                 270

Arg Leu Pro Lys Pro Lys Gly Gln Thr Val Gly Ser Phe Arg Lys Gly
            275                 280                 285

Leu Thr Met Leu Pro Asp Ala Ile Ser Ala Arg Leu Gly Asn Lys Val
    290                 295                 300

Lys Leu Ser Trp Lys Leu Ser Ser Ile Ser Lys Leu Asp Ser Gly Glu
305                 310                 315                 320

Tyr Ser Leu Thr Tyr Glu Thr Pro Glu Gly Val Val Ser Leu Gln Cys
                325                 330                 335

Lys Thr Val Val Leu Thr Ile Pro Ser Tyr Val Ala Ser Thr Leu Leu
                340                 345                 350

Arg Pro Leu Ser Ala Ala Ala Asp Ala Leu Ser Lys Phe Tyr Tyr
            355                 360                 365

Pro Pro Val Ala Ala Val Ser Ile Ser Tyr Pro Lys Glu Ala Ile Arg
    370                 375                 380

Ser Glu Cys Leu Ile Asp Gly Glu Leu Lys Gly Phe Gly Gln Leu His
385                 390                 395                 400

Pro Arg Ser Gln Gly Val Glu Thr Leu Gly Thr Ile Tyr Ser Ser Ser
                405                 410                 415

Leu Phe Pro Asn Arg Ala Pro Pro Gly Arg Val Leu Leu Asn Tyr
                420                 425                 430

Ile Gly Gly Ala Thr Asn Thr Gly Ile Leu Ser Lys Thr Asp Ser Glu
            435                 440                 445

Leu Val Glu Thr Val Asp Arg Asp Leu Arg Lys Ile Leu Ile Asn Pro
    450                 455                 460

Asn Ala Gln Asp Pro Phe Val Val Gly Val Arg Leu Trp Pro Gln Ala
465                 470                 475                 480

Ile Pro Gln Phe Leu Val Gly His Leu Asp Leu Leu Asp Val Ala Lys
                485                 490                 495

Ala Ser Ile Arg Asn Thr Gly Phe Glu Gly Leu Phe Leu Gly Gly Asn
                500                 505                 510

Tyr Val Ser Gly Val Ala Leu Gly Arg Cys Val Glu Gly Ala Tyr Glu
            515                 520                 525

Val Ala Ala Glu Val Asn Asp Phe Leu Thr Asn Arg Val Tyr Lys
    530                 535                 540         543

<210> SEQ ID NO 7
<211> LENGTH: 39
<212> TYPE: DNA
<213> ORGANISM: Artificial Sequence
<220> FEATURE:
<223> OTHER INFORMATION: Designed oligonucleotide primer to amplify bchH
      gene

<400> SEQUENCE: 7
gacatctagt ctagacgacc atatgcacgg tgaagtctc                          39

<210> SEQ ID NO 8
<211> LENGTH: 31
<212> TYPE: DNA
<213> ORGANISM: Artificial Sequence
<220> FEATURE:
<223> OTHER INFORMATION: Designed oligonucleotide primer to amplify bchH
      gene

<400> SEQUENCE: 8
acggaagctt ggtacctcac tcggcggcaa t                               31

<210> SEQ ID NO 9
<211> LENGTH: 35
<212> TYPE: DNA
<213> ORGANISM: Artificial Sequence
<220> FEATURE:
<223> OTHER INFORMATION: Designed oligonucleotide primer to amplify DNA
      fragment having partial sequence of tobacco chlH gene

<400> SEQUENCE: 9
ccaatgtaat gctatggtac ctatgttatt cactc                           35

<210> SEQ ID NO 10
<211> LENGTH: 34
<212> TYPE: DNA
<213> ORGANISM: Artificial Sequence
<220> FEATURE:
<223> OTHER INFORMATION: Designed oligonucleotide primer to amplify DNA
      fragment having partial sequence of tobacco chlH gene

<400> SEQUENCE: 10
gagatcattc ttttgctgt cgacttatcg atcg                             34

<210> SEQ ID NO 11
<211> LENGTH: 36
<212> TYPE: DNA
<213> ORGANISM: Artificial Sequence
<220> FEATURE:
<223> OTHER INFORMATION: Designed oligonucleotide primer to amplify DNA
      fragment having partial sequence of soybean PPO gene

<400> SEQUENCE: 11
ggcggaggcg tcaccatggt ctgcatcgcc caggcc                          36

<210> SEQ ID NO 12
<211> LENGTH: 36
<212> TYPE: DNA
<213> ORGANISM: Artificial Sequence
<220> FEATURE:
<223> OTHER INFORMATION: Designed oligonucleotide primer to amplify DNA
      fragment having partial sequence of soybean PPO gene

<400> SEQUENCE: 12
gcctgcaggt cgacaactgc tactatttgt acactc                          36

<210> SEQ ID NO 13
<211> LENGTH: 33
<212> TYPE: DNA
<213> ORGANISM: Artificial Sequence
<220> FEATURE:
<223> OTHER INFORMATION: Designed oligonucleotide primer to amplify DNA
      fragment having partial sequence of soybean PPO gene

<400> SEQUENCE: 13
cacaggaaag gtaccatggt ctgcatcgcc cag                             33

```
<210> SEQ ID NO 14
<211> LENGTH: 33
<212> TYPE: DNA
<213> ORGANISM: Artificial Sequence
<220> FEATURE:
<223> OTHER INFORMATION: Designed oligonucleotide primer to amplify DNA
      fragment having partial sequence of soybean PPO gene

<400> SEQUENCE: 14
cctgcagctc gagagctcct actatttgta cac                              33

<210> SEQ ID NO 15
<211> LENGTH: 28
<212> TYPE: DNA
<213> ORGANISM: Artificial Sequence
<220> FEATURE:
<223> OTHER INFORMATION: Designed oligonucleotide primer to amplify
      Chlamydomonas PPO gene

<400> SEQUENCE: 15
aatgatgttg acccagactc ctgggacc                                    28

<210> SEQ ID NO 16
<211> LENGTH: 27
<212> TYPE: DNA
<213> ORGANISM: Artificial Sequence
<220> FEATURE:
<223> OTHER INFORMATION: Designed oligonucleotide primer to amplify
      Chlamydomonas PPO gene

<400> SEQUENCE: 16
tactacacat cccagcaagc gccaatg                                     27

<210> SEQ ID NO 17
<211> LENGTH: 1838
<212> TYPE: DNA
<213> ORGANISM: Chlamydomonas reinhardtii CC407
<220> FEATURE:
<221> NAME/KEY: CDS
<222> LOCATION: (1)...(1693)

<400> SEQUENCE: 17 a atg atg ttg acc cag act cct ggg acc gcc acg gct tct agc cgg     46
  Met Met Leu Thr Gln Thr Pro Gly Thr Ala Thr Ala Ser Ser Arg
   1               5                  10                  15 cgg tcg cag atc cgc tcg gct gcg cac gtc tcc gcc aag gtc gcg cct  94
Arg Ser Gln Ile Arg Ser Ala Ala His Val Ser Ala Lys Val Ala Pro
             20                  25                  30 cgg ccc acg cca ttc tcg gtc gcg agc ccc gcg acc gct gcg agc ccc  142
Arg Pro Thr Pro Phe Ser Val Ala Ser Pro Ala Thr Ala Ala Ser Pro
         35                  40                  45 gcg acc gcg gcg gcc cgc cgc aca ctc cac cgc act gct gcg gcg gcc  190
Ala Thr Ala Ala Ala Arg Arg Thr Leu His Arg Thr Ala Ala Ala Ala
     50                  55                  60 act ggt gct ccc acg gcg tcc gga gcc ggc gtc gcc aag acg ctc gac  238
Thr Gly Ala Pro Thr Ala Ser Gly Ala Gly Val Ala Lys Thr Leu Asp
 65                  70                  75 aat gtg tat gac gtg atc gtg gtc ggt gga ggt ctc tcg ggc ctg gtg  286
Asn Val Tyr Asp Val Ile Val Val Gly Gly Gly Leu Ser Gly Leu Val
 80                  85                  90                  95 acc ggc cag gcc ctg gcg gct cag cac aaa att cag aac ttc ctt gtt  334
Thr Gly Gln Ala Leu Ala Ala Gln His Lys Ile Gln Asn Phe Leu Val
                100                 105                 110 acg gag gct cgc gag cgc gtc ggc ggc aac att acg tcc atg tcg ggc  382
Thr Glu Ala Arg Glu Arg Val Gly Gly Asn Ile Thr Ser Met Ser Gly
```

```
                115              120                  125
gat ggc tac gtg tgg gag gag ggc ccg aac agc ttc cag ccc aac gat    430
Asp Gly Tyr Val Trp Glu Glu Gly Pro Asn Ser Phe Gln Pro Asn Asp
        130                 135                 140 agc atg ctg cag att gcg gtg gac tct ggc tgc gag aag gac ctt gtg    478
Ser Met Leu Gln Ile Ala Val Asp Ser Gly Cys Glu Lys Asp Leu Val
    145                 150                 155 ttc ggt gac ccc acg gct ccc cgc ttc gtg tgg tgg gag ggc aag ctg    526
Phe Gly Asp Pro Thr Ala Pro Arg Phe Val Trp Trp Glu Gly Lys Leu
160                 165                 170                 175 cgc ccc gtg ccc tcg ggc ctg gac gcc ttc acc ttc gac ctc atg tcc    574
Arg Pro Val Pro Ser Gly Leu Asp Ala Phe Thr Phe Asp Leu Met Ser
                180                 185                 190 atc ccc ggc aag atc cgc gcc ggg ctg ggc gcc atc ggc ctc atc aac    622
Ile Pro Gly Lys Ile Arg Ala Gly Leu Gly Ala Ile Gly Leu Ile Asn
            195                 200                 205 gga gcc atg ccc tcc ttc gag gag agt gtg gag cag ttc atc cgc cgc    670
Gly Ala Met Pro Ser Phe Glu Glu Ser Val Glu Gln Phe Ile Arg Arg
        210                 215                 220 aac ctg ggc gat gag gtg ttc ttc cgc ctg atc gag ccc ttc tgc tcc    718
Asn Leu Gly Asp Glu Val Phe Phe Arg Leu Ile Glu Pro Phe Cys Ser
    225                 230                 235 ggc gtg tac gcg ggc gac ccc tcc aag ctg tcc atg aag gcg gcc ttc    766
Gly Val Tyr Ala Gly Asp Pro Ser Lys Leu Ser Met Lys Ala Ala Phe
240                 245                 250                 255 aac agg atc tgg att ctg gag aag aac ggc ggc agc ctg gtg gga ggt    814
Asn Arg Ile Trp Ile Leu Glu Lys Asn Gly Gly Ser Leu Val Gly Gly
                260                 265                 270 gcc atc aag ctg ttc cag gaa cgc cag tcc aac ccg gcc ccg ccg cgg    862
Ala Ile Lys Leu Phe Gln Glu Arg Gln Ser Asn Pro Ala Pro Pro Arg
            275                 280                 285 gac ccg cgc ctg ccg ccc aag ccc aag ggc cag acg gtg ggc tcg ttc    910
Asp Pro Arg Leu Pro Pro Lys Pro Lys Gly Gln Thr Val Gly Ser Phe
        290                 295                 300 cgc aag ggc ctg aag atg ctg ccg gac gcc att gag cgc aac atc ccc    958
Arg Lys Gly Leu Lys Met Leu Pro Asp Ala Ile Glu Arg Asn Ile Pro
    305                 310                 315 gac aag atc cgc gtg aac tgg aag ctg gtg tct ctg ggc cgc gag gcg   1006
Asp Lys Ile Arg Val Asn Trp Lys Leu Val Ser Leu Gly Arg Glu Ala
320                 325                 330                 335 gac ggg cgg tac ggg ctg gtg tac gac acg ccc gag ggc cgt gtc aag   1054
Asp Gly Arg Tyr Gly Leu Val Tyr Asp Thr Pro Glu Gly Arg Val Lys
                340                 345                 350 gtg ttt gcc cgc gcc gtg gct ctg acc gcg ccc agc tac gtg gtg gcg   1102
Val Phe Ala Arg Ala Val Ala Leu Thr Ala Pro Ser Tyr Val Val Ala
            355                 360                 365 gac ctg gtc aag gag cag gcg ccc gcc gcc gcc gag gcc ctg ggc tcc   1150
Asp Leu Val Lys Glu Gln Ala Pro Ala Ala Ala Glu Ala Leu Gly Ser
        370                 375                 380 ttc gac tac ccg ccg gtg ggc gcc gtg acg ctg tcg tac ccg ctg agc   1198
Phe Asp Tyr Pro Pro Val Gly Ala Val Thr Leu Ser Tyr Pro Leu Ser
    385                 390                 395 gcc gtg cgg gag gag cgc aag gcc tcg gac ggg tcc gtg ccg ggc ttc   1246
Ala Val Arg Glu Glu Arg Lys Ala Ser Asp Gly Ser Val Pro Gly Phe
400                 405                 410                 415 ggt cag ctg cac ccg cgc acg cag ggc atc acc act ctg ggc acc atc   1294
Gly Gln Leu His Pro Arg Thr Gln Gly Ile Thr Thr Leu Gly Thr Ile
                420                 425                 430 tac agc tcc agc ctg ttc ccc ggc cgc gcg ccc gag ggc cac atg ctg   1342
Tyr Ser Ser Ser Leu Phe Pro Gly Arg Ala Pro Glu Gly His Met Leu
```

```
                                                                                       -continued Tyr Ser Ser Ser Leu Phe Pro Gly Arg Ala Pro Glu Gly His Met Leu
            435                 440                 445 ctg ctc aac tac atc ggc ggc acc acc aac cgc ggc atc gtc aac cag        1390
Leu Leu Asn Tyr Ile Gly Gly Thr Thr Asn Arg Gly Ile Val Asn Gln
            450                 455                 460 acc acc gag cag ctg gtg gag cag gtg gac aag gac ctg cgc aac atg        1438
Thr Thr Glu Gln Leu Val Glu Gln Val Asp Lys Asp Leu Arg Asn Met
        465                 470                 475 gtc atc aag ccc gac gcg ccc aag ccc cgt gtg gtg ggc gtg cgc gtg        1486
Val Ile Lys Pro Asp Ala Pro Lys Pro Arg Val Val Gly Val Arg Val
480                 485                 490                 495 tgg ccg cgc gcc atc ccg cag ttc aac ctg ggc cac ctg gag cag ctg        1534
Trp Pro Arg Ala Ile Pro Gln Phe Asn Leu Gly His Leu Glu Gln Leu
                500                 505                 510 gac aag gcg cgc aag gcg ctg gac gcg gcg ggg ctg cag ggc gtg cac        1582
Asp Lys Ala Arg Lys Ala Leu Asp Ala Ala Gly Leu Gln Gly Val His
            515                 520                 525 ctg ggg ggc aac tac gtc agc ggt gtg gcc ctg ggc aag gtg gtg gag        1630
Leu Gly Gly Asn Tyr Val Ser Gly Val Ala Leu Gly Lys Val Val Glu
            530                 535                 540 cac ggc tac gag tcc gca gcc aac ctg gcc aag agc gtg tcc aag gcc        1678
His Gly Tyr Glu Ser Ala Ala Asn Leu Ala Lys Ser Val Ser Lys Ala
        545                 550                 555 gca gtc aag gcc taa gcggctgcag cagtagcagc agcagcatcg ggctgtagct        1733
Ala Val Lys Ala
560 ggtaaatgcc gcagtggcac cggcagcagc aattggcaag cacttggggc aagcggagtg        1793 gaggcgaggg gggggctacc attggcgctt gctgggatgt gtagt                        1838

<210> SEQ ID NO 18
<211> LENGTH: 563
<212> TYPE: PRT
<213> ORGANISM: Chlamydomonas reinhardtii CC407

<400> SEQUENCE: 18

Met Met Leu Thr Gln Thr Pro Gly Thr Ala Thr Ala Ser Ser Arg
 1               5                  10                  15

Arg Ser Gln Ile Arg Ser Ala Ala His Val Ser Ala Lys Val Ala Pro
                20                  25                  30

Arg Pro Thr Pro Phe Ser Val Ala Ser Pro Ala Thr Ala Ala Ser Pro
            35                  40                  45

Ala Thr Ala Ala Ala Arg Arg Thr Leu His Arg Thr Ala Ala Ala Ala
        50                  55                  60

Thr Gly Ala Pro Thr Ala Ser Gly Ala Gly Val Ala Lys Thr Leu Asp
    65                  70                  75

Asn Val Tyr Asp Val Ile Val Val Gly Gly Gly Leu Ser Gly Leu Val
80                  85                  90                  95

Thr Gly Gln Ala Leu Ala Ala Gln His Lys Ile Gln Asn Phe Leu Val
                100                 105                 110

Thr Glu Ala Arg Glu Arg Val Gly Gly Asn Ile Thr Ser Met Ser Gly
            115                 120                 125

Asp Gly Tyr Val Trp Glu Glu Gly Pro Asn Ser Phe Gln Pro Asn Asp
        130                 135                 140

Ser Met Leu Gln Ile Ala Val Asp Ser Gly Cys Glu Lys Asp Leu Val
    145                 150                 155

Phe Gly Asp Pro Thr Ala Pro Arg Phe Val Trp Trp Glu Gly Lys Leu
160                 165                 170                 175
```

-continued

```
Arg Pro Val Pro Ser Gly Leu Asp Ala Phe Thr Phe Asp Leu Met Ser
            180                 185                 190

Ile Pro Gly Lys Ile Arg Ala Gly Leu Gly Ala Ile Gly Leu Ile Asn
        195                 200                 205

Gly Ala Met Pro Ser Phe Glu Glu Ser Val Glu Gln Phe Ile Arg Arg
        210                 215                 220

Asn Leu Gly Asp Glu Val Phe Phe Arg Leu Ile Glu Pro Phe Cys Ser
        225                 230                 235

Gly Val Tyr Ala Gly Asp Pro Ser Lys Leu Ser Met Lys Ala Ala Phe
240                 245                 250                 255

Asn Arg Ile Trp Ile Leu Glu Lys Asn Gly Ser Leu Val Gly Gly
            260                 265                 270

Ala Ile Lys Leu Phe Gln Glu Arg Gln Ser Asn Pro Ala Pro Pro Arg
            275                 280                 285

Asp Pro Arg Leu Pro Pro Lys Pro Lys Gly Gln Thr Val Gly Ser Phe
            290                 295                 300

Arg Lys Gly Leu Lys Met Leu Pro Asp Ala Ile Glu Arg Asn Ile Pro
305                 310                 315

Asp Lys Ile Arg Val Asn Trp Lys Leu Val Ser Leu Gly Arg Glu Ala
320                 325                 330                 335

Asp Gly Arg Tyr Gly Leu Val Tyr Asp Thr Pro Glu Gly Arg Val Lys
                340                 345                 350

Val Phe Ala Arg Ala Val Ala Leu Thr Ala Pro Ser Tyr Val Val Ala
                355                 360                 365

Asp Leu Val Lys Glu Gln Ala Pro Ala Ala Glu Ala Leu Gly Ser
            370                 375                 380

Phe Asp Tyr Pro Pro Val Gly Ala Val Thr Leu Ser Tyr Pro Leu Ser
    385                 390                 395

Ala Val Arg Glu Glu Arg Lys Ala Ser Asp Gly Ser Val Pro Gly Phe
400                 405                 410                 415

Gly Gln Leu His Pro Arg Thr Gln Gly Ile Thr Thr Leu Gly Thr Ile
                420                 425                 430

Tyr Ser Ser Ser Leu Phe Pro Gly Arg Ala Pro Glu Gly His Met Leu
                435                 440                 445

Leu Leu Asn Tyr Ile Gly Gly Thr Thr Asn Arg Gly Ile Val Asn Gln
            450                 455                 460

Thr Thr Glu Gln Leu Val Glu Gln Val Asp Lys Asp Leu Arg Asn Met
    465                 470                 475

Val Ile Lys Pro Asp Ala Pro Lys Pro Arg Val Val Gly Val Arg Val
480                 485                 490                 495

Trp Pro Arg Ala Ile Pro Gln Phe Asn Leu Gly His Leu Glu Gln Leu
                500                 505                 510

Asp Lys Ala Arg Lys Ala Leu Asp Ala Ala Gly Leu Gln Gly Val His
                515                 520                 525

Leu Gly Gly Asn Tyr Val Ser Gly Val Ala Leu Gly Lys Val Val Glu
            530                 535                 540

His Gly Tyr Glu Ser Ala Ala Asn Leu Ala Lys Ser Val Ser Lys Ala
    545                 550                 555

Ala Val Lys Ala
560             563

<210> SEQ ID NO 19
<211> LENGTH: 32
```

```
<212> TYPE: DNA
<213> ORGANISM: Artificial Sequence
<220> FEATURE:
<223> OTHER INFORMATION: Designed oligonucleotide primer to amplify DNA
      fragment having partial sequence of Chlamydomonas PPO gene

<400> SEQUENCE: 19
ggtcggtgga ggggatccga tgctggtgac cg                                32

<210> SEQ ID NO 20
<211> LENGTH: 32
<212> TYPE: DNA
<213> ORGANISM: Artificial Sequence
<220> FEATURE:
<223> OTHER INFORMATION: Designed oligonucleotide primer to amplify DNA
      fragment having partial sequence of Chlamydomonas PPO gene

<400> SEQUENCE: 20
gctactgctg cgagctctta ggccttgact gc                                32

<210> SEQ ID NO 21
<211> LENGTH: 33
<212> TYPE: DNA
<213> ORGANISM: Artificial Sequence
<220> FEATURE:
<223> OTHER INFORMATION: Designed oligonucleotide primer to amplify DNA
      fragment having partial sequence of cucumber ferrochelatase gene

<400> SEQUENCE: 21
gctttagaat cggatcctat ggcagtggat gac                               33

<210> SEQ ID NO 22
<211> LENGTH: 36
<212> TYPE: DNA
<213> ORGANISM: Artificial Sequence
<220> FEATURE:
<223> OTHER INFORMATION: Designed oligonucleotide primer to amplify DNA
      fragment having partial sequence of cucumber ferrochelatase gene

<400> SEQUENCE: 22
ggtgaacttc tatttgagct ctcaggtaaa tataag                            36

<210> SEQ ID NO 23
<211> LENGTH: 25
<212> TYPE: DNA
<213> ORGANISM: Artificial Sequence
<220> FEATURE:
<223> OTHER INFORMATION: Designed oligonucleotide primer to amplify
      Esherichia coli hemF gene

<400> SEQUENCE: 23
gctgaaggcg tgatcagtta tttcc                                        25

<210> SEQ ID NO 24
<211> LENGTH: 24
<212> TYPE: DNA
<213> ORGANISM: Artificial Sequence
<220> FEATURE:
<223> OTHER INFORMATION: Designed oligonucleotide primer to amplify
      Esherichia coli hemF gene

<400> SEQUENCE: 24
catcagcctg cagtgcgaaa agtg                                         24

<210> SEQ ID NO 25
<211> LENGTH: 26
<212> TYPE: DNA
```

```
<213> ORGANISM: Artificial Sequence
<220> FEATURE:
<223> OTHER INFORMATION: Designed oligonucleotide primer to amplify
      Esherichia coli hemF gene

<400> SEQUENCE: 25
cgaaaaaggg atccgttatg aaaccc                                          26

<210> SEQ ID NO 26
<211> LENGTH: 23
<212> TYPE: DNA
<213> ORGANISM: Artificial Sequence
<220> FEATURE:
<223> OTHER INFORMATION: Designed oligonucleotide primer to amplify
      Esherichia coli hemF gene

<400> SEQUENCE: 26
gctgttttcc gagctcccgt cac                                             23

<210> SEQ ID NO 27
<211> LENGTH: 22
<212> TYPE: DNA
<213> ORGANISM: Artificial Sequence
<220> FEATURE:
<223> OTHER INFORMATION: Designed oligonucleotides to synthesize genes
      encoding random peptides comprising 5 amino acids
<220> FEATURE:
<221> NAME/KEY: unsure
<222> LOCATION: (1)...(22)
<223> OTHER INFORMATION: any n = a, g, c, t, any, unknown, or other

<400> SEQUENCE: 27
tggccnnknn knnknnknnk gc                                              22

<210> SEQ ID NO 28
<211> LENGTH: 29
<212> TYPE: DNA
<213> ORGANISM: Artificial Sequence
<220> FEATURE:
<223> OTHER INFORMATION: Designed oligonucleotides to synthesize genes
      encoding random peptides comprising 5 amino acids
<220> FEATURE:
<221> NAME/KEY: unknown
<222> LOCATION: (1)...(29)
<223> OTHER INFORMATION: any n = a, g, c, t, any, unknown, or other

<400> SEQUENCE: 28
ggccgcmnnm nnmnnmnnmn nggccagct                                       29

<210> SEQ ID NO 29
<211> LENGTH: 22
<212> TYPE: DNA
<213> ORGANISM: Artificial Sequence
<220> FEATURE:
<223> OTHER INFORMATION: Designed oligonucleotide to synthesize the gene
      encoding the peptide HASYS

<400> SEQUENCE: 29
tggcccatgc tagttagtcg gc                                              22

<210> SEQ ID NO 30
<211> LENGTH: 29
<212> TYPE: DNA
<213> ORGANISM: Artificial Sequence
<220> FEATURE:
<223> OTHER INFORMATION: Designed oligonucleotide to synthesize the gene
      encoding the peptide HASYS

<400> SEQUENCE: 30
```
tggcgccgac taactagcat gggccagct                                              29

<210> SEQ ID NO 31
<211> LENGTH: 22
<212> TYPE: DNA
<213> ORGANISM: Artificial Sequence
<220> FEATURE:
<223> OTHER INFORMATION: Designed oligonucleotide to synthesize the gene
      encoding the peptide RASSL

<400> SEQUENCE: 31
tggcccgggc gtcgtcgttg gc                                                     22

<210> SEQ ID NO 32
<211> LENGTH: 29
<212> TYPE: DNA
<213> ORGANISM: Artificial Sequence
<220> FEATURE:
<223> OTHER INFORMATION: Designed oligonucleotide to synthesize the gene
      encoding the peptide RASSL

<400> SEQUENCE: 32
ggccgccaac gacgacgccc gggccagct                                              29

<210> SEQ ID NO 33
<211> LENGTH: 26
<212> TYPE: DNA
<213> ORGANISM: Artificial Sequence
<220> FEATURE:
<223> OTHER INFORMATION: Designed oligonucleotide to synthesize the gene
      encoding the peptide MGHASYS

<400> SEQUENCE: 33
catgggtcac gcttcttact cctaag                                                 26

<210> SEQ ID NO 34
<211> LENGTH: 26
<212> TYPE: DNA
<213> ORGANISM: Artificial Sequence
<220> FEATURE:
<223> OTHER INFORMATION: Designed oligonucleotide to synthesize the gene
      encoding the peptide MGHASYS

<400> SEQUENCE: 34
aattcttagg agtaagaagc gtgacc                                                 26

<210> SEQ ID NO 35
<211> LENGTH: 26
<212> TYPE: DNA
<213> ORGANISM: Artificial Sequence
<220> FEATURE:
<223> OTHER INFORMATION: Designed oligonucleotide to synthesize the gene
      encoding the peptide MGRASSL

<400> SEQUENCE: 35
catgggtcgt gcttcttccc tgtaag                                                 26

<210> SEQ ID NO 36
<211> LENGTH: 26
<212> TYPE: DNA
<213> ORGANISM: Artificial Sequence
<220> FEATURE:
<223> OTHER INFORMATION: Designed oligonucleotide to synthesize the gene
      encoding the peptide MGRASSL

<400> SEQUENCE: 36

-continued aattcttaca gggaagaagc acgacc    26

<210> SEQ ID NO 37
<211> LENGTH: 23
<212> TYPE: DNA
<213> ORGANISM: Artificial Sequence
<220> FEATURE:
<223> OTHER INFORMATION: Designed oligonucleotide to synthesize the gene
      encoding the peptide MGYAGY

<400> SEQUENCE: 37
catgggttac gctggctact aag    23

<210> SEQ ID NO 38
<211> LENGTH: 23
<212> TYPE: DNA
<213> ORGANISM: Artificial Sequence
<220> FEATURE:
<223> OTHER INFORMATION: Designed oligonucleotide to synthesize the gene
      encoding the peptide MGYAGY

<400> SEQUENCE: 38
aattcttagt agccagcgta acc    23

<210> SEQ ID NO 39
<211> LENGTH: 23
<212> TYPE: DNA
<213> ORGANISM: Artificial Sequence
<220> FEATURE:
<223> OTHER INFORMATION: Designed oligonucleotide to synthesize the gene
      encoding the peptide MGYAGF

<400> SEQUENCE: 39
catgggttac gctggcttct aag    23

<210> SEQ ID NO 40
<211> LENGTH: 23
<212> TYPE: DNA
<213> ORGANISM: Artificial Sequence
<220> FEATURE:
<223> OTHER INFORMATION: Designed oligonucleotide to synthesize the gene
      encoding the peptide MGYAGF

<400> SEQUENCE: 40
aattcttaga agccagcgta acc    23

<210> SEQ ID NO 41
<211> LENGTH: 34
<212> TYPE: DNA
<213> ORGANISM: Artificial Sequence
<220> FEATURE:
<223> OTHER INFORMATION: Designed oligonucleotide to synthesize the gene
      encoding the peptide MG(HASYS)4

<400> SEQUENCE: 41
catgggtcac gcttcttact cccatgcatc ttac    34

<210> SEQ ID NO 42
<211> LENGTH: 36
<212> TYPE: DNA
<213> ORGANISM: Artificial Sequence
<220> FEATURE:
<223> OTHER INFORMATION: Designed oligonucleotide to synthesize the gene
      encoding the peptide MG(HASYS)4

<400> SEQUENCE: 42
gtgggagtaa gatgcatggg agtaagaagc gtgacc    36

<210> SEQ ID NO 43
<211> LENGTH: 37
<212> TYPE: DNA
<213> ORGANISM: Artificial Sequence
<220> FEATURE:
<223> OTHER INFORMATION: Designed oligonucleotide to synthesize the gene
      encoding the peptide MG(HASYS)4

<400> SEQUENCE: 43
tcccacgctt cttactccca tgcatcttac tcctaag                          37

<210> SEQ ID NO 44
<211> LENGTH: 35
<212> TYPE: DNA
<213> ORGANISM: Artificial Sequence
<220> FEATURE:
<223> OTHER INFORMATION: Designed oligonucleotide to synthesize the gene
      encoding the peptide MG(HASYS)4

<400> SEQUENCE: 44
aattcttagg agtaagatgc atgggagtaa gaagc                            35

<210> SEQ ID NO 45
<211> LENGTH: 30
<212> TYPE: DNA
<213> ORGANISM: Artificial Sequence
<220> FEATURE:
<223> OTHER INFORMATION: Designed oligonucleotide to synthesize the gene
      encoding the peptide MG(HASYS)8

<400> SEQUENCE: 45
tcccacgctt cttactccca tgcatcttac                                  30

<210> SEQ ID NO 46
<211> LENGTH: 30
<212> TYPE: DNA
<213> ORGANISM: Artificial Sequence
<220> FEATURE:
<223> OTHER INFORMATION: Designed oligonucleotide to synthesize the gene
      encoding the peptide MG(HASYS)8

<400> SEQUENCE: 46
gtgggagtaa gatgcatggg agtaagaagc                                  30

<210> SEQ ID NO 47
<211> LENGTH: 34
<212> TYPE: DNA
<213> ORGANISM: Artificial Sequence
<220> FEATURE:
<223> OTHER INFORMATION: Designed oligonucleotide to synthesize the gene
      encoding the peptide MG(RASSL)4

<400> SEQUENCE: 47
catgggtcgt gcttcttccc tgcgcgcatc ttcc                             34

<210> SEQ ID NO 48
<211> LENGTH: 36
<212> TYPE: DNA
<213> ORGANISM: Artificial Sequence
<220> FEATURE:
<223> OTHER INFORMATION: Designed oligonucleotide to synthesize the gene
      encoding the peptide MG(RASSL)4

<400> SEQUENCE: 48
acgcagggaa gatgcgcgca gggaagaagc acgacc                           36

<210> SEQ ID NO 49
<211> LENGTH: 37
<212> TYPE: DNA
<213> ORGANISM: Artificial Sequence
<220> FEATURE:
<223> OTHER INFORMATION: Designed oligonucleotide to synthesize the gene
      encoding the peptide MG(RASSL)4

<400> SEQUENCE: 49
ctgcgtgctt cttccctgcg cgcatcttcc ctgtaag                                37

<210> SEQ ID NO 50
<211> LENGTH: 35
<212> TYPE: DNA
<213> ORGANISM: Artificial Sequence
<220> FEATURE:
<223> OTHER INFORMATION: Designed oligonucleotide to synthesize the gene
      encoding the peptide MG(RASSL)4

<400> SEQUENCE: 50
aattcttaca gggaagatgc gcgcagggaa gaagc                                  35

<210> SEQ ID NO 51
<211> LENGTH: 30
<212> TYPE: DNA
<213> ORGANISM: Artificial Sequence
<220> FEATURE:
<223> OTHER INFORMATION: Designed oligonucleotide to synthesize the gene
      encoding the peptide MG(RASSL)8

<400> SEQUENCE: 51
ctgcgtgctt cttccctgcg cgcatcttcc                                        30

<210> SEQ ID NO 52
<211> LENGTH: 30
<212> TYPE: DNA
<213> ORGANISM: Artificial Sequence
<220> FEATURE:
<223> OTHER INFORMATION: Designed oligonucleotide to synthesize the gene
      encoding the peptide MG(RASSL)8

<400> SEQUENCE: 52
acgcagggaa gatgcgcgca gggaagaagc                                        30

<210> SEQ ID NO 53
<211> LENGTH: 5
<212> TYPE: PRT
<213> ORGANISM: Artificial Sequence
<220> FEATURE:
<223> OTHER INFORMATION: Protoporphyrin IX binding protein HASYS

<400> SEQUENCE: 53

His Ala Ser Tyr Ser
 1               5

<210> SEQ ID NO 54
<211> LENGTH: 7
<212> TYPE: PRT
<213> ORGANISM: Artificial Sequence
<220> FEATURE:
<223> OTHER INFORMATION: Protoporphyrin IX binding protein MGHASYS

<400> SEQUENCE: 54

Met Gly His Ala Ser Tyr Ser
 1               5

<210> SEQ ID NO 55
<211> LENGTH: 5
<212> TYPE: PRT
<213> ORGANISM: Artificial Sequence
<220> FEATURE:
<223> OTHER INFORMATION: Protoporphyrin IX binding protein RASSL

<400> SEQUENCE: 55

Arg Ala Ser Ser Leu
 1               5

<210> SEQ ID NO 56
<211> LENGTH: 7
<212> TYPE: PRT
<213> ORGANISM: Artificial Sequence
<220> FEATURE:
<223> OTHER INFORMATION: Protoporphyrin IX binding protein MGRASSL

<400> SEQUENCE: 56

Met Gly Arg Ala Ser Ser Leu
 1               5

<210> SEQ ID NO 57
<211> LENGTH: 4
<212> TYPE: PRT
<213> ORGANISM: Artificial Sequence
<220> FEATURE:
<223> OTHER INFORMATION: H2TMpyP binding protein YAGY.

<400> SEQUENCE: 57

Tyr Ala Gly Tyr
 1

<210> SEQ ID NO 58
<211> LENGTH: 6
<212> TYPE: PRT
<213> ORGANISM: Artificial Sequence
<220> FEATURE:
<223> OTHER INFORMATION: H2TMpyP binding protein MGYAGY

<400> SEQUENCE: 58

Met Gly Tyr Ala Gly Tyr
 1               5

<210> SEQ ID NO 59
<211> LENGTH: 4
<212> TYPE: PRT
<213> ORGANISM: Artificial Sequence
<220> FEATURE:
<223> OTHER INFORMATION: H2TMpyP binding protein YAGF

<400> SEQUENCE: 59

Tyr Ala Gly Phe
 1

<210> SEQ ID NO 60
<211> LENGTH: 6
<212> TYPE: PRT
<213> ORGANISM: Artificial Sequence
<220> FEATURE:
<223> OTHER INFORMATION: H2TMpyP binding protein MGYAGF

<400> SEQUENCE: 60

Met Gly Tyr Ala Gly Phe
 1               5

<210> SEQ ID NO 61
<211> LENGTH: 22

```
<212> TYPE: PRT
<213> ORGANISM: Artificial Sequence
<220> FEATURE:
<223> OTHER INFORMATION: Protoporphyrin IX binding protein MG(HASYS)4

<400> SEQUENCE: 61

Met Gly His Ala Ser Tyr Ser His Ala Ser Tyr Ser His Ala Ser Tyr
 1               5                  10                  15

Ser His Ala Ser Tyr Ser
            20

<210> SEQ ID NO 62
<211> LENGTH: 42
<212> TYPE: PRT
<213> ORGANISM: Artificial Sequence
<220> FEATURE:
<223> OTHER INFORMATION: Protoporphyrin IX binding protein MG(HASYS)8

<400> SEQUENCE: 62

Met Gly His Ala Ser Tyr Ser His Ala Ser Tyr Ser His Ala Ser Tyr
 1               5                  10                  15

Ser His Ala Ser Tyr Ser His Ala Ser Tyr Ser His Ala Ser Tyr Ser
            20                  25                  30

His Ala Ser Tyr Ser His Ala Ser Tyr Ser
        35                  40

<210> SEQ ID NO 63
<211> LENGTH: 22
<212> TYPE: PRT
<213> ORGANISM: Artificial Sequence
<220> FEATURE:
<223> OTHER INFORMATION: Protoporphyrin IX binding protein MG(RASSL)4

<400> SEQUENCE: 63

Met Gly Arg Ala Ser Ser Leu Arg Ala Ser Ser Leu Arg Ala Ser Ser
 1               5                  10                  15

Leu Arg Ala Ser Ser Leu
            20

<210> SEQ ID NO 64
<211> LENGTH: 42
<212> TYPE: PRT
<213> ORGANISM: Artificial Sequence
<220> FEATURE:
<223> OTHER INFORMATION: Protoporphyrin IX binding protein MG(RASSL)8.

<400> SEQUENCE: 64

Met Gly Arg Ala Ser Ser Leu Arg Ala Ser Ser Leu Arg Ala Ser Ser
 1               5                  10                  15

Leu Arg Ala Ser Ser Leu Arg Ala Ser Ser Leu Arg Ala Ser Ser Leu
            20                  25                  30

Arg Ala Ser Ser Leu Arg Ala Ser Ser Leu
        35                  40

<210> SEQ ID NO 65
<211> LENGTH: 36
<212> TYPE: DNA
<213> ORGANISM: Artificial Sequence
<220> FEATURE:
<223> OTHER INFORMATION: Designed oligonucleotide primer to introduce
      mutation into arabidopsis PPO gene

<400> SEQUENCE: 65
tgttcaggtg tttatgttgg tgatccttca aaactg                         36
```

<210> SEQ ID NO 66
<211> LENGTH: 32
<212> TYPE: DNA
<213> ORGANISM: Artificial Sequence
<220> FEATURE:
<223> OTHER INFORMATION: Designed oligonucleotide primer to amplify
      herbicide resistant arabidopsis PPO(A220V) gene

<400> SEQUENCE: 66
ccatgcggaa gcttatggag ttatctcttc tc                              32

<210> SEQ ID NO 67
<211> LENGTH: 34
<212> TYPE: DNA
<213> ORGANISM: Artificial Sequence
<220> FEATURE:
<223> OTHER INFORMATION: Designed oligonucleotide primer to amplify
      herbicide resistant arabidopsis PPO(A220V) gene

<400> SEQUENCE: 67
gggagattta atgtcgacca tttacttgta agcg                            34

<210> SEQ ID NO 68
<211> LENGTH: 31
<212> TYPE: DNA
<213> ORGANISM: Artificial Sequence
<220> FEATURE:
<223> OTHER INFORMATION: Designed oligonucleotide primer to amplify
      Arabidopsis chloroplast ferrochelatase gene

<400> SEQUENCE: 68
gatcggttct gaaatttgga tccatgcagg c                               31

<210> SEQ ID NO 69
<211> LENGTH: 31
<212> TYPE: DNA
<213> ORGANISM: Artificial Sequence
<220> FEATURE:
<223> OTHER INFORMATION: Designed oligonucleotide primer to amplify
      Arabidopsis chloroplast ferrochelatase gene

<400> SEQUENCE: 69
cacaaaacca acgagctcct ataggttccg g                               31

<210> SEQ ID NO 70
<211> LENGTH: 30
<212> TYPE: DNA
<213> ORGANISM: Artificial Sequence
<220> FEATURE:
<223> OTHER INFORMATION: Designed oligonucleotide primer to amplify
      soybean coproporphyrinogen III oxidase gene

<400> SEQUENCE: 70
gaatcggatc cgaagcatga tgcattgtgc                                 30

<210> SEQ ID NO 71
<211> LENGTH: 30
<212> TYPE: DNA
<213> ORGANISM: Artificial Sequence
<220> FEATURE:
<223> OTHER INFORMATION: Designed oligonucleotide primer to amplify
      soybean coproporphyrinogen III oxidase gene

<400> SEQUENCE: 71
gggggtcgac tgatgaatta gatccattcc                                 30

-continued

<210> SEQ ID NO 72
<211> LENGTH: 36
<212> TYPE: DNA
<213> ORGANISM: Artificial Sequence
<220> FEATURE:
<223> OTHER INFORMATION: Designed oligonucleotide primer to amplify
      DNA fragment having nucleotide sequence encoding the Petunia
      hybrida EPSPS chloroplast transit peptide and the Agrobacterium
      sp. strain CP4 EPSPS gene

<400> SEQUENCE: 72
ggaagcttca agaatggcac aaattaacaa catggc                              36

<210> SEQ ID NO 73
<211> LENGTH: 32
<212> TYPE: DNA
<213> ORGANISM: Artificial Sequence
<220> FEATURE:
<223> OTHER INFORMATION: Designed oligonucleotide primer to amplify DNA
      fragment having nucleotide sequence encoding the Petunia hybrida
      EPSPS chloroplast transit peptide and the Agrobacterium sp. strain
      CP4 EPSPS gene

<400> SEQUENCE: 73
gagtcgacgg tcatcaggca gccttcgtat cg                                  32

<210> SEQ ID NO 74
<211> LENGTH: 1587
<212> TYPE: DNA
<213> ORGANISM: Petunia hybrida EPSPS chloroplast transit peptide and
      Agrobacterium sp. strain CP4 EPSPS
<220> FEATURE:
<221> NAME/KEY: CDS
<222> LOCATION: (1)...(1581)

<400> SEQUENCE: 74

```
atg gca caa att aac aac atg gct caa ggg ata caa acc ctt aat ccc      48
Met Ala Gln Ile Asn Asn Met Ala Gln Gly Ile Gln Thr Leu Asn Pro
 1               5                  10                  15 aat tcc aat ttc cat aaa ccc caa gtt cct aaa tct tca agt ttt ctt      96
Asn Ser Asn Phe His Lys Pro Gln Val Pro Lys Ser Ser Ser Phe Leu
             20                  25                  30 gtt ttt gga tct aaa aaa ctg aaa aat tca gca aat tct atg ttg gtt     144
Val Phe Gly Ser Lys Lys Leu Lys Asn Ser Ala Asn Ser Met Leu Val
         35                  40                  45 ttg aaa aaa gat tca att ttt atg caa aag ttt tgt tcc ttt agg att     192
Leu Lys Lys Asp Ser Ile Phe Met Gln Lys Phe Cys Ser Phe Arg Ile
     50                  55                  60 tca gca tca gtg gct aca gcc tgc atg ctt cac ggt gca agc agc cgg     240
Ser Ala Ser Val Ala Thr Ala Cys Met Leu His Gly Ala Ser Ser Arg
 65                  70                  75                  80 ccc gca acc gcc cgc aaa tct tct ggc ctt tcc gga acc gtc cgc att     288
Pro Ala Thr Ala Arg Lys Ser Ser Gly Leu Ser Gly Thr Val Arg Ile
                 85                  90                  95 ccc ggc gac aag tcg atc tcc cac cgg tcc ttc atg ttc ggc ggt ctc     336
Pro Gly Asp Lys Ser Ile Ser His Arg Ser Phe Met Phe Gly Gly Leu
            100                 105                 110 gcg agc ggt gaa acg cgc atc acc ggc ctt ctg gaa ggc gag gac gtc     384
Ala Ser Gly Glu Thr Arg Ile Thr Gly Leu Leu Glu Gly Glu Asp Val
        115                 120                 125 atc aat acg ggc aag gcc atg cag gcc atg ggc gcc agg atc cgt aag     432
Ile Asn Thr Gly Lys Ala Met Gln Ala Met Gly Ala Arg Ile Arg Lys
    130                 135                 140 gaa ggc gac acc tgg atc atc gat ggc gtc ggc aat ggc ggc ctc ctg     480
Glu Gly Asp Thr Trp Ile Ile Asp Gly Val Gly Asn Gly Gly Leu Leu
```

-continued

| | | | | | | | | | | | | | | | |
|---|---|---|---|---|---|---|---|---|---|---|---|---|---|---|---|
| Glu | Gly | Asp | Thr | Trp | Ile | Ile | Asp | Gly | Val | Gly | Asn | Gly | Gly | Leu | Leu |
| 145 | | | | | 150 | | | | | 155 | | | | | 160 |

| gcg | cct | gag | gcg | ccg | ctc | gat | ttc | ggc | aat | gcc | gcc | acg | ggc | tgc | cgc | 528 |
|---|---|---|---|---|---|---|---|---|---|---|---|---|---|---|---|---|
| Ala | Pro | Glu | Ala | Pro | Leu | Asp | Phe | Gly | Asn | Ala | Ala | Thr | Gly | Cys | Arg | |
| | | | | 165 | | | | | 170 | | | | | 175 | | |

| ctg | acc | atg | ggc | ctc | gtc | ggg | gtc | tac | gat | ttc | gac | agc | acc | ttc | atc | 576 |
|---|---|---|---|---|---|---|---|---|---|---|---|---|---|---|---|---|
| Leu | Thr | Met | Gly | Leu | Val | Gly | Val | Tyr | Asp | Phe | Asp | Ser | Thr | Phe | Ile | |
| | | | 180 | | | | | 185 | | | | | 190 | | | |

| ggc | gac | gcc | tcg | ctc | aca | aag | cgc | ccg | atg | ggc | cgc | gtg | ttg | aac | ccg | 624 |
|---|---|---|---|---|---|---|---|---|---|---|---|---|---|---|---|---|
| Gly | Asp | Ala | Ser | Leu | Thr | Lys | Arg | Pro | Met | Gly | Arg | Val | Leu | Asn | Pro | |
| | | | 195 | | | | | 200 | | | | | 205 | | | |

| ctg | cgc | gaa | atg | ggc | gtg | cag | gtg | aaa | tcg | gaa | gac | ggt | gac | cgt | ctt | 672 |
|---|---|---|---|---|---|---|---|---|---|---|---|---|---|---|---|---|
| Leu | Arg | Glu | Met | Gly | Val | Gln | Val | Lys | Ser | Glu | Asp | Gly | Asp | Arg | Leu | |
| | 210 | | | | | 215 | | | | | 220 | | | | | |

| ccc | gtt | acc | ttg | cgc | ggg | ccg | aag | acg | ccg | acg | ccg | atc | acc | tac | cgc | 720 |
|---|---|---|---|---|---|---|---|---|---|---|---|---|---|---|---|---|
| Pro | Val | Thr | Leu | Arg | Gly | Pro | Lys | Thr | Pro | Thr | Pro | Ile | Thr | Tyr | Arg | |
| 225 | | | | | 230 | | | | | 235 | | | | | 240 | |

| gtg | ccg | atg | gcc | tcc | gca | cag | gtg | aag | tcc | gcc | gtg | ctg | ctc | gcc | ggc | 768 |
|---|---|---|---|---|---|---|---|---|---|---|---|---|---|---|---|---|
| Val | Pro | Met | Ala | Ser | Ala | Gln | Val | Lys | Ser | Ala | Val | Leu | Leu | Ala | Gly | |
| | | | | 245 | | | | | 250 | | | | | 255 | | |

| ctc | aac | acg | ccc | ggc | atc | acg | acg | gtc | atc | gag | ccg | atc | atg | acg | cgc | 816 |
|---|---|---|---|---|---|---|---|---|---|---|---|---|---|---|---|---|
| Leu | Asn | Thr | Pro | Gly | Ile | Thr | Thr | Val | Ile | Glu | Pro | Ile | Met | Thr | Arg | |
| | | | 260 | | | | | 265 | | | | | 270 | | | |

| gat | cat | acg | gaa | aag | atg | ctg | cag | ggc | ttt | ggc | gcc | aac | ctt | acc | gtc | 864 |
|---|---|---|---|---|---|---|---|---|---|---|---|---|---|---|---|---|
| Asp | His | Thr | Glu | Lys | Met | Leu | Gln | Gly | Phe | Gly | Ala | Asn | Leu | Thr | Val | |
| | | 275 | | | | | 280 | | | | | 285 | | | | |

| gag | acg | gat | gcg | gac | ggc | gtg | cgc | acc | atc | cgc | ctg | gaa | ggc | cgc | ggc | 912 |
|---|---|---|---|---|---|---|---|---|---|---|---|---|---|---|---|---|
| Glu | Thr | Asp | Ala | Asp | Gly | Val | Arg | Thr | Ile | Arg | Leu | Glu | Gly | Arg | Gly | |
| | 290 | | | | | 295 | | | | | 300 | | | | | |

| aag | ctc | acc | ggc | caa | gtc | atc | gac | gtg | ccg | ggc | gac | ccg | tcc | tcg | acg | 960 |
|---|---|---|---|---|---|---|---|---|---|---|---|---|---|---|---|---|
| Lys | Leu | Thr | Gly | Gln | Val | Ile | Asp | Val | Pro | Gly | Asp | Pro | Ser | Ser | Thr | |
| 305 | | | | | 310 | | | | | 315 | | | | | 320 | |

| gcc | ttc | ccg | ctg | gtt | gcg | gcc | ctg | ctt | gtt | ccg | ggc | tcc | gac | gtc | acc | 1008 |
|---|---|---|---|---|---|---|---|---|---|---|---|---|---|---|---|---|
| Ala | Phe | Pro | Leu | Val | Ala | Ala | Leu | Leu | Val | Pro | Gly | Ser | Asp | Val | Thr | |
| | | | | 325 | | | | | 330 | | | | | 335 | | |

| atc | ctc | aac | gtg | ctg | atg | aac | ccc | acc | cgc | acc | ggc | ctc | atc | ctg | acg | 1056 |
|---|---|---|---|---|---|---|---|---|---|---|---|---|---|---|---|---|
| Ile | Leu | Asn | Val | Leu | Met | Asn | Pro | Thr | Arg | Thr | Gly | Leu | Ile | Leu | Thr | |
| | | | 340 | | | | | 345 | | | | | 350 | | | |

| ctg | cag | gaa | atg | ggc | gcc | gac | atc | gaa | gtc | atc | aac | ccg | cgc | ctt | gcc | 1104 |
|---|---|---|---|---|---|---|---|---|---|---|---|---|---|---|---|---|
| Leu | Gln | Glu | Met | Gly | Ala | Asp | Ile | Glu | Val | Ile | Asn | Pro | Arg | Leu | Ala | |
| | | 355 | | | | | 360 | | | | | 365 | | | | |

| ggc | ggc | gaa | gac | gtg | gcg | gac | ctg | cgc | gtt | cgc | tcc | tcc | acg | ctg | aag | 1152 |
|---|---|---|---|---|---|---|---|---|---|---|---|---|---|---|---|---|
| Gly | Gly | Glu | Asp | Val | Ala | Asp | Leu | Arg | Val | Arg | Ser | Ser | Thr | Leu | Lys | |
| | 370 | | | | | 375 | | | | | 380 | | | | | |

| ggc | gtc | acg | gtg | ccg | gaa | gac | cgc | gcg | cct | tcg | atg | atc | gac | gaa | tat | 1200 |
|---|---|---|---|---|---|---|---|---|---|---|---|---|---|---|---|---|
| Gly | Val | Thr | Val | Pro | Glu | Asp | Arg | Ala | Pro | Ser | Met | Ile | Asp | Glu | Tyr | |
| 385 | | | | | 390 | | | | | 395 | | | | | 400 | |

| ccg | att | ctc | gct | gtc | gcc | gcc | gcc | ttc | gcg | gaa | ggg | gcg | acc | gtg | atg | 1248 |
|---|---|---|---|---|---|---|---|---|---|---|---|---|---|---|---|---|
| Pro | Ile | Leu | Ala | Val | Ala | Ala | Ala | Phe | Ala | Glu | Gly | Ala | Thr | Val | Met | |
| | | | | 405 | | | | | 410 | | | | | 415 | | |

| aac | ggt | ctg | gaa | gaa | ctc | cgc | gtc | aag | gaa | agc | gac | cgc | ctc | tcg | gcc | 1296 |
|---|---|---|---|---|---|---|---|---|---|---|---|---|---|---|---|---|
| Asn | Gly | Leu | Glu | Glu | Leu | Arg | Val | Lys | Glu | Ser | Asp | Arg | Leu | Ser | Ala | |
| | | | 420 | | | | | 425 | | | | | 430 | | | |

| gtc | gcc | aat | ggc | ctc | aag | ctc | aat | ggc | gtg | gat | tgc | gat | gag | ggc | gag | 1344 |
|---|---|---|---|---|---|---|---|---|---|---|---|---|---|---|---|---|
| Val | Ala | Asn | Gly | Leu | Lys | Leu | Asn | Gly | Val | Asp | Cys | Asp | Glu | Gly | Glu | |
| | | 435 | | | | | 440 | | | | | 445 | | | | |

| acg | tcg | ctc | gtc | gtg | cgc | ggc | cgc | cct | gac | ggc | aag | ggg | ctc | ggc | aac | 1392 |
|---|---|---|---|---|---|---|---|---|---|---|---|---|---|---|---|---|
| Thr | Ser | Leu | Val | Val | Arg | Gly | Arg | Pro | Asp | Gly | Lys | Gly | Leu | Gly | Asn | |
| | 450 | | | | | 455 | | | | | 460 | | | | | |

-continued

```
gcc tcg ggc gcc gcc gtc gcc acc cat ctc gat cac cgc atc gcc atg     1440
Ala Ser Gly Ala Ala Val Ala Thr His Leu Asp His Arg Ile Ala Met
465                 470                 475                 480 agc ttc ctc gtc atg ggc ctc gtg tcg gaa aac cct gtc acg gtg gac     1488
Ser Phe Leu Val Met Gly Leu Val Ser Glu Asn Pro Val Thr Val Asp
                485                 490                 495 gat gcc acg atg atc gcc acg agc ttc ccg gag ttc atg gac ctg atg     1536
Asp Ala Thr Met Ile Ala Thr Ser Phe Pro Glu Phe Met Asp Leu Met
            500                 505                 510 gcc ggg ctg ggc gcg aag atc gaa ctc tcc gat acg aag gct gcc tga     1584
Ala Gly Leu Gly Ala Lys Ile Glu Leu Ser Asp Thr Lys Ala Ala
        515                 520                 525 tga                                                                  1587

<210> SEQ ID NO 75
<211> LENGTH: 33
<212> TYPE: DNA
<213> ORGANISM: Artificial Sequence
<220> FEATURE:
<223> OTHER INFORMATION: Designed oligonucleotide primer to amplify DNA
      fragment having partial sequence of soybean PPO gene

<400> SEQUENCE: 75
cacaggaaag gtaccatggt ctgcatcgcc cag                                 33

<210> SEQ ID NO 76
<211> LENGTH: 33
<212> TYPE: DNA
<213> ORGANISM: Artificial Sequence
<220> FEATURE:
<223> OTHER INFORMATION: Designed oligonucleotide primer to amplify DNA
      fragment having partial sequence of soybean PPO gene

<400> SEQUENCE: 76
cctgcagctc gagagctcct actatttgta cac                                 33

<210> SEQ ID NO 77
<211> LENGTH: 6
<212> TYPE: PRT
<213> ORGANISM: Artificial Sequence
<220> FEATURE:
<223> OTHER INFORMATION: PPO variant in which a region presumed to be
      FAD binding site of PPO
<220> FEATURE:
<221> NAME/KEY: unknown
<222> LOCATION: (1)...(6)
<223> OTHER INFORMATION: any Xaa = any amino acid, unknown, or other

<400> SEQUENCE: 77

Gly Xaa Gly Xaa Xaa Gly
  1               5

<210> SEQ ID NO 78
<211> LENGTH: 6
<212> TYPE: PRT
<213> ORGANISM: Artificial Sequence
<220> FEATURE:
<223> OTHER INFORMATION: PPO variant in which a region presumed to be
      FAD binding site of PPO

<400> SEQUENCE: 78

Gly Gly Gly Ile Ser Gly
  1               5
```